(12) United States Patent
Damschroder et al.

(10) Patent No.: US 9,718,870 B2
(45) Date of Patent: Aug. 1, 2017

(54) OX40L FUSION PROTEINS AND USES THEREOF

(71) Applicant: MEDIMMUNE, LLC, Gaithersburg, MD (US)

(72) Inventors: Melissa Damschroder, Gaithersburg, MD (US); Michael Oberst, Gaithersburg, MD (US); Scott Hammond, Gaithersburg, MD (US); Hui Feng, Potomac, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 14/722,679

(22) Filed: May 27, 2015

(65) Prior Publication Data

US 2016/0024176 A1 Jan. 28, 2016

Related U.S. Application Data

(60) Provisional application No. 62/004,555, filed on May 29, 2014, provisional application No. 62/111,796, filed on Feb. 4, 2015.

(51) Int. Cl.

| *A61K 39/00* | (2006.01) |
|---|---|
| *A61K 39/385* | (2006.01) |
| *C07K 16/00* | (2006.01) |
| *C12P 21/08* | (2006.01) |
| *C07H 21/04* | (2006.01) |
| *C12P 21/06* | (2006.01) |
| *C12N 15/00* | (2006.01) |
| *C12N 5/00* | (2006.01) |
| *C07K 14/705* | (2006.01) |
| *A61K 39/39* | (2006.01) |

(52) U.S. Cl.
CPC ........ *C07K 14/70575* (2013.01); *A61K 39/39* (2013.01); *A61K 2039/55516* (2013.01); *A61K 2039/6056* (2013.01); *C07K 2319/30* (2013.01)

(58) Field of Classification Search
None
See application file for complete search history.

(56) References Cited

U.S. PATENT DOCUMENTS

| 5,457,035 | A | 10/1995 | Baum et al. |
| 5,892,019 | A | 4/1999 | Schlom et al. |
| 6,312,700 | B1 | 11/2001 | Weinberg |
| 6,413,746 | B1 | 7/2002 | Field |
| 6,660,501 | B2 | 12/2003 | Field |
| 7,056,695 | B2* | 6/2006 | Dahiyat ............... C07K 14/525 424/85.1 |
| 7,148,321 | B2* | 12/2006 | Gillies .................. C07K 16/30 424/130.1 |
| 7,959,925 | B2* | 6/2011 | Weinberg ............. A61K 38/191 424/178.1 |
| 9,079,976 | B2* | 7/2015 | Shirwan ........... C07K 14/70532 |
| 2008/0108560 | A1* | 5/2008 | Beals ................... C07K 14/765 424/85.1 |
| 2008/0187954 | A1 | 8/2008 | Kallmeier et al. |
| 2011/0243966 | A1 | 10/2011 | Farrington et al. |
| 2012/0116056 | A1* | 5/2012 | Sun ........................ C07K 14/61 530/387.3 |
| 2013/0345406 | A1 | 12/2013 | Van De Winkel et al. |

FOREIGN PATENT DOCUMENTS

| WO | WO 95/21915 | 8/1995 |
| WO | WO 02/072605 A2 | 9/2002 |
| WO | WO 2004/009823 A1 | 1/2004 |
| WO | WO 2006/121810 A2 | 11/2006 |
| WO | WO 2016/062722 | * 4/2016 ............. C12N 15/11 |

OTHER PUBLICATIONS

Wu et al. 2005. Nature Biotech. 23:1137.*
Baruah, P., et al., "Decreased levels of alternative co-stimulatory receptors OX40 and 4-1BB characterise T cells from head and neck cancer patients," Immunobiology, vol. 217, Issue 7, pp. 669-675 (Jul. 2012).
Croft, M., "Control of immunity by the TNFR-related molecule OX40 (CD134)," Annual Reviews, vol. 28, pp. 57-78 (2010).
Croft, M., et al., "The significance of OX40 and OX40L to T-cell biology and immune disease," Immunological Reviews, vol. 229, Issue 1, pp. 173-191 (May 2009).
Curti, B. D., et al, "OX40 is a potent immune-stimulating target in late-stage cancer patients," Cancer Research, vol. 73, Issue 24, pp. 7189-7198 (Dec. 15, 2013).
Dall'Acqua, W. F., et al., "Modulation of the effector functions of a human IgG1 through engineering of its hinge region," The Journal of Immunology, vol. 177, Issue 2, pp. 1129-1138 (Jul. 15, 2006).
Innes, H. E., et al., "Significance of the metastasis-inducing protein AGR2 for outcome in hormonally treated breast cancer patients," British Journal of Cancer, vol. 94, Issue 7, pp. 1057-1065 (Apr. 10, 2006).
International Search Report and Written Opinion for International Application No. PCT/US2015/032598, mailed Sep. 11, 2015.
Jensen, S. M., et al., "Signaling through OX40 enhances antitumor immunity," Seminars in Oncology, vol. 37, Issue 5, pp. 524-532 (Oct. 2010).
Kjaergaard, et al., "Therapeutic Efficacy of OX-40 Receptor Antibody Depends on Tumor Immunogenicity and Anatomic Site of Tumor Growth," Cancer Research, vol. 60, pp. 5514-5521 (Oct. 1,2000).
Kobayashi, H., et al., "Tryptophan H33 plays an important role in pyrimidine (6-4) pyrimidone photoproduct binding by a high-affinity antibody," Protein Engineering, vol. 12, Issue 10, pp. 879-884 (Oct. 1999).
Ladanyi, A., et al., "T-cell activation marker expression on tumor-infiltrating lymphocytes as prognostic factor in cutaneous malignant melanoma," Clinical Cancer Research, vol. 10, Issue 2, pp. 521-530 (Jan. 15, 2004).

(Continued)

*Primary Examiner* — Shulamith H Shafer

(57) ABSTRACT

The disclosure provides OX40L huIgG4 fusion polypeptide subunits comprising a human IgG4 Fc domain, a trimerization domain, and the receptor binding domain of Ox40 ligand, where the fusion polypeptide subunits can self-assemble into hexameric proteins. Also provided are methods of making fusion polypeptide subunits and hexameric proteins, and methods of use, e.g., treatment of cancer.

36 Claims, 39 Drawing Sheets

(56) References Cited

OTHER PUBLICATIONS

Figure 1:
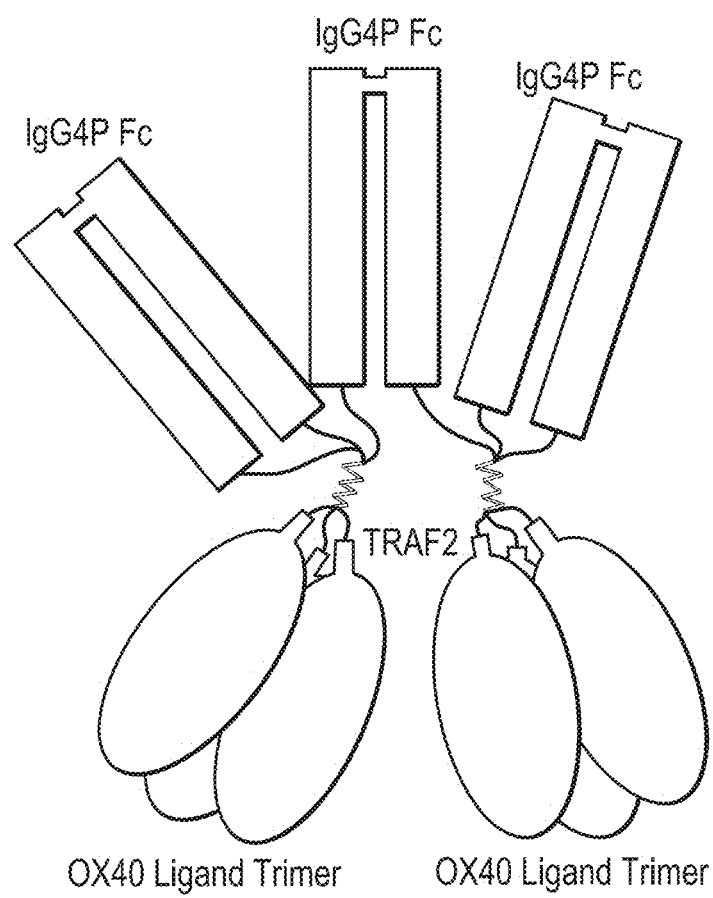

Melero, I., et al., "Clinical development of immunostimulatory monoclonal antibodies and opportunities for combination," Clinical Cancer Research, vol. 19, Issue 5, pp. 997-1008 (Mar. 2013).
Ndhlovu, L. C., et al., "Critical involvement of OX40 ligand signals in the T cell priming events during experimental autoimmune encephalomyelitis," The Journal of Immunolog, vol. 167, Issue 5, pp. 2991-2999 (Sep. 2001).
Petty, J. K., et al., "Survival in human colorectal cancer correlates with expression of the T-cell costimulatory molecule OX-40," The American Journal of Surgery, vol. 183, Issue 5, pp. 512-518 (May 2002).
Piconese, S., et al., "OX40 triggering blocks suppression by regulatory T cells and facilitates tumor rejection," The Journal of Cell Biology, vol. 205, No. 4, pp. 825-839 (Apr. 2008).
Ramstad, T., et al., "Immunohistochemical analysis of primary breast tumors and tumor-draining lymph nodes by means of the T-cell costimulatory molecule OX-40," The American Journal of Surgery, vol. 179, Issue 5, pp. 400-406 (May 2000).
Sarff, M., et al., "OX40 (CD134) expression in sentinel lymph nodes correlates with prognostic features of primary melanomas," The American Journal of Surgery, vol. 195, Issue 5, pp. 621-625 (May 2008).
Vetto, J. T., et al., "Presence of the T-cell activation marker OX-40 on tumor infiltrating lymphocytes and draining lymph node cells from patients with melanoma and head and neck cancers," The American Journal of Surgery, vol. 174, Issue 3, pp. 258-265 (Sep. 1997).
Voo, K. S., et al., "Antibodies Targeting Human OX40 Expand Effector T Cells and Block Inducible and Natural Regulatory T Cell Function," The Journal of Immunology, vol. 191, No. 7, pp. 3641-3650 (2013).
Vu, MD., et al., "OX40 costimulation turns off Foxp3+ Tregs," Blood, vol. 110, Issue 7, pp. 2501-2510 (Nov. 2007).
Weinberg, A. D., et al., "Anti-OX40 (CD134) administration to nonhuman primates: immunostimulatory effects and toxicokinetic study," Journal of Immunotherapy, vol. 29, Issue 6, pp. 575-585 (Nov.-Dec. 2006).
Weinberg, A. D., et al., "Engagement of the OX-40 receptor in vivo enhances antitumor immunity," The Journal of Immunology, vol. 164, Issue 4, pp. 2160-2169 (Feb. 15, 2000).

\* cited by examiner

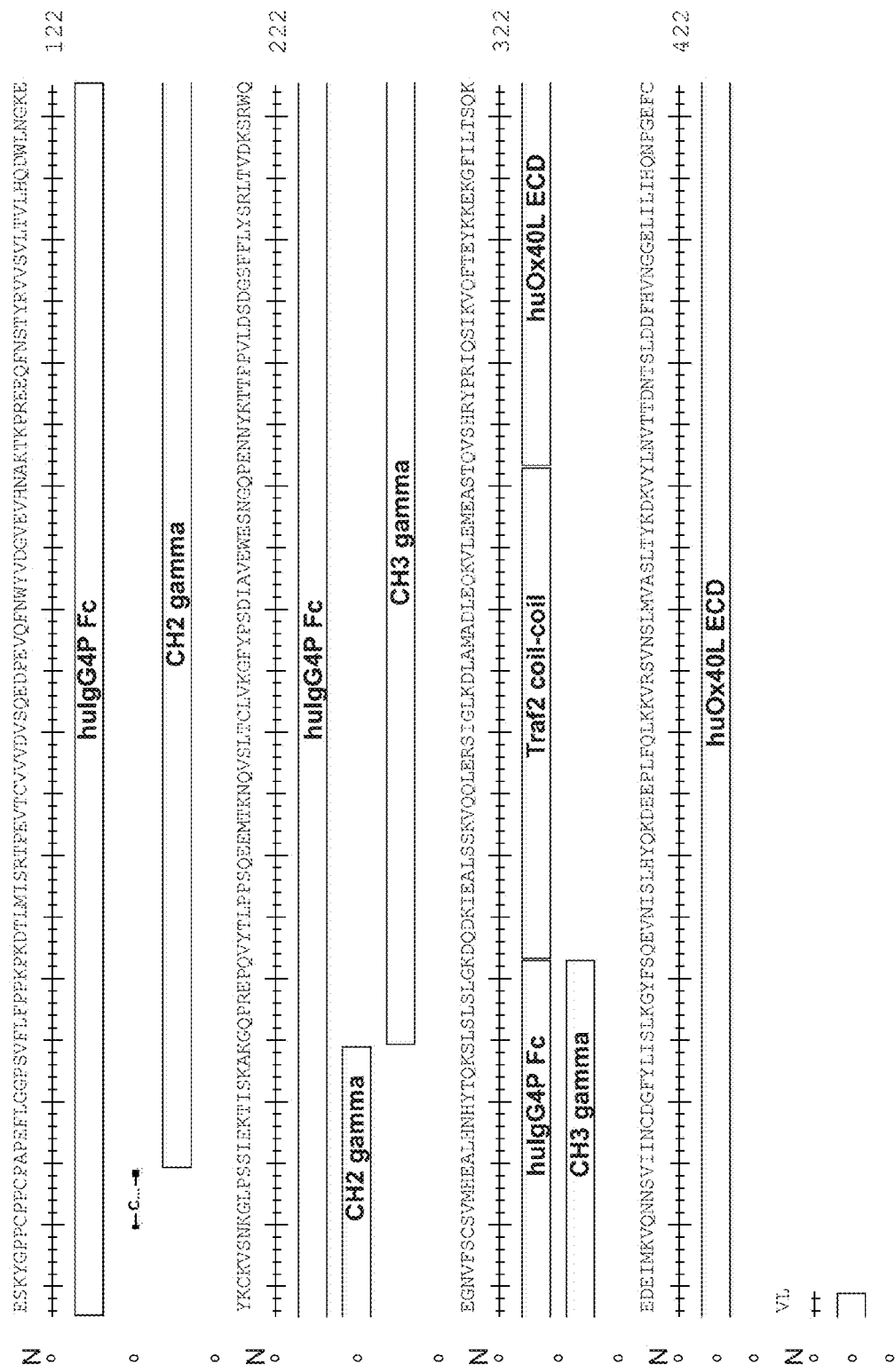

FIG. 2 Contd.

Amino Acid Sequence of huIgG4PFcTF2OX40L F180A (N to C terminus)

```
N ESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKE  122
                                              huIgG4P Fc

N YKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQ  222
                                              huIgG4P Fc

N EGNVFSCSVMHEALHNHYTQKSLSLSLGKDQDKTEALSSRVQQLERSIGLKDIAMADLEQKVIEMEASTQVSHRYPRIQSIKVQFTEYKKEKGFILTSQK  322
                    huIgG4P Fc                         Traf2 coil-coil                huOx40L ECD F180A N EDEIMKVQNNSVIINCDGFYLISLKGYFSQEVNISLHYQKDEEPLFQLKKVPSVNSLMVASLTYKDKVYLNVTTDNTSLDDFHVNGGELILIHQNPGEAC  422
                                              huOx40L ECD F180A

VL ‡ ☐
```

FIG. 3A
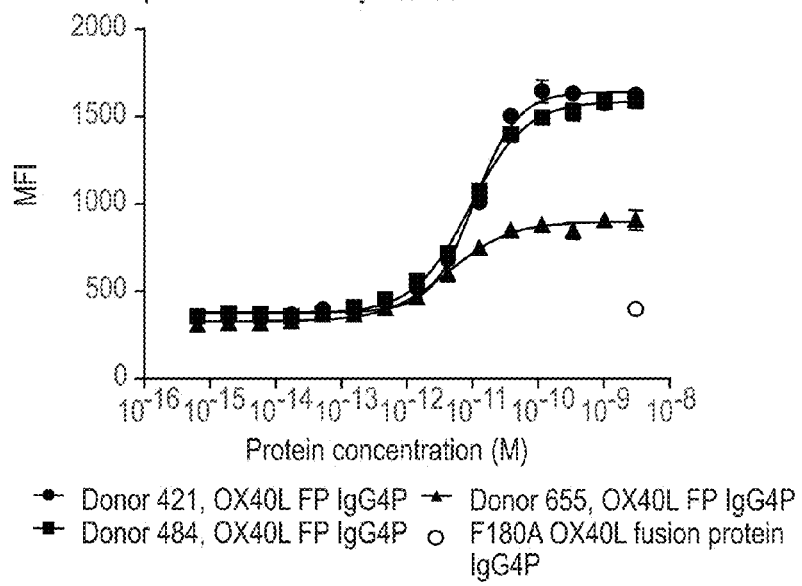
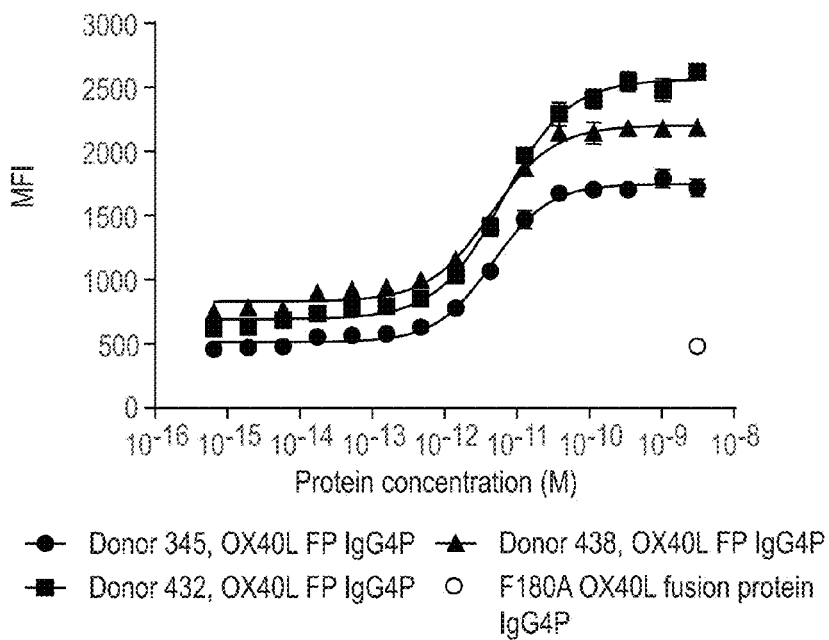

FIG. 3B
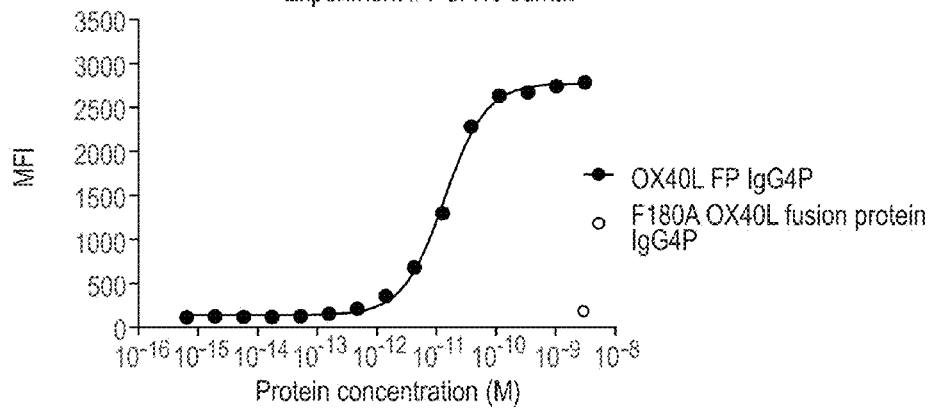
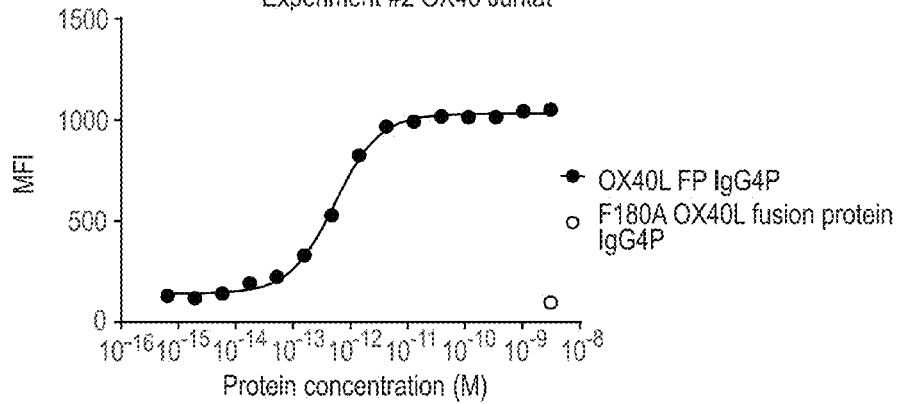
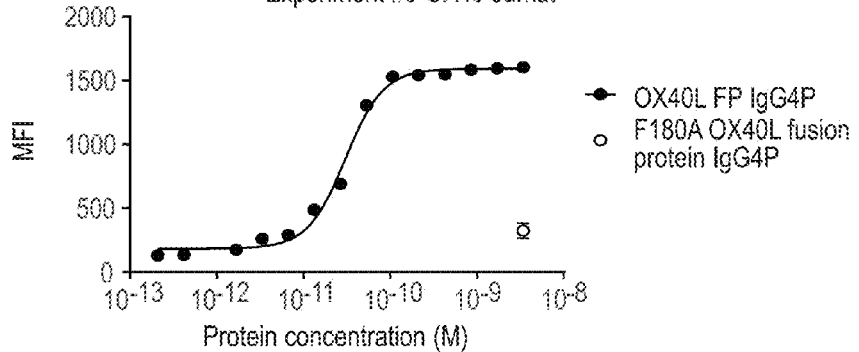

- Clone OX86
- OX40L FP IgG4P
- F180A OX40L Fusion Protein IgG4P
- Rat IgG1 isotype

- OX40L FP IgG4P
- Clone OX40
- Mouse IgG1 isotype
- F180A OX40L Fusion Protein IgG4P FIG. 4C
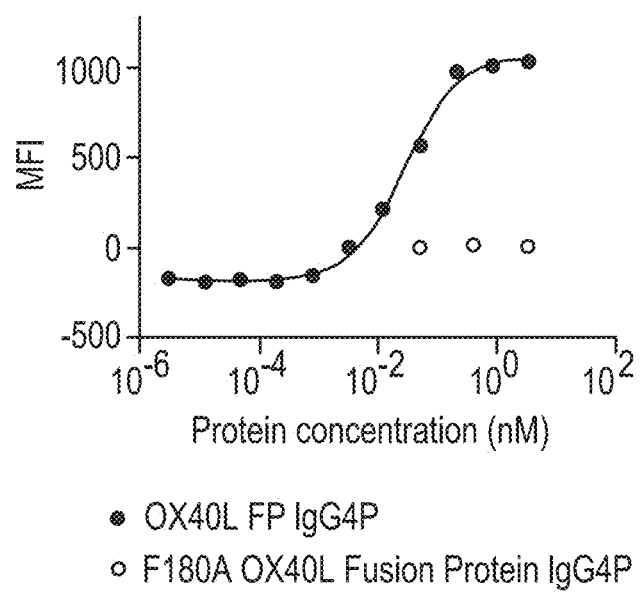
- OX40L FP IgG4P
- F180A OX40L Fusion Protein IgG4P
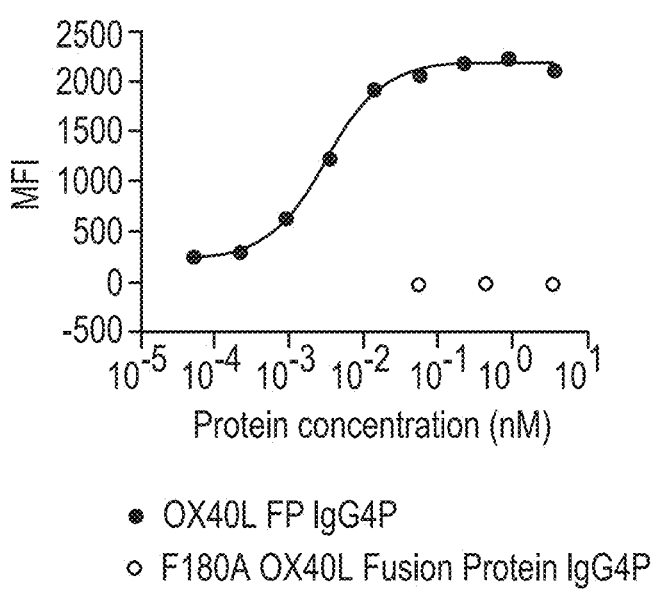
- OX40L FP IgG4P
- F180A OX40L Fusion Protein IgG4P FIG. 4D
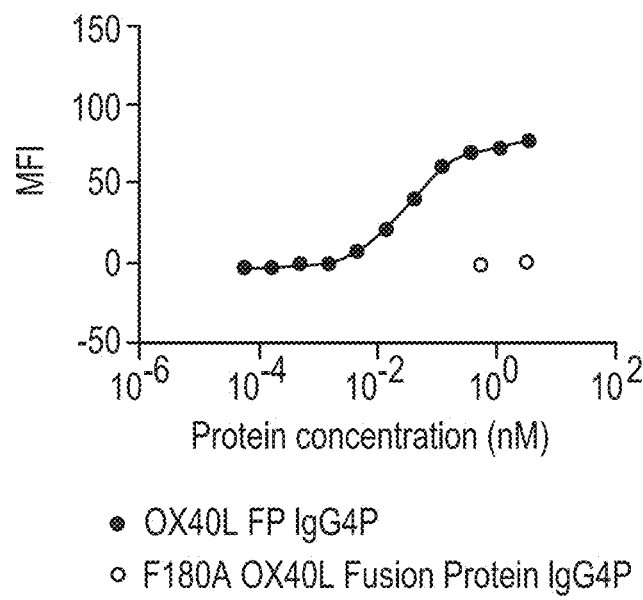
- OX40L FP IgG4P
- F180A OX40L Fusion Protein IgG4P
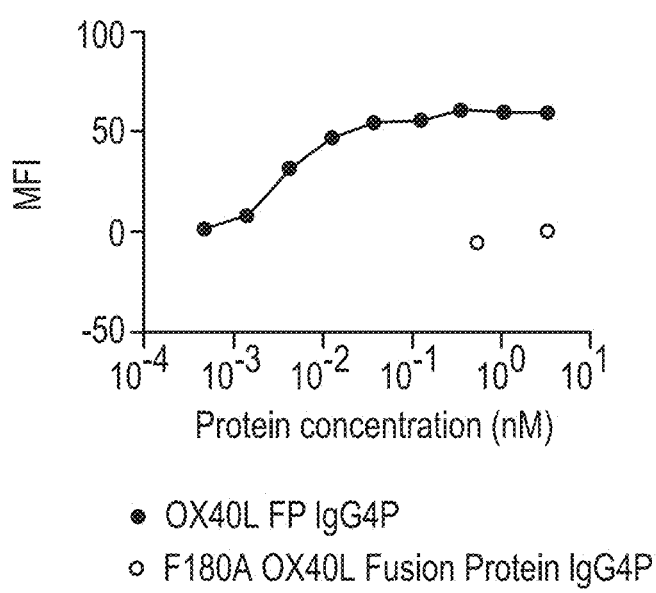
- OX40L FP IgG4P
- F180A OX40L Fusion Protein IgG4P

Figure 5A:
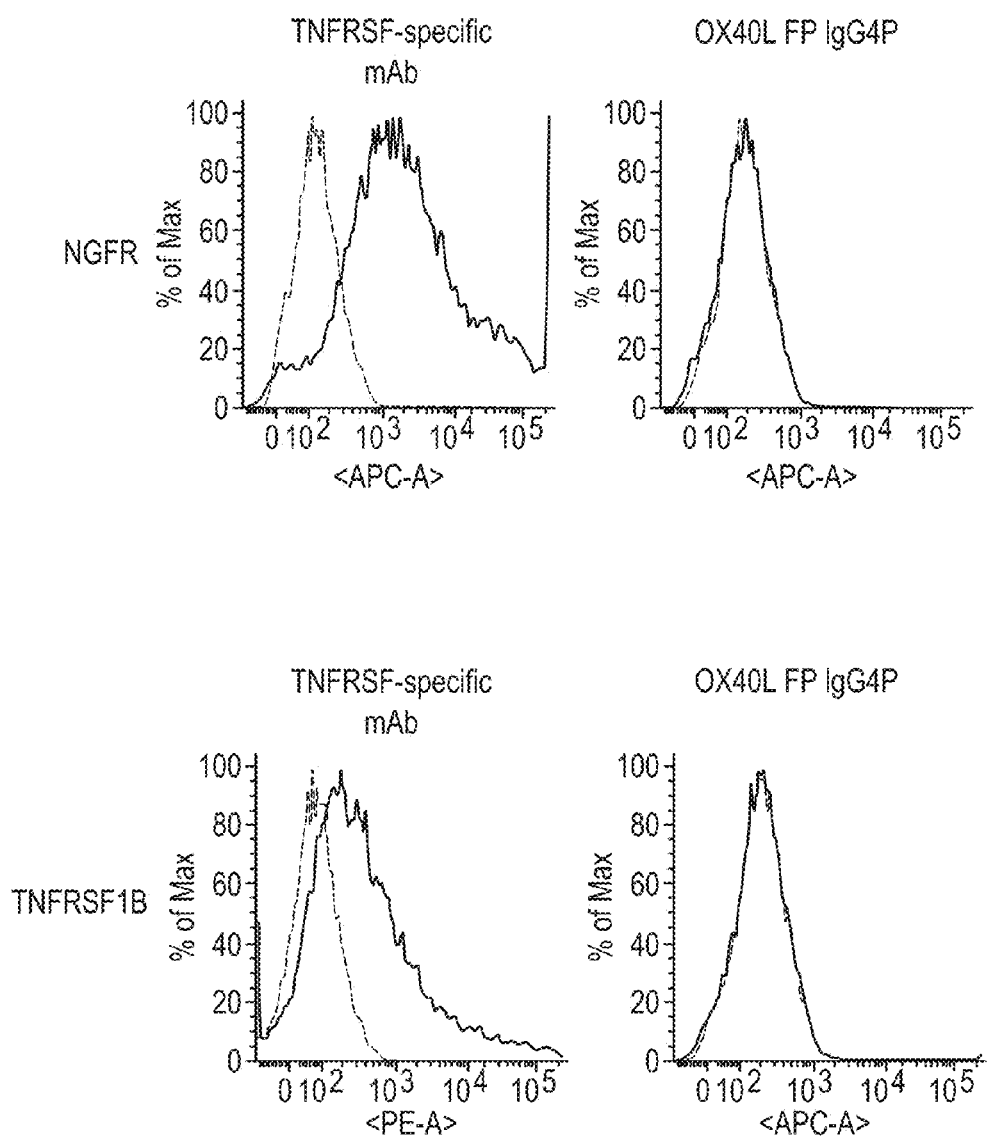

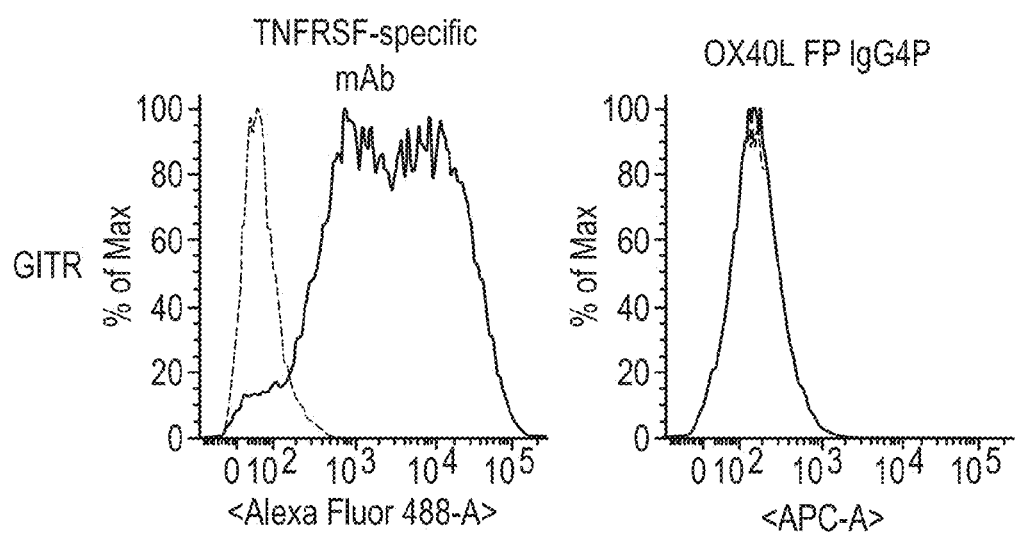
FIG. 5A Contd.

Figure 5B:
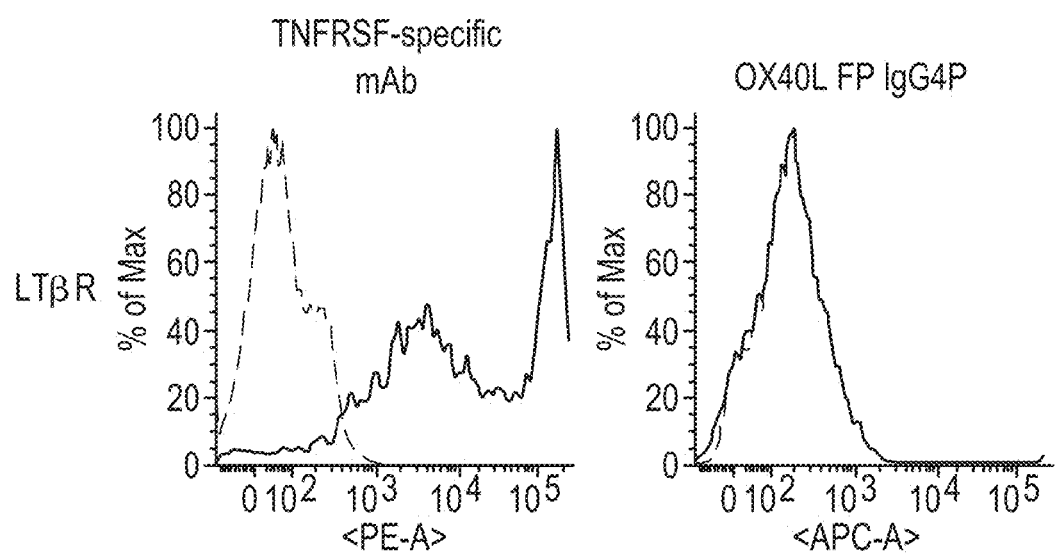

FIG. 5B Contd.
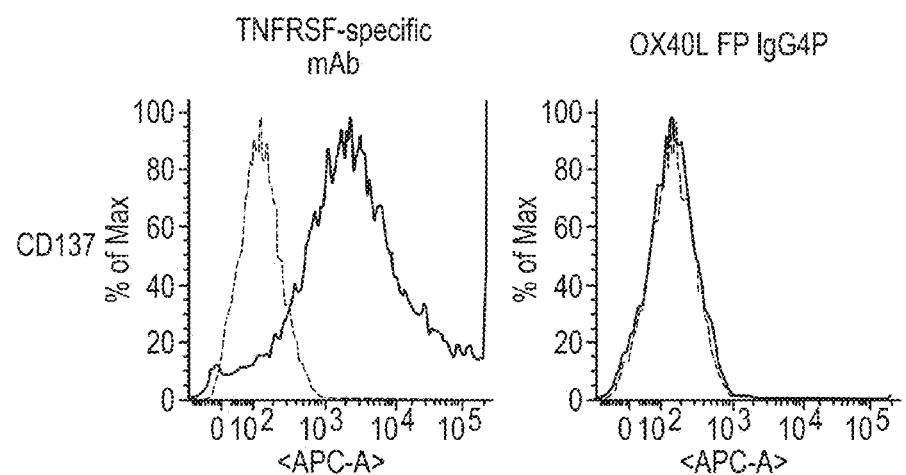
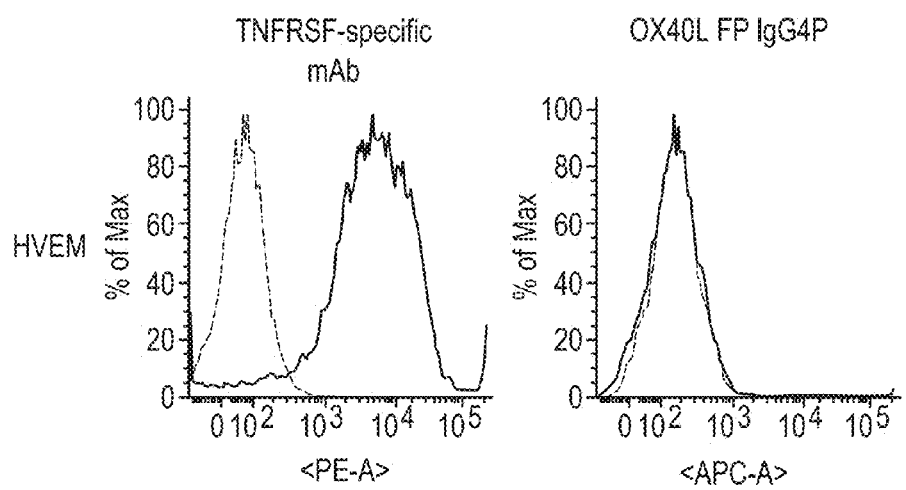

CD4 T cell proliferation

IFNγ Release

TNFα Release

IL-10 Release

IL-13 Release

CD32A-expressing HEK plus OX40 Jurkat reporter

Parental HEK plus OX40 Jurkat reporter

OX40 Jurkat reporter alone

CD32A-expressing HEK293

CD45 positive cells, renal tumor
Experiment 16

FIG. 13
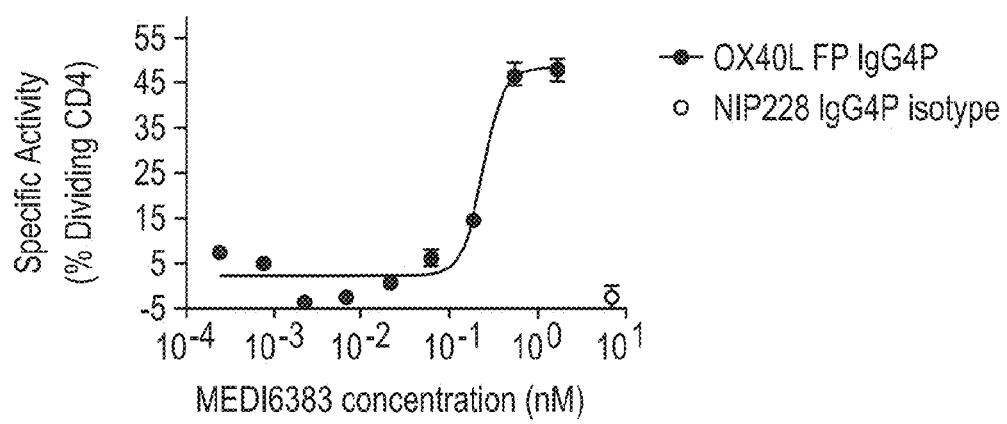
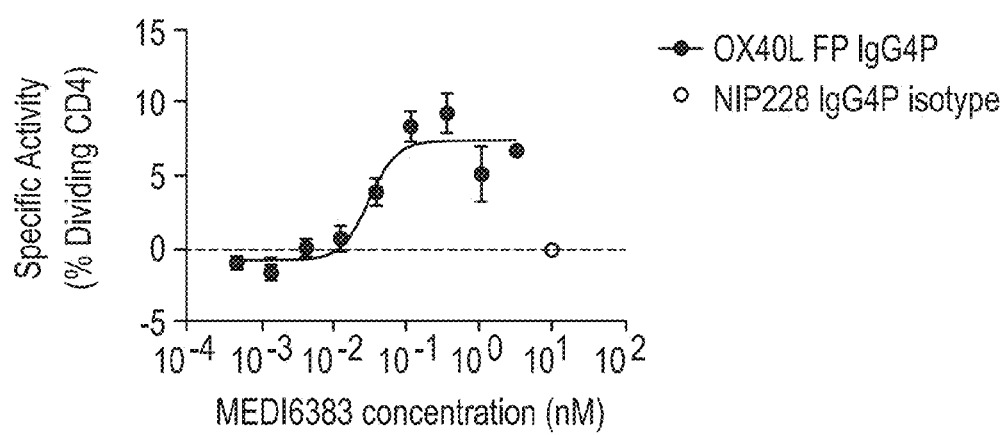

Experiment #1: Donor 1

Experiment #1: Donor 1

Experiment #1: Donor 2

Experiment #1: Donor 2

Experiment #2: Donor 3

FIG. 18
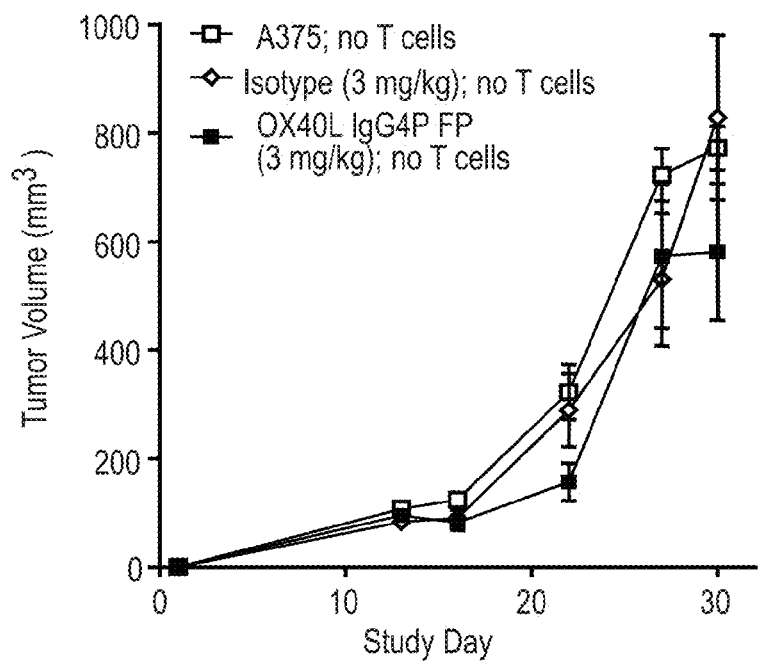
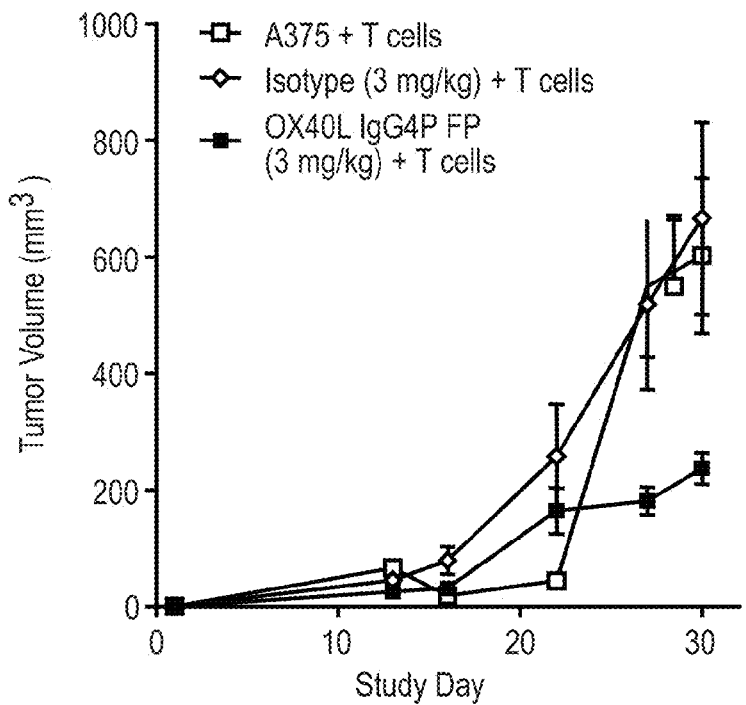

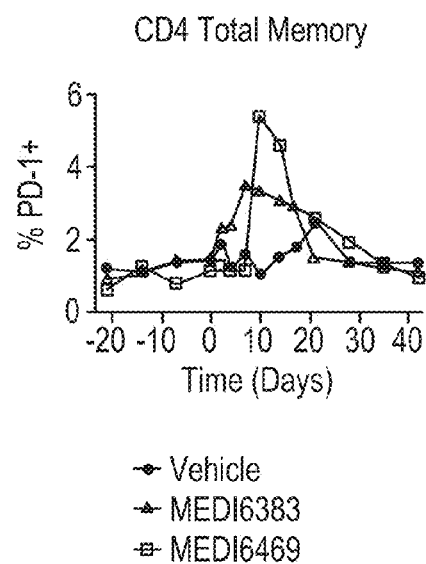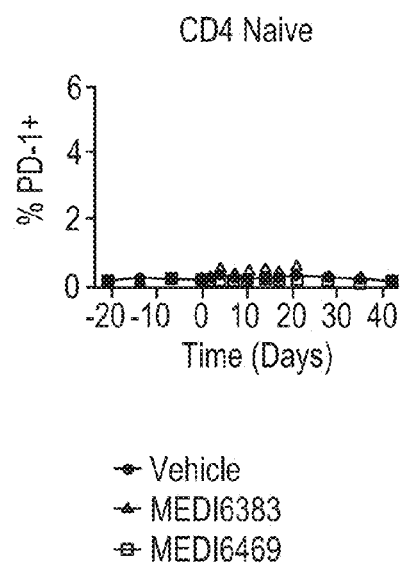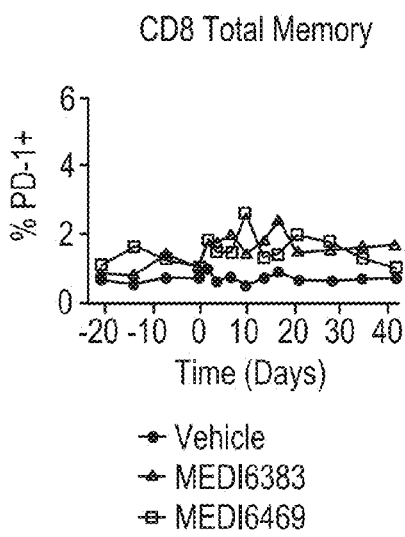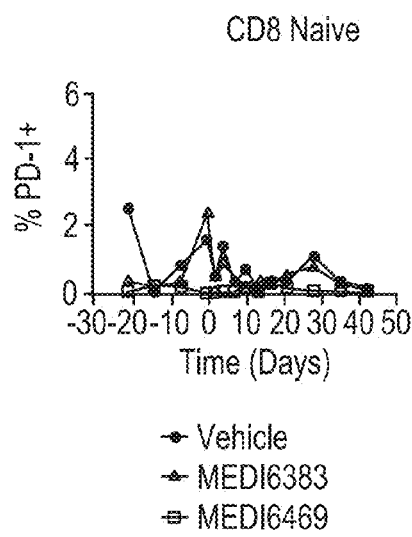

SEQUENCE LISTING

```
<160> NUMBER OF SEQ ID NOS: 12

<210> SEQ ID NO 1
<211> LENGTH: 183
<212> TYPE: PRT
<213> ORGANISM: Homo sapiens

<400> SEQUENCE: 1

Met Glu Arg Val Gln Pro Leu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60
```

```
Gln Phe Thr Glu Tyr Lys Lys Glu Lys Gly Phe Ile Leu Thr Ser Gln
 65                  70                  75                  80

Lys Glu Asp Glu Ile Met Lys Val Gln Asn Asn Ser Val Ile Ile Asn
                 85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 2
<211> LENGTH: 501
<212> TYPE: PRT
<213> ORGANISM: Homo sapiens

<400> SEQUENCE: 2

Met Ala Ala Ser Val Thr Pro Pro Gly Ser Leu Glu Leu Leu Gln
  1               5                  10                  15

Pro Gly Phe Ser Lys Thr Leu Leu Gly Thr Lys Leu Glu Ala Lys Tyr
                 20                  25                  30

Leu Cys Ser Ala Cys Arg Asn Val Leu Arg Arg Pro Phe Gln Ala Gln
             35                  40                  45

Cys Gly His Arg Tyr Cys Ser Phe Cys Leu Ala Ser Ile Leu Ser Ser
         50                  55                  60

Gly Pro Gln Asn Cys Ala Ala Cys Val His Glu Gly Ile Tyr Glu Glu
 65                  70                  75                  80

Gly Ile Ser Ile Leu Glu Ser Ser Ala Phe Pro Asp Asn Ala Ala
                 85                  90                  95

Arg Arg Glu Val Glu Ser Leu Pro Ala Val Cys Pro Ser Asp Gly Cys
                100                 105                 110

Thr Trp Lys Gly Thr Leu Lys Glu Tyr Glu Ser Cys His Glu Gly Arg
            115                 120                 125

Cys Pro Leu Met Leu Thr Glu Cys Pro Ala Cys Lys Gly Leu Val Arg
        130                 135                 140

Leu Gly Glu Lys Glu Arg His Leu Glu His Glu Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
                180                 185                 190

Gly Lys Lys Lys Ile Pro Arg Glu Lys Phe Gln Asp His Val Lys Thr
            195                 200                 205

Cys Gly Lys Cys Arg Val Pro Cys Arg Phe His Ala Ile Gly Cys Leu
        210                 215                 220

Glu Thr Val Glu Gly Glu Lys Gln Gln Glu His Glu Val Gln Trp Leu
225                 230                 235                 240

Arg Glu His Leu Ala Met Leu Leu Ser Ser Val Leu Glu Ala Lys Pro
                245                 250                 255
```

Leu Leu Gly Asp Gln Ser His Ala Gly Ser Glu Leu Leu Gln Arg Cys
            260                 265                 270

Glu Ser Leu Glu Lys Lys Thr Ala Thr Phe Glu Asn Ile Val Cys Val
        275                 280                 285

Leu Asn Arg Glu Val Glu Arg Val Ala Met Thr Ala Glu Ala Cys Ser
    290                 295                 300

Arg Gln His Arg Leu Asp Gln Asp Lys Ile Glu Ala Leu Ser Ser Lys
305                 310                 315                 320

Val Gln Gln Leu Glu Arg Ser Ile Gly Leu Lys Asp Leu Ala Met Ala
                325                 330                 335

Asp Leu Glu Gln Lys Val Leu Glu Met Glu Ala Ser Thr Tyr Asp Gly
            340                 345                 350

Val Phe Ile Trp Lys Ile Ser Asp Phe Ala Arg Lys Arg Gln Glu Ala
        355                 360                 365

Val Ala Gly Arg Ile Pro Ala Ile Phe Ser Pro Ala Phe Tyr Thr Ser
    370                 375                 380

Arg Tyr Gly Tyr Lys Met Cys Leu Arg Ile Tyr Leu Asn Gly Asp Gly
385                 390                 395                 400

Thr Gly Arg Gly Thr His Leu Ser Leu Phe Phe Val Val Met Lys Gly
                405                 410                 415

Pro Asn Asp Ala Leu Leu Arg Trp Pro Phe Asn Gln Lys Val Thr Leu
            420                 425                 430

Met Leu Leu Asp Gln Asn Asn Arg Glu His Val Ile Asp Ala Phe Arg
        435                 440                 445

Pro Asp Val Thr Ser Ser Ser Phe Gln Arg Pro Val Asn Asp Met Asn
    450                 455                 460

Ile Ala Ser Gly Cys Pro Leu Phe Cys Pro Val Ser Lys Met Glu Ala
465                 470                 475                 480

Lys Asn Ser Tyr Val Arg Asp Asp Ala Ile Phe Ile Lys Ala Ile Val
                485                 490                 495

Asp Leu Thr Gly Leu
            500

<210> SEQ ID NO 3
<211> LENGTH: 1206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gagagcaagt acggccctcc ctgcccccct tgccctgccc ccgagttcct gggcggacct     60
agcgtgttcc tgttcccccc caagcccaag gacaccctga tgatcagcag aaccccgag    120 gtgacctgcg tggtggtgga cgtgtcccag gaggacccg aggtccagtt taattggtac    180
gtggacggcg tggaagtgca taacgccaag accaagccca gagaggagca gttcaacagc    240
acctacagag tggtgtccgt gctgaccgtg ctgcaccagg actggctgaa cggcaaggaa    300
tacaagtgca aggtctccaa caagggcctg cctagcagca tcgagaagac catcagcaag    360
gccaagggcc agccacggga gccccaggtc tacaccctgc acctagcca agaggagatg    420 accaagaacc aggtgtccct gacctgtctg gtgaaaggct tctatcccag cgatatcgcc    480
gtggagtggg agagcaacgg ccagcccgag aacaactaca agaccacccc ccctgtgctg    540
gacagcgacg gcagcttctt cctgtactcc agactgaccg tggacaagtc cagatggcag    600

```
gagggcaacg tcttcagctg ctccgtgatg cacgaggccc tgcacaacca ctacacccag    660
aagtccctga gcctgagcct gggcaaggac caggataaga tcgaggctct gtcctccaag    720
gtgcagcagc tggaacggtc catcggcctg aaggacctgg ccatggctga cctggaacag    780
aaagtgctgg aaatggaagc ctccacacag gtgtcacaca gatacccccg gatccagtcc    840
attaaggtgc agttcaccga gtacaagaaa gagaagggct ttatcctgac ctcccagaaa    900
gaggacgaga tcatgaaggt gcagaacaac tccgtgatca tcaactgcga cgggttctac    960
ctgatctccc tgaagggcta cttcagccag gaagtgaaca tctccctgca ctaccagaag   1020
gacgaggaac ccctgttcca gctgaagaaa gtgcggagcg tgaactccct gatggtggcc   1080
tctctgacct acaaggacaa ggtgtacctg aacgtgacca ccgacaacac ctccctggac   1140
gacttccacg tgaacggcgg cgagctgatc ctgatccacc agaaccctgg cgagttctgc   1200
gtgctg                                                              1206
```

<210> SEQ ID NO 4
<211> LENGTH: 402
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Asp Gln Asp Lys Ile Glu Ala Leu Ser Ser Lys
225                 230                 235                 240
```

```
Val Gln Gln Leu Glu Arg Ser Ile Gly Leu Lys Asp Leu Ala Met Ala
                245                 250                 255

Asp Leu Glu Gln Lys Val Leu Glu Met Glu Ala Ser Thr Gln Val Ser
            260                 265                 270

His Arg Tyr Pro Arg Ile Gln Ser Ile Lys Val Gln Phe Thr Glu Tyr
        275                 280                 285

Lys Lys Glu Lys Gly Phe Ile Leu Thr Ser Gln Lys Glu Asp Glu Ile
    290                 295                 300

Met Lys Val Gln Asn Asn Ser Val Ile Ile Asn Cys Asp Gly Phe Tyr
305                 310                 315                 320

Leu Ile Ser Leu Lys Gly Tyr Phe Ser Gln Glu Val Asn Ile Ser Leu
                325                 330                 335

His Tyr Gln Lys Asp Glu Glu Pro Leu Phe Gln Leu Lys Lys Val Arg
            340                 345                 350

Ser Val Asn Ser Leu Met Val Ala Ser Leu Thr Tyr Lys Asp Lys Val
        355                 360                 365

Tyr Leu Asn Val Thr Thr Asp Asn Thr Ser Leu Asp Asp Phe His Val
    370                 375                 380

Asn Gly Gly Glu Leu Ile Leu Ile His Gln Asn Pro Gly Glu Phe Cys
385                 390                 395                 400

Val Leu

<210> SEQ ID NO 5
<211> LENGTH: 1206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gagagcaagt acggccctcc ctgccccct tgccctgccc ccgagttcct gggcggacct      60
agcgtgttcc tgttccccc caagcccaag gacaccctga tgatcagcag aacccccgag     120
gtgacctgcg tggtggtgga cgtgtcccag gaggaccccg aggtccagtt taattggtac    180
gtggacggcg tggaagtgca taacgccaag accaagccca gagaggagca gttcaacagc    240
acctacagag tggtgtccgt gctgaccgtg ctgcaccagg actggctgaa cggcaaggaa    300
tacaagtgca aggtctccaa caagggcctg cctagcagca tcgagaagac catcagcaag    360
gccaagggcc agccacggga gccccaggtc tacaccctgc cacctagcca agaggagatg    420
accaagaacc aggtgtccct gacctgtctg gtgaaaggct tctatcccag cgatatcgcc    480
gtggagtggg agagcaacgg ccagcccgag aacaactaca agaccacccc ccctgtgctg    540
gacagcgacg gcagcttctt cctgtactcc agactgaccg tggacaagtc cagatggcag    600
gagggcaacg tcttcagctg ctccgtgatg cacgaggccc tgcacaacca ctacacccag    660
aagtccctga gcctgagcct gggcaaggac caggataaga tcgaggctct gtcctccaag    720
gtgcagcagc tggaacggtc catcggcctg aaggacctgg ccatggctga cctggaacag    780
aaagtgctgg aaatggaagc ctccacacag gtgtcacaca gatacccccg gatccagtcc    840
attaaggtgc agttcaccga gtacaagaaa gagaagggct tatcctgac ctcccagaaa    900 gaggacgaga tcatgaaggt gcagaacaac tccgtgatca tcaactgcga cgggttctac    960
ctgatctccc tgaagggcta cttcagccag gaagtgaaca tctccctgca ctaccagaag   1020
gacgaggaac ccctgttcca gctgaagaaa gtgcggagcg tgaactccct gatggtggcc   1080
```

-continued

```
tctctgacct acaaggacaa ggtgtacctg aacgtgacca ccgacaacac ctccctggac    1140
gacttccacg tgaacggcgg cgagctgatc ctgatccacc agaaccctgg cgaggcctgc    1200
gtgctg                                                                1206
```

```
<210> SEQ ID NO 6
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Asp Gln Asp Lys Ile Glu Ala Leu Ser Ser Lys
225                 230                 235                 240

Val Gln Gln Leu Glu Arg Ser Ile Gly Leu Lys Asp Leu Ala Met Ala
                245                 250                 255

Asp Leu Glu Gln Lys Val Leu Glu Met Glu Ala Ser Thr Gln Val Ser
            260                 265                 270

His Arg Tyr Pro Arg Ile Gln Ser Ile Lys Val Gln Phe Thr Glu Tyr
        275                 280                 285

Lys Lys Glu Lys Gly Phe Ile Leu Thr Ser Gln Lys Glu Asp Glu Ile
    290                 295                 300

Met Lys Val Gln Asn Asn Ser Val Ile Ile Asn Cys Asp Gly Phe Tyr
305                 310                 315                 320

Leu Ile Ser Leu Lys Gly Tyr Phe Ser Gln Glu Val Asn Ile Ser Leu
                325                 330                 335

```
His Tyr Gln Lys Asp Glu Glu Pro Leu Phe Gln Leu Lys Lys Val Arg
            340                 345                 350

Ser Val Asn Ser Leu Met Val Ala Ser Leu Thr Tyr Lys Asp Lys Val
            355                 360                 365

Tyr Leu Asn Val Thr Thr Asp Asn Thr Ser Leu Asp Asp Phe His Val
        370                 375                 380

Asn Gly Gly Glu Leu Ile Leu Ile His Gln Asn Pro Gly Glu Ala Cys
385                 390                 395                 400

Val Leu

<210> SEQ ID NO 7
<211> LENGTH: 1200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gataagaccc acacctgtcc cccttgtcct gccctgaac tgctgggcgg accttccgtg       60
ttcctgttcc cccaaagcc caaggacacc ctgatgatct cccggacccc cgaagtgacc      120
tgcgtggtgg tggatgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggattggc tgaacggcaa agagtacaag    300
tgcaaggtgt ccaacaaggc cctgcctgcc cccatcgaaa agaccatctc caaggccaag    360
ggccagcccc gggaacccca ggtgtacaca ctgcccccta gccgggaaga gatgaccaag    420
aaccaggtgt ccctgacctg tctcgtgaag ggcttctacc cctccgatat cgccgtggaa    480
tgggagtcca acggccagcc tgagaacaac tacaagacca cccccctgt gctggactcc     540 gacggctcat tcttcctgta ctccaagctg acagtggaca gtcccggtg cagcagggc     600 aacgtgttct cctgctccgt gatgcacgag gccctgcaca accactacac ccagaagtcc    660
ctgtccctga gccccggcaa ggaccaggat aagatcgagg ctctgtcctc caaggtgcag    720
cagctggaac ggtccatcgg cctgaaggac ctggccatgg ctgacctgga acagaaagtg    780
ctggaaatgg aagcctccac acaggtgtca cacagatacc cccggatcca gtccattaag    840
gtgcagttca ccgagtacaa gaaagagaag ggctttatcc tgacctccca gaaagaggac    900
gagatcatga aggtgcagaa caactccgtg atcatcaact gcgacgggtt ctacctgatc    960 tcccctgaagg gctacttcag ccaggaagtg aacatctccc tgcactacca gaaggacgag   1020
gaacccctgt tccagctgaa gaaagtgcgg agcgtgaact ccctgatggt ggcctctctg   1080
acctacaagg acaaggtgta cctgaacgtg accaccgaca cacctccct ggacgacttc    1140 cacgtgaacg gcggcgagct gatcctgatc caccagaacc ctggcgagtt ctgcgtgctg   1200

<210> SEQ ID NO 8
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Lys Thr His Thr Cys Pro Pro Cys Pro Ala Pro Glu Leu Leu Gly
1               5                   10                  15
```

-continued

Gly Pro Ser Val Phe Leu Phe Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Asp Gln Asp Lys Ile Glu Ala Leu Ser Ser Lys Val Gln
225                 230                 235                 240

Gln Leu Glu Arg Ser Ile Gly Leu Lys Asp Leu Ala Met Ala Asp Leu
                245                 250                 255

Glu Gln Lys Val Leu Glu Met Glu Ala Ser Thr Gln Val Ser His Arg
            260                 265                 270

Tyr Pro Arg Ile Gln Ser Ile Lys Val Gln Phe Thr Glu Tyr Lys Lys
        275                 280                 285

Glu Lys Gly Phe Ile Leu Thr Ser Gln Lys Glu Asp Glu Ile Met Lys
290                 295                 300

Val Gln Asn Asn Ser Val Ile Ile Asn Cys Asp Gly Phe Tyr Leu Ile
305                 310                 315                 320

Ser Leu Lys Gly Tyr Phe Ser Gln Glu Val Asn Ile Ser Leu His Tyr
                325                 330                 335

Gln Lys Asp Glu Glu Pro Leu Phe Gln Leu Lys Lys Val Arg Ser Val
            340                 345                 350

Asn Ser Leu Met Val Ala Ser Leu Thr Tyr Lys Asp Lys Val Tyr Leu
        355                 360                 365

Asn Val Thr Thr Asp Asn Thr Ser Leu Asp Asp Phe His Val Asn Gly
370                 375                 380

Gly Glu Leu Ile Leu Ile His Gln Asn Pro Gly Glu Phe Cys Val Leu
385                 390                 395                 400

<210> SEQ ID NO 9
<211> LENGTH: 1248
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 9

```
gtgcctagag attgcggctg caagccctgc atctgcaccg tgcccgaggt gtccagcgtg      60
ttcatcttcc cacccaagcc caaggacgtg ctgaccatca ccctgacccc caaagtgacc     120
tgcgtggtgg tggacatcag caaggacgac cccgaggtgc agttcagttg gttcgtggac     180
gacgtggaag tgcacaccgc ccagacccag cccagagagg aacagttcaa cagcaccttc     240
agaagcgtgt ccgagctgcc catcatgcac caggactggc tgaacggcaa agaattcaag     300
tgcagagtga acagcgccgc cttccctgcc cccatcgaga aaaccatcag caagaccaag     360
ggcagaccca aggcccccca ggtgtacacc atcccccac ccaaagaaca gatggccaag     420
gacaaggtgt ccctgacctg catgatcacc gatttcttcc cagaggacat caccgtggaa     480
tggcagtgga acggccagcc cgccgagaac tacaagaaca cccagcccat catggacacc     540
gacggcagct acttcgtgta cagcaagctg aacgtgcaga agtccaactg ggaggccggc     600
aacaccttca cctgtagcgt gctgcacgag ggcctgcaca accaccacac cgagaagtcc     660
ctgagccaca gccccggcaa gcggctggac caggacaaga tcgaggccct gagcaacaag     720
gtgcagcagc tggaacggtc tatcggcctg aaggacctgg ctatggccga cctggaacag     780
aaagtgtctg agctggaagt gtccaccagc agccccgcca aggaccctcc catccagaga     840
ctgagaggcg ccgtgaccag atgcgaggac ggccagctgt tcatcagcag ctacaagaac     900
gagtaccaga ccatggaagt gcagaacaac agcgtggtca tcaagtgcga cggcctgtac     960
atcatctacc tcaagggcag cttcttccag gaagtgaaga tcgacctgca cttcagagag    1020
gaccacaacc ccatcagcat ccccatgctg aacgacggca cgcgatcgt gttcaccgtg    1080
gtggctagcc tggccttcaa ggacaaagtg tatctgaccg tgaacgcccc cgacaccctg    1140
tgcgagcatc tgcagatcaa cgacggcgag ctgatcgtgg tgcagctgac ccccggctac    1200
tgtgcccctg agggcagcta ccacagcacc gtgaaccagg tgcccctg                 1248
```

<210> SEQ ID NO 10
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Val Pro Arg Asp Cys Gly Cys Lys Pro Cys Ile Cys Thr Val Pro Glu
1               5                   10                  15
Val Ser Ser Val Phe Ile Phe Pro Pro Lys Pro Lys Asp Val Leu Thr
            20                  25                  30
Ile Thr Leu Thr Pro Lys Val Thr Cys Val Val Val Asp Ile Ser Lys
        35                  40                  45
Asp Asp Pro Glu Val Gln Phe Ser Trp Phe Val Asp Asp Val Glu Val
    50                  55                  60
His Thr Ala Gln Thr Gln Pro Arg Glu Glu Gln Phe Asn Ser Thr Phe
65                  70                  75                  80
Arg Ser Val Ser Glu Leu Pro Ile Met His Gln Asp Trp Leu Asn Gly
                85                  90                  95
Lys Glu Phe Lys Cys Arg Val Asn Ser Ala Ala Phe Pro Ala Pro Ile
            100                 105                 110
```

```
Glu Lys Thr Ile Ser Lys Thr Lys Gly Arg Pro Lys Ala Pro Gln Val
            115                 120                 125

Tyr Thr Ile Pro Pro Lys Glu Gln Met Ala Lys Asp Lys Val Ser
130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
210                 215                 220

Pro Gly Lys Arg Leu Asp Gln Asp Lys Ile Glu Ala Leu Ser Asn Lys
225                 230                 235                 240

Val Gln Gln Leu Glu Arg Ser Ile Gly Leu Lys Asp Leu Ala Met Ala
                245                 250                 255

Asp Leu Glu Gln Lys Val Ser Glu Leu Glu Val Ser Thr Ser Ser Pro
            260                 265                 270

Ala Lys Asp Pro Pro Ile Gln Arg Leu Arg Gly Ala Val Thr Arg Cys
        275                 280                 285

Glu Asp Gly Gln Leu Phe Ile Ser Ser Tyr Lys Asn Glu Tyr Gln Thr
290                 295                 300

Met Glu Val Gln Asn Asn Ser Val Val Ile Lys Cys Asp Gly Leu Tyr
305                 310                 315                 320

Ile Ile Tyr Leu Lys Gly Ser Phe Phe Gln Glu Val Lys Ile Asp Leu
                325                 330                 335

His Phe Arg Glu Asp His Asn Pro Ile Ser Ile Pro Met Leu Asn Asp
            340                 345                 350

Gly Arg Arg Ile Val Phe Thr Val Val Ala Ser Leu Ala Phe Lys Asp
        355                 360                 365

Lys Val Tyr Leu Thr Val Asn Ala Pro Asp Thr Leu Cys Glu His Leu
370                 375                 380

Gln Ile Asn Asp Gly Glu Leu Ile Val Val Gln Leu Thr Pro Gly Tyr
385                 390                 395                 400

Cys Ala Pro Glu Gly Ser Tyr His Ser Thr Val Asn Gln Val Pro Leu
                405                 410                 415

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
1               5

<210> SEQ ID NO 12
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 12

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Asp Gln Asp Lys Ile Glu Ala Leu Ser Ser Lys
225                 230                 235                 240

Val Gln Gln Leu Glu Arg Ser Ile Gly Leu Lys Asp Leu Ala Met Ala
                245                 250                 255

Asp Leu Glu Gln Lys Val Leu Glu Met Glu Ala Ser Thr Gln Val Ser
            260                 265                 270

His Arg Tyr Pro Arg Ile Gln Ser Ile Lys Val Gln Phe Thr Glu Tyr
        275                 280                 285

Lys Lys Glu Lys Gly Phe Ile Leu Thr Ser Gln Lys Glu Asp Glu Ile
    290                 295                 300

Met Lys Val Gln Asn Asn Ser Val Ile Ile Asn Cys Asp Gly Phe Tyr
305                 310                 315                 320

Leu Ile Ser Leu Lys Gly Tyr Phe Ser Gln Glu Val Asn Ile Ser Leu
                325                 330                 335

His Tyr Gln Lys Asp Glu Glu Pro Leu Phe Gln Leu Lys Lys Val Arg
            340                 345                 350

Ser Val Asn Ser Leu Met Val Ala Ser Leu Thr Tyr Lys Asp Lys Val
        355                 360                 365

Tyr Leu Asn Val Thr Thr Asp Asn Thr Ser Leu Asp Asp Phe His Val
    370                 375                 380

```
Asn Gly Gly Glu Leu Ile Leu Ile His Gln Asn Pro Gly Glu Ala Cys
385                 390                 395                 400
Val Leu
```

OX40L FUSION PROTEINS AND USES THEREOF

SEQUENCE LISTING

The instant application contains a Sequence Listing which has been submitted electronically in ASCII format and is hereby incorporated by reference in its entirety. Said ASCII copy, created on May 21, 2015, is named OX40F-101WO1_SL.txt and is 31,496 bytes in size.

BACKGROUND

OX40 (CD134; TNFRSF4) is a tumor necrosis factor receptor found primarily on activated CD4+ and CD8+ T-cells, regulatory T cells (Treg) and natural killer (NK) cells (Croft et al., 2009, *Immunol Rev.* 229:173-91). OX40 has one known endogenous ligand, OX40 ligand (OX40L; CD152; TNFSF4), that exists in a trimeric form and can cluster OX40 resulting in potent cell signaling events within T cells (Croft et al., 2009, *Immunol Rev.* 229:173-91). Signaling through OX40 on activated CD4+ and CD8+ T cells leads to enhanced cytokine production, granzyme and perforin release and expansion of effector and memory T cell pools (Jensen et al., 2010, *Semin Oncol.* 37:524-32). In addition, OX40 signaling on Treg cells inhibits expansion of Tregs, shuts down the induction of Tregs and blocks Treg-suppressive function (Voo et al., 2013, *J Immunol.* 191: 3641-50; Vu et al., 2007, *Blood.* 110:2501-10).

Immunohistochemistry studies and early flow cytometry analyses showed that OX40 is expressed on T cells infiltrating a broad range of human cancers (Baruah et al., 2011, *Immunobiology* 217:668-675; Curti et al, 2013, *Cancer Res.* 73:7189-98; Ladanyi et al, 2004, *Clin Cancer Res.* 10:521-30; Petty et al, 2002, *Am J Surg.* 183:512-8; Ramstad et al, 2000, *Am J Surg.* 179:400-6; Sarff et al, 2008, *Am J Surg.* 195:621-5; discussion 625; Vetto et al, 1997, *Am J Surg.* 174:258-65). OX40 expression on tumor-infiltrating lymphocytes correlates with longer survival in several human cancers, suggesting that OX40 signals may play a critical role in establishing an antitumor immune response (Ladanyi et al., 2004, *Clin Cancer Res.* 10:521-30; Petty et al., 2002, *Am J Surg.* 183:512-8).

In a variety of nonclinical mouse tumor models, agonists of OX40, including antibodies and OX40 ligand fusion proteins, have been used successfully with promising results (Kjaergaard et al., 2000, *Cancer Res.* 60:5514-21; Ndhlovu et al., 2001, *J Immunol.* 167:2991-9; Weinberg et al., 2000, *J Immunol.* 164:2160-9). Co-stimulating T cells through OX40 promoted anti-tumor activity that in some cases was durable, providing long-lasting protection against subsequent tumor challenge (Weinberg et al., 2000, *J Immunol.* 164:2160-9). Treg cell inhibition and co-stimulation of effector T cells were shown to be necessary for tumor growth inhibition of OX40 agonists (Piconese et al., 2008, *J Exp Med.* 205:825-39). Many strategies and technologies have been explored to enhance the anti-tumor effect of OX40 agonist therapy through combinations with vaccines, chemotherapy, radiotherapy, and immunotherapy (Jensen et al., 2010, *Semin Oncol.* 37:524-32; Melero et al., 2013, *Clin Cancer Res.* 19:997-1008).

SUMMARY

This disclosure relates to polypeptide subunits, each including, as a fusion polypeptide, the receptor-binding domain of OX40 Ligand (OX40L), a trimerization domain and a human IgG4 Fc domain, which are capable of forming stable multimeric, e.g., hexameric proteins. Compositions and methods are provided that are useful for cancer immunotherapy.

The disclosure provides a single-chain polypeptide subunit that includes: a human IgG4 Fc domain; a functional trimerization domain; and a receptor binding domain of OX40L. In certain aspects, a polypeptide subunit as provided can self-assemble into a trimeric or a hexameric protein. In certain aspects, the polypeptide subunit includes, from the amino terminus to the carboxy terminus, the human IgG4 Fc domain, followed by the trimerization domain, followed by the OX40L receptor binding domain. The carboxy terminus of the human IgG4 Fc domain can be fused directly to the amino terminus of the trimerization domain, and the carboxy terminus of the trimerization domain can be fused directly to the amino terminus of the OX40L receptor binding domain.

In further aspects of the polypeptide subunit provided by the disclosure, the IgG4 Fc domain includes an IgG4 hinge region, which can include a mutation that confers complete inter heavy chain disulfide bond formation, e.g., a serine to proline mutation at position 228 (S228P) according to EU numbering. In certain aspects, the hinge region includes amino acids 1 to 12 of SEQ ID NO: 4. The human IgG4 Fc domain can further include a CH2 region, and/or a CH3 region. In certain aspects the human IgG4 Fc domain includes amino acids 1 to 229 of SEQ ID NO: 4.

The trimerization domain provided by the disclosure can include an alpha-helical coiled coil domain, a leucine zipper domain, or a combination thereof. For example, the trimerization domain can be derived from TRAF2; Thrombospondin 1; Matrilin-4; CMP (matrilin-1); HSF1; or Cubilin. In certain aspects, the trimerization domain includes a human TRAF2 trimerization domain. In certain aspects the TRAF2 trimerization domain includes amino acids 310 to 349 of human TRAF2 (SEQ ID NO: 2).

In additional aspects of the polypeptide subunit provided by the disclosure, the OX40L receptor binding domain can include amino acids 51 to 183 of human OX40L (SEQ ID NO: 1). In certain aspects the polypeptide subunit provided by the disclosure can self-assemble into a hexameric fusion protein that can specifically bind to human OX40. In certain aspects the polypeptide subunit includes the amino acid sequence SEQ ID NO: 4.

A polypeptide subunit as provided herein can further include an associated heterologous agent. A heterologous agent as provided herein can be a heterologous polypeptide that is fused to the polypeptide subunit via a peptide bond. The heterologous polypeptide can be fused, for example, to the N-terminus of the IgG4-Fc domain, to the C-terminus of the receptor binding domain of OX40L, between the C-terminus of the IgG4-Fc domain and to the N-terminus of the trimerization domain, or between the C-terminus of the trimerization domain and to the N-terminus of the receptor binding domain of OX40L. In certain aspects the heterologous agent can be chemically conjugated to the polypeptide subunit and can be, for example a cytotoxic molecule, a stabilizing agent, an immune response modifier, or a detectable agent.

In certain aspects, the disclosure provides polypeptide subunits that can be used as controls. For example, the disclosure provides a polypeptide subunit where the OX40L receptor binding domain includes amino acids 51 to 183 of human OX40L (SEQ ID NO: 1), except for a single phenylalanine to alanine substitution at position 180 (F180A). A hexameric fusion protein that self-assembles from this polypeptide subunit is incapable of binding to human OX40. In certain aspects, this control polypeptide subunit includes the amino acid sequence SEQ ID NO: 6.

In certain aspects, the disclosure provides a trimeric protein that includes three polypeptide subunits as provided herein.

The disclosure provides a hexameric protein that includes six polypeptide subunits as described above. In certain aspects, the six polypeptide subunits each include the amino acid sequence SEQ ID NO: 4. An exemplary hexameric fusion protein is OX40L IgG4P Fusion Protein.

In certain aspects, a hexameric protein as provided by the disclosure can specifically bind to OX40 as expressed on activated CD4$^+$ or CD8$^+$ T cells from human, cynomolgus monkey, and/or rhesus monkey. For example, the hexameric protein can specifically bind to OX40 as expressed on primary activated CD4$^+$ T cells from human, cynomolgus monkey, and/or rhesus monkey. In certain aspects, the binding affinity for human OX40 expressed on primary activated human CD4$^+$ T cells is about 1.0 pM to about 8.0 pM, e.g., about 3.6 pM as measured by flow cytometry. In certain aspects the hexameric protein can achieve 20% receptor occupancy on primary activated human CD4$^+$ T cells ($EC_{20}$) at about 0.5 to about 3.0 pM, e.g., about 1.8 pM, 50% receptor occupancy on primary activated human CD4$^+$ T cells ($EC_{50}$) at about 3.0 to about 10 pM, e.g., about 6.6 pM, and 90% receptor occupancy on primary activated human CD4$^+$ T cells ($EC_{90}$) at about 35 to about 70 pM, e.g., about 53 pM, all as measured by flow cytometry.

In certain aspects a hexameric protein as provided by the disclosure has a binding affinity for human OX40 expressed on OX40-overexpressing Jurkat cells of about 1.0 pM to about 24 pM, e.g., about 12 pM, as measured by flow cytometry. In certain aspects the hexameric protein can achieve $EC_{20}$ on OX40-overexpressing Jurkat cells at about 1.0 to about 15 pM, e.g., about 7.2 pM, $EC_{50}$ on OX40-overexpressing Jurkat cells at about 1.0 to about 40 pM, e.g., about 16 pM, and $EC_{90}$ on OX40-overexpressing Jurkat cells at about 10 to about 100 pM, e.g., about 57 pM, all as measured by flow cytometry.

In certain aspects a hexameric protein as provided by the disclosure has a binding affinity for cynomolgus monkey OX40 expressed on primary activated cynomolgus monkey CD4$^+$ T cells is about 1.0 pM to about 50 pM, e.g., about 24 pM, as measured by flow cytometry. In certain aspects a hexameric protein as provided by the disclosure has a binding affinity for rhesus monkey OX40 expressed on primary activated rhesus monkey CD4$^+$ T cells is about 1.0 pM to about 50 pM, e.g., about 21 pM, as measured by flow cytometry.

In certain aspects a hexameric protein as provided by the disclosure can induce dose-dependent proliferation of activated CD4$^+$ T cells and dose-dependent cytokine release from activated CD4$^+$ T cells in a plate-based assay. In certain aspects, a 20% maximal proliferation response ($EC_{20}$) can be achieved in primary activated human CD4$^+$ T cells at a hexameric protein concentration of about 1.0 pM to about 15 pM, e.g., about 8.0 pM, a 50% maximal proliferation response ($EC_{50}$) can be achieved in primary activated human CD4$^+$ T cells at a hexameric protein concentration of about 5.0 pM to about 25 pM, e.g., about 14 pM, and a 90% maximal proliferation response ($EC_{90}$) can be achieved in primary activated human CD4$^+$ T cells at a hexameric protein concentration of about 50 pM to about 65 pM, e.g., about 57 pM, all as measured by flow cytometry. In certain aspects the hexameric protein can induce dose-dependent release of IFNγ, TNFα, IL-5, IL-10, IL-2, IL-4, IL-13, IL-8, IL-12 p70, and/or IL-1β. In certain aspects the cytokines released include IFNγ, TNFα, IL-5, and/or IL-10.

In certain aspects a hexameric protein as provided by the disclosure can achieve CD4$^+$ T cell proliferation and cytokine release in primary activated cynomolgus monkey CD4$^+$ T cells and in primary activated rhesus monkey CD4$^+$ T cells.

In certain aspects a hexameric protein as provided by the disclosure can activate the NFκB pathway in OX40 expressing T cells in the presence of FcγR-expressing cells. For example, the OX40-expressing T cells can be OX40-expressing Jurkat NFκB-luciferase reporter cells that produce luciferase in response to stimulation of the NFκB signaling pathway. The OX40 expressed by these cells can be, e.g., human OX40, cynomolgus monkey OX40 or rhesus monkey OX40.

In certain aspects a hexameric protein as provided by the disclosure, when administered as an effective dose to a subject in need of cancer treatment, can inhibit tumor growth in the subject, for example, in the presence of T-cells. In certain aspects, tumor growth can be inhibited by at least 10%, at least 20%, at least 30%, at least 40%, and least 50%, at least 60%, or at least 70% compared to administration of an isotype-matched control.

In certain aspects a hexameric protein as provided by the disclosure can induce proliferation of activated, OX40-expressing CD4$^+$ T cells through binding to OX40, but does not substantially trigger complement-dependent or antibody-dependent cytotoxicity against the activated CD4$^+$ T cells. For example, in certain aspects a hexameric protein as provided herein does not bind to C1q or trigger NK cell-mediated antibody-dependent cellular cytotoxicity of activated CD4$^+$ T cells.

In certain aspects a hexameric protein as provided by the disclosure, upon co-administration with a vaccine antigen to a subject, can increase CD4+ central memory (cM) T-cell proliferation, effector memory (eM) CD8+T cell proliferation, NK cell proliferation, and/or B cell proliferation. In certain aspects, CD4+cM T-cell proliferation. CD8+eM T-cell proliferation, NK cell proliferation, B cell proliferation, or any combination thereof is measured as intracellular Ki67 expression in peripheral blood mononuclear cells.

In certain aspects a hexameric protein as provided by the disclosure, upon co-administration with a vaccine antigen, including, but not limited to an antigen from respiratory syncytial virus (RSV), hepatitis B or C virus, Ebola virus, influenza virus, *Pseudomonas aeruginosa*, *Clostridium difficile*, or *Staphylococcus aureus*, to a subject, can increase antigen-specific T-cell response that can be measured, e.g., as increased interferon gamma (IFN-gamma) expression.

In certain aspects a hexameric protein as provided by the disclosure, upon co-administration with a vaccine antigen to a subject, can increase antigen-specific IgG titers. In certain aspects the antigen can be a soluble F glycoprotein of respiratory syncytial virus (RSV sF), and co-administration of the hexameric protein and the RSV antigen to a subject can increase titers of RSV-neutralizing antibodies.

In certain aspects, the subject to which the hexameric protein and vaccine antigen is co-administered is a non-human primate.

In certain aspects a hexameric protein as provided by the disclosure can inhibit regulatory T cell (Treg) mediated suppression of effector T cell proliferation, e.g., in a plate-based assay. In certain aspects the effector T cells are effector CD4+T cells. In certain aspects, the ratio of effector cells to Treg cells can be about 1:0.5 to about 1:3, e.g., about 1:1 or about 1:2.

The disclosure further provides a composition that includes a hexameric protein as provided herein, and a carrier.

In certain aspects, the disclosure provides a polynucleotide that includes a nucleic acid encoding a polypeptide subunit as provided herein, or a hexameric protein as provided herein. In certain aspects, the polynucleotide can include the nucleic acid sequence SEQ ID NO: 3.

The disclosure further provides a vector that incorporates the polynucleotide as provided and a host cell that incorporates the polynucleotide or the vector as provided. In a related aspect, the disclosure provides a method of producing a polypeptide subunit of as provided herein or a hexameric protein as provided herein, where the method includes culturing the provided host cell under conditions in which the polypeptide subunit or hexameric protein encoded by the polynucleotide is expressed, and recovering the polypeptide subunit or hexameric protein.

In further aspects, the disclosure provides a method to promote survival or proliferation of activated T cells, where the method includes contacting activated T cells with a hexameric protein as provided herein such that the hexameric protein can specifically bind to OX40 on the surface of the T cells. The disclosure further provides a method of inducing cytokine release from activated T cells, where the method includes contacting activated T cells with a hexameric protein as provided herein such that the hexameric protein can specifically bind to OX40 on the surface of the T cells. In certain aspects, the cytokine can be IFNγ, TNFα, IL-5, IL-10, IL-2, IL-4, IL-13, IL-8, IL-12 p70, and/or IL-1β, e.g., IFNγ, TNFα, IL-5, and/or IL-10. In certain aspects the activated T cells are activated CD4$^+$ T cells and/or activated CD8$^+$ T cells. For example, the activated CD4$^+$ T cells can be human CD4$^+$ T cells, cynomolgus monkey CD4$^+$ T cells, and/or rhesus monkey CD4$^+$ T cells.

In further aspects, the disclosure provides a method to reduce regulatory T cell (Treg)-mediated suppression of activated T cell proliferation, where the method includes contacting a mixture of activated T cells and Treg cells with the hexameric protein as disclosed herein, wherein the hexameric protein can specifically bind to OX40 on the surface of the T cells.

In yet another aspect the disclosure provides a method of promoting T cell activation, where the method includes contacting T cells with a hexameric protein as provided herein such that the hexameric protein can specifically bind to OX40 on the surface of the T cells. In certain aspects, this method further includes cross-linking of the hexameric protein through interaction of the IgG4-Fc domain with a cell expressing FcγR. The cell expressing FcγR can be, e.g., a B cell, a monocyte, a macrophage, a myeloid or plasmacytoid dendritic cell, a follicular dendritic cell, a Langerhans cell, an endothelial cell, an NK cell, an activated T cell, a neutrophil, an eosinophil, a platelet, a mast cell, a CD45$^+$ cell from a primary human tumor or tumor-draining or non-draining lymph node, and/or a CD45+ cell from other secondary or tertiary lymphoid structures. In certain aspects, T cell activation can be measured through stimulation of the NFκB signal transduction pathway, and in certain aspects the activated T cells are activated CD4$^+$ T cells and/or activated CD8$^+$ T cells, for example, human CD4$^+$ T cells, cynomolgus monkey CD4$^+$ T cells, and/or rhesus monkey CD4$^+$ T cells.

In certain aspects, the methods provided above include administering an effective amount of the hexameric protein or composition as provided by the disclosure to a subject in need of treatment. In a related aspect, the disclosure provides a method of treating cancer in a subject, where the method includes administering to a subject in need of treatment an effective amount of a hexameric protein as provided herein. In certain aspects, the cancer is a solid tumor. In certain aspects, administration of the hexameric protein or composition can inhibit tumor growth, can promote tumor reduction, or both. In certain aspects tumor growth inhibition is achieved in the presence of T-cells.

In yet another aspect, the disclosure provides a method of enhancing an immune response in a subject, where the method includes administering to a subject in need thereof a therapeutically effective amount of a hexameric protein as provided by the disclosure, or a composition as provided by the disclosure. For any of the treatment methods provided in this disclosure, the subject can be a human subject.

In an additional aspect, the disclosure provides a method of inducing expression of ICOS on T cells, comprising contacting T cells with a hexameric protein as provided by the disclosure, wherein the hexameric protein can specifically bind to OX40 on the surface of the T cells.

In another aspect, the disclosure provides a method of inducing expression of PD-1 on T cells, comprising contacting T cells with the hexameric protein as provided by the disclosure, wherein the hexameric protein can specifically bind to OX40 on the surface of the T cells.

BRIEF DESCRIPTION OF THE DRAWINGS/FIGURES

FIG. 1. Schematically illustrates an exemplary multimeric protein, namely an OX40L fusion protein.

FIG. 2. Amino Acid Sequence of OX40L IgG4P Fusion Protein (N to C terminus, SEQ ID NO: 4). Amino Acid Sequence huIgG4PFcTF2OX40L F180A is disclosed as SEQ ID NO: 12.

FIG. 3A. OX40L IgG4P Fusion Protein and control protein binding to OX40 expressed on the surface of primary activated human CD4$^+$ T cells. Data was used for determination of apparent affinity ($K_d$) and apparent concentrations to achieve receptor occupancy of 20%, 50% and 90% ($EC_{20}$, $EC_{50}$, and $EC_{90}$ values).

FIG. 3B. OX40L IgG4P Fusion Protein and control protein binding to human OX40 expressed on Jurkat T cells. Data was used for determination of apparent affinity ($K_d$) and apparent concentrations to achieve receptor occupancy of 20%, 50% and 90% ($EC_{20}$, $EC_{50}$, and $EC_{90}$ values).

Figure 4A:
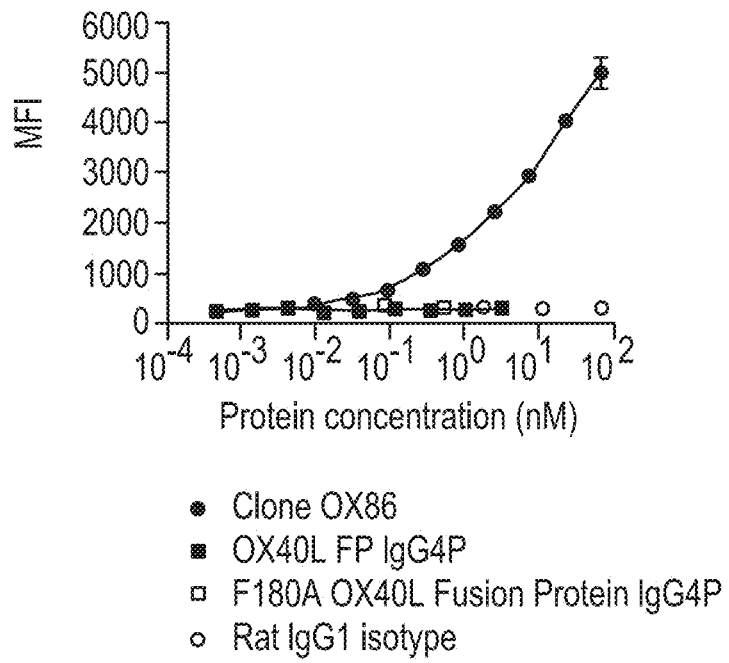

FIG. 4A. OX40L IgG4P Fusion Protein lacks binding to OX40 expressed on primary activated mouse CD4$^+$ T cells. MFI=mean fluorescence intensity. nM=nanomolar. Error bars=SEM.

Figure 4B:
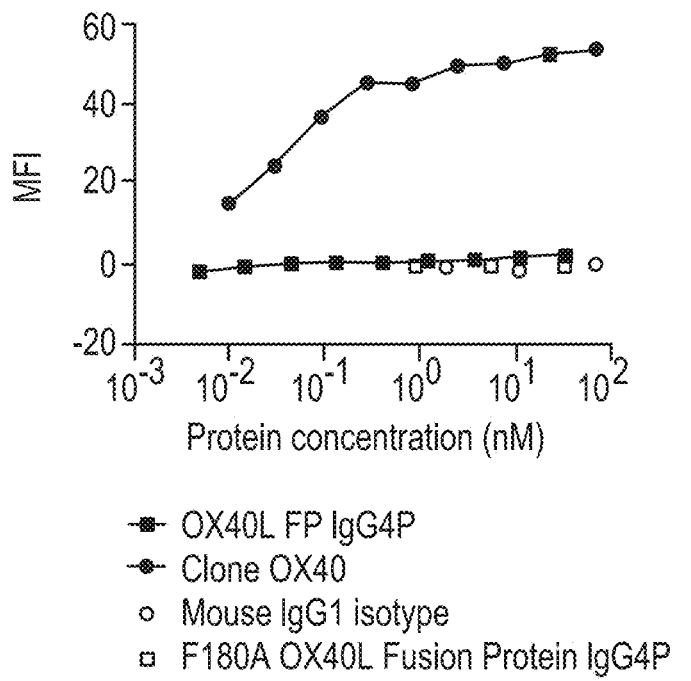

FIG. 4B. OX40L IgG4P Fusion Protein lacks binding to OX40 expressed on primary activated rat CD4$^+$ T cells. MFI=mean fluorescence intensity. nM=nanomolar. Error bars=SEM.

FIG. 4C. Binding of OX40L IgG4P Fusion Protein to OX40 expressed on primary activated cynomolgous monkey CD4$^+$ T cells. Single well data averaged from two independent assays was used for determination of apparent affinity ($K_d$) values. MFI=mean fluorescence intensity. nM=nanomolar.

Figure 5C:
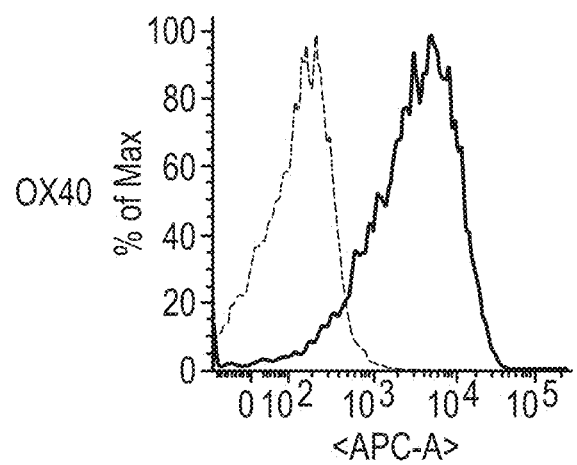

FIG. 4D. Binding of OX40L IgG4P Fusion Protein to OX40 expressed on primary activated rhesus macaque CD4$^+$ T cells. Data averaged from two independent assays was used for determination of apparent affinity (Kd) values. MFI=mean fluorescence intensity. nM=nanomolar. Error bars=SEM FIG. 5A-C. Binding of OX40L IgG4P Fusion Protein to TNFRSF-expressing HEK293 and OX40-expressing Jurkat. (A-B) Transient expression of TNFRSF members, as indicated to left of histograms, in HEK293 cells and binding to TNFRSF-specific mAbs or to OX40L IgG4P Fusion Protein, as indicated above histograms. Gray histogram, fluorochrome-conjugated isotype control antibody binding for TNFRSF-specific mAb or goat anti-human AlexaFluor® 647 secondary antibody binding control for OX40L IgG4P Fusion Protein; Open histogram, TNFRSF-specific mAb or OX40L IgG4P Fusion Protein binding. (C) Binding of OX40L IgG4P Fusion Protein to OX40-expressing Jurkat as a positive control. Gray histogram, goat anti-human AlexaFluor® 647 secondary antibody binding control; Open histogram, OX40L IgG4P Fusion Protein binding.

Figure 6:
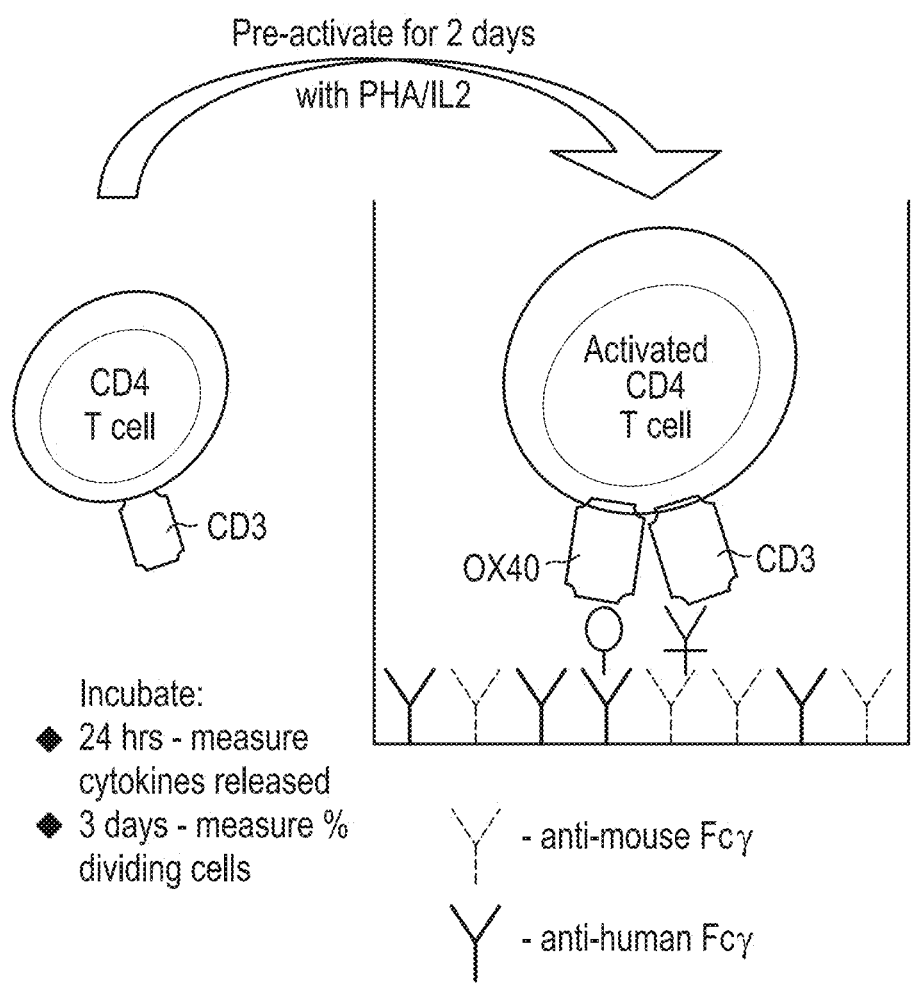
Figure 7A:
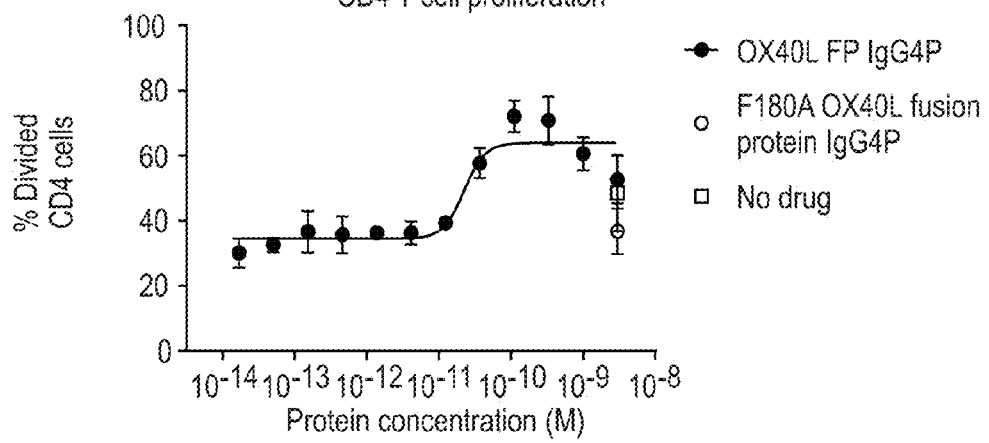
Figure 7B:
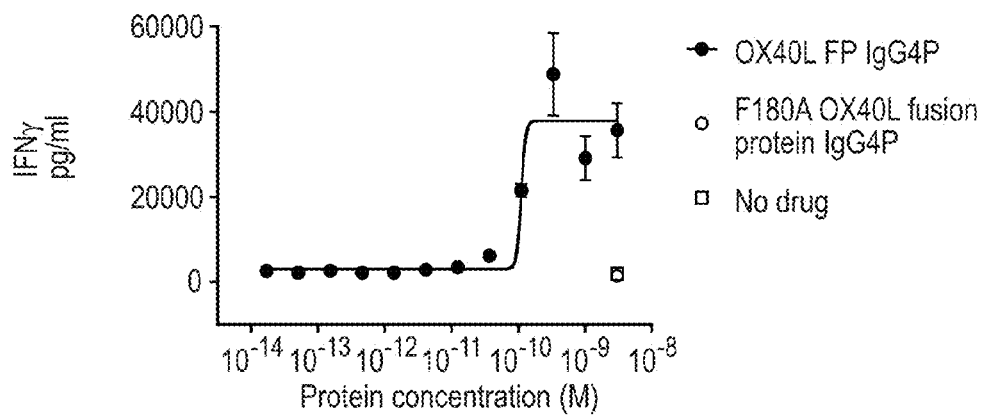
Figure 7C:
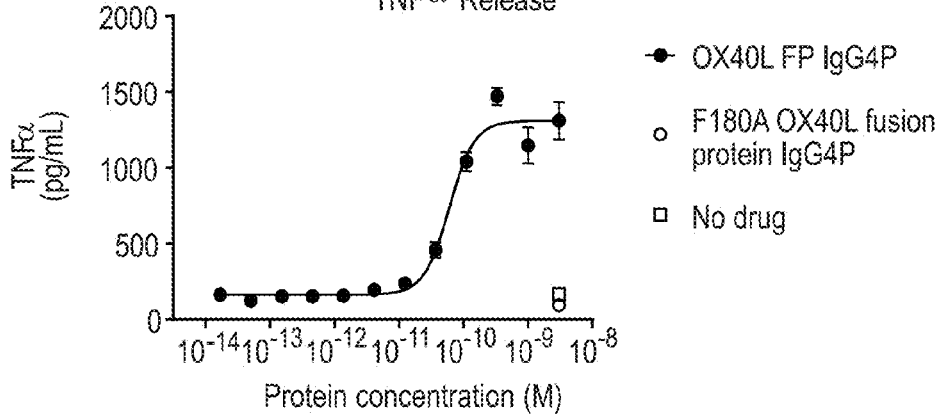
Figure 7D:
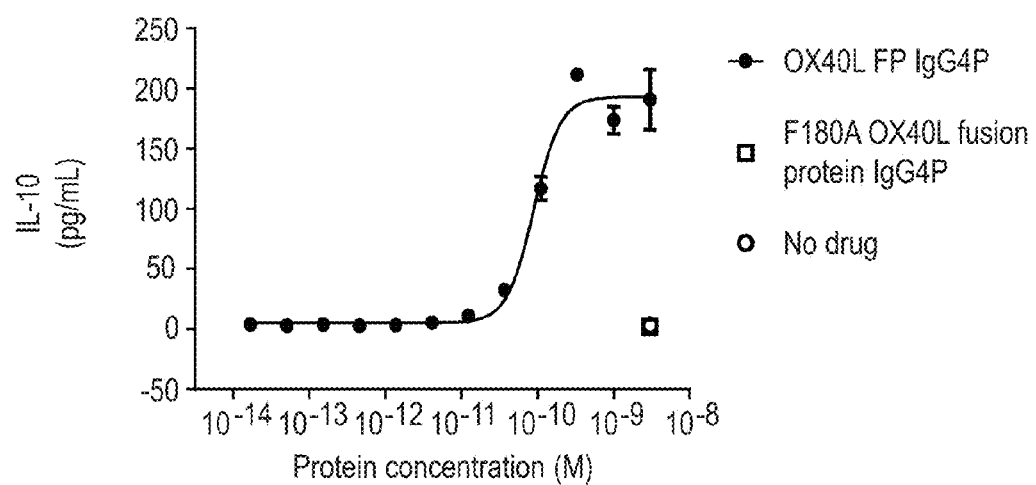
Figure 7E:
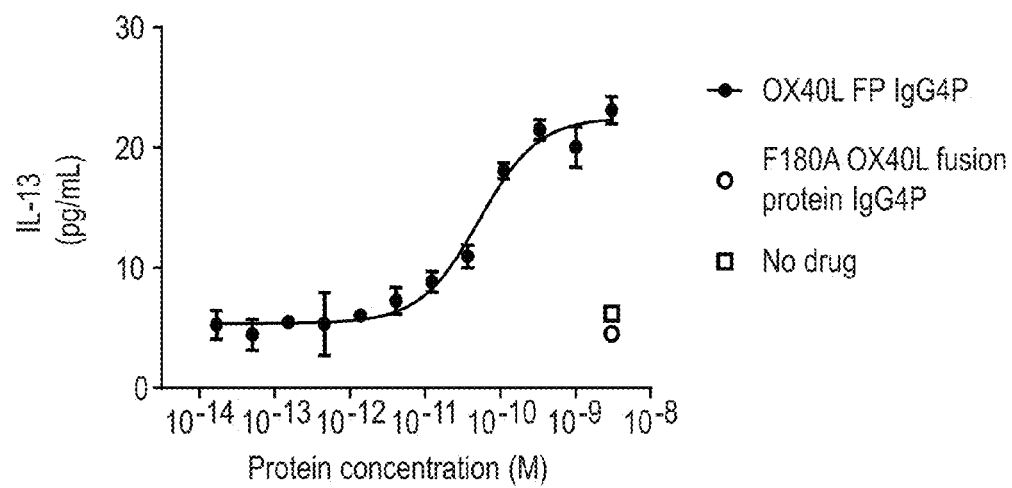

FIG. 6. Schematic diagram of the OX40L IgG4P Fusion Protein plate-bound bioactivity assay. Q, OX40L IgG4P Fusion Protein., anti-CD3 clone OKT3.

FIG. 7A-E. OX40L IgG4P Fusion Protein co-stimulates primary CD4 T cell to proliferate and release cytokines in a plate-based bioactivity assay. Representative data for donor 4 presented for (A) CD4 T cell proliferation and release of (B) IFNγ, (C) TNFα, (D) IL-10, (E) IL-13; similar results were found for donors 1, 2, and 3. Symbols, mean values; Error bars, standard deviation of the mean.

Figure 8:
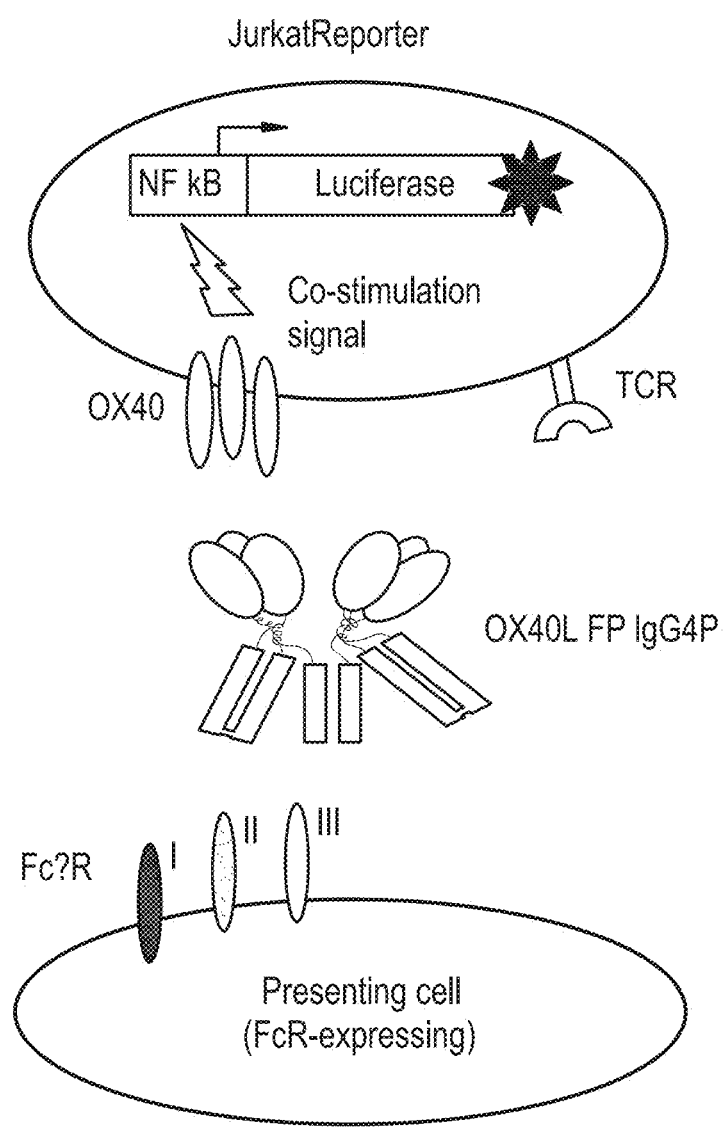

FIG. 8. Cell systems used for measuring OX40L IgG4P Fusion Protein bioactivity. OX40L IgG4P Fusion Protein cross linking by FcγR-expressing cells mediates the clustering of OX40 on the OX40-expressing Jurkat NFκB-luciferase clone 64 reporter cell line, resulting in NFκB-dependent production of luciferase that can be measured as a surrogate for NFκB activity and T cell activation.

Figure 9A:
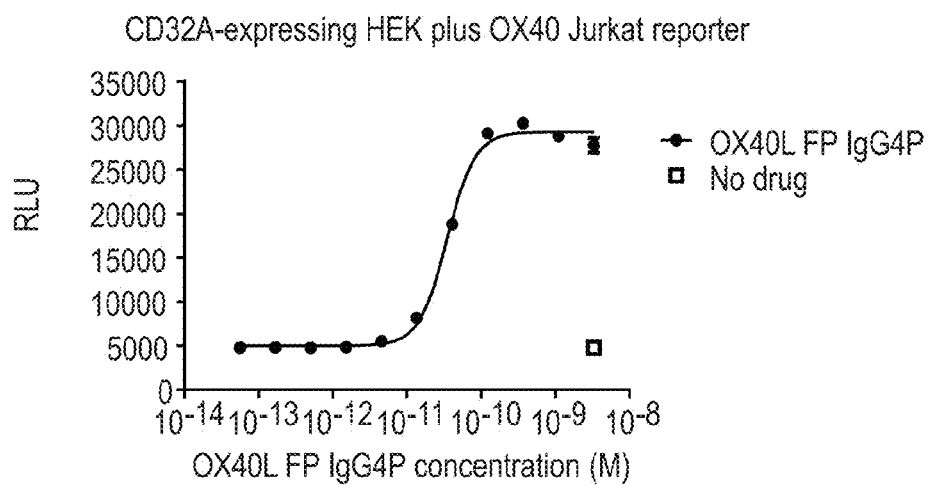
Figure 9B:
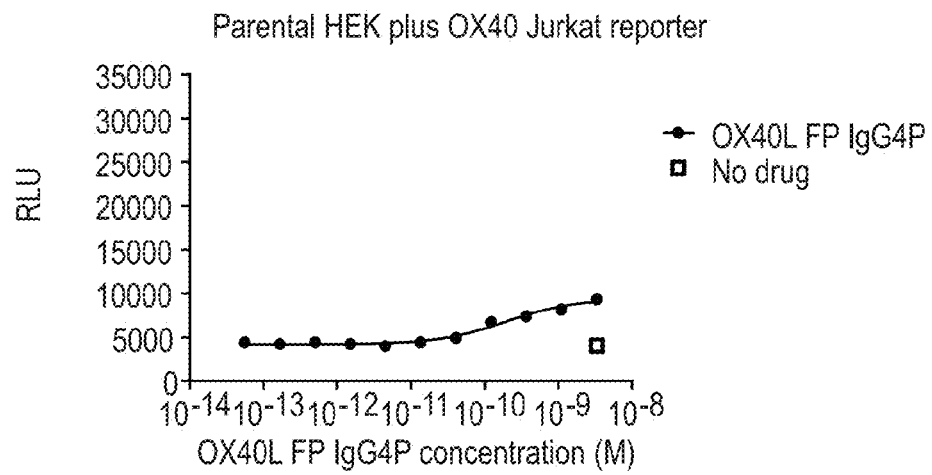
Figure 9C:
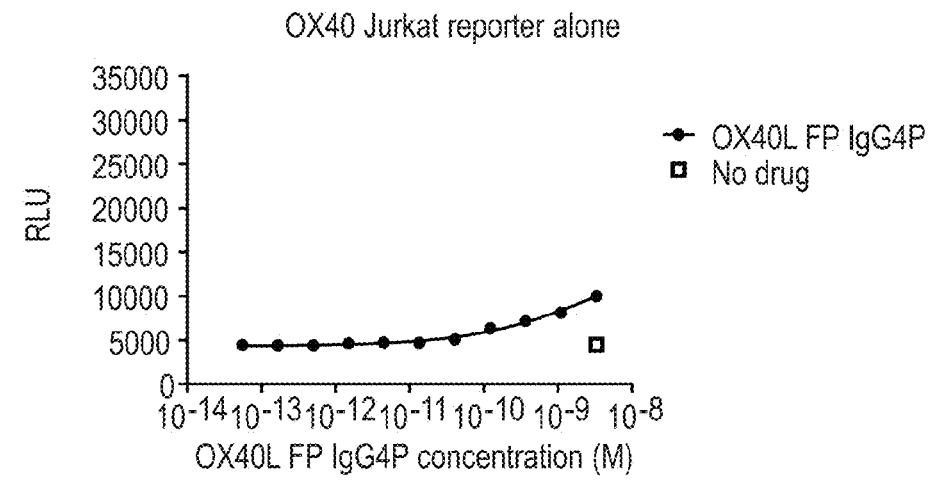
Figure 10A:
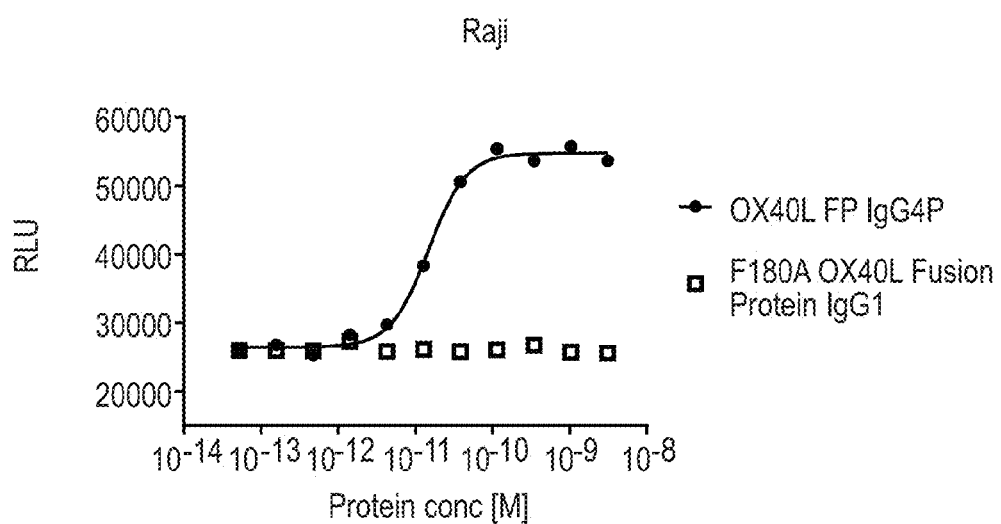
Figure 10B:
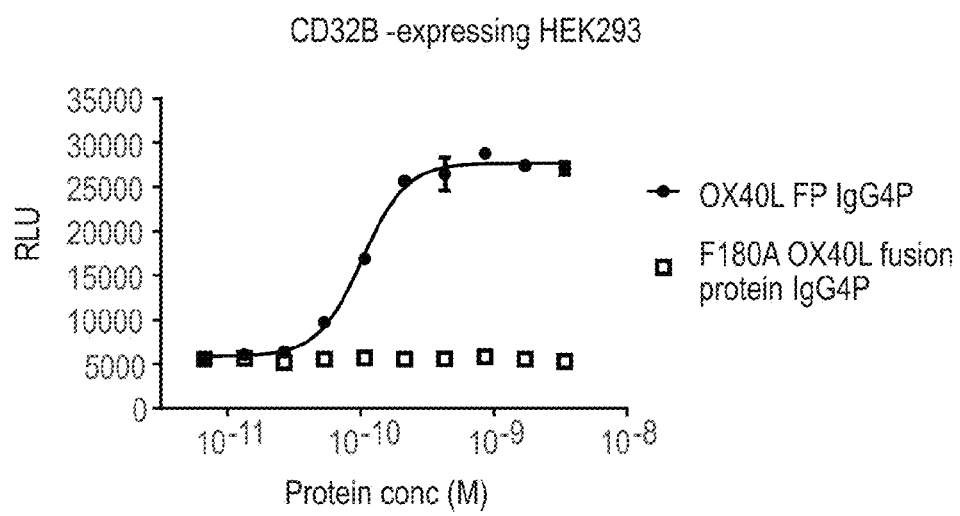
Figure 10C:
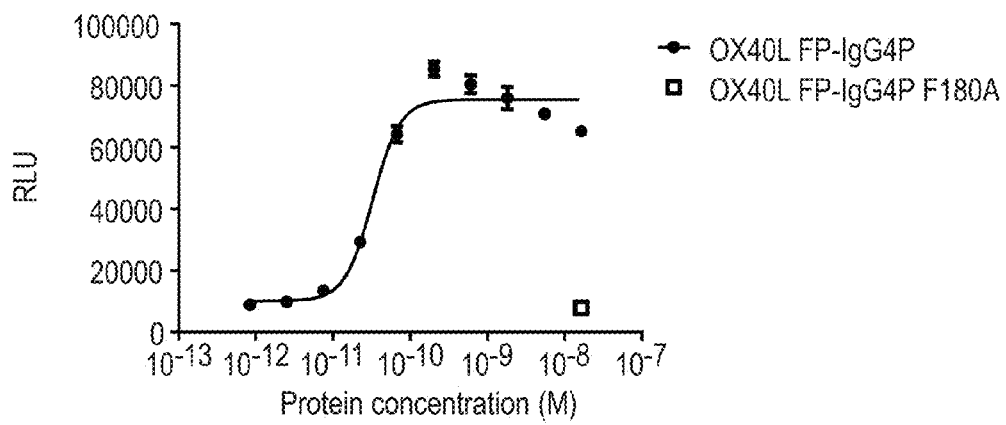
Figure 10D:
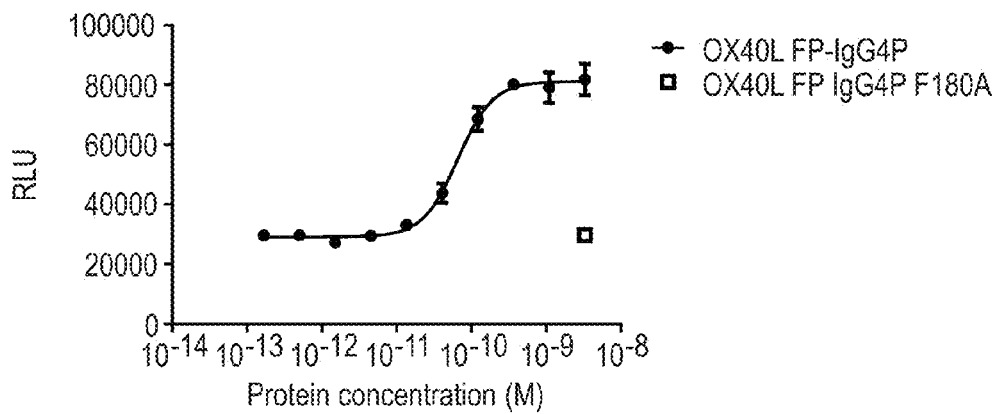

FIG. 9A-C. Bioactivity of OX40L IgG4P Fusion Protein when cross-linked or not by FcγR. (A) Reporter activity after cross-linking of OX40L IgG4P Fusion Protein by CD32A-expressing HEK293. (B) Reporter activity in the presence of HEK293 parental cells without FcγR expression. (C) Reporter activity with drug and without HEK293 cells. RLU, relative light units.

FIG. 10A-D. Examples of OX40L IgG4P Fusion Protein bioactivity using Raji, CD32B-expressing HEK293, CD32A-expressing HEK293, or CD45+ cells isolated from primary human tumors for FcγR mediated drug cross-linking and the OX40-expressing Jurkat NFκB-luciferase clone 64 reporter cells for bioactivity readout. (A) OX40L IgG4P Fusion Protein activity clustered by Raji B cells; (B) CD32B-expressing HEK293; (C) CD32A-expressing HEK293; (D) CD45+ cells isolated from primary human tumors. RLU=Relative Light Units. M=Molarity.

Figure 11:
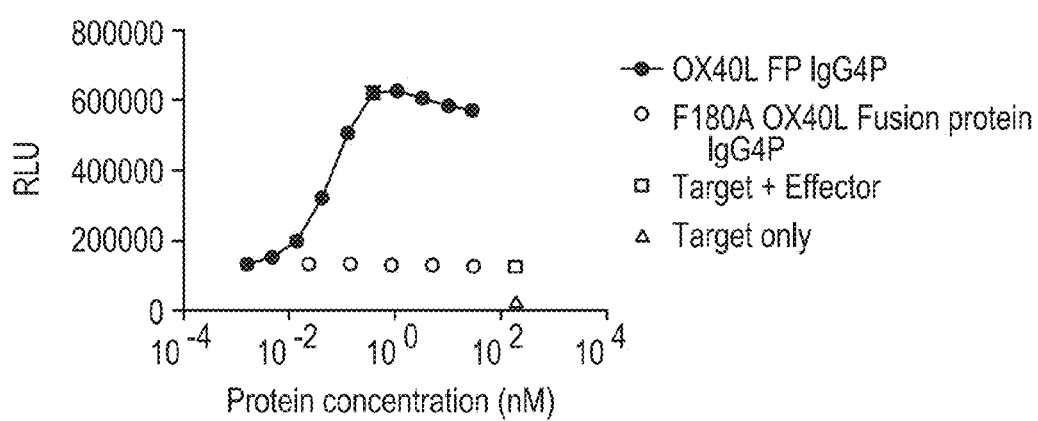

FIG. 11. OX40L IgG4P Fusion Protein is Active in Cyno/Rhesus OX40-expressing Jurkat NFκB-luciferase Clone B2 and LCL8664 Rhesus B Cell Bioactivity Assays. Concentration-dependent activity in RLU of OX40L IgG4P Fusion Protein to induce signaling through cyno/rhesus OX40 expressed on the cell surface of a Jurkat NFκB-luciferase reporter cell line. 4 replicates per data point. Error bars=SEM. RLU, relative light units; n=2 assays; nM=nanomolar FIG. 12. OX40L IgG4P Fusion Protein is active in a Cyno/Rhesus OX40-expressing Jurkat NFκB-luciferase and Fc Gamma Receptor Expressing Rhesus Immune Cells Bioactivity Assay. Concentration-dependent activity in RLU of OX40L IgG4P Fusion Protein to induce signaling through cyno/rhesus OX40 expressed on the cell surface of a Jurkat NFκB-luciferase reporter cell line. 2 replicates per data point. Error bars=SEM. RLU, relative light units; nM=nanomolar.

FIG. 13. OX40L IgG4P Fusion Protein Causes Proliferation of Primary activated Rhesus CD4+ T Cells. Concentration-dependent activity of OX40L IgG4P Fusion Protein to induce primary activated rhesus CD4+ T cells into the cell cycle and divide. Specific activity of OX40L IgG4P Fusion Protein was calculated by subtracting the average value for stimulated cells with anti-CD3 antibody only from the percent CD4 divided value. Data shown for 2 independent assays with triplicate wells. nM=nanomolar. Error bars=SEM.

FIG. 14A-D. Assessment of natural killer cell-mediated antibody-dependent cellular cytotoxicity of OX40L IgG4P Fusion Protein, OX40L IgG1 Fusion Protein and anti-CD20 antibodies, Experiment #1. Specific killing of OX40-expressing CD4+ T cells by primary activated NK cells mediated by the OX40L fusion protein IgG1, but not by OX40L IgG4P Fusion Protein nor by F180A OX40L fusion protein IgG1 and IgG4P controls: (A) Donor 1 NK cells incubated with activated CD4+ T cells; (B) Donor 1 NK cells incubated with Toledo B cells; (C) Donor 2 NK cells incubated with activated CD4+ T cells. Primary activated NK cells used in the ADCC assays were capable of mediating efficient lysis of the Toledo B cells bound to rituximab: (D) Donor 2 NK cell combined with Toledo B cells. Experimental replicates were conducted in triplicate. Error bars represent standard deviation of the mean.

Figure 15:
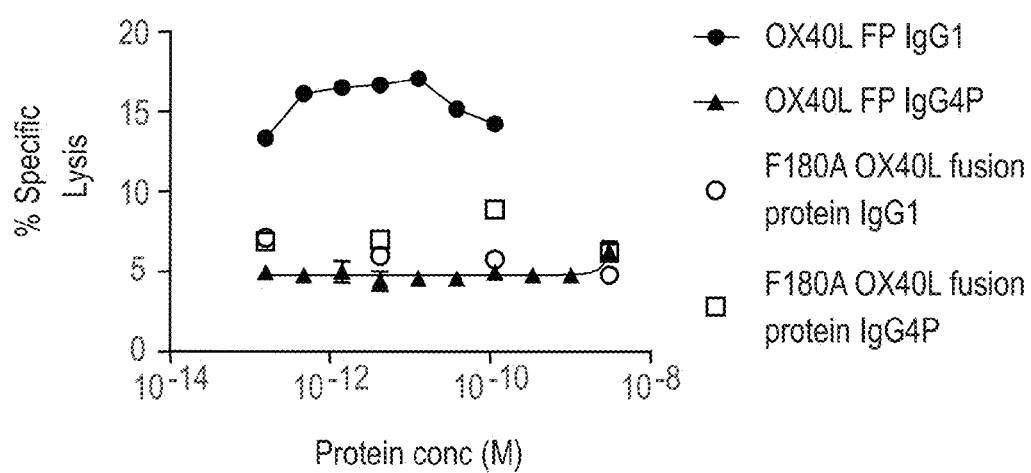

FIG. 15. Assessment of natural killer cell-mediated antibody-dependent cellular cytotoxicity of OX40L IgG4P Fusion Protein and the OX40 ligand fusion protein IgG1, Experiment #2. Specific killing of OX40-expressing CD4+ T cells by primary activated NK cells mediated by the OX40L fusion protein IgG1, but not by OX40L IgG4P Fusion Protein nor by F180A OX40L fusion protein IgG1 and IgG4P controls. Experimental replicates were conducted in triplicate. Error bars represent standard deviation of the mean.

Figure 16A:
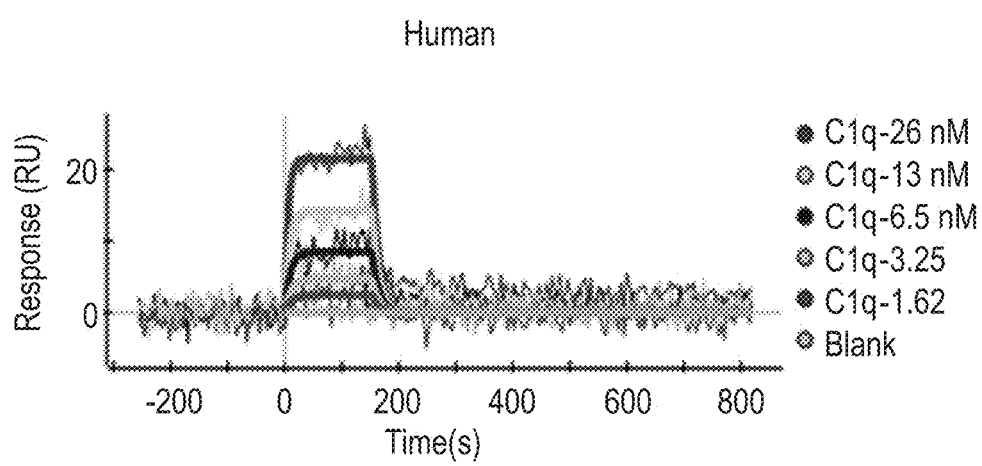
Figure 16B:
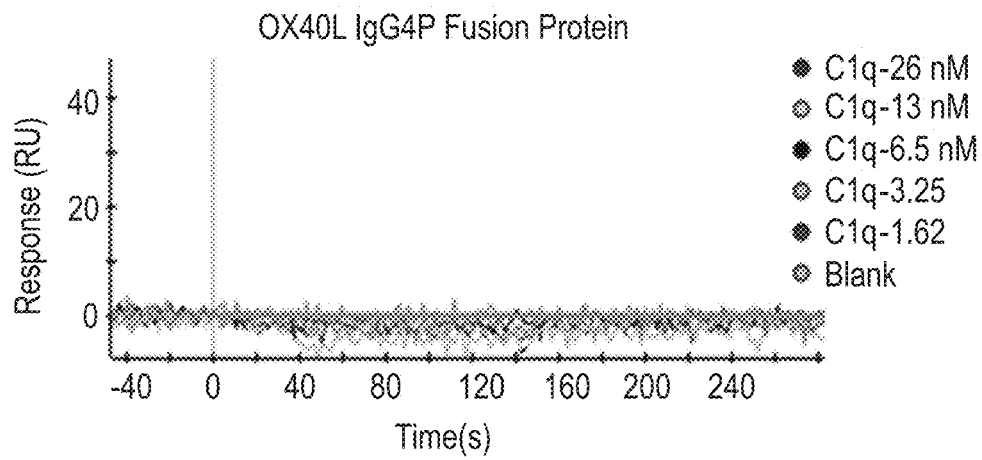

FIG. 16A-B. Assessment of OX40L IgG4P Fusion Protein binding to purified C1q protein. (A) The indicated concentrations of purified human C1q protein were injected onto the biosensor chip. Blank represents injections of PBS/0.005% Tween 20 vehicle alone. (B) In the same experiment, control human IgG1 bound purified human C1q.

Figure 17:
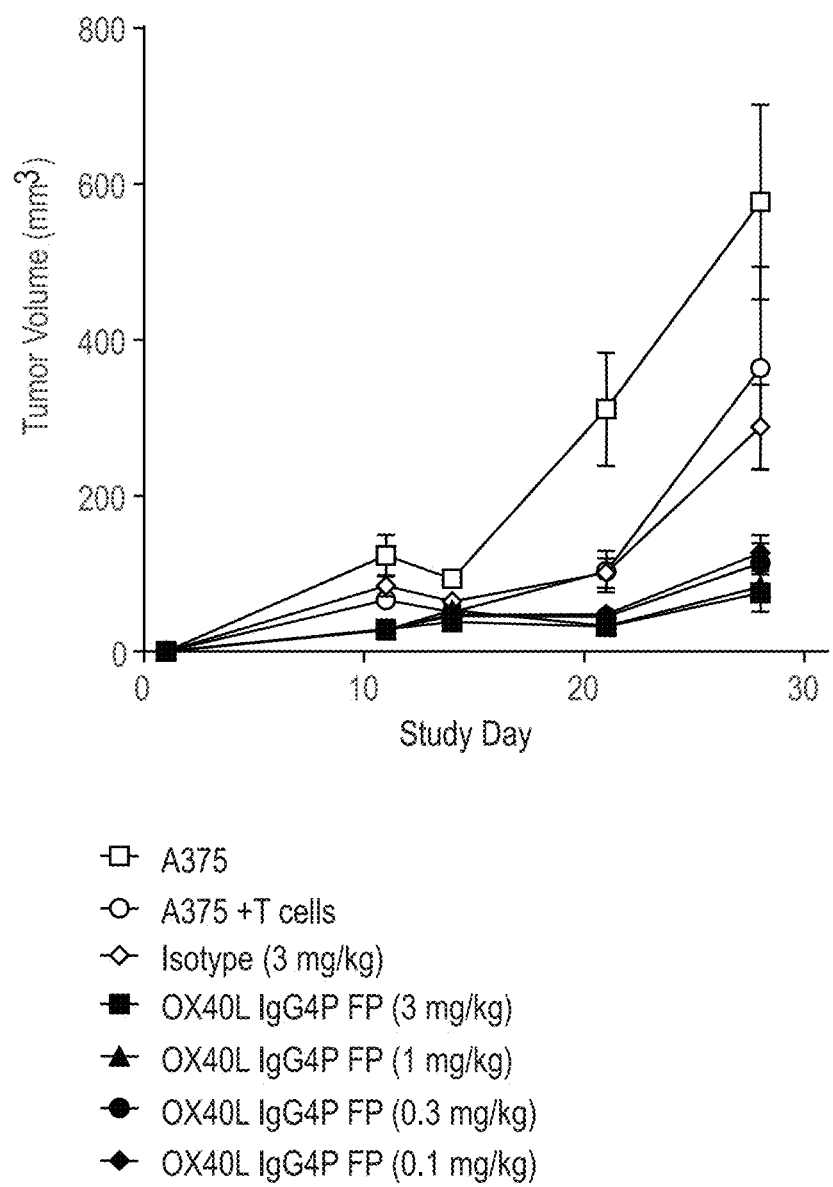

FIG. 17. Effect of OX40L IgG4P Fusion Protein on Growth of A375 Cells in a Mouse Xenograft Model. Six NOD/SCID mice in each group were engrafted SC on Day 1 with A375 cells mixed with alloreactive human CD4+ and CD8+ T cell lines at E:T ratio 1:6. Test article (Isotype control or OX40L IgG4P Fusion Protein) was administered IP on Days 4, 7, 9 and 12. Mean values of tumor volumes are shown. A comparison between OX40L IgG4P Fusion Protein-treated and the Isotype control-treated animals was made, and intergroup differences were analyzed for statistical significance by a Mann-Whitney rank sum test. Error bars represent standard error of the mean. *: TGI>50%, $P \leq 0.05$ as compared to the isotype-control group. NOD/SCID=nonobese diabetic/severe combined immunodeficient; SC=subcutaneous; E:T=effector-to-target ratio; IP=intraperitoneal; TGI=tumor growth inhibition FIG. 18. Effect of OX40L IgG4P Fusion Protein on Growth of A375 Cells in a Mouse Xenograft Model. Six NOD/SCID mice in each group were engrafted SC on Day 1 with A375 cells alone (no T cells) or mixed with alloreactive human CD4+ and CD8+ T cell lines (ratio of 2:1) at E:T ratio 1:6 Test article (Isotype control or OX40L IgG4P Fusion Protein) was administered IP on Days 3, 6, 8 and 10. Mean values of tumor volumes are shown. A comparison between OX40L IgG4P Fusion Protein-treated and the Isotype control-treated animals was made, and intergroup differences were analyzed for statistical significance by a Mann-Whitney rank sum test. Error bars represent standard error of the mean. *: TGI>50%, P≤0.05 as compared to the isotype control group. NOD/SCID=nonobese diabetic/severe combined immunodeficient; SC=subcutaneous; E:T=effector-to-target ratio; IP=intraperitoneal; TGI=tumor growth inhibition.

Figure 19A:
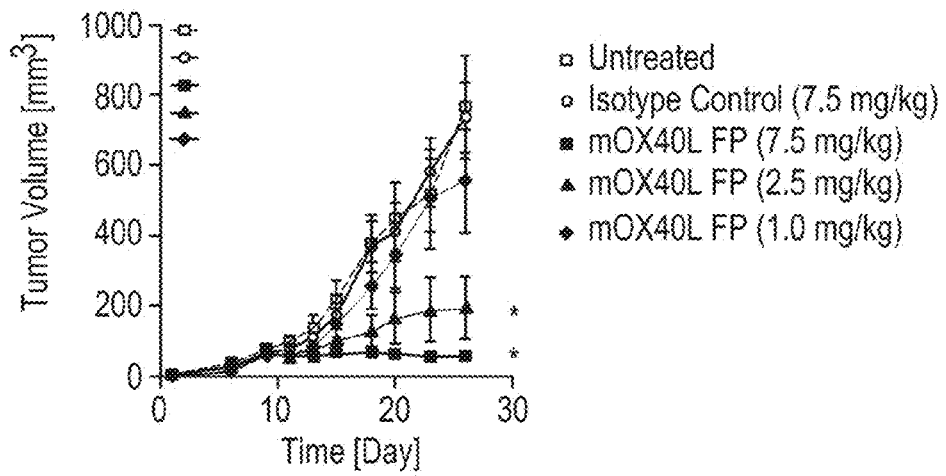
Figure 19B:
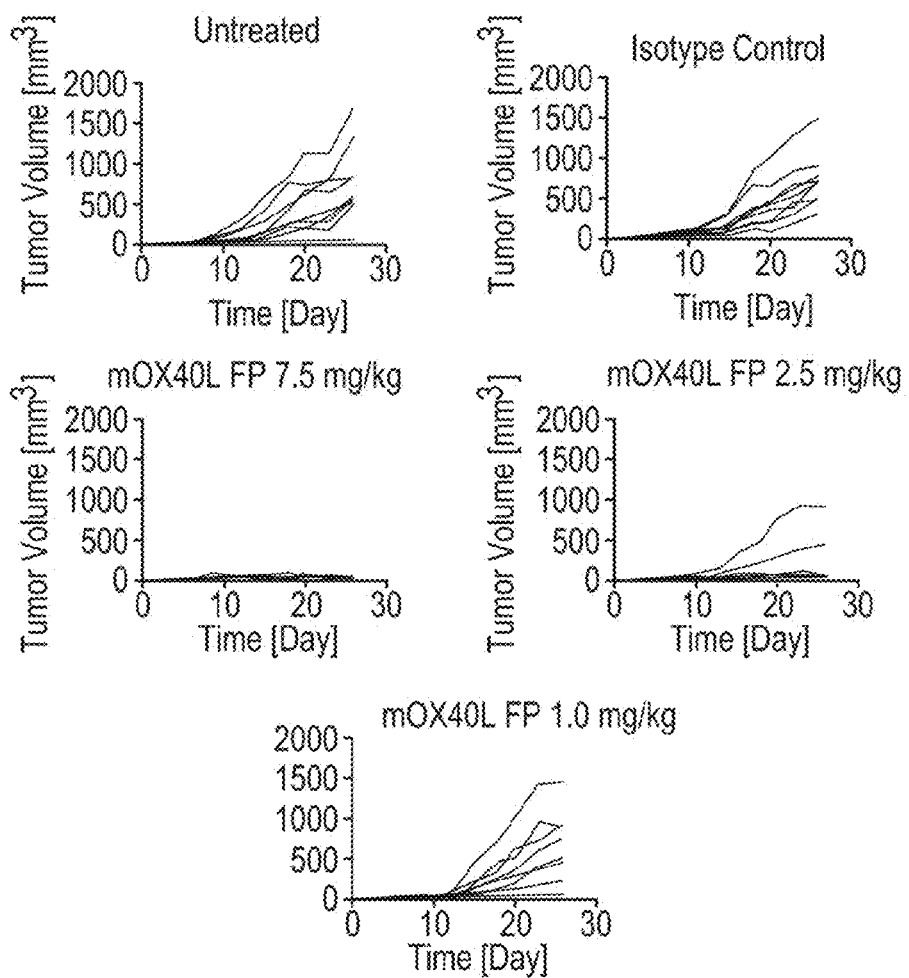

FIG. 19A-B. Effect of Murine OX40 Ligand Fusion Protein on Growth of Renca Cell Line in a Mouse Syngeneic Model. Ten BALB/c mice in each group were inoculated SC on Day 1 with Renca cells. Control article (isotype control) and test article (mOX40L FP) were administered IP on Days 4 and 7. Mean (panel A) and individual (pane B) values of tumor volumes are shown. A comparison between mOX40L FP-treated and the Isotype control-treated animals was made, and intergroup differences were analyzed for statistical significance by the method described in Section 6.8 using GraphPad Prism 6.0 software. Error bars represent standard error of the mean. *: TGI>50%, P≤0.0001 as compared to the isotype-control group on Day 26. SC=subcutaneous; IP=intraperitoneal; TGI=tumor growth inhibition.

Figure 20A:
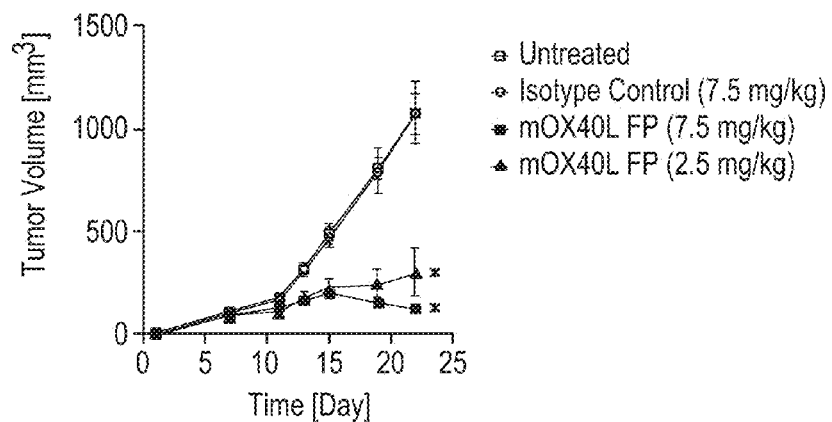
Figure 20B:
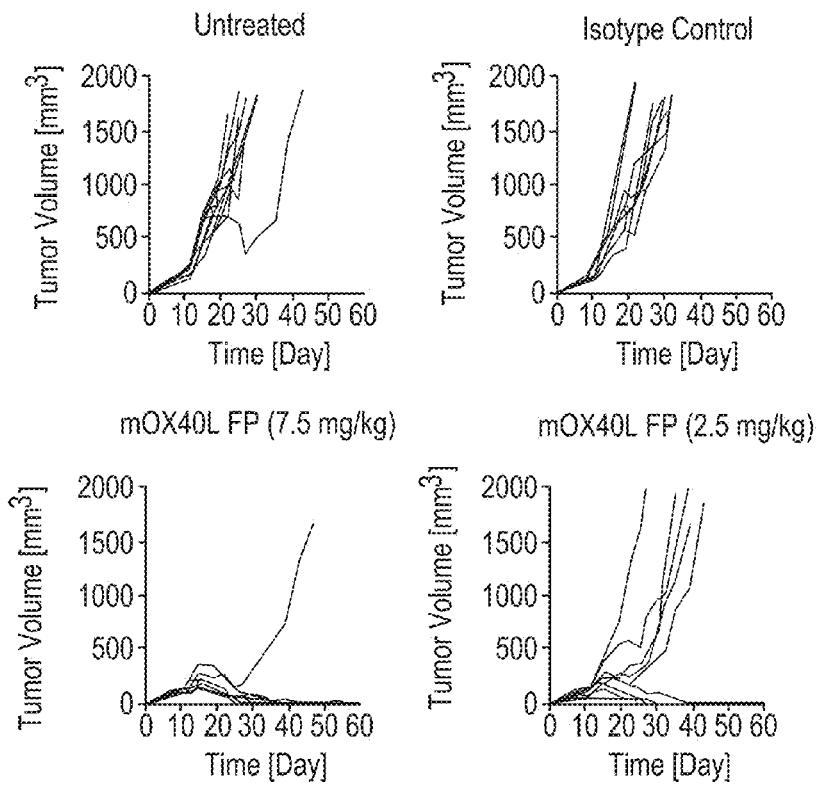

FIG. 20A-B. Effect of Murine OX40 Ligand Fusion Protein on Growth of CT26 Cell Line in a Mouse Syngeneic Model. Ten BALB/c mice in each group were inoculated SC on Day 1 with CT26 cells. Control article (isotype control) and test article (mOX40L FP) were administered IP on Days 4 and 6. Mean (panel A) and individual (panel B) values of tumor volumes are shown. A comparison between mOX40L FP-treated and the isotype control-treated animals was made, and intergroup differences were analyzed for statistical significance by the method described in Section 6.8 using GraphPad Prism 6.0 software. Error bars represent standard error of the mean. *: TGI>50%, P≤0.0001 as compared to the isotype-control group on study day 22. SC=subcutaneous; IP=intraperitoneal; TGI=tumor growth inhibition.

Figure 21A:
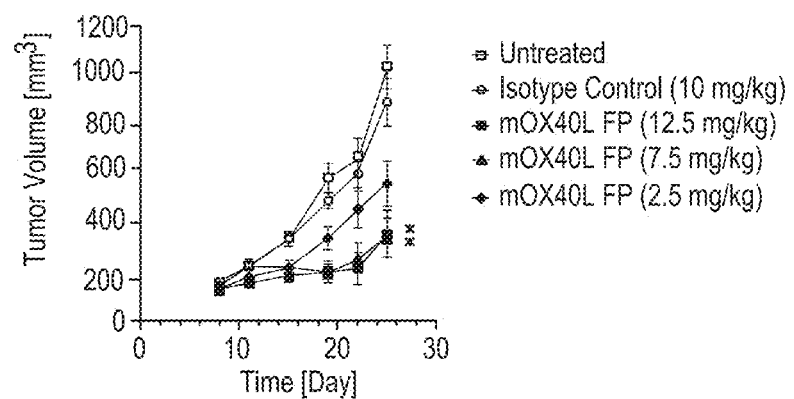
Figure 21B:
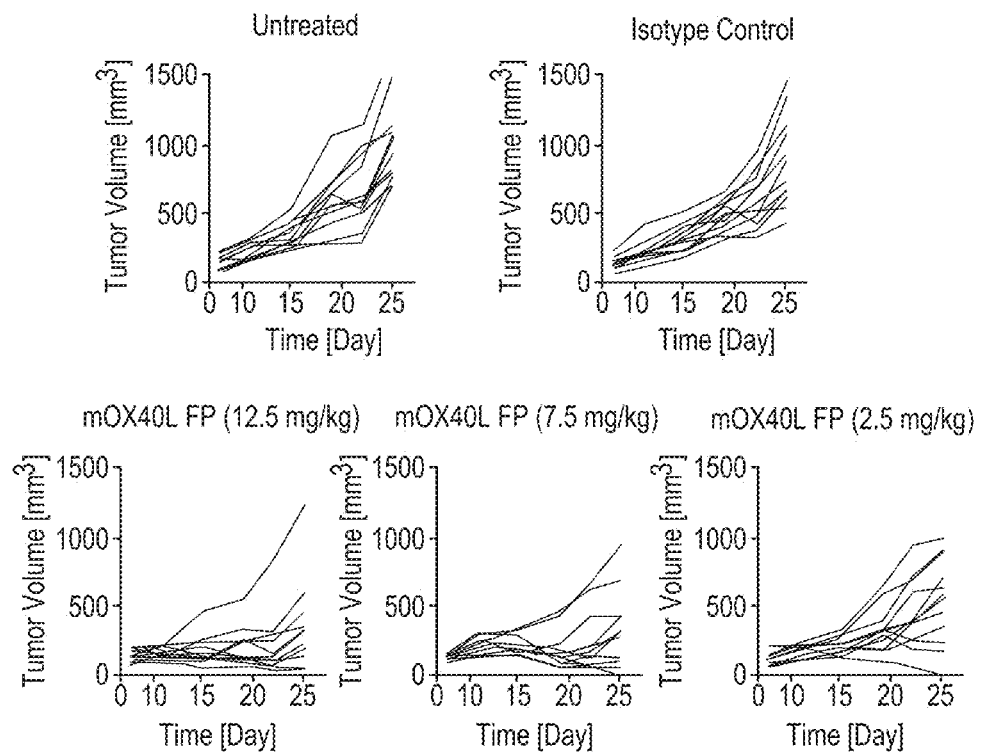

FIG. 21A-B. Effect of Murine OX40 Ligand Fusion Protein on Growth of 4T1 Cell Line in a Mouse Syngeneic Model. Twelve BALB/c mice in each group were inoculated SC on Day 1 with 4T1 cells. Control article (isotype control) and test article (mOX40L FP) were administered IP on Days 4 and 7. Mean (panel A) and individual (panel B) values of tumor volumes are shown. A comparison between mOX40L FP-treated and the Isotype control-treated animals was made, and intergroup differences were analyzed for statistical significance by the method described in Section 6.8 using GraphPad Prism 6.0 software. Error bars represent standard error of the mean. *: TGI>50%, P≤0.0006 as compared to the isotype-control group on study day 25. SC=subcutaneous; IP=intraperitoneal; TGI=tumor growth inhibition.

Figure 22A:
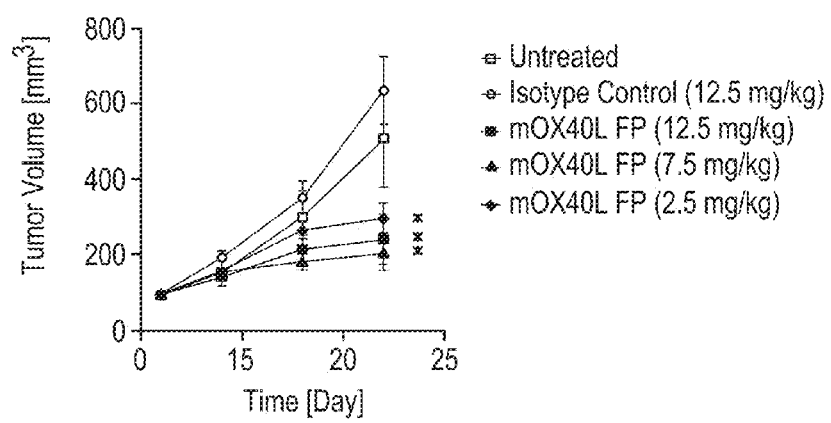
Figure 22B:
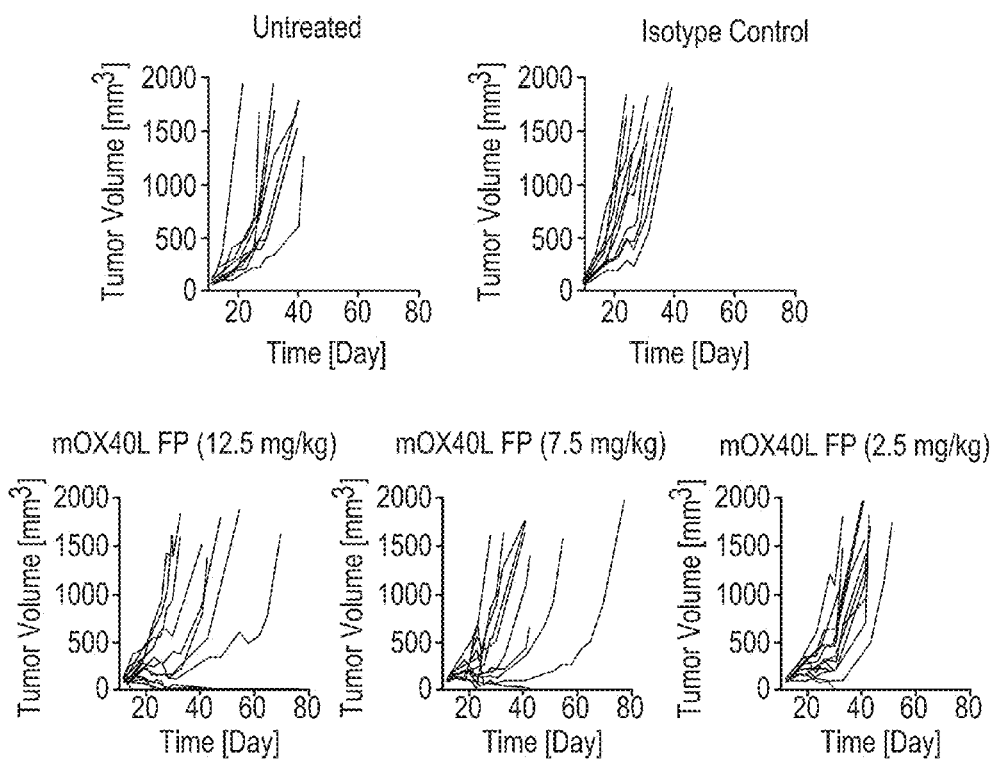

FIG. 22A-B. Effect of Murine OX40 Ligand Fusion Protein on Growth of MCA205 Cell Line in a Mouse Syngeneic Model. Fourteen C57BL/6 mice in each group were inoculated SC on Day 1 with MCA205 cells. Control article (isotype control) and test article (OX40L FP) were administered IP on Days 11 and 14. Mean (panel A) and individual (panel B) values of tumor volumes are shown. A comparison between mOX40L FP-treated and the isotype control-treated animals was made, and intergroup differences were analyzed for statistical significance by the method described in Section 6.8 using GraphPad Prism 6.0 software. Error bars represent standard error of the mean. *: TGI>50%, P≤0.028 as compared to the isotype-control group on study day 22. SC=subcutaneous; IP=intraperitoneal; TGI=tumor growth inhibition.

Figure 23:
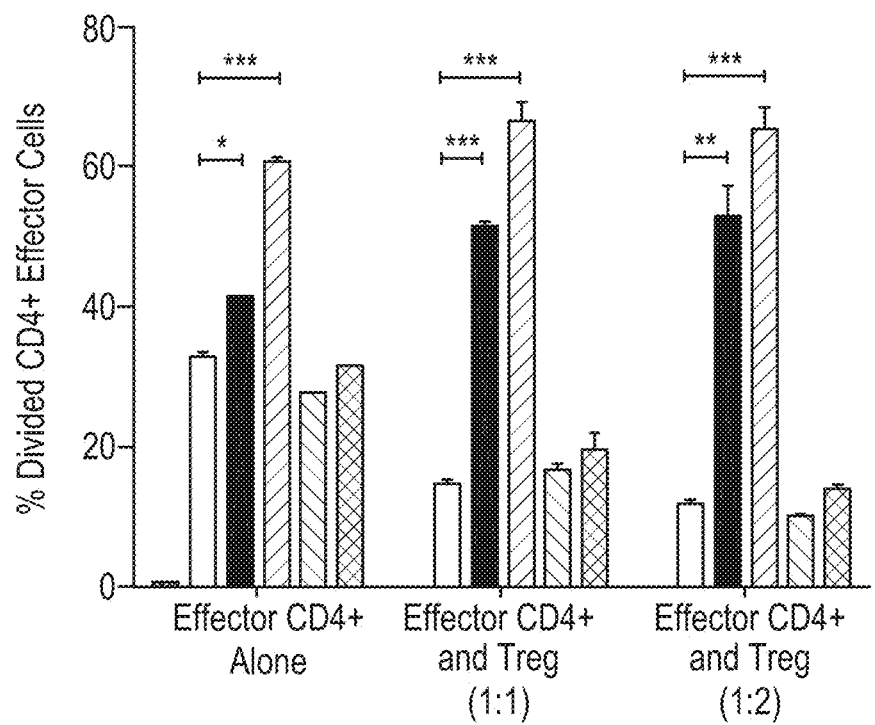

FIG. 23. OX40L IgG4P Fusion Protein Overcomes Regulatory T Cell Suppression of Effector CD4+T cells. Effector CD4+T cells were labelled with carboxyfluorescein diacetate succinimidyl ester (CFSE) and cultured, with and without regulatory T cells (Tregs) at the ratios indicated, for 4 days in the presence of anti-CD3, anti-CD28 and test or control articles. The percentage of divided effector CD4+T cells at the end of the assay was assessed by flow cytometry. Error bars represent the standard error of the mean from duplicate assay wells. Significance was calculated using the Student's T test where *p=0.0042; p=0.0002; *p<0.0001.

Figure 24:
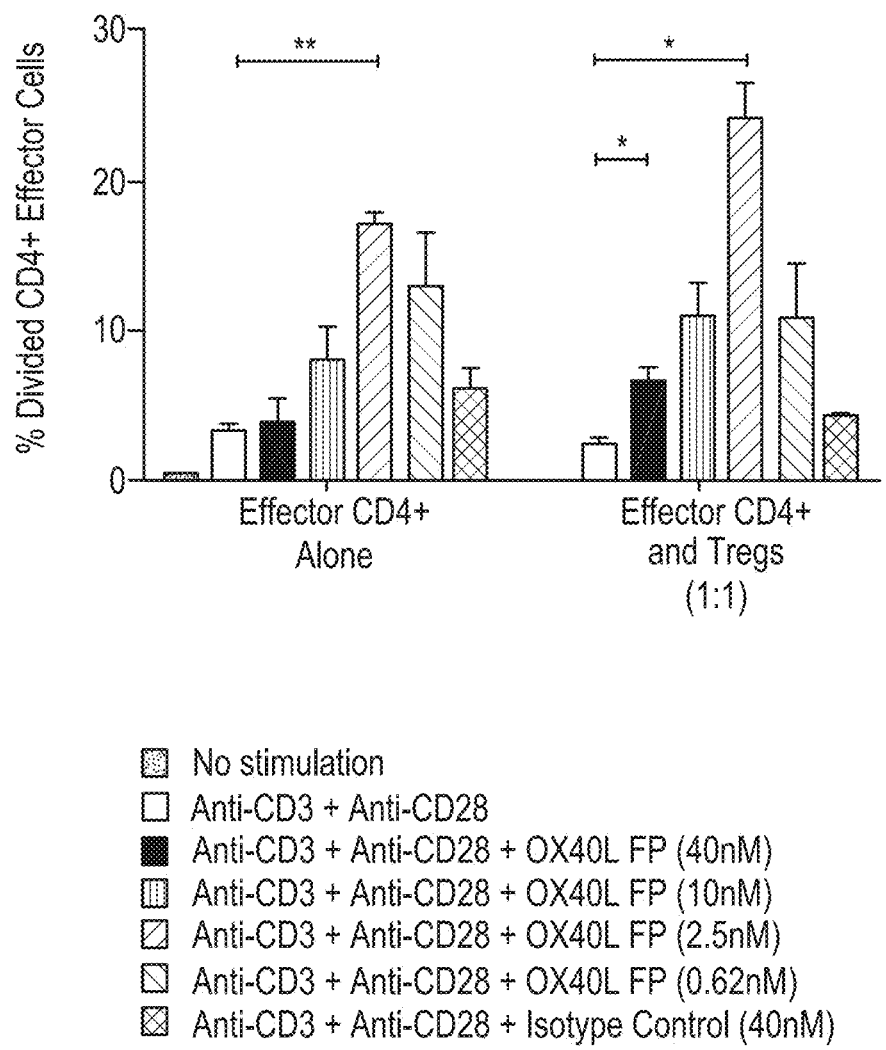

FIG. 24. OX40L IgG4P Fusion Protein Effects on Regulatory T Cell Suppression of Effector CD4+T cells are Concentration Dependent. Effector CD4+T cells were labelled with carboxyfluorescein diacetate succinimidyl ester (CFSE) and cultured, with and without regulatory T cells (Tregs) at a 1:1 ratio, for 4 days in the presence of anti-CD3, anti-CD28 and test or control articles. The percentage of divided effector CD4+T cells at the end of the assay was assessed by flow cytometry. Error bars represent the standard error of the mean from duplicate assay wells. Significance was calculated using the Student's T test where *p<0.05; **p<0.01.

Figure 25:
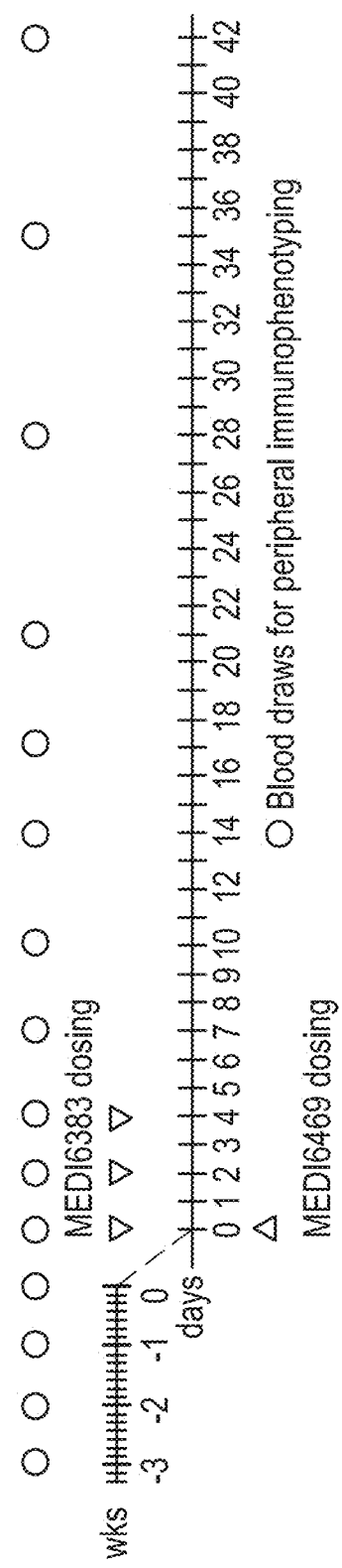
Figure 26A:
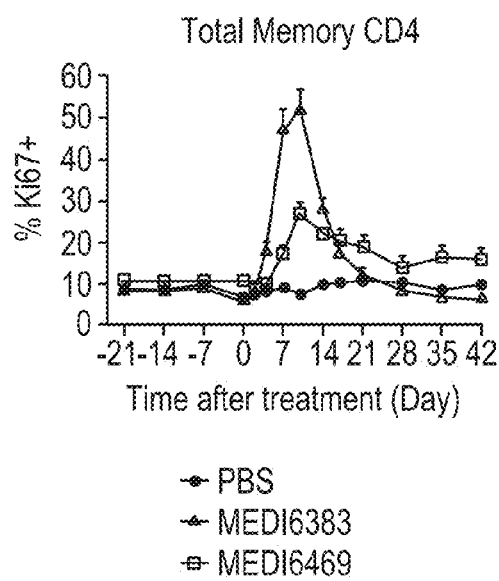
Figure 26B:
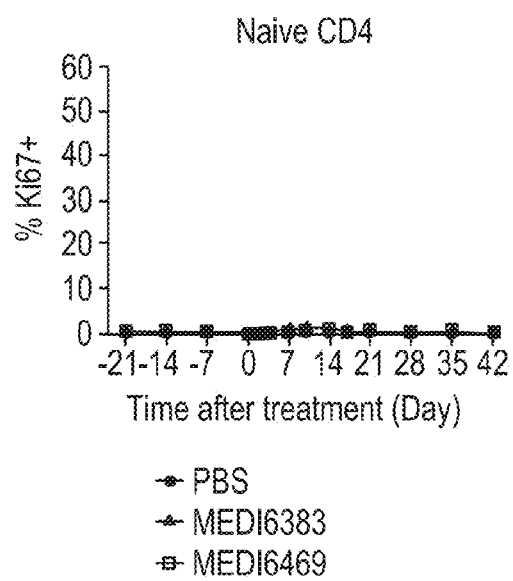
Figure 26C:
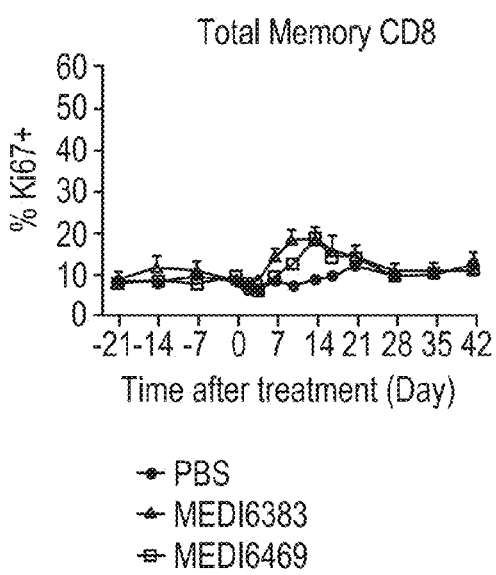
Figure 26D:
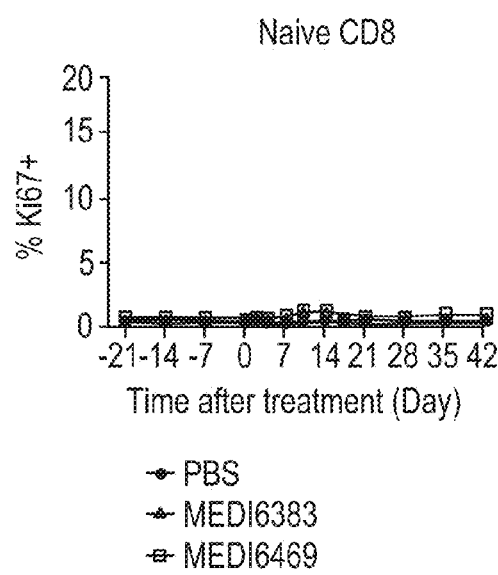
Figure 27A:
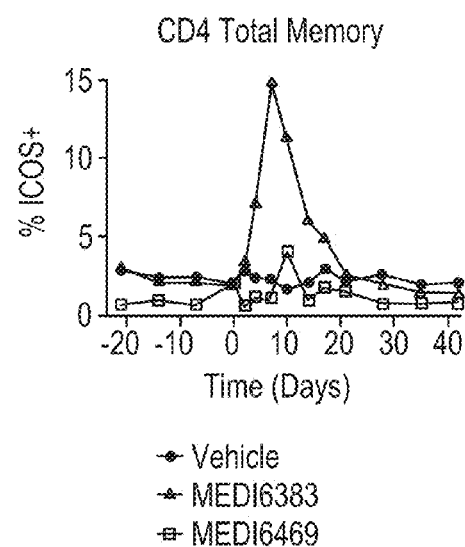
Figure 27B:
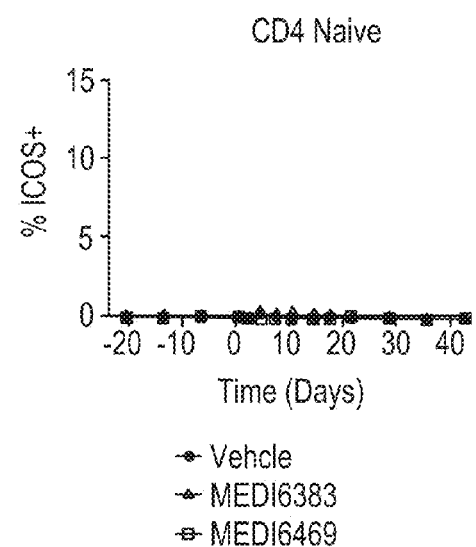
Figure 27C:
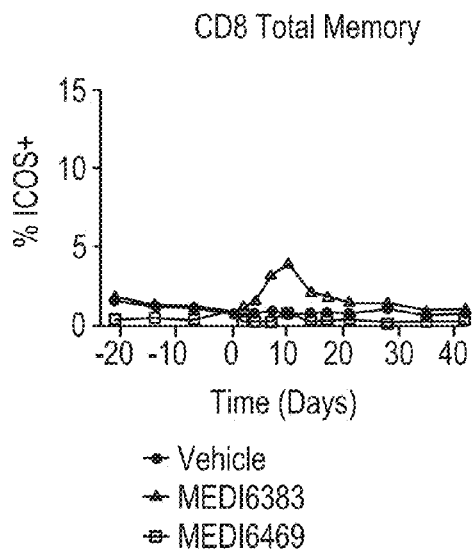
Figure 27D:
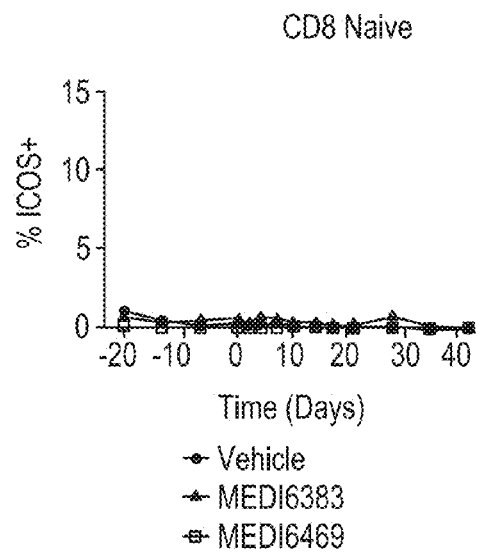

FIG. 25. Study design for monitoring pharmacodynamics effects of OX40L fusion protein IgG4-FP administered via the intravenous route to Rhesus monkeys.

FIG. 26 A-D. Pharmacodynamics (as measured by Ki-67 expression) of total CD4 memory T-cells (A), naïve CD4 T cells (B), total memory CD8 T-cells (C), and naïve CD8 T-cells (D).

FIG. 27 A-D. Pharmacodynamics (as measured by ICOS expression) of total CD4 memory T-cells (A), naïve CD4 T cells (B), total memory CD8 T-cells (C), and naïve CD8 T-cells (D).

FIG. 28 A-D. Pharmacodynamics (as measured by PD-1 expression) of total CD4 memory T-cells (A), naïve CD4 T cells (B), total memory CD8 T-cells (C), and naïve CD8 T-cells (D).

Figure 29:
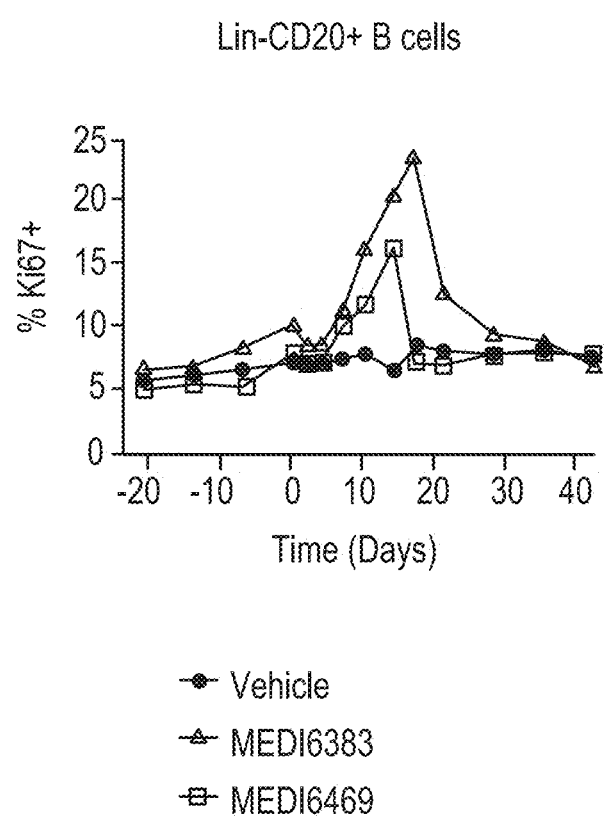

FIG. 29. Pharmacodynamics (as measured by Ki-67 expression) as proliferation of Lin-CD20+B cells.

DETAILED DESCRIPTION

Engagement of the OX40 receptor on T cells, e.g., CD4$^+$ T-cells during, or shortly after, priming by an antigen results in an increased response of the T cells, e.g., CD4$^+$ T-cells to the antigen. In the context of the present disclosure, the term "engagement" refers to binding to and stimulation of at least one activity mediated by the OX40 receptor. For example, engagement of the OX40 receptor on antigen specific T cells, e.g., CD4$^+$ T-cells results in increased T cell proliferation as compared to the response to antigen alone, and increased cytokine production. The elevated response to the antigen can be maintained for a period of time substantially longer than in the absence of OX40 receptor engagement. Thus, stimulation via the OX40 receptor enhances the antigen specific immune response by boosting T-cell recognition of antigens, e.g., tumor antigens.

OX40 agonists can enhance antigen specific immune responses in a subject, such as a human subject, when administered to the subject during or shortly after priming of T-cells by an antigen. OX40 agonists include OX40 ligand ("OX40L"), such as soluble OX40L fusion proteins and anti-OX40 antibodies or fragments thereof. A specific example is a fusion polypeptide subunit comprising the receptor binding domain of OX40L, a trimerization domain, e.g., an isoleucine zipper domain from TRAF-2, and a human IgG4 Fc domain, where the polypeptide subunit self-assembles into a multimeric (e.g., trimeric or hexameric) fusion protein. Also described are nucleic acids including polynucleotide sequences that encode such fusion polypeptides. This disclosure also provides methods for enhancing an antigen specific immune response in a subject using the multimeric OX40L fusion polypeptides. The compositions and methods disclosed herein with respect to OX40L fusion proteins can be more generally applied to the production and use of multimeric (e.g., trimeric and hexameric) receptor-binding fusion proteins.

Definitions

The term "a" or "an" entity refers to one or more of that entity; for example, "polypeptide subunit" is understood to represent one or more polypeptide subunits. As such, the terms "a" (or "an"), "one or more," and "at least one" can be used interchangeably herein.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-standard amino acids. A polypeptide can be derived from a natural biological source or produced by recombinant technology, but is not necessarily translated from a designated nucleic acid sequence. It can be generated in any manner, including by chemical synthesis.

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein. As used herein, the term "polypeptide subunit" refers to a polypeptide chain of amino acids which can interact with other polypeptide subunits, either identical or different, to form a multimeric protein, e.g., a hexameric protein as described herein.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, and are referred to as unfolded.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides that have been separated, fractionated, or partially or substantially purified by any suitable technique.

Other polypeptides disclosed herein are fragments, derivatives, analogs, or variants of the foregoing polypeptides, and any combination thereof. The terms "fragment," "variant," "derivative" and "analog" when referring to polypeptide subunit or multimeric protein as disclosed herein can include any polypeptide or protein that retain at least some of the activities of the complete polypeptide or protein, but which is structurally different. Fragments of polypeptides include, for example, proteolytic fragments, as well as deletion fragments. Variants include fragments as described above, and also polypeptides with altered amino acid sequences due to amino acid substitutions, deletions, or insertions. Variants can occur spontaneously or be intentionally constructed. Intentionally constructed variants can be produced using art-known mutagenesis techniques. Variant polypeptides can comprise conservative or non-conservative amino acid substitutions, deletions or additions. Derivatives are polypeptides that have been altered so as to exhibit additional features not found on the native polypeptide. Examples include fusion proteins. Variant polypeptides can also be referred to herein as "polypeptide analogs." As used herein a "derivative" refers to a subject polypeptide having one or more amino acids chemically derivatized by reaction of a functional side group. Also included as "derivatives" are those peptides that contain one or more standard or synthetic amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate protein activity are well-known in the art (see, e.g., Brummell et al., *Biochem.* 32: 1180-1 187 (1993); Kobayashi et al., *Protein Eng.* 12(10):879-884 (1999); and Burks et al., *Proc. Natl. Acad. Sci. USA* 94: 412-417 (1997)).

As used herein, the term "antibody" (or a fragment, variant, or derivative thereof) refers to at least the minimal portion of an antibody which is capable of binding to antigen, e.g., at least the variable domain of a heavy chain (VH) and the variable domain of a light chain (VL) in the context of a typical antibody produced by a B cell. Basic antibody structures in vertebrate systems are relatively well understood. See, e.g., Harlow et al., Antibodies: A Laboratory Manual, (Cold Spring Harbor Laboratory Press, 2nd ed. 1988).

Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "coding region" is a portion of nucleic acid comprising codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can encode heterologous coding regions, either fused or unfused to a nucleic acid encoding a polypeptide subunit or fusion protein as provided herein. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association or linkage is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA).

Polynucleotide and nucleic acid coding regions can be associated with additional coding regions that encode secretory or signal peptides, which direct the secretion of a polypeptide encoded by a polynucleotide as disclosed herein, e.g., a polynucleotide encoding a polypeptide subunit provided herein. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

A "vector" is nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art.

A "transformed" cell, or a "host" cell, is a cell into which a nucleic acid molecule has been introduced by molecular biology techniques. As used herein, the term transformation encompasses all techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

By "specifically binds," it is generally meant that a molecule, e.g., an OX40L or receptor-binding fragment thereof, binds to another molecule, e.g., OX40, via its receptor-binding domain, and that the binding entails some complementarity between the antigen binding domain and the epitope. According to this definition, a ligand is said to "specifically bind" to a receptor when it binds to that receptor, via its receptor-binding domain more readily than it would bind to a random, unrelated molecule. The term "specificity" is used herein to qualify the relative affinity by which a certain ligand binds to a certain receptor. For example, ligand "A" can be deemed to have a higher specificity for a given receptor than ligand "B," or ligand "A" can be said to bind to receptor "C" with a higher specificity than it has for related receptor "D."

By "a receptor-binding domain," it is intended a binding domain comprised in a ligand, e.g., an OX40L as disclosed herein.

A ligand, e.g., an OX40L-IgG4-Fc polypeptide subunit or multimeric fusion protein as disclosed herein can bind to a receptor, e.g., OX40, with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. A ligand, e.g., an OX40L-IgG4-Fc polypeptide subunit or multimeric fusion protein as disclosed herein can bind to a receptor, e.g., OX40, with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

The terms "inhibit," "block," and "suppress" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity.

As used herein, the term "affinity" refers to a measure of the strength of the binding of a ligand to its cognate receptor. As used herein, the term "avidity" refers to the overall stability of the complex between a population of ligands and receptors, that is, the functional combining strength of a combination of ligands and receptors, e.g., interaction of a hexameric OX40L-IgG4 Fusion Protein to cell surface OX40. Avidity is related to both the affinity of individual receptor binding domains in the population with specific receptors, and also the valencies of the ligands and the receptors.

A ligand, e.g., an OX40L-IgG4-Fc polypeptide subunit or multimeric fusion protein as disclosed herein can also be described or specified in terms of its binding affinity to a ligand. For example, a ligand can bind to a receptor with a dissociation constant or $K_D$ no greater than $5\times10^{-2}$ M, $10^{-2}$M, $5\times10^{-3}$M, $10^{-3}$M, $5\times10^{-4}$ M, $10^{-4}$M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$ M, $10^{-10}$M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$M, or $10^{-15}$M.

A ligand, e.g., an OX40L-IgG4-Fc polypeptide subunit or multimeric fusion protein as disclosed herein can bind to a receptor, e.g., OX40, with an on rate (k(on)) of greater than or equal to $10^3$ M$^{-1}$ sec$^{-1}$, $5\times10^3$M$^{-1}$ sec$^{-1}$, $10^{-4}$ M$^{-1}$ sec$^{-1}$ or $5\times10^{-4}$ M$^{-1}$ sec$^{-1}$. A ligand, e.g., an OX40L-IgG4-Fc polypeptide subunit or multimeric fusion protein as disclosed herein can bind to a receptor, e.g., OX40, with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

OX40, or "OX40 receptor" is a protein (also variously termed CD134, tumor necrosis factor receptor superfamily member 4, and ACT-35) expressed on the surface of activated T cells, e.g., CD4$^+$ and CD8$^+$ T-cells, as well as on Foxp3$^+$ CD4$^+$ regulatory T cells (Tregs). Naive CD4$^+$ and CD8$^+$ T cells do not express OX40 (Croft, M., (2010) *Ann Rev Immunol* 28:57-78).

"OX40 ligand" ("OX40L") (also variously termed tumor necrosis factor ligand superfamily member 4, gp34, TAX transcriptionally-activated glycoprotein-1, and CD252) is found largely on antigen presenting cells (APCs), and can be induced on activated B cells, dendritic cells (DCs), Langerhans cells, plamacytoid DCs, and macrophages (Croft, M., (2010) *Ann Rev Immunol* 28:57-78). Other cells, including activated T cells, NK cells, mast cells, endothelial cells, and smooth muscle cells can express OX40L in response to inflammatory cytokines (Id.). OX40L specifically binds to the OX40 receptor. The human protein is described in PCT Publication No. WO 95/21915. The mouse OX40L is described in U.S. Pat. No. 5,457,035. OX40L is expressed on the surface of cells and includes an intracellular, a transmembrane and an extracellular receptor-binding domain. A functionally active soluble form of OX40L can be produced by deleting the intracellular and transmembrane domains as described, e.g., in U.S. Pat. Nos. 5,457,035 and 6,312,700, and WO 95/21915, the disclosures of which are incorporated herein for all purposes. A functionally active form of OX40L is a form that retains the capacity to bind specifically to OX40, that is, that possesses an OX40 "receptor binding domain." An example is amino acids 51 to 183 of SEQ ID NO: 1, human OX40L. Methods of determining the ability of an OX40L molecule or derivative to bind specifically to OX40 are discussed below. Methods of making and using OX40L and its derivatives (such as derivatives that include an OX40 binding domain) are described in WO 95/21915, which also describes proteins comprising the soluble form of OX40L linked to other peptides, such as human immunoglobulin ("Ig") Fc regions, that can be produced to facilitate purification of OX40 ligand from cultured cells, or to enhance the stability of the molecule after in vivo administration to a mammal (see also, U.S. Pat. No. 5,457,035 and PCT Publication No. WP 2006/121810, both of which are incorporated by reference herein in their entireties).

As used herein, the term "OX40L" includes the entire OX40 ligand, soluble OX40 ligand, and functionally active portions of the OX40 ligand. Also included within the definition of OX40L are OX40 ligand variants which vary in amino acid sequence from naturally occurring OX40 ligand molecules but which retain the ability to specifically bind to an OX40 receptor. Such variants are described in U.S. Pat. No. 5,457,035 and WO 95/21915. In a related embodiment, the disclosure provides mutants of OX40L which have lost the ability to specifically bind to OX40, for example amino acids 51 to 183 of SEQ ID NO: 1, in which the phenylalanine at position 180 of the receptor-binding domain of human OX40L has been replaced with alanine (F180A).

A "trimerization domain" is an amino acid sequence within a polypeptide that promotes assembly of the polypeptide into trimers. For example, a trimerization can promote assembly into trimers via associations with other trimerization domains (of additional polypeptides with the same or a different amino acid sequence). The term is also used to refer to a polynucleotide that encodes such a peptide or polypeptide.

The term "Fc" domain refers to a portion of an antibody constant region. Traditionally, the term Fc domain refers to a protease (e.g., papain) cleavage product encompassing the paired CH2, CH3 and hinge regions of an antibody. In the context of this disclosure, the term Fc domain or Fc refers to any polypeptide (or nucleic acid encoding such a polypeptide), regardless of the means of production, that includes all or a portion of the CH2, CH3 and hinge regions of an immunoglobulin polypeptide, e.g., a human IgG4 Fc.

As used herein the term "CH2 domain" includes the portion of the Fc domain of a heavy chain molecule that extends, e.g., from about amino acid 244 to amino acid 360 of an antibody using conventional numbering schemes (amino acids 244 to 360, Kabat numbering system; and amino acids 231-340, EU numbering system). It is also well documented that the CH3 domain extends from the CH2 domain to the C-terminal of the IgG molecule and comprises approximately 108 amino acids.

As used herein, the term "hinge region" includes the portion of the Fc domain of a heavy chain molecule that joins the CH1 domain to the CH2 domain. This hinge region comprises approximately 25 amino acids and is flexible, thus allowing the two N-terminal antigen binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In certain aspects provided herein, a human IgG4 Fc domain can be mutated in the hinge region to insure disulfide bond formation between two hinge regions, specifically, a serine to proline mutation at position 228 (according to EU numbering). Human IgG4 Fc domains comprising the S228P mutation are referred to herein as "IgG4P Fc domains."

As used herein, the terms "linked," "fused" or "fusion" can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature.), e.g., an OX40L IgG4P fusion protein as provided herein. Although the reading frame is thus made continuous throughout the fused segments, the segments can be physically or spatially separated by, for example, in-frame linker sequence.

In the context of polypeptides, a "linear sequence" or a "sequence" is an order of amino acids in a polypeptide in an amino to carboxyl terminal direction in which amino acids that neighbor each other in the sequence are contiguous in the primary activated structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein the terms "treat," "treatment," or "treatment of" (e.g., in the phrase "treating a cancer patient") refers to reducing the potential for disease pathology, reducing the occurrence of disease symptoms, e.g., to an extent that the subject has a longer survival rate or reduced discomfort. For example, treating can refer to the ability of a therapy when administered to a subject, to reduce disease symptoms, signs, or causes. Treating also refers to mitigating or decreasing at least one clinical symptom and/or inhibition or delay in the progression of the condition and/or prevention or delay of the onset of a disease or illness.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals, including, e.g., humans, non-human primates, dogs, cats, guinea pigs, rabbits, rats, mice, horses, cattle, bears, and so on.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

An "effective amount" of an antibody as disclosed herein is an amount sufficient to carry out a specifically stated purpose. An "effective amount" can be determined empirically and in a routine manner, in relation to the stated purpose. OX40L IgG4 Fusion Polypeptide Subunits The present disclosure relates to an OX40L fusion polypeptide subunit that can assemble into a hexameric protein with an increased ability to stimulate human T cells. The polypeptide subunit provided herein comprises a human IgG4 Fc domain, e.g., a human IgG4P Fc domain, a trimerization domain, e.g., a TRAF-2 isoleucine zipper trimerization domain, and the receptor binding domain of human OX40L. An exemplary embodiment is illustrated schematically in FIG. 1. Typically, the IgG4 Fc domain, the trimerization domain and the OX40L receptor binding domain are arranged in an N-terminal to C-terminal direction. An exemplary OX40L fusion polypeptide subunit is represented by SEQ ID NO: 4.

In an exemplary embodiment, the OX40L receptor binding domain is an extracellular domain of a human OX40L. The sequence of one such a domain is represented by amino acids 51 to 183 of SEQ ID NO: 1.

```
>sp|P23510|TNFL4_HUMAN Tumor necrosis factor
ligand superfamily member 4 OS = Homo sapiens
GN = TNFSF4 PE = 1 SV = 1
MERVQPLEENVGNAARPRFERNKLLLVASVIQGLGLLLCFTYICLHFSAL

QVSHRYPRIQSIKVQFTEYKKEKGFILTSQKEDEIMKVQNNSVIINCDGF

YLISLKGYFSQEVNISLHYQKDEEPLFQLKKVRSVNSLMVASLTYKDKVY

LNVTTDNTSLDDFHVNGGELILIHQNPGEFCVL
```

Any OX40L polypeptide sequence that retains the desired property of binding to the OX40 receptor is suitable in the fusion polypeptides and methods described herein.

Adjacent to the OX40L receptor binding domain is a trimerization domain. The term "adjacent" includes, for example, contiguous with, or associated via a linker or heterologous agent. The trimerization domain serves to promote self-assembly of individual OX40L fusion polypeptide molecules into a trimeric protein. Thus, an OX40L fusion polypeptide with a trimerization domain self-assembles into a trimeric OX40L fusion protein. In one embodiment, the trimerization domain is a leucine zipper domain. An exemplary leucine zipper domain is the engineered yeast GCN4 leucine variant described by Harbury et al. (1993) Science 262:1401-1407, the disclosure of which is incorporated herein for all purposes. Exemplary trimerization domains include: TNF receptor-associated factor-2 (TRAF2) (GENBANK® Accession No. Q12933 [gi: 23503103]; amino acids 310-349); Thrombospondin 1 (Accession No. P07996 [gi:135717]; amino acids 291-314); Matrilin-4 (Accession No. O95460 [gi:14548117]; amino acids 594-618; cartilage matrix protein (matrilin-1) (Accession No. NP002370 [gi:4505111]; amino acids 463-496; Heat shock transcription factor (HSF) (Accession No. AAX42211 [gi:61362386]; amino acids 165-191; and Cubilin (Accession No. NP001072 [gi:4557503]; amino acids 104-138. In certain aspects, the trimerization domain comprises amino acids 310 to 349 of human TRAF2 (SEQ ID NO: 2).

```
>sp|Q12933|TRAF2_HUMAN TNF receptor-associated
factor 2 OS = Homo sapiens GN = TRAF2 PE = 1
SV = 2
MAAASVTPPGSLELLQPGFSKTLLGTKLEAKYLCSACRNVLRRPFQAQC

GHRYCSFCLASILSSGPQNCAACVHEGIYEEGISILESSSAFPDNAARR

EVESLPAVCPSDGCTWKGTLKEYESCHEGRCPLMLTECPACKGLVRLGE

KERHLEHECPERSLSCRHCRAPCCGADVKAHHEVCPKFPLTCDGCGKKK

IPREKFQDHVKTCGKCRVPCRFHAIGCLETVEGEKQQEHEVQWLREHLA

MLLSSVLEAKPLLGDQSHAGSELLQRCESLEKKTATFENIVCVLNREVE

RVAMTAEACSRQHRLDQDKIEALSSKVQQLERSIGLKDLAMADLEQKVL

EMEASTYDGVFIWKISDFARKRQEAVAGRIPAIFSPAFYTSRYGYKMCL

RIYLNGDGTGRGTHLSLFFVVMKGPNDALLRWPFNQKVTLMLLDQNNRE

HVIDAFRPDVTSSSFQRPVNDMNIASGCPLFCPVSKMEAKNSYVRDDAI

FIKAIVDLTGL
```

In addition to the OX40L receptor binding domain and the trimerization domain, the fusion polypeptide includes an immunoglobulin domain, such as a constant region or "Fc" domain. The present disclosure provides a human IgG4 Fc domain including at least the hinge region. In certain aspects the human IgG4 Fc domain further includes the CH2 domain. In certain aspects the human IgG4 Fc domain further includes the CH3 domain. In certain aspects the hinge region comprises a serine to proline mutation at position 228 (according to EU numbering) which confers complete inter-heavy chain disulfide bond formation. In certain aspects the hinge region comprises amino acids 1 to 12 of SEQ ID NO: 4. In certain aspects the human IgG4 Fc domain comprises amino acids 1 to 229 of SEQ ID NO: 4.

In combination with the trimerization domain which brings together three OX40L receptor binding domains, the disulfide bond formation between two IgG4 Fc domains results in the formation of a hexameric protein (FIG. 1). Thus, the immunoglobulin domain serves as a dimerization domain that promotes assembly between two trimeric fusion polypeptides into a stable hexamer (that is a multimer that contains six OX40L fusion polypeptide subunits) via interactions between unpaired immunoglobulin domains. In certain aspects, the human IgG4 Fc domain provides stability to the hexameric protein without promoting effector functions such as antibody dependent cellular cytotoxicity (ADCC) or complement-dependent cellular cytotoxicity.

In certain aspects, this disclosure provides a single-chain polypeptide subunit that self-assembles to form a hexameric protein that can specifically binds to OX40. An exemplary polypeptide subunit comprises a human IgG4 Fc domain, a functional trimerization domain, and a receptor binding domain of OX40L. In specific aspects the polypeptide subunit can self-assemble into a trimeric or a hexameric protein. In certain aspects, the polypeptide subunit is arranged, from the amino terminus to the carboxy terminus, as follows: the human IgG4 Fc domain, followed by the trimerization domain, followed by the OX40L receptor binding domain. The three domains can be immediately adjacent. For example, in certain aspects the carboxy terminus of the human IgG4 Fc domain is fused directly to the amino terminus of the trimerization domain, and the carboxy terminus of the trimerization domain is fused directly to the amino terminus of the OX40L receptor binding domain. Alternatively, the three domains can be separated by one or more linkers, spacers, or other heterologous polypeptides In certain aspects, an OX40L fusion polypeptide subunit as provided herein can specifically bind to human OX40. In certain aspects, an OX40L fusion polypeptide subunit as provided herein can specifically bind to a non-human primate OX40, e.g., cynomolgus monkey OX40 or rhesus monkey OX40. In certain aspects, an OX40L fusion polypeptide subunit as provided herein does not bind to mouse OX40 or to rat OX40.

An OX40L subunit polypeptide as provided herein can contain one or more conservative amino acid changes, e.g., up to ten conservative changes (e.g., two substituted amino acids, three substituted amino acids, four substituted amino acids, or five substituted amino acids, etc.), provided that the changes can be made in the polypeptide without changing a biochemical function of the OX40L fusion polypeptide subunit or hexameric protein.

For example, one or more conservative changes can be made in an OX40L receptor binding domain without changing its ability to bind to OX40. Similarly, one or more conservative changes can be made in trimerization domain without altering its ability to trimerize.

Additionally, part of a polypeptide domain can be deleted without impairing or eliminating all of its functions. Similarly, insertions or additions can be made in the polypeptide chain, for example, adding epitope tags, without impairing or eliminating its functions, as described below. Other modifications that can be made without materially impairing one or more functions of a polypeptide include, for example, in vivo or in vitro chemical and biochemical modifications that incorporate unusual amino acids. Such modifications include, for example, acetylation, carboxylation, phosphorylation, glycosylation, labeling, e.g., with radionuclides, and various enzymatic modifications, as will be readily appreciated by those of ordinary skill in the art. A variety of methods for labeling polypeptides, and labels useful for such purposes, are well known in the art, and include radioactive isotopes such as $^{32}$P, fluorophores, chemiluminescent agents, enzymes, and antiligands.

The fusion polypeptide subunit can further include a heterologous agent, e.g., a stabilizing agent, an immune response modifier, or a detectable agent. In certain aspects the heterologous agent comprises one or more additional polypeptide sequences fused to the polypeptide subunit via a peptide bond, such as a signal sequence (e.g., a secretory signal sequence), a linker sequence, an amino acid tag or label, or a peptide or polypeptide sequence that facilitates purification. In certain aspects, the heterologous polypeptide can be fused to the N-terminus of the IgG4-Fc domain, the heterologous polypeptide can be fused to the C-terminus of the receptor binding domain of OX40L, the heterologous polypeptide can be fused to the C-terminus of the IgG4-Fc domain and to the N-terminus of the trimerization domain, or the heterologous polypeptide can be fused to the C-terminus of the trimerization domain and to the N-terminus of the receptor binding domain of OX40L. Alternatively the heterologous polypeptide can be fused internally within any of the IgG4 Fc domain, the trimerization domain, or the OX40L receptor binding domain, as long as the functional characteristics of the domains are maintained.

In certain aspects, the heterologous agent can be chemically conjugated to the polypeptide subunit. Exemplary heterologous agents that can be chemically conjugated to the polypeptide subunit include, without limitation, linkers, drugs, toxins, imaging agents, radioactive compounds, organic and inorganic polymers, and any other compositions which might provide a desired activity that is not provided by the polypeptide subunit itself. Specific agents include, without limitation, polyethylene glycol (PEG), a cytotoxic agent, a radionuclide, an imaging agent, biotin.

In certain aspects, the disclosure provides certain OX40L-related polypeptide subunits to be used as controls or research tools. For example, the disclosure provides an OX40L-related subunit polypeptide as described above, where the OX40L receptor binding domain comprises amino acids 51 to 183 of human OX40L (SEQ ID NO: 1), except for a single phenylalanine to alanine substitution at position 180 (F180A). This OX40L-related polypeptide subunit, comprising SEQ ID NO: 6, is incapable of binding to human OX40. In another example, the disclosure provides OX40L polypeptide subunits that can form a hexameric protein as described above, but where the OX40L receptor binding domain is a mouse or rat OX40L receptor binding domain, and the Fc domain is a murine IgG1 Fc domain, and the trimerization domain is a mouse TRAF2 trimerization domain. This mouse-derived construct can be used to conduct in vivo experiments in rodents.

Multimeric OX40L IgG4P Fusion Proteins

An OX40L fusion polypeptide subunit as described above can self-assemble into a trimeric or hexameric OX40L fusion protein. Accordingly, the disclosure provides a hexameric protein comprising six polypeptide subunits as described above. An exemplary polypeptide subunit described in the Examples self-assembles into a hexameric protein designated herein as "OX40L IgG4P Fusion Protein." Except where specifically noted, the term "OX40L IgG4P Fusion Protein" as used herein refers to a human OX40L IgG4P Fusion Protein. The amino acid sequence of the polypeptide subunit that self-assembles into the hexameric protein OX40 IgG4P Fusion Protein is provided in SEQ ID NO: 4. Nonetheless, one of ordinary skill in the art will recognize that numerous other sequences also fulfill the criteria set forth herein for hexameric OX40L fusion proteins.

In certain aspects, an OX40L fusion polypeptide subunit can also self-assemble into a trimeric protein comprising three polypeptide subunits. This could occur, for example, where an Fc domain does not exhibit complete dimerization.

A hexameric protein as provided herein, e.g., OX40L IgG4P Fusion Protein, can specifically bind to OX40 as expressed on primary activated T cells, e.g., primary activated CD4$^+$ T cells, from human, cynomolgus monkey, rhesus monkey, or any combination thereof. In certain aspects, a hexameric protein as provided herein, e.g., OX40L IgG4P Fusion Protein, can bind to human OX40 expressed on primary activated human CD4$^+$ T cells with a binding affinity of about 0.01 pM to about 1 nM, e.g., about 0.1 pM to about 100 pM, e.g., about 1 pM to about 10 pM, e.g., about 1.0 pM to about 8.0 pM, all as measured by flow cytometry. For example, a hexameric protein as provided herein, e.g., OX40L IgG4P Fusion Protein, can bind to human OX40 expressed on primary activated human CD4$^+$ T cells with a binding affinity of about 0.1 pM, about 0.5 pM, about 1 pM, about 2 pM, about 3 pM, about 4 pM, about 5 pM, about 6 pM, about 7 pM, about 8 pM, about 9 pM, about 10 pM, about 20 pM, about 30 pM, about 40 pM, about 50 pM, about 60 pM, about 70 pM, about 80 pM, about 90 pM, about 100 pM, about 500 pM, or about 1 nM, all as measured by flow cytometry. In certain aspects, a hexameric protein as provided herein, e.g., OX40L IgG4P Fusion Protein, can bind to human OX40 expressed on primary activated human CD4$^+$ T cells with a binding affinity of about 3.6 pM. Binding affinity can be measured by a number of different methods and/or instruments, and the relative binding affinities can vary depending on the method or instrument, as is well understood by persons or ordinary skill in the art.

A hexameric protein as provided herein, e.g., OX40L IgG4P Fusion Protein, given its multivalent characteristic can occupy and cross-link some or all of the OX40 molecules on the surface of a cell, e.g., a primary activated human CD4+ T cell. In certain aspects, a hexameric protein as provided herein, e.g., OX40L IgG4P Fusion Protein, can bind to human OX40 expressed on primary activated human CD4+ T cells, and can achieve 20% receptor occupancy on primary activated human CD4+ T cells ($EC_{20}$) at a concentration of about 0.01 pM to about 1 nM, e.g., about 0.1 pM to about 100 pM, e.g., about 0.5 pM to about 10 pM, e.g., or about 0.5 to about 3.0 pM, e.g., about 0.5 pM, about 0.6 pM, about 0.7 pM, about 0.8 pM, about 0.9 pM, about 2 pM, about 2 pM, or about 3 pM, as measured by flow cytometry. In certain aspects, a hexameric protein as provided herein, e.g., OX40L IgG4P Fusion Protein, can bind to human OX40 expressed on primary activated human CD4+ T cells, and can achieve 50% receptor occupancy on primary activated human CD4+ T cells ($EC_{50}$) at a concentration of about 0.01 pM to about 1 nM, e.g., about 0.1 pM to about 100 pM, e.g., about 0.5 pM to about 10 pM, e.g., or about 3.0 pM to about 10 pM, e.g., about 2 pM, about 3 pM, about 4 pM, about 5 pM, about 6 pM, about 7 pM, about 8 pM, about 9 pM, or about 10 pM, as measured by flow cytometry. In certain aspects, a hexameric protein as provided herein, e.g., OX40L IgG4P Fusion Protein, can bind to human OX40 expressed on primary activated human CD4+ T cells, and can achieve 90% receptor occupancy on primary activated human CD4+ T cells ($EC_{90}$) at a concentration of about 0.1 pM to about 10 nM, e.g., about 1 pM to about 1 nM, e.g., about 10 pM to about 100 pM, e.g., or about 35 to about 70 pM, e.g., about 30 pM, about 40 pM, about 50 pM, about 60 pM, or about 70 pM, as measured by flow cytometry.

In certain aspects, a hexameric protein as provided herein, e.g., OX40L IgG4P Fusion Protein, can bind to human OX40 expressed on primary activated human CD4+ T cells, and can achieve $EC_{20}$ a concentration of about 1.8 pM, $EC_{50}$ at a concentration about 6.6 pM, and $EC_{90}$ at a concentration of about 53 pM, all as measured by flow cytometry.

For example, a hexameric protein as provided herein, e.g., OX40L IgG4P Fusion Protein, can bind to human OX40 expressed on OX40-overexpressing Jurkat cells with a binding affinity of about 1.0 pM to about 24 pM, e.g., about 12 pM as measured by flow cytometry.

In certain aspects, a hexameric protein as provided herein, e.g., OX40L IgG4P Fusion Protein, can bind to human OX40 expressed on OX40-overexpressing Jurkat cells, and can achieve $EC_{20}$ at a concentration of about 1.0 to about 15 pM, $EC_{50}$ at a concentration of about 1.0 to about 40 pM, and $EC_{90}$ at a concentration about 10 to about 100 pM as measured by flow cytometry. In certain aspects, a hexameric protein as provided herein, e.g., OX40L IgG4P Fusion Protein, can bind to human OX40 expressed on OX40-overexpressing Jurkat cells and can achieve $EC_{20}$ at a concentration of about 7.2 pM, $EC_{50}$ at a concentration of about 16 pM, and $EC_{90}$ at a concentration of about 57 pM, as measured by flow cytometry.

In another example, a hexameric protein as provided herein, e.g., OX40L IgG4P Fusion Protein, can bind to cynomolgus monkey OX40 expressed on primary activated cynomolgus monkey CD4+ T cells with a binding affinity of about 1.0 pM to about 50 pM, e.g., about 24 pM, as measured by flow cytometry. In another example, a hexameric protein as provided herein, e.g., OX40L IgG4P Fusion Protein, can bind to rhesus monkey OX40 expressed on primary activated rhesus monkey CD4+ T cells with a binding affinity of about 1.0 pM to about 50 pM, e.g., about 21 pM, as measured by flow cytometry.

In certain aspects, a hexameric protein as provided herein, e.g., OX40L IgG4P Fusion Protein, can induce dose-dependent proliferation of activated CD4+ T cells in a plate-based assay. For example, in an in vitro assay using a hexameric protein as provided herein, e.g., OX40L IgG4P Fusion Protein, a 20% maximal proliferation response ($EC_{20}$) can be achieved in primary activated human CD4+ T cells at a hexameric protein concentration of about 1.0 pM to about 15 pM, e.g., about 8.0 pM, a 50% maximal proliferation response ($EC_{50}$) can be achieved in primary activated human CD4+ T cells at a hexameric protein concentration of about 5.0 pM to about 25 pM, e.g., about 14 pM, and a 90% maximal proliferation response ($EC_{90}$) can be achieved in primary activated human CD4+ T cells at a hexameric protein concentration of about 50 pM to about 65 pM, e.g., about 57 pM, all as measured by flow cytometry.

In certain aspects, a hexameric protein as provided herein, e.g., OX40L IgG4P Fusion Protein, can induce dose-dependent cytokine release from activated CD4+ T cells, e.g., human primary activated CD4+ T cells. In certain aspects, the released cytokine is IFNγ, TNFα, IL-5, IL-10, IL-2, IL-4, IL-13, IL-8, IL-12 p70, IL-1β, or any combination thereof. In certain aspects, the cytokine is IFNγ, TNFα, IL-5, IL-10, or any combination thereof. Similarly, a hexameric protein as provided herein, e.g., OX40L IgG4P Fusion Protein, can achieve CD4+ T cell proliferation and cytokine release in primary activated cynomolgus monkey CD4+ T cells and in primary activated rhesus monkey CD4+ T cells.

In additional aspects, a hexameric protein as provided herein, e.g., OX40L IgG4P Fusion Protein, can activate the NFκB pathway in OX40 expressing T cells in the presence of FcγR-expressing cells. For example, a hexameric protein as provided herein, e.g., OX40L IgG4P Fusion Protein can activate the NFκB pathway in OX40-expressing Jurkat NFκB-luciferase reporter cells that produce luciferase in response to stimulation of the NFκB signaling pathway. Alternatively, a hexameric protein as provided herein, e.g., OX40L IgG4P Fusion Protein can activate the NFκB pathway in cells expressing human OX40, cynomolgus monkey OX40 or rhesus monkey OX40.

In yet another aspect a hexameric protein as provided herein, e.g., OX40L IgG4P Fusion Protein can facilitate cancer treatment, e.g., by slowing tumor growth, stalling tumor growth, or reducing the size of existing tumors, when administrated as an effective dose to a subject in need of cancer treatment. In certain aspects the facilitation of cancer treatment can be achieved in the presence of T-cells. In certain aspects, a hexameric protein as provided herein, e.g., OX40L IgG4P Fusion Protein, when administered as an effective dose to a subject in need of treatment, can reduce tumor growth by at least 10%, at least 20%, at least 30%, at least 40%, and least 50%, at least 60%, or at least 70% compared to administration of an isotype-matched control molecule.

In yet further aspects, a hexameric protein as provided herein, e.g., OX40L IgG4P Fusion Protein, can induce proliferation of activated, OX40-expressing CD4+ T cells through binding to OX40, but does not substantially trigger complement-dependent or antibody-dependent cytotoxicity against the activated CD4+ T cells. Moreover in certain aspects, a hexameric protein as provided herein, e.g., OX40L IgG4P Fusion Protein, can induce proliferation of activated, OX40-expressing CD4+ T cells through binding to OX40, but does not bind to C1q or trigger NK cell-mediated antibody-dependent cellular cytotoxicity of activated CD4+ T cells.

Polynucleotides Encoding OX40L Fusion Proteins

The disclosure further provides a polynucleotide comprising a nucleic acid that encodes an OX40L fusion polypeptide subunit, or a hexameric protein as provided herein, e.g., OX40L IgG4P Fusion Protein. An exemplary polynucleotide sequence that encodes a polypeptide subunit of OX40L IgG4P Fusion Protein is represented by SEQ ID NO: 3. In certain aspects, nucleic acid sequences encoding the IgG4 Fc domain, the trimerization domain and the OX40L receptor binding domains are joined in a 5' to 3' orientation, e.g., contiguously linked in a 5' to 3' orientation. In other aspects, the provided polynucleotide can further comprise a signal sequence encoding, e.g., a secretory signal peptide or membrane localization sequence. Polynucleotides encoding any and all OX40L fusion polypeptide subunits or multimeric, e.g., hexameric proteins comprising the subunits, are provided by this disclosure.

In certain aspects, the disclosure provides a polynucleotide comprising a nucleic acid that encodes OX40L IgG4P Fusion Protein. In certain aspects the nucleic acid sequence comprises SEQ ID NO: 3. Polynucleotides encoding control proteins provided herein, e.g., the disclosure provides a polynucleotide comprising a nucleic acid that encodes HuIgG-4FcPTF2OX40L F180A. In certain aspects the nucleic acid comprises SEQ ID NO: 5.

Polynucleotides encoding an OX40L fusion polypeptide subunit, or a hexameric protein as provided herein, e.g., OX40L IgG4P Fusion Protein include deoxyribonucleotides (DNA, cDNA) or ribodeoxynucletides (RNA) sequences, or modified forms of either nucleotide, which encode the fusion polypeptides described herein. The term includes single and double stranded forms of DNA and/or RNA.

Also provided are polynucleotides comprising nucleic acid sequences comprising one or a small number of deletions, additions and/or substitutions. Such changes can be contiguous or can be distributed at different positions in the nucleic acid. A substantially identical nucleic acid sequence can, for example, have 1, or 2, or 3, or 4, or even more nucleotide deletions, additions and/or substitutions. In certain aspects, the one or more deletions, additions and/or substitutions do not alter the reading frame encoded by the polynucleotide sequence, such that a modified ("mutant") but substantially identical polypeptide is produced upon expression of the nucleic acid.

The similarity between amino acid (and/or nucleic acid) sequences is expressed in terms of the similarity between the sequences, otherwise referred to as sequence identity. Sequence identity is frequently measured in terms of percentage identity (or similarity); the higher the percentage, the more similar are the primary activated structures of the two sequences. "Percent (%) identity" is defined herein as the percentage of amino acid residues in a candidate sequence that are identical with the amino acid residues in a selected sequence, after aligning the sequences and introducing gaps in the candidate and/or selected sequence, if necessary, to achieve the maximum percent sequence identity, and not considering any conservative amino acid substitutions as part of the sequence identity.

Thus, a polynucleotide comprising a nucleic acid that encodes an OX40L fusion polypeptide subunit, or a hexameric protein as provided herein, e.g., OX40L IgG4P Fusion Protein, can be at least about 95%, or at least 96%, frequently at least 97%, 98%, or 99% identical to SEQ ID NO: 4 or to at least one subsequence thereto. Alignment for purposes of determining percent homology (i.e., sequence similarity) or percent identity can be achieved in various ways that are within the skill in the art, for instance, using publicly or proprietary algorithms. For instance, sequence similarity can be determined using pairwise alignment methods, e.g., BLAST, BLAST-2, ALIGN, or ALIGN-2 or multiple sequence alignment methods such as Megalign (DNASTAR), ClustalW or T-Coffee software. Those skilled in the art can determine appropriate scoring functions, e.g., gap penalties or scoring matrices for measuring alignment, including any algorithms needed to achieve optimal alignment quality over the full-length of the sequences being compared. In addition, sequence alignment can be achieved using structural alignment methods (e.g., methods using secondary or tertiary structure information to align two or more sequences), or hybrid methods combining sequence, structural, and phylogenetic information to identify and optimally align candidate protein sequences.

The NCBI Basic Local Alignment Search Tool (BLAST) (Altschul et al., J. Mol. Biol. (1990) 215:403) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Thus, a nucleic acid sequence that is substantially identical, or substantially similar to SEQ ID NO: 4 is encompassed within the present disclosure. A sequence is substantially identical to SEQ ID NO: 4 if the sequence is identical, on a nucleotide by nucleotide basis, with at least a subsequence of the reference sequence (e.g., SEQ ID NO: 4). Such nucleic acids can include, e.g., insertions, deletions, and substitutions relative to SEQ ID NO: 4. For example, such nucleic acids can be at least about 70%, 80%, 90%, 95%, 96%, 97%, 98% or even 99% identical to a reference nucleic acid, or encode a polypeptide at least about 70%, 80%, 90%, 95%, 96%, 97%, 98% or even 99% identical to the reference polypeptide sequence, e.g., SEQ ID NO: 4.

Additionally, a polynucleotide comprising a nucleic acid encoding an OX40L fusion polypeptide subunit, or a hexameric protein as provided herein, e.g., OX40L IgG4P Fusion Protein, can also include polynucleotide sequences, such as expression regulatory sequences and/or vector sequences that facilitate the expression or replication of the nucleic acids. Similarly, a polynucleotide comprising a nucleic acid encoding an OX40L fusion polypeptide subunit, or a hexameric protein as provided herein, e.g., OX40L IgG4P Fusion Protein, can include additional coding sequences that confer functional attributes on the encoded polypeptide. Such sequences include secretory signal sequences and membrane localization signals.

A polynucleotide comprising a nucleic acid encoding an OX40L fusion polypeptide subunit, or a hexameric protein as provided herein, e.g., OX40L IgG4P Fusion Protein, can be introduced into a vector, such as a eukaryotic expression vector, by conventional techniques. Accordingly, the disclosure provides a vector comprising a polynucleotide as provided herein. An expression vector is designed to permit the transcription of the polynucleotide sequence encoding an OX40L fusion polypeptide subunit, or a hexameric protein as provided herein, e.g., OX40L IgG4P Fusion Protein in cells by providing regulatory sequences that initiate and enhance the transcription of the cDNA and ensure its proper splicing and polyadenylation. Numerous expression vectors are known to those of skill in the art, and are available commercially, or can be assembled from individual components according to conventional molecular biology procedures.

The choice of expression control sequence and expression vector will depend upon the choice of host cell. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

Suitable host cells for expression of an OX40L fusion polypeptide subunit, or a hexameric protein as provided herein, e.g., OX40L IgG4P Fusion Protein include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 2004/009823, each of which is hereby incorporated by reference herein in its entirety.

Also provided is a host cell comprising a polynucleotide or vector as provided herein. Various mammalian or insect cell culture systems can be advantageously employed to express polypeptide subunits or hexameric proteins provided herein. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, BioTechnology 6:47 (1988).

The expression and purification of proteins, such as an OX40L fusion polypeptide subunit, or a hexameric protein as provided herein, e.g., OX40L IgG4P Fusion Protein, can be performed using standard laboratory techniques. Examples of such methods are discussed or referenced herein. After expression, purified proteins have many uses, including for instance functional analyses, antibody production, and diagnostics, as well as the prophylactic and therapeutic uses described below. For example, polypeptide subunits or hexameric proteins provided herein can be used to produce pharmaceutical compositions, including vaccine compositions suitable for prophylactic and/or therapeutic administration.

An OX40L fusion polypeptide subunit, or a hexameric protein as provided herein, e.g., OX40L IgG4P Fusion Protein produced by a transformed host, can be purified according to any suitable method. Such standard methods include chromatography (e.g., ion exchange, affinity and sizing column chromatography), centrifugation, differential solubility, or by any other standard technique for protein purification. Affinity tags such as hexahistidine (SEQ ID NO: 11), maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an influenza B/Yamagata virus-binding molecule. Some or all of the foregoing purification steps, in various combinations, can also be employed to provide a homogeneous recombinant protein.

An OX40L fusion polypeptide subunit, or a hexameric protein as provided herein, e.g., OX40L IgG4P Fusion Protein produced in bacterial culture, can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Pharmaceutical Compositions and Administration Methods

Methods of preparing and administering a hexameric protein as provided herein, e.g., OX40L IgG4P Fusion Protein as provided herein, to a subject in need thereof, e.g., to enhance an immune response in a cancer patient, e.g., to inhibit or reduce tumor growth, are well known to or can be readily determined by those skilled in the art. The route of administration of a hexameric protein as provided herein, e.g., OX40L IgG4P Fusion Protein can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as suitable forms, another example of a form for administration would be a solution for injection, in particular for intravenous or intraarterial injection or drip. Usually, a suitable pharmaceutical composition can comprise, without limitation, a buffer (e.g. acetate, phosphate or citrate buffer), a surfactant (e.g. polysorbate), a stabilizer agent (e.g. human albumin), etc. In other methods compatible with the teachings herein, a hexameric protein as provided herein, e.g., OX40L IgG4P Fusion Protein as provided herein can be delivered directly to the site of the adverse cellular population thereby increasing the exposure of the diseased tissue to the therapeutic agent.

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of a hexameric protein as provided herein, e.g., OX40L IgG4P Fusion Protein that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

By "therapeutically effective dose or amount" or "effective amount" is intended an amount of a hexameric protein as provided herein, e.g., OX40L IgG4P Fusion Protein, that when administered brings about a positive therapeutic response with respect to treatment of a patient with a disease or condition to be treated.

Kits

This disclosure further provides kits that comprise a hexameric protein as provided herein, e.g., OX40L IgG4P Fusion Protein described herein and that can be used to perform the methods described herein. In certain embodiments, a kit comprises at least one purified a hexameric protein as provided herein, e.g., OX40L IgG4P Fusion Protein, in one or more containers. One skilled in the art will readily recognize that the disclosed hexameric protein as provided herein, e.g., OX40L IgG4P Fusion Protein, can be readily incorporated into one of the established kit formats that are well known in the art.

Immunoassays

A hexameric protein as provided herein, e.g., OX40L IgG4P Fusion Protein can be assayed for specific and/or selective binding by any method known in the art. The immunoassays that can be used include but are not limited to competitive and non-competitive assay systems using techniques such as Western blots, radioimmunoassays, ELISA (enzyme linked immunosorbent assay), fluorescent focus assay (FFA), microneutralization assay, hemagglutination inhibition assay (HAI), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety). FFA, microneutralization assay, and HAI will be discussed in details in the Examples below.

Methods and reagents suitable for determination of binding characteristics of a hexameric protein as provided herein are known in the art and/or are commercially available. Equipment and software designed for such kinetic analyses are commercially available (e.g., BTAcore®, BTAevaluation® software, GE Healthcare; KINEXA® Software, Sapidyne Instruments).

Methods of Immune Enhancement and Treatment

The enhancement of an antigen-specific immune response in a subject (e.g., a mammalian subject, such as a human subject) by engaging OX40 on activated T cells, e.g., activated CD4$^+$ T-cells during or after antigen activation can be accomplished using a wide variety of methods. The method of choice will primarily depend upon the type of antigen against which it is desired to enhance the immune response, and various methods available are discussed below. Whatever method is selected, a hexameric protein as provided herein, e.g., OX40L IgG4P Fusion Protein, can be administered to a subject, e.g., a human patient such that it is presented to T-cells of the subject during or shortly after priming of the T-cells by antigen. Exemplary methods of activating an immune response in a subject, e.g., a human subject using a hexameric protein as provided herein, e.g., OX40L IgG4P Fusion Protein, are presented in PCT Publication No. WO 2006/121810, which is incorporated by reference herein in its entirety.

In certain aspects, the disclosure provides a method to promote survival or proliferation of activated T cells, e.g., activated CD4$^+$ T cells, comprising contacting the activated T cells, e.g., activated CD4$^+$ T cells, with a hexameric protein as provided herein, e.g., OX40L IgG4P Fusion Protein, under conditions where the hexameric protein can specifically bind to OX40 on the surface of the T cells, e.g., activated CD4$^+$ T cells. In certain aspects the contacting is in vitro. In certain aspects the contacting is in vivo, e.g. via administration of an effective dose of the hexameric protein to a subject in need of treatment. In certain aspects the contacting can occur at the same time as T cell activation, e.g., antigen activation, in certain aspects the contacting can occur after T cell activation.

In further aspects, the disclosure provides a method of inducing cytokine release from activated T cells, e.g., activated CD4$^+$ T cells, comprising contacting the activated T cells, e.g., activated CD4$^+$ T cells, with a hexameric protein as provided herein, e.g., OX40L IgG4P Fusion Protein, wherein the hexameric protein can specifically bind to OX40 on the surface of the activated T cells, e.g., activated CD4$^+$ T cells. In certain aspects the contacting is in vitro. In certain aspects the contacting is in vivo, e.g. via administration of an effective dose of the hexameric protein to a subject in need of treatment. In certain aspects the contacting can occur at the same time as T cell activation, e.g., antigen activation, in certain aspects the contacting can occur after T cell activation. In certain aspects the cytokine can be IFNγ, TNFα, IL-5, IL-10, IL-2, IL-4, IL-13, IL-8, IL-12 p70, IL-1β, or any combination thereof. In certain aspects the cytokine is IFNγ, TNFα, IL-5, IL-10, or any combination thereof.

In certain aspects, the activated T cells, e.g., activated CD4$^+$ T cells are human CD4$^+$ T cells, cynomolgus monkey CD4$^+$ T cells, rhesus monkey CD4$^+$ T cells, or a combination thereof.

The disclosure further provides a method of promoting T cell activation, comprising contacting T cells with a hexameric protein as provided herein, e.g., OX40L IgG4P Fusion Protein, wherein the hexameric protein can specifically bind to OX40 on the surface of the T cells. In certain aspects the contacting occurs in the presence of antigen, e.g., a tumor antigen. In certain aspects the method further comprising cross-linking of the hexameric protein through interaction of the IgG4-Fc domain with a cell expressing FcγR, e.g., a B cell, monocyte, macrophage, myeloid or plasmacytoid dendritic cell, follicular dendritic cell, Langerhans cell, endothelial cell, NK cell, activated T cell, neutrophil, eosinophil, platelet, mast cell, a CD45$^+$ cell from a primary human tumor or tumor-draining or non-draining lymph node, a CD45+ cell from other secondary or tertiary lymphoid structures, or a combination thereof. In certain aspects, the T cell activation can be measured through stimulation of the NFκB signal transduction pathway. In certain aspects the contacting is in vitro. In certain aspects the contacting is in vivo, e.g. via administration of an effective dose of the hexameric protein to a subject in need of treatment.

The disclosure further provides a method of inducing expression of ICOS or Programmed cell death protein 1 (PD-1) on T-cells, comprising contacting T-cells with a hexameric protein as provided herein, e.g., OX40L IgG4P Fusion Protein, wherein the hexameric protein can specifically bind to OX40 on the surface of the T cells.

The disclosure further provides a method of treating cancer in a subject, comprising administering to a subject in need of treatment an effective amount of a hexameric protein as provided herein, e.g., OX40L IgG4P Fusion Protein, or a composition or formulation comprising the hexameric protein. In certain aspects, the cancer is a solid tumor. According to this method, administration of the hexameric protein or composition can inhibit tumor growth; can promote tumor reduction, or both. In certain aspects, the tumor growth inhibition is achieved in the presence of T-cells.

The terms "cancer", "tumor", "cancerous", and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer including, but not limited to, squamous cell cancers, and cancers of mucinous origins, such as, mucinous ovarian cancer, cholangiocarcinoma (liver) and renal papillary carcinoma.

Some embodiments are directed to a method of preventing or treating a cancer in a subject in need thereof, comprising administering to the subject an effective amount of a hexameric protein as provided herein, e.g., OX40L IgG4P Fusion Protein, a composition or formulation comprising the hexameric protein, or a polynucleotide, a vector, or a host cell as described herein.

Effective doses of compositions for treatment of cancer vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

The compositions of the disclosure can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The disclosure further provides a method of enhancing an immune response in a subject comprising administering to a subject in need thereof a therapeutically effective amount of a hexameric protein as provided herein, e.g., OX40L IgG4P Fusion Protein, or a composition or formulation comprising the hexameric protein.

The subject to be treated can be any animal, e.g., mammal, in need of treatment, in certain aspects, subject is a human subject.

In its simplest form, a preparation to be administered to a subject is a hexameric protein as provided herein, e.g., OX40L IgG4P Fusion Protein, administered in conventional dosage form, and in some aspects, combined with a pharmaceutical excipient, carrier or diluent as described elsewhere herein.

A hexameric protein as provided herein, e.g., OX40L IgG4P Fusion Protein can be administered by any suitable method as described elsewhere herein, e.g., via IV infusion. In certain aspects, a hexameric protein as provided herein, e.g., OX40L IgG4P Fusion Protein, can be introduced into a tumor, or in the vicinity of a tumor cell.

All types of tumors are potentially amenable to treatment by this approach including, without limitation, carcinoma of the breast, lung, pancreas, ovary, kidney, colon and bladder, as well as melanomas, sarcomas and lymphomas.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

TABLE 1-1

List of Abbreviations and Definitions of Terms

| Abbreviation or Term | Definition |
| --- | --- |
| 1A7 | A mouse IgG1 kappa isotype control antibody |
| A | Alanine |
| A375 | human melanoma cell line |
| ADCC | Antibody-dependent cellular cytotoxicity |
| BSA | Bovine serum albumin |
| ° C. | Degrees Celsius |
| CI | Confidence Interval |
| CDC | Complement-dependent cytotoxicity |
| CR | complete response |
| Cyno | cynomolgus |
| DM-L | Density Media- Lymphocyte |
| EC | Effective concentration |
| ECf | Effective concentration resulting in f % of maximal effect |
| EC20 | Effective concentration resulting in 20% of maximal effect |
| EC50 | Half maximal effective concentration |
| EC90 | Effective concentration resulting in 90% of maximal effect |
| E:T | effector-to-target |
| F | Fraction of maximal |
| F | Phenylalanine |
| FACS | Fluorescence Activated Cell Sorting |
| FBS | Fetal bovine serum |
| Fc | Crystallizable fragment of IgG |
| G | Force of gravity |
| H+L | Heavy plus light chains |

TABLE 1-1-continued

List of Abbreviations and Definitions of Terms

| Abbreviation or Term | Definition |
| --- | --- |
| IgG | Immunoglobulin |
| IL-2 | interleukin 2 |
| IP | intraperitoneal |
| IU | International Units |
| Kd | Equilibrium binding dissociation constant |
| LSM | Lymphocyte separation medium |
| M | molarity |
| mAb | monoclonal antibody |
| OX40L IgG4P Fusion Protein | human OX40 ligand IgG4P fusion protein |
| μg | micrograms |
| MFI | Mean fluorescence intensity |
| min | minutes |
| mL | milliliter |
| mOX40L FP | A mouse OX40 ligand mouse IgG1 fusion protein |
| mOX40L FP (Y182A) | A mouse OX40 ligand mouse IgG1 fusion protein with a point mutation in the OX40L that renders the fusion protein incapable of binding to murine OX40 |
| NA | Not applicable |
| NIP228 | A mouse IgG1 kappa monoclonal antibody against 4-hydroxy-3-iodo-5-nitrophenylacetic acid |
| NK | Natural killer |
| NOD/SCID | non-obese diabetic/severe combined immunodeficient |
| OX40L FP IgG4P Y180A | human OX40 ligand IgG4P fusion protein engineered to have reduced binding to OX40 |
| PBMC | peripheral blood mononuclear cells |
| PBS | Phosphate buffered saline |
| PHA-L | Phytohemaglutinin-Leucoagglutinin |
| PI | Propidium iodide |
| pM | picomolar |
| RBC | Red blood cell |
| RED | receptor binding domain |
| Rh | Recombinant human |
| ROA | route of administration |
| rpm | Revolutions per minute |
| RT | Room temperature |
| SC | subcutaneous |
| SD | Standard Deviation |
| TCR | T cell receptor |
| TGI | tumor growth inhibition |
| TNFR | Tumor necrosis factor receptor |
| TRAF2 | tumor necrosis associated factor 2 |
| Treg | T regulatory |
| V | volume |

Example 1

Engineering of OX40L IgG4P Fc Fusion Protein

OX40L IgG4P Fusion Protein is a genetically engineered human OX40 ligand (OX40L) hexameric fusion protein composed of three distinct domains (FIG. 1): a human IgG4P Fc, the isoleucine zipper of TRAF2, and the receptor binding domain of human OX40L. The N-terminal Fc consists of the hinge region (HC) and the gamma heavy chain constant domains 2 and 3 (CH2, CH3) of human immunoglobulin G4 (IgG4). The core hinge region contains a serine to proline mutation at position 228 (according to EU numbering) which confers complete inter-heavy chain disulfide bond formation. The IgG4P Fc domain is fused directly to an isoleucine zipper trimerization domain derived from amino acid residues 310-349 of human tumor necrosis factor 2 (TRAF2). Fused to the c-terminus of the TRAF2 domain are amino acid residues 51-183 of the extracellular receptor binding domain (RBD) of human OX40L (gene name TNFSF4). The TRAF2 domain stabilizes the homotrimeric structure of OX40L RBDs to enable OX40 binding and activation, while the IgG4P Fc domain confers serum stability, dimerization of OX40L trimers, and facilitates Fcγ receptor clustering of the hexameric fusion protein.

OX40L IgG4P Fusion Protein was genetically engineered by fusing two separate DNA fragments together and then cloning the fused DNA into a plasmid vector, thereby generating a single gene encoding the complete fusion protein termed huIgG4PFcTF2OX40L. An in-house plasmid containing the S228P IgG4P mutation previously introduced into the IgG4 DNA sequence by site-directed mutagenesis was used as a template in polymerase chain reaction (PCR) to generate the IgG4P Fc DNA fragment. A separate in-house plasmid containing a DNA sequence encoding a fusion of the TRAF2 and OX40L RBD was used as a PCR template to generate the second DNA fragment. The latter fragment was recombined with the IgG4P Fc fragment by overlap extension PCR resulting in a single DNA fragment encoding the full-length fusion protein. The oligonucleotide primers used in the PCR were designed to introduce a 5' BssHII restriction site and a 3' NheI restriction site to digest, ligate and clone the full-length fragment into an in-house pOE plasmid expression vector. The nucleotide sequence of the insert comprises the following nucleotide sequence (SEQ ID NO: 3), and the expression product from this construct, also referred to herein as huIgGFcPTF2OX40L comprises the following amino acid sequence (SEQ ID NO: 4):

```
SEQ ID NO: 3: DNA Sequence of huIgG4FcPTF2OX40L
(5' to 3' Open Reading Frame)
GAGAGCAAGTACGGCCCTCCCTGCCCCCCTTGCCCTGCCCCCGAGTTCCT

GGGCGGACCTAGCGTGTTCCTGTTCCCCCCCAAGCCCAAGGACACCCTGA

TGATCAGCAGAACCCCCGAGGTGACCTGCGTGGTGGTGGACGTGTCCCAG

GAGGACCCCGAGGTCCAGTTTAATTGGTACGTGGACGGCGTGGAAGTGCA

TAACGCCAAGACCAAGCCCAGAGAGGAGCAGTTCAACAGCACCTACAGAG

TGGTGTCCGTGCTGACCGTGCTGCACCAGGACTGGCTGAACGGCAAGGAA

TACAAGTGCAAGGTCTCCAACAAGGGCCTGCCTAGCAGCATCGAGAAGAC

CATCAGCAAGGCCAAGGGCCAGCCACGGGAGCCCCAGGTCTACACCCTGC

CACCTAGCCAAGAGGAGATGACCAAGAACCAGGTGTCCCTGACCTGTCTG

GTGAAAGGCTTCTATCCCAGCGATATCGCCGTGGAGTGGGAGAGCAACGG

CCAGCCCGAGAACAACTACAAGACCACCCCCCCTGTGCTGGACAGCGACG

GCAGCTTCTTCCTGTACTCCAGACTGACCGTGGACAAGTCCAGATGGCAG

GAGGGCAACGTCTTCAGCTGCTCCGTGATGCACGAGGCCCTGCACAACCA

CTACACCCAGAAGTCCCTGAGCCTGAGCCTGGGCAAGGACCAGGATAAGA

TCGAGGCTCTGTCCTCCAAGGTGCAGCAGCTGGAACGGTCCATCGGCCTG

AAGGACCTGGCCATGGCTGACCTGGAACAGAAAGTGCTGGAAATGGAAGC

CTCCACACAGGTGTCACACAGATACCCCCGGATCCAGTCCATTAAGGTGC

AGTTCACCGAGTACAAGAAAGAGAAGGGCTTTATCCTGACCTCCCAGAAA

GAGGACGAGATCATGAAGGTGCAGAACAACTCCGTGATCATCAACTGCGA

CGGGTTCTACCTGATCTCCCTGAAGGGCTACTTCAGCCAGGAAGTGAACA

TCTCCCTGCACTACCAGAAGGACGAGGAACCCCTGTTCCAGCTGAAGAAA

GTGCGGAGCGTGAACTCCCTGATGGTGGCCTCTCTGACCTACAAGGACAA

GGTGTACCTGAACGTGACCACCGACAACACCTCCCTGGACGACTTCCACG
```

TGAACGGCGGCGAGCTGATCCTGATCCACCAGAACCCTGGCGAGTTCTGC

GTGCTG

```
SEQ ID NO: 4: Amino Acid Sequence of
huIgG4FcPTF2OX40L (N to C terminus)
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGKDQDKIEALSSKVQQLERSIGL

KDLAMADLEQKVLEMEASTQVSHRYPRIQSIKVQFTEYKKEKGFILTSQK

EDEIMKVQNNSVIINCDGFYLISLKGYFSQEVNISLHYQKDEEPLFQLKK

VRSVNSLMVASLTYKDKVYLNVTTDNTSLDDFHVNGGELILIHQNPGEFC

VL
```

The IgG4P-Fc domain is shown in regular font with the S228P mutation underlined, the TRAF2 trimerization domain is underlined, and the RBD of OX40L is depicted in BOLD.

In addition to this construct, a variant (F180A) was also produced that encodes a phenylalanine (F) to alanine (A) mutation at the amino acid corresponding to position 180 in OX40L. This mutation ablates OX40 receptor binding activity of the OX40L protein, thus the resulting molecule can serve as an experimental control to validate the specific activity of the fusion protein. This variant was generated by site-directed mutagenesis using a primer encoding alanine at position 180 and the plasmid encoding the fusion protein as template. The nucleotide sequence of the insert comprises the following nucleotide sequence (SEQ ID NO: 5), and the expression product from this construct, also referred to herein as huIgGFcPTF2OX40L F180A comprises the following amino acid sequence (SEQ ID NO: 6):

```
DNA Sequence of huIgG4FcPTF2OX40L F180A
(5' to 3' Open Reading Frame)
GAGAGCAAGTACGGCCCTCCCTGCCCCCCTTGCCCTGCCCCCGAGTTCCT

GGGCGGACCTAGCGTGTTCCTGTTCCCCCCCAAGCCCAAGGACACCCTGA

TGATCAGCAGAACCCCCGAGGTGACCTGCGTGGTGGTGGACGTGTCCCAG

GAGGACCCCGAGGTCCAGTTTAATTGGTACGTGGACGGCGTGGAAGTGCA

TAACGCCAAGACCAAGCCCAGAGAGGAGCAGTTCAACAGCACCTACAGAG

TGGTGTCCGTGCTGACCGTGCTGCACCAGGACTGGCTGAACGGCAAGGAA

TACAAGTGCAAGGTCTCCAACAAGGGCCTGCCTAGCAGCATCGAGAAGAC

CATCAGCAAGGCCAAGGGCCAGCCACGGGAGCCCCAGGTCTACACCCTGC

CACCTAGCCAAGAGGAGATGACCAAGAACCAGGTGTCCCTGACCTGTCTG

GTGAAAGGCTTCTATCCCAGCGATATCGCCGTGGAGTGGGAGAGCAACGG

CCAGCCCGAGAACAACTACAAGACCACCCCCCCTGTGCTGGACAGCGACG

GCAGCTTCTTCCTGTACTCCAGACTGACCGTGGACAAGTCCAGATGGCAG

GAGGGCAACGTCTTCAGCTGCTCCGTGATGCACGAGGCCCTGCACAACCA

CTACACCCAGAAGTCCCTGAGCCTGAGCCTGGGCAAGGACCAGGATAAGA

TCGAGGCTCTGTCCTCCAAGGTGCAGCAGCTGGAACGGTCCATCGGCCTG
```

AAGGACCTGGCCATGGCTGACCTGGAACAGAAAGTGCTGGAAATGGAAGC

CTCCACACAGGTGTCACACAGATACCCCCGGATCCAGTCCATTAAGGTGC

AGTTCACCGAGTACAAGAAAGAGAAGGGCTTTATCCTGACCTCCCAGAAA

GAGGACGAGATCATGAAGGTGCAGAACAACTCCGTGATCATCAACTGCGA

CGGGTTCTACCTGATCTCCCTGAAGGGCTACTTCAGCCAGGAAGTGAACA

TCTCCCTGCACTACCAGAAGGACGAGGAACCCCTGTTCCAGCTGAAGAAA

GTGCGGAGCGTGAACTCCCTGATGGTGGCCTCTCTGACCTACAAGGACAA

GGTGTACCTGAACGTGACCACCGACAACACCTCCCTGGACGACTTCCACG

TGAACGGCGGCGAGCTGATCCTGATCCACCAGAACCCTGGCGAGGCCTGC

GTGCTG

Amino Acid Sequence of huIgG4PFcTF2OX40L F180A
(N to C terminus)
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK<u>DQDKIEALSSKVQQLERSIGL</u>

<u>KDLAMADLEQKVLEMEAST</u>QVSHRYPRIQSIKVQFTEYKKEKGFILTSQK

EDEIMKVQNNSVIINCDGFYLISLKGYFSQEVNISLHYQKDEEPLFQLKK

VRSVNSLMVASLTYKDKVYLNVTTDNTSLDDFHVNGGELILIHQNPGEA<u>C</u>

VL

The IgG4P-Fc domain is shown in regular font with the S228P mutation underlined, the TRAF2 trimerization domain is <u>underlined</u>, the RBD of OX40L is depicted in BOLD, and the F180A mutation is double-underlined.

The huIgG4PFcTF2OX40L and huIgG4PFcTF2OX40L F180A constructs are depicted graphically in FIG. 2.

A third variant, huIgG1FcTF2OX40L, was also constructed, which replaced the IgG4P Fc domain with a human IgG1 Fc domain. Rather than utilizing overlap extension PCR, this construct was designed in silico and prepared by gene synthesis (GeneArt®, Life Technologies). As previously described, the synthesized gene fragment was used as PCR template to introduce BssHII and NheI restriction sites for digestion and ligation into the pOE plasmid expression vector. The nucleotide sequence of the insert comprises the following nucleotide sequence (SEQ ID NO: 7), and the expression product from this construct, also referred to herein as huIgGFcPTF2OX40L F180A comprises the following amino acid sequence (SEQ ID NO: 8):

SEQ ID NO: 7: DNA Sequence of huIgG1TF2OX40L
(5' to 3' Open Reading Frame)
GATAAGACCCACACCTGTCCCCCTTGTCCTGCCCCTGAACTGCTGGGCGG

ACCTTCCGTGTTCCTGTTCCCCCCAAAGCCCAAGGACACCCTGATGATCT

CCCGGACCCCCGAAGTGACCTGCGTGGTGGTGGATGTGTCCCACGAGGAC

CCTGAAGTGAAGTTCAATTGGTACGTGGACGGCGTGGAAGTGCACAACGC

CAAGACCAAGCCCAGAGAGGAACAGTACAACTCCACCTACCGGGTGGTGT

CCGTGCTGACCGTGCTGCACCAGGATTGGCTGAACGGCAAAGAGTACAAG

TGCAAGGTGTCCAACAAGGCCCTGCCTGCCCCCATCGAAAAGACCATCTC

CAAGGCCAAGGGCCAGCCCCGGGAACCCCAGGTGTACACACTGCCCCCTA

GCCGGGAAGAGATGACCAAGAACCAGGTGTCCCTGACCTGTCTCGTGAAG

GGCTTCTACCCCTCCGATATCGCCGTGGAATGGGAGTCCAACGGCCAGCC

TGAGAACAACTACAAGACCACCCCCCCTGTGCTGGACTCCGACGGCTCAT

TCTTCCTGTACTCCAAGCTGACAGTGGACAAGTCCCGGTGGCAGCAGGGC

AACGTGTTCTCCTGCTCCGTGATGCACGAGGCCCTGCACAACCACTACAC

CCAGAAGTCCCTGTCCCTGAGCCCCGGCAAGGACCAGGATAAGATCGAGG

CTCTGTCCTCCAAGGTGCAGCAGCTGGAACGGTCCATCGGCCTGAAGGAC

CTGGCCATGGCTGACCTGGAACAGAAAGTGCTGGAAATGGAAGCCTCCAC

ACAGGTGTCACACAGATACCCCCGGATCCAGTCCATTAAGGTGCAGTTCA

CCGAGTACAAGAAAGAGAAGGGCTTTATCCTGACCTCCCAGAAAGAGGAC

GAGATCATGAAGGTGCAGAACAACTCCGTGATCATCAACTGCGACGGGTT

CTACCTGATCTCCCTGAAGGGCTACTTCAGCCAGGAAGTGAACATCTCCC

TGCACTACCAGAAGGACGAGGAACCCCTGTTCCAGCTGAAGAAAGTGCGG

AGCGTGAACTCCCTGATGGTGGCCTCTCTGACCTACAAGGACAAGGTGTA

CCTGAACGTGACCACCGACAACACCTCCCTGGACGACTTCCACGTGAACG

GCGGCGAGCTGATCCTGATCCACCAGAACCCTGGCGAGTTCTGCGTGCTG

SEQ ID NO: 8: Amino Acid Sequence of
huIgG1FcTF2OX40L (N to C terminus)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGK<u>DQDKIEALSSKVQQLERSIGLKD</u>

<u>LAMADLEQKVLEMEAST</u>QVSHRYPRIQSIKVQFTEYKKEKGFILTSQKED

EIMKVQNNSVIINCDGFYLISLKGYFSQEVNISLHYQKDEEPLFQLKKVR

SVNSLMVASLTYKDKVYLNVTTDNTSLDDFHVNGGELILIHQNPGEFCVL

The IgG1-Fc domain is shown in regular font, the TRAF2 trimerization domain is <u>underlined</u>, and the RBD of OX40L is depicted in BOLD.

The generated pOE plasmids encoding for the fusion proteins were transfected into HEK293 cells for transient expression, then the soluble fusion proteins was purified from the culture media by Protein A chromatography and gel filtration. The purified fusion proteins underwent biochemical characterization using a homogenous time-resolved fluorescence (HTRF) epitope competition assay (Cisbio, catalog #62C16PAE). The HTRF competition assay was performed to assess the binding activity of the huIgG4PFcTF2OX40L to the V158 high affinity variant of CD16a (FcγRIIIa) which mediates antibody-dependent cellular cytotoxicity (ADCC). In this assay, FcγRIIIa and γ-chain are co-expressed in HEK293 cells and labeled with SNAP-terbium donor dye. Preparations of huIgG4PFcTF2OX40L protein at concentrations between 0.1-1 μM are added to the labeled cells, followed by addition of acceptor dye-labeled human IgG (IgG-d2). IgG-d2 bound to labeled FcγRIIIa and triggered a measurable FRET signal. Competition of IgG-d2 binding by huIgG4PFcTF2OX40L inhibited FRET, and this negative signal is inversely proportional to the binding affinity of the fusion protein for FcγRIIIa. HuIgG4PFcTF2OX40L bound to FcγRIIIa, with a half maximal response (EC50) of 500 nM. In comparison, human IgG1 monoclonal antibody bound with an EC50 of 220 nM, indicating that the fusion protein has ~2.3 fold decreased affinity for FcγRIIIa relative to a typical IgG1 antibody. The huIgG1FcTF2OX40L variant was also tested in the HTRF assay and it bound FcγRIIIa with an EC50 of 4 nM, or ~55 fold increased affinity relative to the IgG1 antibody.

Example 2

Binding Affinity and Receptor Occupancy of OX40L IgG4P Fusion Protein to Native OX40 Expressed on the Surface of Activated Human, Non-Human Primate, Rat and Mouse T Cells In this example, cell-based equilibrium binding assays were performed to measure the apparent affinity of binding of OX40L IgG4P Fusion Protein to OX40 expressed on the cell surface of human, non-human primate, rat and mouse T cells. Additionally, the equilibrium binding assays were conducted to determine what concentrations of OX40L IgG4P Fusion Protein achieved 20%, 50%, or 90% human OX40 receptor occupancy ($EC_{20}$, $EC_{50}$, and $EC_{90}$).

Binding of OX40L IgG4P Fusion Protein to Primary Activated Human CD4$^+$ T Cells and OX40-Expressing Jurkat T Cells The equilibrium binding constant ($K_d$) for OX40L IgG4P Fusion Protein binding to human OX40 and the concentrations to bind 20%, 50%, or 90% of human OX40 receptor ($EC_{20}$, $EC_{50}$, and $EC_{90}$) at equilibrium were calculated from binding curves of OX40L IgG4P Fusion Protein to OX40-expressing activated primary human CD4$^+$ T cells or human OX40-expressing Jurkat T cells.

For binding to activated primary activated human CD4$^+$ T cells, CD4$^+$ cells were first isolated from sodium heparin anti-coagulated whole blood obtained from healthy donors through the MedImmune Blood Donor Program according to the following protocol:

1. 1 mL of Stem Cell Technologies RosetteSep CD4$^+$ T cell isolation kit antibody mix was added per 20 mL of whole blood, mixed, and incubated for 20 minutes (min) at room temperature (RT).
2. Blood was diluted 1:1 with sterile room temperature FACS buffer (2% heat inactivated newborn calf serum in PBS, pH 7.2) and layered onto DM-L media followed by centrifugation at 380 g (1200 rpm) in a table-top centrifuge for 20 min with the break off.
3. After centrifugation, the buffy coat containing human CD4$^+$ T cells was removed with a 10 mL pipette and the cells washed once with RT FACS buffer and once with RT complete RPMI media.
4. Cells were counted on a ViCell counter to determine cell number and viability and CD4$^+$ T cells were suspended in complete RPMI media at a concentration of $1.0 \times 10^6$ per ml Primary activated human CD4$^+$ T cells ($1.0 \times 10^6$ per mL in complete RPMI media) were cultured in a humidified tissue culture incubator at 37° C. and 5% $CO_2$ for 48 hours in the presence of 2 μg/mL PHA-L and 20 IU/mL rhIL-2 to activate T cells and up-regulate OX40. These cells were subsequently used in OX40L IgG4P Fusion Protein binding experiments. All donors in the tables and figures below represent separate individuals; that is, CD4$^+$ T cells were not isolated from the same donor for repeat binding experiments.

Human OX40-expressing Jurkat NFκB-luciferase clone 64 cells were cultured in complete RPMI prior to binding experiments, but without activation.

Cells for binding experiments were subsequently collected by centrifugation (380 g for 5 min at RT), suspended in FACS buffer and counted on a Beckman Coulter ViCell counter to determine cell viability. Cells determined to be >95% viable were subsequently used for binding assays after dilution to $1.0 \times 10^6$ cells per mL in FACS buffer. Then, 100 μL of viable cells (100,000) were added to each well of a non-TC treated 96-well round-bottom plate for binding assays.

To bind OX40L IgG4P Fusion Protein to cells, the drug was diluted to 1 μg/mL in 4° C. FACS buffer and diluted 3-fold over a 15 point dilution series. After dilution, cells added to 96 well plates were spun down at 380 g to pellet cells, and FACS buffer removed. 100 μL of FACS buffer containing OX40L IgG4P Fusion Protein was then added to cells and incubated for 1 hour at 4° C. Following OX40L IgG4P Fusion Protein incubation, cells were washed three times with 4° C. FACS buffer using 200 μL per wash. Cells were then incubated with 100 μL of FACS buffer containing 25 μg/mL AlexaFluor® 647 labeled goat anti-human secondary antibody and 1 μg/mL propidium iodide (PI) for 30 minutes at 4° C. in the dark. Following secondary antibody incubation, cells were washed two times with 4° C. FACS buffer (200 μL per wash) and then suspended in 100 μL FACS buffer for flow cytometry analysis on a BD LSRII flow cytometer. For compensation, wells containing OX40-expressing cells bound to 10 μg/mL antibody (no PI), cells bound to secondary AlexaFluor® 647 labeled Ab reagent only or cells permeabilized with 0.1% saponin and treated with 1 μg/mL PI were prepared for single-stain compensation controls. For background subtraction, cells containing secondary antibody in the absence of primary antibody was also prepared as described above. F180A mutant OX40L fusion protein IgG4P control was used at the same concentrations as OX40L IgG4P Fusion Protein in early experiments to demonstrate that OX40L IgG4P Fusion Protein binding was mediated specifically by OX40L binding to OX40 on activated T cells. This mutated control protein represents OX40L IgG4P Fusion Protein with a single amino acid mutation at position 180 (F to A amino acid change) that prevents OX40L binding to OX40 but does not affect the overall structure of OX40L IgG4P Fusion Protein; it does not bind to native OX40 and thus demonstrates that receptor occupancy on activated T cells is mediated specifically by OX40L:OX40 interactions.

For analysis of OX40L IgG4P Fusion Protein and control protein binding to cells, Flow Jo cytometry analysis software (TreeStar) was used. After fluorescence compensation using compensation controls to define the compensation matrix, live (PI negative) cells were gated and the mean fluorescence intensity (MFI) of secondary antibody determined. MFI of OX40L IgG4P Fusion Protein binding was plotted versus protein concentration (M) to determine binding curves, and the apparent equilibrium dissociation binding constant ($K_d$) and concentrations representing receptor occupancy of 20, 50 and 90% ($EC_{20}$, $EC_{50}$, and $EC_{90}$ respectively) were determined in GraphPad prism using a single site (hyperbola) non-linear regression equations and $EC_f$ calculations using sigmoidal dose-response curves (variable slope), respectively. P-values, if any, determined from 2-tailed Student's T tests comparing apparent Kd and $EC_{20}$, $EC_{50}$, and $EC_{90}$ values derived using primary human CD4 T cells and derived using OX40-expressing Jurkat cells are presented in the summary tables.

OX40L IgG4P Fusion Protein bound to activated human CD4$^+$ T cells with a mean $K_d$ of 3.6±4.3 pM and $EC_{20}$, $EC_{50}$, and $EC_{90}$ receptor occupancy values of 1.8±1.1, 6.6±2.8, and 53±17 pM, respectively (Table 2-1 and FIG. 3A).

OX40L IgG4P Fusion Protein bound to OX40-expressing Jurkat T cells with a mean $K_d$ of 12±12 pM and $EC_{20}$, $EC_{50}$, and $EC_{90}$ receptor occupancy values of 7.2±8.8, 16±16, and 57±46 pM, respectively (Table 2-2 and FIG. 3B). No statistical differences in binding affinity or receptor occupancy values were calculated between OX40-expressing activated primary activated human CD4$^+$ T cells and OX40-expressing Jurkat cells as shown in Table 2-3

TABLE 2-1

Apparent Affinity ($K_d$) and Receptor Occupancy Values ($EC_{20}$, $EC_{50}$, $EC_{90}$) for Binding of OX40L IgG4P Fusion Protein to OX40-expressing Activated Primary activated Human CD4$^+$ T Cells

| Binding Protein | N donors | $K_d$ ± SD (pM) | $EC_{20}$ ± SD (pM) | $EC_{50}$ ± SD (pM) | $EC_{90}$ ± SD (pM) |
|---|---|---|---|---|---|
| OX40L IgG4P Fusion Protein | 6 | 3.6 ± 4.3 | 1.8 ± 1.1 | 6.6 ± 2.8 | 53 ± 17 |
| F180A OX40L fusion protein human IgG4P | 2 | No binding | No binding | No binding | No binding |

TABLE 2-2

Apparent Affinity ($K_d$) and Receptor Occupancy Values ($EC_{20}$, $EC_{50}$, $EC_{90}$) for Binding of OX40L IgG4P Fusion Protein to human OX40-expressing Jurkat NFkB-luciferase Clone 64 cells

| Binding Protein | N experiments | $K_d$ ± SD (pM) | $EC_{20}$ ± SD (pM) | $EC_{50}$ ± SD (pM) | $EC_{90}$ ± SD (pM) |
|---|---|---|---|---|---|
| OX40L IgG4P Fusion Protein | 3 | 12 ± 12 | 7.2 ± 8.8 | 16 ± 16 | 57 ± 46 |
| F180A OX40L fusion protein human IgG4P | 3 | No binding | No binding | No binding | No binding |

TABLE 2-3

Statistical Comparison of Apparent Affinity and Receptor Occupancy Values between Primary activated Human CD4$^+$ T cells and Human OX40-expressing Jurkat

| | Experimental Parameter measured | | | |
|---|---|---|---|---|
| | Apparent Affinity | Apparent $EC_{20}$ | Apparent $EC_{50}$ | Apparent $EC_{90}$ |
| Statistical P value, significance | p = 0.34, not significant | p = 0.28, not significant | p = 0.43, not significant | p = 0.90, not significant |

OX40L IgG4P Fusion Protein Binding to Mouse CD4$^+$ T Cells

OX40L IgG4P Fusion Protein binding to mouse OX40 was investigated using OX40-expressing activated primary activated mouse CD4$^+$ T cells. Mouse CD4$^+$ T cells were isolated from harvested normal Balb/C mouse spleens according to the following protocol:

1. Spleens were mashed against a 70 μM nylon filter with the back of a sterile 3 mL syringe plunger to release splenocytes and the filter rinsed with 1 mL complete media (RPMI 1640 with 10% fetal bovine serum (FBS), 1% antibiotic/antimycotic solution, and 55 μM beta mercaptoethanol (BME).
2. Splenocytes were centrifuged at 330×g (1200 rpm) for 10 min at RT in a tabletop centrifuge to pellet cells.
3. Supernatant was discarded and pellet was treated with 5 mL of 1×red blood cell (RBC) lysis buffer and incubated at RT for 5 minutes to lyse RBCs. 45 mL of complete media was added to the mix to restore osmolarity at the end of incubation time.
4. Cells were pelleted in a centrifuge at 330×g for 10 min and washed twice in Miltenyi MACS buffer (PBS pH 7.2+0.5% bovine serum albumin (BSA)+2 mM ethylenediamine tetraacetic acid (EDTA)).
5. Supernatant was discarded and the cell pellet was suspended in cold MACS buffer and counted with a ViCell counter to determine cell number and viability.
6. Mouse CD4$^+$ T cell isolation was performed with a Miltenyi process kit according to manufacturer's instructions. Next, the CD4$^+$ positive T cells were suspended at 1.5×10$^6$ per mL in complete media.

Mouse CD4$^+$ T cells (150,000 per well in 100 μL complete media) were cultured in 96-well plates coated with 2 μg/mL hamster anti-mouse CD3 and hamster anti-mouse CD28 antibodies to activate T cells and induce OX40 expression and incubated overnight in a humidified tissue culture incubator at 37° C. and 5% CO$_2$. Activated CD4$^+$ T cells were removed from the incubation plate and 100,000 cells were transferred to each well of a non-tissue culture treated 96-well round-bottom plate for binding assays and cells washed once with FACS buffer (PBS pH 7.2 with 2% FBS). Binding was performed with 1 μg/mL OX40L IgG4P Fusion Protein and rat anti-mouse clone OX86 (positive control) antibodies serially diluted 3-fold in FACS buffer for a 10-point data curve, and 1 μg/mL F180A mutant OX40L fusion protein IgG4P (negative control) was diluted in deep well polypropylene plates 6-fold for a 3 point data curve. 50 μL of FACS buffer containing OX40L IgG4P Fusion Protein or antibodies were added to cells in duplicate and incubated for 45 minutes at 4° C. Following primary activated incubation, cells were washed twice with 200 μL of cold (4° C.) FACS buffer per wash. Cells were then incubated for 30 minutes at 4° C. in the dark with 50 μL of FACS buffer containing 10 μg/mL AlexaFluor®488 labeled goat anti-human secondary or AlexaFluor®488 labeled goat anti-rat secondary antibody and 5 μg/mL propidium iodide (PI). Following secondary antibody incubation, cells were washed twice with 4° C. FACS buffer (200 μL per wash) and suspended in 100 μL FACS buffer for flow cytometry analysis on a BD LSRII flow cytometer. Wells containing OX40-expressing cells (no PI), cells bound to secondary AlexaFluor® 488 labeled antibody reagent only or cells permeabilized with 0.1% saponin and treated with 10 μg/mL PI were prepared for single-stain compensation controls.

Flow Jo cytometry analysis software (TreeStar, Ashland, Oregon) was used to determine OX40L IgG4P Fusion Protein and control protein binding to cells. Using compensation controls to define the compensation matrix, live (PI negative) cells were gated and the mean fluorescence intensity (MFI) of secondary antibody determined. MFI of OX40L IgG4P Fusion Protein binding was plotted versus protein concentration (nM) to determine binding curves, and the apparent equilibrium dissociation binding constant ($K_d$) was determined using GraphPad prism (La Jolla, Calif.) and using a single-site (hyperbola) non-linear regression equation.

Binding assay results for activated mouse CD4⁺ T cells are shown in FIG. 4A.

OX40L IgG4P Fusion Protein does not bind to activated mouse CD4⁺ T cells.

OX40L IgG4P Fusion Protein binding to rat CD4⁺ T cells

OX40L IgG4P Fusion Protein binding to rat OX40 was investigated with OX40-expressing activated primary activated rat CD4⁺ T cells. Rat CD4⁺ cells were isolated from fresh harvested normal Sprague Dawley rat spleens according to the following protocol:

1. Spleens were mashed against a 70 μM nylon filter with the back of a sterile 3 mL syringe plunger to release splenocytes and the filter rinsed with complete media (RPMI 1640 with 10% FBS, 1% antibiotic/antimycotic solution, and 55 μM BME).
2. Splenocytes were centrifuged at 330×g (1200 rpm) for 10 min at RT in a tabletop centrifuge to pellet cells.
3. Supernatant was discarded and the pellet was treated with 5 mL of 1×RBC lysis buffer and incubated at RT for 5 minutes. 45 mL of complete media was added to the pellet to stop lysis at the end of incubation time.
4. Cells were pelleted in a centrifuge at 330×g for 10 min and washed twice in Miltenyi MACS buffer (PBS pH 7.2+0.5% BSA+2 mM EDTA).
5. Supernatant was discarded and cell pellet was suspended in cold MACS buffer and counted with a ViCell counter to determine cell number and viability.
6. Rat CD4⁺ T cell isolation was performed with an R&D Systems Magcellect kit according to manufacturer's instructions. Next, the CD4⁺ positive T cells were suspended at $1.5 \times 10^6$ per mL in complete media.

Rat CD4⁺ T cells ($1 \times 10^6$ per mL complete media) were cultured in a T75 cell culture flask with 1 μg/mL concanavalin A (Con A) and 500 IU/mL IL-2 to activate T cells and induce OX40 expression and incubated overnight in a humidified tissue culture incubator at 37° C. and 5% CO₂. Activated CD4⁺ T cells were removed from the flask and 100,000 cells were transferred to each well of a non-tissue culture treated 96-well round-bottom plate for binding assays and cells washed once with FACS buffer. Binding was performed with 10 μg/mL OX40L IgG4P Fusion Protein and mouse anti-rat clone OX40 (positive control) antibodies serially diluted 3-fold for a 10 point data curve in FACS buffer and 10 μg/mL F180A mutant OX40L fusion protein IgG4P (negative control) serially diluted 6-fold for a 3 point data curve in deep well polypropylene plates. 100 μL of OX40L IgG4P Fusion Protein, control protein, or antibodies were added to cells in duplicate and incubated for 1 hour at 4° C. Following primary activated incubation, cells were washed twice with 200 μL of cold (4° C.) FACS buffer per wash. Cells were then incubated for 30 minutes at 4° C. in the dark with 100 μL of FACS buffer containing 10 μg/mL AlexaFluor® 488 labeled goat anti-human or AlexaFluor®488 labeled goat anti-mouse secondary antibody and 5 μg/mL propidium iodide (PI). Following secondary antibody incubation, cells were washed twice with 4° C. FACS buffer (200 μL per wash) and resuspended in 100 μL FACS buffer for flow cytometry analysis on a BD LSRII flow cytometer. Wells containing OX40-expressing cells (no PI), cells bound to secondary AlexaFluor® 488 labeled antibody reagent only or cells permeabilized with 0.1% saponin and treated with 10 μg/mL PI were prepared for single-stain compensation controls.

Flow Jo cytometry analysis software (TreeStar, Ashland, Oreg.) was used to determine OX40L IgG4P Fusion Protein and control protein binding to cells. Using compensation controls to define the compensation matrix, live (PI negative) cells were gated and the mean fluorescence intensity (MFI) of secondary antibody determined. MFI of OX40L IgG4P Fusion Protein binding was plotted versus protein concentration (nM) to determine binding curves, and the apparent equilibrium dissociation binding constant ($K_d$) was determined using GraphPad prism (San Diego, Calif.) and using a single-site (hyperbola) non-linear regression equation.

Binding assay results for activated rat CD4⁺ T cells are shown in FIG. 4B. OX40L IgG4P Fusion Protein does not bind to activated rat CD4⁺ T cells.

OX40L IgG4P Fusion Protein binding to cynomolgus monkey CD4⁺ T cells

The equilibrium binding constant ($K_d$) for OX40L IgG4P Fusion Protein binding to cynomolgous monkey (cyno) OX40 was determined using OX40-expressing activated primary activated cyno CD4⁺ T cells. Cyno CD4⁺ T cells were isolated from sodium heparin anti-coagulated whole blood obtained from healthy cyno donors (N=2) from World Wide Primates (Miami, Fla.) according to the following protocol:

1. (Assay 1) 60% Percoll was prepared by combining 52.8 mL Percoll Plus, 1.2 mL of 1M HEPES, 6 mL of 10×PBS pH 7.2 and 40 mL of 1×PBS pH 7.2, then 10 mL of whole blood was layered onto 30 mL of 60% Percoll in a 50 ml conical centrifuge tube. (Assay 2) Lymphocyte separation media (LSM) was diluted to 85% by adding 15 mL of PBS to 85 mL of LSM at RT, then 20 mL of whole blood was layered onto 15 mL of 85% LSM.
2. (Assay 1) Blood was centrifuged at 400×g for 30 min at RT in a tabletop centrifuge without the brake. (Assay 2) Blood was centrifuged at 1100×g for 20 min at RT in a tabletop centrifuge without the brake.
3. Peripheral blood mononuclear cells (PBMC) were collected at the interphase and washed twice with cold (4° C.) Miltenyi MACS buffer at 1200 RPM for 10 minutes.
4. Supernatant was discarded and pellet was treated with 5 mL of 1×RBC lysis buffer and incubated at RT for 5 minutes. 45 mL of complete media (RPMI with 10% FBS and 1% antibiotics/antimycotics) was added to the pellet to stop the lysing process at the end of incubation time.
5. Cells were then pelleted in a centrifuge at 330×g for 10 min and washed twice with 20 mL of cold (4° C.) Miltenyi MACS buffer.
6. Supernatant was discarded and cell pellet was suspended in cold (4° C.) MACS buffer and counted with a ViCell counter to determine cell number and viability.
7. Cyno CD4⁺ T cell isolation was performed with a Miltenyi non-human primate kit according to manufacturer's instructions, then CD4⁺ T cells counted on a ViCell counter and suspended at $1 \times 10^6$ per mL in complete media as described above.

Cyno CD4⁺ T cells ($1 \times 10^6$ per mL in complete media) were cultured in a T75 cell culture flask with 2 μg/mL PHA-L and 20 IU/mL IL-2 to activate T cells and induce OX40 expression and incubated 48 hours in a humidified tissue culture incubator at 37° C. and 5% CO₂. Activated CD4⁺ T cells were removed from the flask and 100,000 cells were transferred to each well of a non-tissue culture treated 96-well round-bottom plate for binding assays and cells washed once with 200 μL FACS buffer. Binding was performed with 1 μg/mL OX40L IgG4P Fusion Protein serially diluted 3-fold in FACS buffer for a 10 point data curve and 1 μg/mL F180A mutant OX40L fusion protein IgG4P (negative control) serially diluted 8-fold in deep well polypropylene plates for a 3 point data curve. 100 μL of FACS buffer containing OX40L IgG4P Fusion Protein or control protein was added to cells in duplicate and incubated for 1 hour at 4° C. Following primary activated incubation, cells were washed twice with 200 µL of cold (4° C.) FACS buffer per wash. Cells were then incubated for 30 minutes at 4° C. in the dark with 100 µL of FACS buffer containing 10 µg/mL AlexaFluor®488 labeled goat anti-human secondary antibody and 5 µg/mL propidium iodide (PI). Following secondary antibody incubation, cells were washed twice with 4° C. FACS buffer (200 µL per wash) and suspended in 100 µL FACS buffer for flow cytometry analysis on a BD LSRII flow cytometer. Wells containing OX40-expressing cells (no PI), cells bound to secondary AlexaFluor® 488 labeled antibody reagent only or cells permeabilized with 0.1% saponin and treated with 10 µg/mL PI were prepared for single-stain compensation controls.

Flow Jo cytometry analysis software (TreeStar, Ashland, Oreg.) was used to determine OX40L IgG4P Fusion Protein and control protein binding to cells. Using compensation controls to define the compensation matrix, live (PI negative) cells were gated and the mean fluorescence intensity (MFI) of secondary antibody determined. MFI of OX40L IgG4P Fusion Protein binding was plotted versus protein concentration (nM) to determine binding curves, and the apparent equilibrium dissociation binding constant ($K_d$) was determined using GraphPad prism (San Diego, Calif.) and using a single site (hyperbola) non-linear regression equation.

Results for binding assays using OX40-expressing activated primary activated cyno CD4+ T cells (N=2) are shown in Table 2-4 and FIG. 4C. Calculation of the equilibrium dissociation constants ($K_d$) demonstrated that OX40L IgG4P Fusion Protein bound to activated cyno CD4+ T cells with a mean $K_d$ of 24.2±31.4 pM. The ratio between cyno $K_d$ and human $K_d$ measurements is seven-fold.

TABLE 2-4

Apparent Affinity ($K_d$) for Binding of OX40L IgG4P Fusion Protein to cynomolgous monkey OX40-expressing Activated Primary activated CD4+ T cells

| Binding Protein | N experiments | $K_d$ ± SD (pM) |
| --- | --- | --- |
| OX40L IgG4P Fusion Protein | 2 | 24.2 ± 31.4 |
| F180A OX40L fusion protein human IgG4P | 2 | No binding |

OX40L IgG4P Fusion Protein Binding to Rhesus Monkey CD4+ T Cells

The equilibrium binding constant ($K_d$) for OX40L IgG4P Fusion Protein binding to rhesus monkey OX40 was determined using OX40-expressing activated primary activated rhesus CD4+ T cells. Rhesus CD4+ T cells were isolated from sodium heparin anti-coagulated whole blood obtained from healthy rhesus donors (N=2) from World Wide Primates (Miami, Fla.) according to the following protocol:
1. Lymphocyte separation media (LSM) was diluted to 95% by adding 5 ml of PBS to 95 mL of LSM at RT.
2. Heparinized rhesus blood was diluted 1:1 with PBS at RT and 20 mL of diluted whole blood was layered onto 15 ml of 95% LSM in a 50 ml conical centrifuge tube.
3. Blood was centrifuged at 400×g for 30 min at RT in a tabletop centrifuge without the brake.
4. Peripheral blood mononuclear cells (PBMC) were collected at the interphase and washed twice with cold Miltenyi MACS buffer at 1200 RPM for 10 minutes.
5. Supernatant was discarded and pellet was treated with 5 mL of 1×RBC lysis buffer and incubated at RT for 5 minutes. 45 mL of complete media (RPMI with 10% FBS and 1% antibiotics/antimycotics) was added to the pellet to stop the lysing process at the end of incubation time.
6. Cells were then pelleted in a centrifuge at 330×g for 10 min and washed twice with 20 mL of cold Miltenyi MACS buffer.
7. Supernatant was discarded and cell pellet was suspended in cold MACS buffer and counted with a ViCell counter to determine cell number and viability.
8. Rhesus CD4+ T cell isolation was performed with a Miltenyi non-human primate kit according to manufacturer's instructions, then CD4+ T cells counted on a ViCell counter and resuspended at 1×10$^6$ per mL in complete media as described above.

Rhesus CD4+ T cells (1×10$^6$ per mL in complete media) were cultured in a T75 cell culture flask with 2 µg/mL PHA-L and 20 IU/mL IL-2 to activate T cells and induce OX40 expression and incubated 48 hours in a humidified tissue culture incubator at 37° C. and 5% $CO_2$. Activated CD4+ T cells were removed from the flask and 100,000 cells were transferred to each well of a non-tissue culture treated 96-well round-bottom plate for binding assays and cells washed once with 200 µL FACS buffer. Binding was performed with 1 µg/mL OX40L IgG4P Fusion Protein serially diluted 3-fold in FACS buffer in deep well polypropylene plates for a 10 point (assay 1) or 12 point data curve (assay 2) and 1 µg/mL F180A mutant OX40L fusion protein IgG4P (negative control) was diluted 6-fold for a 2 data points. 100 µL of FACS buffer containing OX40L IgG4P Fusion Protein or control protein were added to cells in duplicate wells and incubated for 1 hour at 4° C. Following primary activated incubation, cells were washed twice with 200 µL of cold (4° C.) FACS buffer per wash. Cells were then incubated for 30 minutes at 4° C. in the dark with 100 µL of FACS buffer containing 10 µg/mL AlexaFluor®488 labeled goat anti-human or AlexaFluor®488 labeled goat anti-mouse secondary antibody and 5 µg/mL propidium iodide (PI). Following secondary antibody incubation, cells were washed twice with 4° C. FACS buffer (200 µL per wash) and suspended in 100 µL FACS buffer for flow cytometry analysis on a BD LSRII flow cytometer. Wells containing OX40-expressing cells (no PI), cells bound to secondary AlexaFluor® 488 labeled Ab reagent only or cells permeabilized with 0.1% saponin and treated with 10 µg/mL PI were prepared for single-stain compensation controls.

Flow Jo cytometry analysis software (TreeStar, Ashland, Oreg.) was used to determine OX40L IgG4P Fusion Protein and control protein binding to cells. Using compensation controls to define the compensation matrix, live (PI negative) cells were gated and the mean fluorescence intensity (MFI) of secondary antibody determined. MFI of OX40L IgG4P Fusion Protein binding was plotted versus protein concentration (nM) to determine binding curves, and the apparent equilibrium dissociation binding constant ($K_d$) was determined using GraphPad prism (San Diego, Calif.) and using a single site (hyperbola) non-linear regression equation.

Results for binding assays using OX40-expressing activated primary activated rhesus CD4+ T cells (N=2) are shown in Table 2-5 and FIG. 4D. Calculation of the equilibrium dissociation constants ($K_d$) demonstrated that OX40L IgG4P Fusion Protein bound to activated rhesus CD4+ T cells with a mean $K_d$ of 20.65±22.56 pM. The ratio between cyno $K_d$ and human $K_d$ measurements is six-fold.

TABLE 2-5

Apparent Affinity ($K_d$) for Binding of OX40L
IgG4P Fusion Protein to rhesus macaque OX40-expressing
Activated Primary CD4+ T cells

| Binding Protein | N experiments | $K_d$ ± SD (pM) |
|---|---|---|
| OX40L IgG4P Fusion Protein | 2 | 20.65 ± 22.56 |
| F180A OX40L fusion protein human IgG4P | 2 | No binding |

SD = Standard Deviation

Statistical Methods

To determine the apparent dissociation equilibrium binding constants ($K_d$) for OX40L IgG4P Fusion Protein binding to human, mouse, rat, cyno, rhesus monkey OX40, a non-linear regression (curve fit) equation for one site binding (hyperbola) was employed using GraphPad Prism version 5.01 for Windows, GraphPad Software, San Diego Calif. USA, www.graphpad.com.

For the determination of the concentration at which 20%, 50%, and 90% of OX40 receptors were occupied by antibody, the concentration values (M) were first transformed using the equation $X=\log[X]$, and subsequently the EC Anything (ECf) was determined for f=20, f=50 and f=90 from sigmoidal dose-response (variable slope concentration-MFI) binding curves using Graphpad Prism software. ECf is the concentration of agonist that gives a response f percent of the way between Bottom and Top, and in this case represents 20, 50, and 90% receptor occupancy when set to 20, 50, or 90, respectively, and where the Top of the calculated curve represents 100% receptor occupancy.

To determine the statistical significance between apparent $K_d$ values or apparent $EC_{20}$, $EC_{50}$ or $EC_{90}$ values determined from binding assays from primary activated human T cells or OX40 expressing Jurkat, a 2-sided unpaired Student's t test with 95% confidence level and Welch's correction to account for data sets with different standard deviations was utilized in Graphpad Prism software.

Significant p-values, if any, obtained from the data are presented in the summary tables and figures adjacent to the descriptive statistics (i.e. mean and standard deviation).

Materials used in this study are listed in Table 2-6.

TABLE 2-6

Materials

| Item | Source |
|---|---|
| AlexaFluor ® A488 goat anti-human IgG (H + L) | Life Technologies, Carlsbad, CA |
| AlexaFluor ® A488 goat anti-mouse IgG (H + L) | Life Technologies, Carlsbad, CA |
| AlexaFluor ® A488 goat anti-rat IgG (H + L) | Life Technologies, Carlsbad, CA |
| Antibiotic/antimycotic solution, 100X | Life Technologies, Carlsbad, CA |
| Anti-rat CD134 (OX40 clone) antibody | Biolegend, San Jose, CA |
| Anti-rat CD3 antibody, purified NA/LE | BD Biosciences, San Jose, CA |
| Anti-mouse CD 134 (OX86 clone) antibody | MedImmune, Gaithersburg, MD |
| Balb/C mouse | Harlan, Indianapolis, IN |
| Betamercaptoethanol | Life Technologies, Carlsbad, CA |
| Bovine serum albumin (BSA) | Sigma, St Louis, MO |
| Complete RPMI media: RPMI-1640 + 10% FBS | Materials from Life Technologies, Carlsbad, CA |
| Concanavalin A | Sigma, St Louis, MO |
| Deep well plates, polypropylene, 2 mL | VWR, Radnor, PA |
| Ethylenediaminetetraacetic acid (EDTA) | Life Technologies, Carlsbad, CA |
| Heat inactivated fetal bovine serum | Life Technologies, Carlsbad, CA |
| Hamster anti-mouse CD3 antibody, purified NA/LE | BD Biosciences, San Jose, CA |
| Hamster anti-mouse CD28 antibody, purified NA/LE | BD Biosciences, San Jose, CA |
| IL-2, recombinant human | Preprotech, Rocky Hill, NJ |
| LSR II flow cytometer | BD Biosciences, San Jose, CA |
| Lymphocyte separation media (LSM) | MP Biomedicals, Santa Ana, CA |
| Magcellect rat CD4+ T cell isolation kit | R&D Systems, Minneapolis, MN |
| Miltenyi MACS buffer | Miltenyi, San Diego, CA |
| Mouse CD4+ T cell isolation kit | Miltenyi, San Diego, CA |
| Non-human primate CD4+ T cell isolation kit | Miltenyi, San Diego, CA |
| Non-TC treated round-bottom 96 well plates | VWR, Radnor, PA |
| Nylon mesh filter, 70 micron | BD Biosciences, San Jose, CA |
| PBS, phosphate buffered saline, pH 7.2 | Life Technologies, Carlsbad, CA |
| Percoll | Sigma, St. Louis, MO |
| PHA-L | Roche Applied Science, Indianapolis, IN |
| Phosphate Buffer Saline (PBS) pH 7.2 without Calcium and Magnesium | Life Technologies, Carlsbad, CA |
| Propidium iodide (1 mg/mL solution) | Sigma, Saint Louis, MO |
| Red blood cell lysis buffer | Biolegend, San Diego, CA |
| RPMI-1640 | Life Technologies, Carlsbad, CA |
| Sprague Dawley rat | Harlan, Indianapolis, IN |
| ViCell counter | Beckman Coulter, Indianapolis, IN |
| Whole blood, sodium heparin anti-coagulated | MedImmune Blood Donor Program, Gaithersburg, MD |

Conclusions

OX40L IgG4P Fusion Protein bound to OX40 expressed on the cell surface of primary activated CD4+ T cells with an apparent $K_d$ of 3.6 pM for human, 24 pM for cynomolgous monkey and OX40 and 21 pM for rhesus macaque. The resulting ratios of the mean $K_d$ values for OX40L IgG4P Fusion Protein bound to OX40 on the cell surface of cynomolgous monkey compared to human primary activated T cells and rhesus macaque compared to human primary activated T cells was calculated to be 7 and 6, respectively. OX40L IgG4P Fusion Protein did not bind to OX40 expressed on the cell surface of rat or mouse T cells. Additionally, the concentration of OX40L IgG4P Fusion Protein that achieves 20%, 50%, or 90% human OX40 receptor occupancy ($EC_{20}$, $EC_{50}$, and $EC_{90}$) at equilibrium was calculated to be 1.8 pM, 6.6 pM and 53 pM, respectively.

Example 3

Determination of the Binding Specificity of OX40L IgG4P Fusion Protein for OX40 Compared to Related Human Tumor Necrosis Factor Receptor Superfamily Members Expressed on the Surface of Cells In this example, the specificity of OX40L IgG4P Fusion Protein was determined in flow-cytometry-based cell binding assays using human embryonic kidney (HEK293) cells transiently transfected with cDNA constructs directing the expression of TNFR superfamily (TNFRSF) members with high sequence identity to OX40.

Methods

Search for Proteins with Close Sequence Homology to Human OX40

In order to identify human proteins with close amino acid sequence identify to human OX40, a sequence homology search was conducted using the protein sequence of OX40. The UniProt website (http://www.uniprot.org) was used for the search and to determine the percentage of amino acid identity between human OX40 and the identified human proteins (Table 3-1).

TABLE 3-1

Amino acid Sequence identity of twelve TNFRSF members with the highest homology to human OX40.

| TNFRSF member | Common Designation | Amino Acid Sequence Identity with Human OX40 (%) | Uniprot Accession No. |
|---|---|---|---|
| TNFRSF 11A | RANK, CD265 | 32.4 | Q9Y6Q6 |
| TNFRSF 16 | NGF receptor | 30.7 | P08138.1 |
| TNFRSF 6B | DcR3 | 28.9 | O95407 |
| TNFRSF 3 | LTβR, TNFRIII | 28.5 | P36941 |
| TNFRSF 1β | NA | 27.7 | P20333 |
| TNFRSF 21 | DR6 | 27.4 | O75509 |
| TNFRSF 18 | GITR, AITR | 26.7 | Q9Y5U5 |
| TNFRSF 5 | CD40 | 25.1 | P25942 |
| TNFRSF 9 | CD137, 4-1BB | 24.8 | Q07011 |
| TNFRSF 11B | Osteoprotegerin | 23.9 | O00300 |
| TNFRSF 1β iso.2 | NA | 22.0 | P20333-2 |
| TNFRSF 6 | Fas | 19.8 | AAH12479.1 |
| TNFRSF 14 | TR2, HVEM-A | 10.5 | Q92956 |

NA = not applicable

Binding Specificity of OX40L IgG4P Fusion Protein cDNA constructs capable of directing the expression of individual TNFRSF members when transfected into mammalian cells were obtained from Origene Technologies. These cDNA constructs were amplified and purified by the Protein Sciences group at MedImmune in Gaithersburg, Md. for use in transient transfections. For expression of each of the TNFRSF members, HEK293 cells were individually transfected using Lipofectamine 2000 combined with 2.5 μg DNA of an expression vector encoding one of the TNFRSF members; manufacturer's suggested protocol for Lipofectamine 2000 was followed. Forty eight hours post transfection, cells were removed from tissue culture plates by trypsinization and trypsin neutralized by the addition of serum-containing complete media followed by cell pelleting and washes in complete media. Cells were then suspended in cold FACS buffer (PBS+2% FBS) and plated into 96 well non-TC treated plates for binding studies with TNFRSF-specific mAbs and OX40L IgG4P Fusion Protein.

For binding to antibodies, cells were pelleted, FACS buffer removed, and cells suspended in FACS buffer containing 1 μg/mL propidium iodide (PI) and either a fluorochrome-labeled mAb specific for the transfected TNFRSF member at a volume recommended by the manufacturer, or with OX40L IgG4P Fusion Protein at a concentration of 1 μg/ml For binding controls, cells were separately incubated with fluorochrome-labeled isotype control antibodies. Cells were incubated with antibodies for 1 hour at 4° C. in the dark. Thereafter, cells incubated with fluorochrome-labeled monoclonal antibodies were washed 2 times in cold FACS buffer and then events analyzed by flow cytometry using an LSRII flow cytometer. Cells incubated with OX40L IgG4P Fusion Protein were washed three times in ice cold FACS buffer and then suspended in 25 μg/mL of AlexaFluor® 647 goat anti-human IgG (H+L) secondary antibody and incubated for a further 30 minutes at 4° C. in the dark. For binding control, some cells were incubated in the absence of OX40L IgG4P Fusion Protein but in the presence of fluorochrome-labeled secondary antibody alone. Thereafter, cells were washed an additional two times with cold FACS buffer and suspended in cold FACS buffer for analysis on an LSRII flow cytometer.

For flow cytometry analysis, flow cytometry standard (FCS) data was examined using FlowJo software. To analyze mAb binding, cells were first gated for viable (PI negative) cells, and then the MFI plotted versus number of events to generate binding histograms. Also, the geometric mean fluorescence intensity of viable cells was determined for each binding so that the fold MFI over background (isotype control or secondary antibody alone) could be determined.

Materials used in this study are listed in Table 3-2.

TABLE 3-2

Materials

| Item | Source |
|---|---|
| AlexaFluor ®647 goat anti-human IgG (H + L) | Life Technologies, Carlsbad, CA |
| Bovine serum albumin (BSA) | Sigma, Saint Louis, MO |
| CD137 (TNFRSF9) pCMV6-XL5 expression vector | Origene Technologies, Inc., Rockville, MD |

TABLE 3-2-continued

Materials

| Item | Source |
| --- | --- |
| Complete RPMI media: RPMI-1640 + 10% FBS | Materials from Life Technologies, Carlsbad, CA |
| FACS buffer: PBS + 2% heat inactivated newborn calf serum | Materials from Life Technologies, Carlsbad, CA |
| GITR (TNFRSF18) pCMV6-XL5 expression vector | Origene Technologies, Inc., Rockville, MD |
| Heat inactivated newborn calf serum | Life Technologies, Carlsbad, CA |
| HVEM (TNFRSF14) pCMV6-XL4 expression vector | Origene Technologies, Inc., Rockville, MD |
| Lipofectamine 2000 | Life Technologies, Carlsbad, CA |
| LSR II flow cytometer | BD Biosciences, San Jose, CA |
| AF488 anti-mouse IgG1 isotype | Biolegend |
| AF488 anti-human GITR | Ebioscience, San Diego, CA |
| AF647 anti-human NGFR | BD, San Jose, CA |
| APC anti-human CD137 | BD, San Jose, CA |
| APC anti-mouse IgG1 isotype | Biolegend, San Diego, CA |
| LTβR (TNFRSF3) pCMV6-XL4 expression vector | Origene Technologies, Inc., Rockville, MD |
| Newborn calf serum, heat inactivated (FBS) | Life Technologies, Carlsbad, CA |
| NGFR (TNFRSF16) pCMV6-XL5 expression vector | Origene Technologies, Inc., Rockville, MD |
| Non-TC treated round-bottom 96 well plates | VWR, Radnor, PA |
| OX40-expressing Jurkat T cell line, clone 64 | Biopharmaceutical Development Group, Gaithersburg, MD |
| PBS, phosphate buffered saline, pH 7.2 | Life Technologies, Carlsbad, CA |
| PE anti-human HVEM | Ebioscience, San Diego, CA |
| PE anti-human LTβR | R&D systems, Minneapolis, MN |
| PE anti-human TNFRSF 1B | BD, San Jose, CA |
| PE anti-mouse IgG1 isotype | Biolegend |
| PE anti-rat isotype | Ebioscience, San Diego, CA |
| Phosphate Buffered Saline (PBS) pH 7.2 without Calcium and Magnesium | Life Technologies, Carlsbad, CA |
| Propidium iodide (1 mg/mL solution) | Sigma, Saint Louis, MO |
| RPMI-1640 | Life Technologies, Carlsbad, CA |
| TNFRSF1β pCMV6-XL5 expression vector | Origene Technologies, Inc., Rockville, MD |
| ViCell counter | Beckman Coulter, Indianapolis, IN |

The sequence homology BLAST search on OX40 identified 12 human TNFRSF proteins that shared 10% or more amino acid sequence identity with OX40. The proteins and the percentage of sequence identity are listed in Table 3-1.

To confirm the specificity of binding of OX40L IgG4P Fusion Protein for human OX40, binding of OX40L IgG4P Fusion Protein to a Jurkat cell line engineered to express human OX40 or to transiently transfected HEK293 cells that expressed human NGFR, LTβR, TNFR2, GITR, CD137 or HVEM was assessed by flow cytometry. Binding of OX40L IgG4P Fusion Protein to a Jurkat cell line that expressed OX40 as determined by MFI was 17-fold greater than the MFI of the secondary antibody alone (FIG. 5A-B). Cell surface expression of human NGFR, LTβR, TNFR2, GITR, CD137 and HVEM was confirmed using commercially available antibodies specific for each human TNFRSF protein; fold increase in MFI as compared to isotype control antibodies for each TNFRSF protein is shown in Table 12-2. Binding of OX40L IgG4P Fusion Protein to HEK293 cells that expressed human NGFR, LTβR, TNFR2, GITR, CD137 or HVEM was not above that seen for binding of the secondary antibody alone to those same cells (Table 3-3, FIG. 5C).

TABLE 3-3

Fold binding of fluorochrome-labeled TNFRSF-specific mAbs and OX40L IgG4P Fusion Protein to TNFRSF-expressing HEK293 cells or OX40L IgG4P Fusion Protein to OX40-expressing Jurkat cells.

| TNFRSF member expressed | Cell Line Transfected with TNFRSF Member | Commercial mAb binding (fold isotype control MFI) | OX40L IgG4P Fusion Protein binding (fold secondary antibody alone MFI) |
| --- | --- | --- | --- |
| OX40 | Jurkat | ND | 17 |
| TNFRSF16 (NGFR) | HEK293 | 27 | 2.0 |
| TNFRSF3 (LTβR) | HEK293 | 51 | 0.94 |
| TNFRSF1β | HEK293 | 2.0 | 1.0 |
| TNFRSF18 (GITR) | HEK293 | 17 | 1.0 |
| TNFRSF9 (CD137) | HEK293 | 18 | 1.0 |
| TNFRSF14 (HVEM) | HEK293 | 25 | 1.0 |

MFI = mean fluorescence intensity; ND = not determined.

Conclusions

Binding of OX40L IgG4P Fusion Protein to human OX40 is specific. OX40L IgG4P Fusion Protein is not cross-reactive to highly related antigens of the TNFRSF.

Example 4

In Vitro Bioactivity of OX40L IgG4P Fusion Protein: Plate-Based Bioassay Using Primary Activated Human CD4+ T Cells In this example, the bioactivity of OX40L IgG4P Fusion Protein was determined using primary activated human CD4+ T cells in a plate-based assay. Activated primary activated human CD4+ cells were plated onto plate-captured sub-optimal anti-CD3 (OKT3) monoclonal antibody for TCR stimulation together with a dose titration of OX40L IgG4P Fusion Protein for OX40 receptor-mediated co-stimulation. CD4+ T cell proliferation as well as cytokine release were determined to measure OX40 bioactivity.

To determine the ability of OX40L IgG4P Fusion Protein to enhance activation of T cells concomitantly with activation through the TCR (co-stimulation), plate-based bioactivity assays were performed and T cell activation assessed. Measurements of T cell co-stimulation included determination of CD4+ T cell proliferation and cytokine release. A mutated version of OX40L IgG4P Fusion Protein containing an OX40L ECD that is incapable of binding OX40 (F180A OX40L fusion protein IgG4P) was used in place of OX40L IgG4P Fusion Protein to demonstrate the requirement of OX40 engagement for co-stimulation.

The bioactivity of OX40L IgG4P Fusion Protein was determined using activated primary activated human CD4+ T cells in a plate-based drug capture assay with CD4+ T cell proliferation as well as cytokine release as activity readouts (FIG. 6).

To measure OX40L IgG4P Fusion Protein bioactivity, the following protocol was used:

Day 0:
Human immune cells in the form of a leuko pak was obtained from AllCells. CD4+ T cells were subsequently purified using an EasySep CD4+ T cell enrichment kit according to the manufacturer's protocol.
Suspend CD4+ T cells in complete RPMI culture media and adjust cell concentration to $1.0 \times 10^6$ per ml Add media containing PHA-L and recombinant human IL-2 to final concentrations of 2 µg/mL and 20 IU/mL, respectively, and culture cells at 37° C. and 5% CO2 in a humidified tissue culture incubator for 2 days to activate T cells.

Day 1:
Coat non-TC treated round-bottom 96 well assay plates with 100 µL of 2 µg/mL of goat anti mouse IgG, Fcγ-specific and 2 µg/mL goat anti human, Fcγ-specific in PBS
Incubate overnight at 4° C.

Day 2:
Wash the plate with 200 µL of PBS
Block the plate for 90 minutes at 37° C. with 1% BSA in PBS (1% BSA/PBS)
Wash the plate 3 times with PBS
Add 2 ng/mL of anti CD3 clone OKT3 reconstituted in 1% BSA/PBS for 90 minutes at 37° C.
Wash the plate 3 times with PBS
Add OX40L IgG4P Fusion Protein or control F180A-mutated OX40L fusion protein IgG4P diluted in 1% BSA/PBS starting at 1 µg/mL (100 µL per well; 3 nM) and continuing over a 3-fold dilution series. Incubate for 90 minutes at 37° C.
In the meantime, collect activated primary activated human CD4+ T cells and adjust concentration to $1.0 \times 10^6$ viable cells/mL in room temperature (RT) complete RPMI
Label cells with CFSE according to the manufacturer's instructions, with the exception of using 1.25 µM CFSE as opposed to the recommended 5 µM with an incubation of 10 minutes at 37° C. After labeling, suspend cells in complete RPMI and adjust concentration to $0.5 \times 10^6$ per ml
Wash the plate 3 times with PBS
Add 200 µL of cells (100,000) per well. Gently pellet cells by centrifugation at 100×g on tabletop centrifuge. Place in a humidified tissue culture incubator at 37° C. and 5% $CO_2$ for 3 days Day 3
The next day (24 hours incubation time), remove 40 µL of cell culture supernatant for cytokine release measurement Day 5
After 72 hours incubation time, remove 40 µL of cell culture supernatant for cytokine release measurement
Pellet CD4+ T cells at 380 g, and wash once with 4° C. PBS containing 2% FBS (FACS buffer)
Suspend cells in binding mix containing antibodies for the labeling of CD4+ T cells and propidium iodide for live/non-viable cell discrimination. Incubate for 30 minutes followed by 2 washes in 4° C. FACS buffer. Re-suspend in 4° C. FACS buffer and analyze events by flow cytometry using an LSRII flow cytometer and FlowJo software for analysis of FCS flow cytometry data.

For analysis of cytokine release, cell culture supernatants obtained after 72 hours of culture were analyzed for cytokine content using a 10-plex Th1/Th2 cytokine analysis kit from MSD according to the manufacturer's protocol. This kit employs an electrochemical detection method to quantitatively measure the following cytokines: IFNγ, IL-2, IL-4, IL-5, IL-8, IL-10, IL-12 p70, IL-13, and IL-1β. In previous experiments, a 72 hour time point has been shown to qualitatively reflect cytokine release at earlier time points, and therefore does not bias for or against the detection of certain Th1/Th2 cytokines under these conditions.

For the analysis of cell proliferation, live (PI negative) events were gated using FlowJo software, and the percentage of CD4+ T cells showing dilution of CFSE determined as a measure of the percentage of cells undergoing proliferation. The concentration of OX40L IgG4P Fusion Protein that produces a half-maximal response in terms of proliferation or cytokine release ($EC_{50}$), as well as the concentrations of drug for 20% and 90% of maximal response ($EC_{20}$ and $EC_{90}$) was determined using non-linear regression analysis in GraphPad Prism, version 5.01.

Materials used in this study are listed in Table 4-1.

TABLE 4-1

Materials

| Item | Source |
|---|---|
| AlexaFluor ®647 goat anti-human IgG (H + L) | Life Technologies, Carlsbad, CA |
| Bovine serum albumin (BSA) | Sigma, Saint Louis, MO |
| CFSE cell labeling kit | Life Technologies, Carlsbad, CA |
| Complete RPMI media: RPMI-1640 + 10% FBS | Materials from Life Technologies, Carlsbad, CA |
| Deep well plates, polypropylene, 2 mL | VWR, Radnor, PA |
| EasySep CD4+ T cell enrichment kit | Stem Cell Technologies, Vancouver, BC Canada |
| FACS buffer: PBS + 2% heat inactivated newborn calf serum | Materials from Life Technologies, Carlsbad, CA |
| Heat inactivated newborn calf serum | Life Technologies, Carlsbad, CA |
| IL-2, recombinant human | Preprotech, Rocky Hill, NJ |
| Leuko Pak | AllCells, Alameda, CA |
| LSM | MP Biomedicals, Santa Ana, CA |
| LSR II flow cytometer | BD Biosciences, San Jose, CA |
| Newborn calf serum, heat inactivated (FBS) | Life Technologies, Carlsbad, CA |
| Non-TC treated round-bottom 96 well plates | VWR, Radnor, PA |
| PBS, phosphate buffered saline, pH 7.2 | Life Technologies, Carlsbad, CA |
| PHA-L | Roche Applied Science, Indianapolis, IN |
| Phosphate Buffer Saline (PBS) pH 7.2 without Calcium and Magnesium | Life Technologies, Carlsbad, CA |
| Propidium iodide (1 mg/mL solution) | Sigma, Saint Louis, MO |
| RPMI-1640 | Life Technologies, Carlsbad, CA |
| Th1/Th2 multi-cytokine detection array | Mesoscale Discovery (MSD), Rockville, MD |
| Vi cell counter | Beckman Coulter, Indianapolis, IN |
| Whole blood, sodium heparin anti-coagulated | MedImmune Blood Donor Program, Gaithersburg, MD |

Enriched CD4+ T cells showed dose-dependent responses to OX40L IgG4P Fusion Protein with regard to induction of proliferation and cytokine release for IFNγ, TNFα, IL-5, IL-10, with poorly formed curves for IL-2, IL-4, IL-13, IL-8, IL-12 p70, and IL-1β. Example of outcomes that gave dose-responses for one of four donors is shown in FIG. 7A-E. A summary of data for the donors is summarized in Table 4-2. Because poorly formed dose-response curves were observed for IL-2, IL-4, IL-13, IL-8, IL-12 p70, and IL-1β cytokine release, potency values were not available for these measures.

The mean $EC_{20}$, $EC_{50}$, and $EC_{90}$ values for four donors with respect to CD4+ T cell proliferation were 8.0±7.6, 14±11, and 57±5.8 pM. The mean $EC_{20}$, $EC_{50}$, and $EC_{90}$ values for cytokine release were as follows: INFγ, 45±39, 65±41, and 140±45 pM; TNFα, 22±17, 48±26, and 230±132 pM; IL-10, 32±20, 53±34, and 137±70 pM; IL-5, 43±28, 59±40, and 134±57 pM. Thus, the proliferation of CD4+ T cells was the most sensitive measure of OX40L IgG4P Fusion Protein potency in this format.

TABLE 4-2

Proliferation and cytokine release activity of OX40L IgG4P Fusion Protein in a plate-based bioactivity assay.

| Donor Number | Readout | $EC_{20}$ (pM) | $EC_{50}$ (pM) | $EC_{90}$ (pM) |
|---|---|---|---|---|
| 1 | Proliferation | 3 | 9 | 65 |
| 2 | Proliferation | 15 | 25 | 63 |
| 3 | Proliferation | 0.02 | 0.5 | 53 |
| 4 | Proliferation | 14 | 22 | 47 |
| | Mean ± Standard Deviation (pM) | 8.0 ± 7.6 | 14 ± 11 | 57 ± 8.5 |
| 1 | Cytokine: IFNγ | 3 | 12 | 96 |
| 2 | Cytokine: IFNγ | 42 | 81 | 202 |
| 3 | Cytokine: IFNγ | 36 | 58 | 127 |
| 4 | Cytokine: IFNγ | 98 | 110 | 132 |
| | Mean ± Standard Deviation (pM) | 45 ± 39 | 65 ± 41 | 140 ± 45 |
| 1 | Cytokine: TNFα | 2 | 18 | 381 |
| 2 | Cytokine: TNFα | 31 | 65 | 145 |
| 3 | Cytokine: TNFα | ~37 | ~38 | ~48 |
| 4 | Cytokine: TNFα | 32 | 60 | 162 |
| | Mean ± Standard Deviation (pM) | 22 ± 17 | 48 ± 26 | 230 ± 132 |
| 1 | Cytokine: IL-10 | 12 | 22 | 86 |
| 2 | Cytokine: IL-10 | 32 | 49 | 109 |
| 3 | Cytokine: IL-10 | ~36 | ~40 | ~50 |
| 4 | Cytokine: IL-10 | 51 | 89 | 217 |
| | Mean ± Standard Deviation (pM) | 32 ± 20 | 53 ± 34 | 137 ± 70 |
| 1 | Cytokine: IL-5 | 23 | 30 | 93 |
| 2 | Cytokine: IL-5 | 62 | 87 | 174 |
| 3 | Cytokine: IL-5 | ND | ND | ND |
| 4 | Cytokine: IL-5 | ND | ND | ND |
| | Mean ± Standard Deviation (pM) | 43 ± 28 | 59 ± 40 | 134 ± 57 |

Example 5

In Vitro Activity of OX40L IgG4P Fusion Protein: 2-Cell Based Bioactivity Assays Using Jurkat NFκB-Luciferase Reporter T Cells In this example, the bioactivity of OX40L IgG4P Fusion Protein was determined using an OX40-expressing Jurkat NFκB-luciferase reporter cell line in two-cell based activity assays. Specifically, OX40 Jurkat NFκB-luciferase reporter cells were plated together with FcγR-expressing HEK293 cells, tumor cell lines, or with CD45+ cells isolated from primary human tumors together with a dose titration of OX40L IgG4P Fusion Protein for OX40 receptor-mediated activation of NFκB signaling. NFκB signaling is a well-known downstream event in OX40 signaling, and correlates well qualitatively with other measures of T cell activation such as proliferation and cytokine release.

To determine the ability of OX40L IgG4P Fusion Protein to enhance activation of T cells, a set of 2-cell reporter bioactivity assays were performed and T cell activation assessed. Measurement of T cell activation was accomplished by using an OX40-expressing Jurkat NFκB-luciferase T cell reporter line that produces luciferase in response to stimulation of the NFκB signaling pathway (FIG. 8), a quintessential result of primary activated human T cell activation. The amount of luciferase, and thus T cell activation, can be measured by adding a luciferase substrate to cell lysates and measuring light emitted by a reaction product using a luminometer. T cell activation was measured for soluble OX40L IgG4P Fusion Protein as well as FcγR cross-linked OX40L IgG4P Fusion Protein using cells that express different complements of FcγRs. Likewise, a mutated version of OX40L IgG4P Fusion Protein containing a single F to A amino acid substitution in the OX40L ECD (F180A OX40L FP IgG4P), that renders the ECD incapable of binding OX40, was used in place of OX40L IgG4P Fusion Protein to demonstrate the specificity of the effects for OX40 engagement.

Assay 1

OX40L IgG4P Fusion Protein was tested for bioactivity using a 2-cell bioactivity assay that uses the human OX40-expressing Jurkat NFκB-luciferase reporter clone 64 (OX40 Jurkat reporter) for readout of OX40 agonism (NFκB activity) and a second FcγR-expressing cell line that mediates OX40L IgG4P Fusion Protein cross linking that clusters OX40 on the OX40-expressing Jurkat reporter cells (FIG. 8). The FcγR-expressing cell lines used for drug cross linking included the Raji B cell tumor line, CD32B-expressing HEK293, CD32A-expressing HEK293 or CD45$^+$ immune cells isolated from primary human tumors or normal adjacent tissue. To determine the soluble activity of OX40L IgG4P Fusion Protein, bioactivity assays were conducted using parental HEK293 cells (FcγR null) in place of FcγR-expressing cell lines, or in the absence of a second cross-linking cell line altogether. To demonstrate the requirement of OX40 engagement on reporter cells, a mutated OX40L fusion protein IgG4P or a mutated OX40L fusion protein IgG1 reduced for OX40 binding was used in place of OX40L IgG4P Fusion Protein.

Prior to use, OX40 Jurkat reporter cells were cultured in complete RPMI at 37° C. and 5% CO2 in a humidified tissue culture incubator at a density of 0.5-1.5e6 per ml Cells were passaged the day prior to the bioassay to a concentration of 1e6 per ml The bioassay of OX40L IgG4P Fusion Protein was set up using the following protocol:

Day 0
  Collect OX40 Jurkat reporter cells and FcγR-expressing cell lines, or HEK parental cells, in 50 mL centrifuge tubes and pellet cells at 380 g (1200 rpm). For CD45$^+$ cells isolated from primary activated human tumors and normal adjacent tissues, tissues were dissociated and CD45$^+$ cells isolated and re-suspended in complete RPMI media for use in bioactivity assays, as described below.
  Re-suspend each cell type in complete RPMI and set aside while diluting antibodies.
  Make a serial dilution of OX40L IgG4P Fusion Protein starting at μg/mL range and diluting 3-fold in complete RPMI media to sub-ng/mL concentrations. Dilute F180A OX40L fusion protein in complete RPMI media as a control.
  Place OX40 reporter cells plus FcγR-expressing cell lines or HEK parental cells (each at 100,000 cells per well) in a 96 well plate.
  Add OX40L IgG4P Fusion Protein to cells in complete RPMI media, to a final concentration starting at 1 μg/mL diluting down 3-fold as described above. F180A OX40L fusion protein is diluted to a final concentration of 1 μg/mL as a control.

Day 1
  The next day (16-24 hours incubation time), add 100 μL of RT reconstituted SteadyGlo luciferase assay solution from Promega to each well and mix well to lyse cells.
  Incubate for 5 minutes at RT to equilibrate luciferase signal, and transfer 150 μL of steady glow/sample lysate using reverse pipetting technique (to avoid air bubbles) from each well to a 96 well white walled assay plate for detection and read luminescence signal using a Perkin Elmer Envision luminescence reader.
Analyze data by plotting concentration of OX40L IgG4P Fusion Protein (x-axis in log 10 of Molarity) versus RLU of luminescence (y-axis). $EC_{20}$, $EC_{50}$, and $EC_{90}$ values were determined via non-linear regression analysis using GraphPad prism version 5.01 software.

The following protocol was used to isolate primary human CD45$^+$ cells from human tumors and normal adjacent tissue:
  Remove tumor or normal adjacent tissue sample from transport media and place in sterile petri dish. Add Hank's Buffer Salt Solution and dissect visible necrotic tissue or any normal tissue from tumor sample.
  Using forceps and scissors, mince tissue into small pieces (~1 mm) and place in a 50 mL conical tube and add 10-20 mL of Collagenase III enzyme mix (250 IU/mL collagenase III, 3 mM $CaCl_2$, 315 μg/mL DNAase I). Mix well and incubate at 30° C. incubator for approximately ½ hour.
  Filter the digested sample through a 70 micron filter. Gently press material against the filter with the back end of a 1 mL syringe plunger, and use cold MACS buffer to wash the filter frequently, to help wash cells through.

Pellet dissociated cells at 900 rpm (190 g RCF) for 15 mM at 4° C.

Determine cell number and viability using a Vi cell counter.

For each 10 million cells, suspend in 80 μL MACS buffer (PBS pH7.2 plus 0.5% BSA and 2 mM EDTA) and add 20 μL of CD45 microbeads.

Incubate on ice for 15 min at 4° C.

Wash cells in 2 mL cold MACS buffer per 10 million cells.

Re-suspend in 500 μL cold MACS buffer

Pre-wet one LS column for each selection tumor and normal tissue sample with 3 mL of cold MACS buffer Apply 500 μL of bead-bound cell suspension to column and add 3×3 mL of cold MACS buffer (total of 9 mL) to wash unbound cells through the column.

Elute bead-bound CD45$^+$ cells by removing the column from the magnet and adding 5 mL of MACS buffer. Gently push MACS buffer together with cells through the column with a plunger. Pellet and re-suspend the CD45$^+$ cells in complete RPMI media and use in bioactivity assays as described above.

Materials used in this study are listed in Table 5-1

TABLE 5-1

| Materials | |
|---|---|
| Item | Source |
| Bovine serum albumin (BSA) | Sigma, Saint Louis, MO |
| Calcium Chloride solution, 1M | Sigma, Saint Louis, MO |
| CD45$^+$ microbeads | Miltenyi, San Diego, CA |
| Collagenase III | Worthington Biochemical Corporation, Lakewood, NJ |
| Complete RPMI media: RPMI-1640 + 10% FBS | Materials from Life Technologies, Carlsbad, CA |
| Deep well plates, polypropylene, 2 mL | VWR, Radnor, PA |
| DNAse I, from bovine pancreas | Sigma, Saint Louis, MO |
| EDTA, 0.5M pH 8.0 | Life Technologies, Carlsbad, CA |
| Hank's Buffered Salt Solution (HBSS) | Life Technologies, Carlsbad, CA |
| Heat inactivated newborn calf serum | Life Technologies, Carlsbad, CA |
| LS column | Miltenyi, San Diego, CA |
| MACS buffer: PBS + 0.5% BSA + 2 mM EDTA | Materials from Life Technologies, Carlsbad, CA |
| Newborn calf serum, heat inactivated (FBS) | Life Technologies, Carlsbad, CA |
| Non-TC treated round-bottom 96 well plates | VWR, Radnor, PA |
| PBS, phosphate buffered saline, pH 7.2 | Life Technologies, Carlsbad, CA |
| Phosphate Buffer Saline (PBS) pH 7.2 without Calcium and Magnesium | Life Technologies, Carlsbad, CA |
| RPMI-1640 | Life Technologies, Carlsbad, CA |
| Steady Glow Luciferase Assay Solution | Promega, Madison, WI |
| Vi cell counter | Beckman Coulter, Indianapolis, IN |

Results of 2-Cell Bioactivity Assays

The bioactivity of OX40L IgG4P Fusion Protein was tested as a soluble protein using OX40-expressing Jurkat NFκB-luciferase reporter cells plus OX40L IgG4P Fusion Protein in the absence of a second cell type or in the presence of HEK293 cells lacking exogenously expressed FcγRs. Under these conditions, OX40L IgG4P Fusion Protein exhibited little reporter activity. However, in the presence of an FcR-expressing cell line, such as CD32A-expressing HEK293, OX40L IgG4P Fusion Protein demonstrates potent T cell stimulation activity as measured by NFκB pathway stimulation (FIG. 9).

As in the presence of CD32A-expressing HEK, OX40L IgG4P Fusion Protein demonstrates potent bioactivity in 2-cell assays using Raji B cells, CD32B-expressing HEK293 cells, CD32A-expressing HEK293, or CD45+ cell isolated from primary human tumors for drug cross-linking (FIG. 10).

Potency values ($EC_{20}$, $EC_{50}$, and $EC_{90}$) for the two-cell bioassays are summarized in Table 5-2. The mean±standard deviation $EC_{20}$, $EC_{50}$, and $EC_{90}$ values for the assays were 35±29 pM, 59±47, and 141±114 pM, respectively.

TABLE 5-2

2-cell bioactivity of OX40L IgG4P Fusion Protein. As indicated, assays used Raji, CD32B-expressing HEK293, CD32A-expressing HEK293, or CD45+ cells isolated from primary human tumors with OX40-expressing Jurkat NFkB-luciferase clone 64 reporter cells.

| Experiment Number | FcγR-expressing cell | $EC_{20}$ (pM) | $EC_{50}$ (pM) | $EC_{90}$ (pM) |
|---|---|---|---|---|
| 1 | Raji | 7.2 | 12 | 25 |
| 2 | CD32B-expressing HEK | 11 | 12 | 16 |
| 3 | CD32B-expressing HEK | 3.5 | 5.6 | 12 |
| 3 | Raji | 6.8 | 15 | 51 |
| 4 | Raji | 9.3 | 15 | 31 |
| 5 | CD32B-expressing HEK | 72 | 112 | 223 |
| 6 | CD32B-expressing HEK | 70 | 104 | 200 |
| 7 | CD32B-expressing HEK | 60 | 102 | 240 |

TABLE 5-2-continued 2-cell bioactivity of OX40L IgG4P Fusion Protein. As indicated, assays used Raji, CD32B-expressing HEK293, CD32A-expressing HEK293, or CD45+ cells isolated from primary human tumors with OX40-expressing Jurkat NFkB-luciferase clone 64 reporter cells.

| Experiment Number | FcγR-expressing cell | $EC_{20}$ (pM) | $EC_{50}$ (pM) | $EC_{90}$ (pM) |
|---|---|---|---|---|
| 8 | CD32B-expressing HEK | 78 | 117 | NC |
| 9 | CD32B-expressing HEK | 82 | 134 | 290 |
| 10 | CD32A-expressing HEK | 19 | 35 | 90 |
| 11 | CD32A-expressing HEK | 21 | 25 | 76 |

TABLE 5-2-continued 2-cell bioactivity of OX40L IgG4P Fusion Protein. As indicated, assays used Raji, CD32B-expressing HEK293, CD32A-expressing HEK293, or CD45+ cells isolated from primary human tumors with OX40-expressing Jurkat NFκB-luciferase clone 64 reporter cells.

| Experiment Number | FcγR-expressing cell | $EC_{20}$ (pM) | $EC_{50}$ (pM) | $EC_{90}$ (pM) |
|---|---|---|---|---|
| 12 | CD32A-expressing HEK | 18 | 33 | 81 |
| 13 | CD45+ cells, renal tumor | 19 | 42 | 145 |
| 14 | CD45+ cells, renal tumor | 64 | 131 | 404 |
| 15 | CD45+ cells, lung tumor | 15 | 37 | 158 |
| 16 | CD45+ cells, renal tumor | 31 | 66 | 215 |
| | Mean ± Stdev | 35 ± 29 | 59 ± 47 | 141 ± 114 |

OX40L IgG4P Fusion Protein mediates the activation of human T cells as measured through the activation of the NFκB pathway in the OX40-expressing Jurkat NFκB-luciferase reporter line. This bioactivity is low in the absence of cells that express FcRs capable of cross linking the drug via the Fc domains of OX40L IgG4P Fusion Protein. In 2-cell systems using FcR-expressing cells (Raji, CD32A- or CD32B-expressing HEK293) for drug cross-linking and the Jurkat NFκB-luciferase reporter line for readout of T cell activation, MEDI mediated potent T cell activation with a mean $EC_{50}$ value of 60±52 pM.

Example 6

In Vitro Comparability Studies with OX40L IgG4P Fusion Protein and Cynomolgus and Rhesus Monkey T Cells Cynomolgus (cyno) and rhesus macaque monkeys have been used for safety and pharmacokinetic/pharmacodynamic (PK/PD) modeling for OX40L IgG4P Fusion Protein and the species share identical OX40 sequence. In this example, the bioactivity of OX40L IgG4P Fusion Protein was determined using a Jurkat NFκB-luciferase reporter cell line expressing cyno/rhesus monkey OX40 in a two-cell based activity assay. Cyno/rhesus OX40 Jurkat NFκB-luciferase reporter cells were plated together with an Fcγ receptor-expressing rhesus B cell line or isolated rhesus cells containing antigen presenting cells, then treated with a dose titration of OX40L IgG4P Fusion Protein for OX40 receptor-mediated activation of NFκB signaling. NFκB signaling is a well-known downstream event in OX40 signaling, and can correlate with other measures of T cell activation such as proliferation and cytokine release.

In addition, the bioactivity of OX40L IgG4P Fusion Protein was determined using primary activated rhesus $CD4^+$ T cells in a plate-based proliferation assay. Primary activated rhesus $CD4^+$ T cells were plated onto plate-captured sub-optimal anti-CD3 monoclonal antibody for TCR stimulation together with a dose titration of OX40L IgG4P Fusion Protein for OX40 receptor-mediated co-stimulation. $CD4^+$ T cell proliferation was measured to determine OX40 bioactivity.

Cyno/Rhesus 2-Cell Bioactivity Assays

OX40L IgG4P Fusion Protein was tested for bioactivity using a two-cell assay with Fcγ receptor-expressing cells used to mediate OX40L IgG4P Fusion Protein cross linking and consequently, OX40 clustering on Jurkat reporter cells. Since cyno and rhesus monkeys share identical OX40 sequence, the first cell type is a cyno/rhesus OX40-expressing Jurkat NFκB-luciferase reporter cell line (clone B2) used for readout of OX40 agonism (NFκB activity). The second cell type is an Fcγ receptor-expressing cell line, rhesus B cell line LCL8664, or Fcγ receptor-expressing immune cells from whole blood of a normal rhesus monkey. To determine the activity of soluble OX40L IgG4P Fusion Protein, a control was conducted in the absence of a second cross-linking cell line ("target only"). Background bioactivity was assessed without the addition of OX40L IgG4P Fusion Protein ("target+ effector"). To demonstrate the requirement of OX40 engagement on reporter cells, the mutated F180A OX40L fusion protein IgG4P with reduced OX40 binding was used in place of OX40L IgG4P Fusion Protein. The OX40L IgG4P Fusion Protein 2-cell bioactivity assay with LCL8664 was performed according to the following protocol:

Day before assay:
1. Complete medium (RPMI with 10% FBS) was added to cyno/rhesus OX40-expressing Jurkat NFκB-luciferase reporter clone B2 and rhesus B cell line LCL8664 to achieve cell density at approximately 500,000 and 400,000 cells per mL, respectively, to promote good cell viability in the assay.

Day 0:
1. Cyno/rhesus OX40-expressing Jurkat NFκB-luciferase reporter clone B2 and rhesus B cell line LCL8664 were collected in separate 50 mL conical centrifuge tubes, pelleted at 330×g and the supernatants discarded. Cells were then suspended in 10 mL complete medium, the cell suspensions counted using a ViCell counter and cell concentration for both cell lines adjusted to 2.5× $10^6$ in complete medium previously described.
2. 10 μg/mL OX40L IgG4P Fusion Protein was serially diluted in 3-fold increments in complete medium in deep well polypropylene plates for an 11-point data curve. 10 μg/mL F180A mutant OX40L fusion protein and IgG4P antibody (negative isotype control) were similarly diluted in 6-fold increments for a 5 point data curve.
3. Cyno/rhesus OX40-expressing Jurkat NFκB-luciferase reporter clone B2 and rhesus B cell line LCL8664 were mixed at equal volume to a final concentration of 1.25×$10^6$ of each cell per mL, then 80 μL of the mixed cell suspension was dispensed to each well of a 96-well bottom non-tissue culture treated plate.
4. 20 μL of OX40L IgG4P Fusion Protein or F180A mutant OX40L fusion protein IgG4P was then added to each well, and the plates transferred to a 37° C. incubator with a humidified 5% $CO_2$ atmosphere.

Day 1:
1. After 16 hours incubation, plates were acclimated to room temperature for 30 minutes; then 100 μL of reconstituted room temperature SteadyGlo luciferase assay solution (Promega) was added to each well to lyse the cells.
2. Plates were incubated for 5 minutes at RT on a rotary shaker to equilibrate luciferase signal. 150 μL of SteadyGlo/sample lysate from each well was transferred to wells of a 96-well white-walled assay plate and luminescence signal in each well determined using a Perkin Elmer Envision luminescence reader.

The following protocol was used to isolate immune cells expressing Fcγ receptors from sodium heparin anti-coagulated whole blood obtained from a healthy Indian-origin rhesus macaque donor (World Wide Primates, Miami, Fla.):

1. 5 mL of fresh whole blood was added to a 50 mL conical tube and 45 mL of ammonium chloride solution was added. The cell mixture was incubated for 10 minutes on ice.
2. The cell mixture was centrifuged at 300×g for 10 minutes; then the supernatant was discarded.
3. Cell pellets were washed twice with 40 mL of complete cell culture medium as previously described, and then cells were ready for use in the 2-cell bioactivity assay.

The 2-cell bioactivity assay with rhesus whole lysed blood was performed as previously described with the LCL8664 rhesus B cell line, except NIP228 IgG4P was used as the negative control antibody at 10 µg/mL concentration only.

Rhesus CD4+ T Cell Proliferation Assay

OX40L IgG4P Fusion Protein bioactivity was determined using activated primary activated rhesus CD4+ T cells in a plate-based drug capture assay and CD4+ T cell proliferation was measured. OX40L IgG4P Fusion Protein bioactivity was assessed according to the following protocol using Rhesus CD4+ T cells isolated from sodium heparin anti-coagulated whole blood obtained from healthy rhesus donors (N=2) from World Wide Primates (Miami, Fla.):

Day 1:
1. Lymphocyte separation media (LSM) was diluted to 95% by adding 5 mL of PBS to 95 mL of LSM at RT.
2. Fresh heparinized rhesus blood was diluted 1:1 with PBS at RT, and then 20 mL of diluted whole blood was overlayed onto 15 mL of 95% LSM in a 50 mL conical centrifuge tube.
3. Blood was centrifuged at 400×g for 30 min at RT in a tabletop centrifuge without the brake.
4. Peripheral blood mononuclear cells (PBMC) were collected at the interphase and washed twice with cold Miltenyi MACS buffer at 1200 RPM for 10 minutes.
5. Supernatant was discarded and the cell pellet was treated with 5 mL of RT 1×RBC lysis buffer and incubated at RT for 5 minutes. 45 mL of complete medium (Advanced RPMI with 10% FBS and 1% antibiotics/antimycotics) was added to the pellet to stop the lysing process at the end of the incubation time.
6. PBMC cells were then pelleted in a centrifuge at 330×g for 10 min and washed twice with 20 mL of cold Miltenyi MACS buffer.
7. Supernatant was discarded and cell pellet was suspended in cold MACS buffer and counted with a ViCell counter to determine cell number and viability.
8. Rhesus CD4+ T cell isolation was performed with a Miltenyi non-human primate kit according to manufacturer's instructions, then CD4+ T cells counted on a ViCell counter and suspended at $1 \times 10^6$ per mL in complete cell culture medium as previously described.
9. Rhesus CD4+ T cells ($1 \times 10^6$ per mL in complete medium) were cultured for 48 hours in a humidified tissue culture incubator at 37° C. and 5% $CO_2$ in a T75 cell culture flask with 5 µg/mL Concanavalin A and 1000 IU/mL IL-2 to activate T cells and induce OX40 expression.

Day 2:
1. Non-tissue culture treated round-bottom 96 well assay plates were coated with 100 µL of 2 µg/mL of goat anti-mouse IgG (Fcγ-specific) and 2 µg/mL goat anti-human IgG (Fcγ-specific) in PBS, then incubated overnight at 4° C.

Day 3:
1. The antibody-coated plates were washed once with 200 µL of PBS, and then the plates were blocked with 1% BSA in PBS (1% BSA/PBS) for 90 minutes at 37° C.
2. Plates were washed twice with 200 µL of PBS; then 100 µL of 2 ng/mL anti-CD3 clone SP34-2 in 1% BSA/PBS was added per well and incubated for 90 minutes at 37° C.
3. Plates were washed twice with 200 µL of PBS, then 100 µL of 0.5 µg/mL (assay 1) or 1 µg/mL (assay 2) OX40L IgG4P Fusion Protein serially diluted in 1% BSA/PBS 3-fold for a 10 point data curve or control NIP228 IgG4P isotype at 1 µg/mL was added per well. Plates were incubated for 90 minutes at 37°.
4. Activated Rhesus CD4+ T cells were adjusted to $1 \times 10^6$ viable cells/mL in RT complete medium as previously described.
5. Rhesus CD4+ T cells were labeled with carboxy fluorescein diacetate succinimidyl ester (CFSE) according to the manufacturer's instructions, with the exception of using 1.25 µM CFSE as opposed to the recommended 5 µM, and incubated 10 minutes at 37° C. After cell labeling, cells were suspended in complete medium and previously described and concentration adjusted to $1.5 \times 10^6$ per ml
6. 100 µL of activated rhesus CD4+ T cells (150,000) were added per well, and the plates placed in a humidified tissue culture incubator at 37° C. and 5% $CO_2$ for three days.

Day 5:
1. Rhesus CD4+ T cells were pelleted in a centrifuge at 330×g, then washed once with 200 µL of 4° C. PBS containing 2% FBS (FACS buffer)
2. Cells were suspended in a 4° C. binding mix containing 2.5 µL CD4-V450 antibody for the labeling of rhesus CD4+ T cells and 0.5 µL of propidium iodide (PI) for live/non-viable cell discrimination.
3. Cell plates were incubated at 4° C. for 30 minutes then washed twice with 200 µL of 4° C. FACS buffer per well. Cell were suspended in 100 µL 4° C. buffer per well and analyzed by flow cytometry using an LSRII flow cytometer and FlowJo software (TreeStar, Ashland, Oreg.) for analysis of FCS flow cytometry data.

The assay was repeated in two independent assays using primary activated rhesus CD4+ T cells, as shown in Table 6-3.

For the analysis of cell proliferation, live (PI negative) events were gated using FlowJo software and the percentage of CD4-gated cells showing dilution of CFSE determined as a measure of the percentage of cells undergoing proliferation.

The concentration of OX40L IgG4P Fusion Protein that produces a half-maximal ($EC_{50}$) response in terms of bioactivity and proliferation was determined using non-linear regression analysis (log dose-response, 4-parameter fit curves) in GraphPad Prism, version 5.01 (San Diego, Calif.). Standard deviation was determined as a measure of deviation between individual experiments and donors.

Materials used in this study are listed in Table 6-1.

TABLE 6-1

Materials

| Item | Source |
| --- | --- |
| Antibiotic-Anti-mycotic solution | Life Technologies, Carlsbad, CA |
| Advanced RPMI media | Life Technologies, Carlsbad, CA |
| Bovine serum albumin (BSA) | Sigma, Saint Louis, MO |
| Ammonium Chloride | StemCell Technologies, Vancouver, BC |
| Anti-human CD3 antibody, clone SP34-2 | BD Biosciences, San Jose, CA |
| Anti-human CD4-V450 antibody, clone L200 | BD Biosciences, San Jose, CA |
| Anti-human CD28 antibody, clone CD28.2 | BD Biosciences, San Jose, CA |
| Goat anti human Fcγ antibody | Jackson Immunoresearch, West Grove, PA |
| Goat anti-mouse Fcγ antibody | Jackson Immunoresearch, West Grove, PA |
| CFSE cell labeling kit | Life Technologies, Carlsbad, CA |
| Concanavalin A | Sigma, St. Louis, MO |
| Deep well plates, polypropylene, 2 mL | VWR, Radnor, PA |
| Envision multilabel plate reader | Perkin Elmer, Waltham, MA |
| FACS buffer: PBS + 2% heat inactivated newborn calf serum | Materials from Life Technologies, Carlsbad, CA |
| Fetal bovine serum, heat inactivated (FBS) | Life Technologies, Carlsbad, CA |
| Goat anti human Fcγ antibody | Jackson Immunoresearch, West Grove, PA |
| Goat anti-mouse Fcγ antibody | Jackson Immunoresearch, West Grove, PA |
| Heat inactivated fetal bovine serum | Life Technologies, Carlsbad, CA |
| IL-2, recombinant human | Preprotech, Rocky Hill, NJ |
| LSR II flow cytometer | BD Biosciences, San Jose, CA |
| Lymphocyte separation media (LSM) | MP Biomedicals, Santa Ana, CA |
| MACS buffer | Miltenyi, San Diego, CA |
| Non-human primate CD4+ T cell isolation kit | Miltenyi, San Diego, CA |
| Non-TC treated round-bottom 96 well plates | VWR, Radnor, PA |
| PBS, phosphate buffered saline, pH 7.2 | Life Technologies, Carlsbad, CA |
| Phosphate Buffer Saline (PBS) pH 7.2 without Calcium and Magnesium | Life Technologies, Carlsbad, CA |
| Propidium iodide (1 mg/mL solution) | Sigma, Saint Louis, MO |
| RBC Lysis Buffer | Biolegend, San Jose, CA |
| Rhesus monkey (Indian Origin) whole blood, sodium heparin anti-coagulated | Worldwide Primates, Miami, CA |
| RPMI-1640 | Life Technologies, Carlsbad, CA |
| Steady Glow Luciferase Assay Solution | Promega, Madison, WI |
| Vi cell counter | Beckman Coulter, Indianapolis, IN |

TABLE 6-2

Mean EC50 Value for OX40L IgG4P Fusion Protein in Cyno/Rhesus OX40-expressing Jurkat NFκB-luciferase Clone B2 and LCL8664 Rhesus B Cell Bioactivity Assays

| Binding Protein | Number of Experiments | Mean EC50 ± SD (pM) |
| --- | --- | --- |
| OX40L IgG4P Fusion Protein | 2 | 49.9 ± 4.60 |
| F180A OX40L Fusion Protein Human IgG4P | 2 | No Activity |

SD = standard deviation

Results
Results of Cyno/Rhesus 2-Cell Bioactivity Assay

Figure 12:
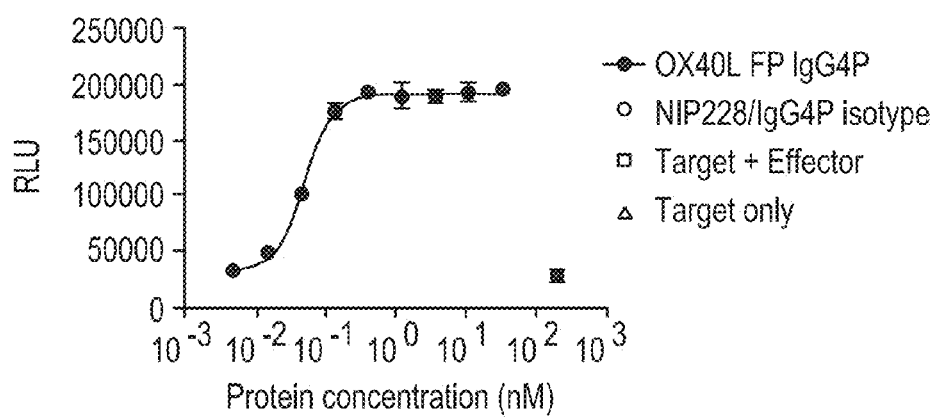
Figure 14A:
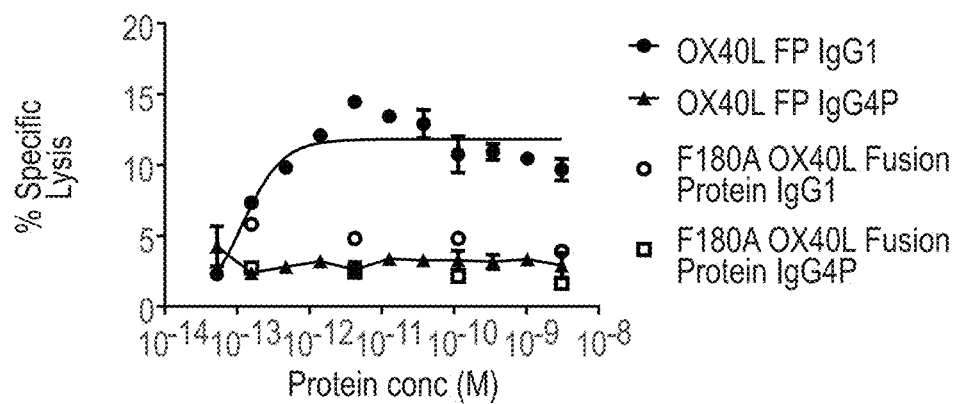
Figure 14B:
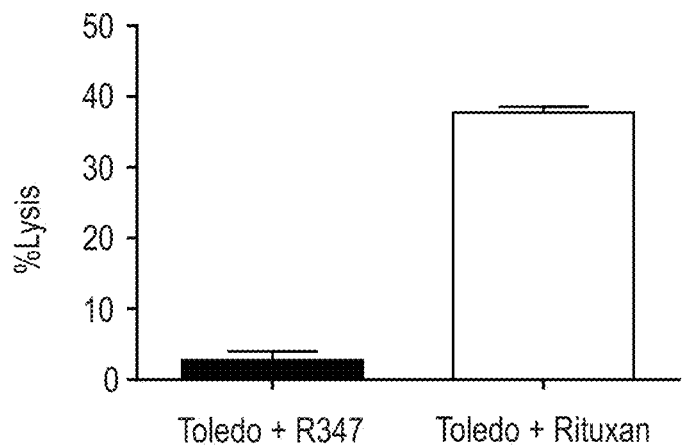
Figure 14C:
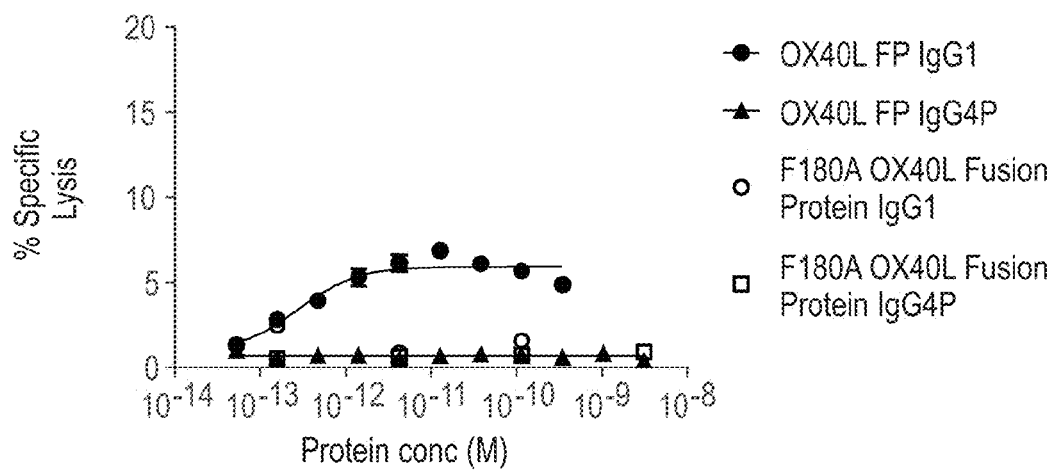
Figure 14D:
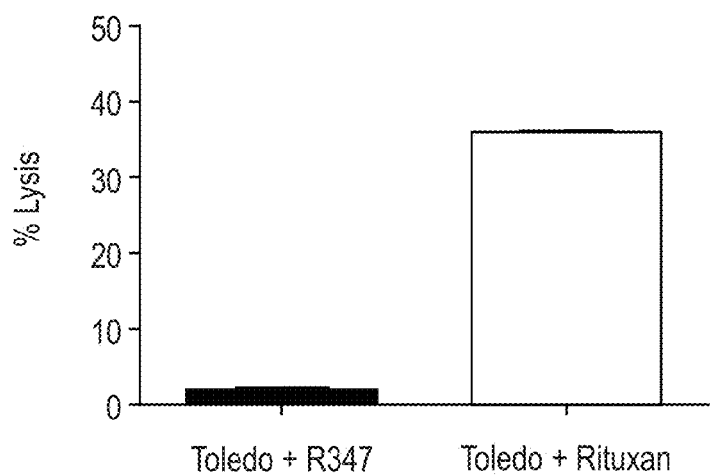

Results for the cyno/rhesus 2-cell bioactivity assays are shown in Tables 6-2 and 6-3 and FIGS. 11 and 12. OX40L IgG4P Fusion Protein demonstrated the ability to activate OX40 signaling pathway in Jurkat T cells in the presence of the rhesus B cell line, LCL8664, with a mean $EC_{50}$ of 49.9+4.60 pM (N=2 assays). As shown in Table 6-5, the $EC_{50}$ value for OX40L IgG4P Fusion Protein activity in the cyno/rhesus 2-cell assay compared to human 2-cell assays with the Raji B cell line is 3.6 fold higher. In addition, OX40L IgG4P Fusion Protein activated OX40 signaling pathway in Jurkat T cells in the presence of total rhesus immune cells expressing Fcγ receptors, with an $EC_{50}$ of 50.8 (95% CI 45.7, 56.4) pM (N=1 assay).

TABLE 6-3

EC50 value for OX40L IgG4P Fusion Protein in Cyno/Rhesus OX40 Expressing Jurkat NFκB Luciferase Clone B2 and Fc Gamma Receptor Expressing Rhesus Immune Cells Bioactivity Assay

| Binding Protein | Number of Experiments | EC50 (95% CI) |
| --- | --- | --- |
| OX40L IgG4P Fusion Protein | 1 | 50.8 (45.7, 56.4) |
| NIP228 IgG4P isotype | 1 | No activity |

CI = confidence interval

Results of Rhesus Primary Activated T Cell Proliferation Assay

Results for the rhesus primary activated T cell proliferation assay (N=2) are shown in Table 6-4 and FIG. 13.

OX40L IgG4P Fusion Protein induced proliferation of primary activated rhesus CD4+ T cells with a mean $EC_{50}$ of 134+144 pM (N=2 assays). As shown in Table 6-6, the $EC_{50}$ value for OX40L IgG4P Fusion Protein activity in the rhesus CD4+ T cell proliferation assay compared to human CD4+ T cell proliferation is 9.6 fold higher.

TABLE 6-4

Mean $EC_{50}$ for OX40L IgG4P Fusion Protein in Primary activated Rhesus CD4+ T Cell Proliferation Assays

| Binding Protein | Number of Experiments | Mean EC50 ± SD (pM) |
| --- | --- | --- |
| OX40L IgG4P Fusion Protein | 2 | 134 ± 144 |
| NIP228 IgG4P isotype | 2 | No activity |

SD = standard deviation

TABLE 6-5

Mean EC50 Values for OX40L IgG4P Fusion Protein in Cyno/Rhesus OX40-expressing Jurkat NFκB-luciferase Clone B2 and LCL8664 Rhesus B Cell Bioactivity Assays Compared to Human OX40-Expressing Jurkat NFκB-luciferase Clone 64 and Raji Human B Cell Bioactivity Assays

| Binding Protein | (Cyno/Rhesus) Mean EC50 ± SD (pM) | (Human) Mean EC50 ± SD (pM) |
| --- | --- | --- |
| OX40L IgG4P Fusion Protein | 49.9 ± 4.60 | 14.0 ± 1.73 |
| F180A OX40L fusion protein human IgG4P | No activity | No Activity |

SD = standard deviation

TABLE 6-6

Mean EC50 Values for OX40L IgG4P Fusion Protein in Rhesus Compared to Human CD4+ T Cell Proliferation Assays

| Binding Protein | Rhesus Mean EC50 ± SD (pM) | (Human) Mean EC50 ± SD (pM) |
| --- | --- | --- |
| OX40L IgG4P Fusion Protein | 134 ± 144 | 14.0 ± 11.0 |
| F180A OX40L fusion protein human IgG4P | No Activity | No Activity |

SD = standard deviation

OX40L IgG4P Fusion Protein activated the OX40 signaling pathway in cyno/rhesus OX40 expressing T cells in the presence of rhesus B cells or rhesus immune cells expressing Fcγ receptors from whole lysed blood. In addition, OX40L IgG4P Fusion Protein induced proliferation of primary activated rhesus CD4+ T cells.

Example 7

Determination of the Ability of OX40L IgG4P Fusion Protein to Trigger Effector Function This example assesses the ability of OX40L IgG4P Fusion Protein to bind to C1q, and to trigger natural killer (NK) cell-mediated antibody-dependent cellular cytotoxicity (ADCC) against primary activated human CD4+ T cells expressing high levels of OX40. A version of OX40L IgG4P Fusion Protein bearing a human IgG1 Fc domain (OX40L FP IgG1) was generated to assess the contribution of an Fc domain known and capable of triggering ADCC or binding to C1q. A version of OX40L IgG4P Fusion Protein and of the OX40L FP IgG1 bearing a point mutation (F180A) in the OX40L receptor binding domain has reduced binding capacity for OX40 and was produced to evaluate the contribution of the OX40 binding-domain to trigger ADCC against cells expressing OX40. The anti-CD20 antibody rituximab binds to B cells expressing CD20 and was used as a positive control for ADCC experiments. Because primary activated human CD4+ T cells do not express CD20, a separate assay using the Toledo B cell line, which does express CD20, was conducted to confirm that the ADCC assay system was valid. A human IgG1 control antibody was used as a positive control for C1q binding assays.

Antibody-Dependent Cellular Cytotoxicity

The ADCC activity of OX40L IgG4P Fusion Protein relative to that of OX40L fusion protein IgG1 and rituximab was tested using enriched primary activated human NK cells as effectors and OX40-expressing primary activated human CD4+ T cells as targets. For the isolation of primary activated human CD4+ T cells, heparin anti-coagulated whole blood obtained from healthy donors through the MedImmune Blood Donor Program and processed according to the following protocol:

1. 1 mL of Stem Cell Technologies RosetteSep CD4+ T cell isolation kit antibody mix was added per 20 mL of whole blood, mixed, and incubated for 20 minutes (min) at room temperature (RT).
2. Blood was diluted 1:1 with sterile room temperature FACS buffer (2% heat inactivated newborn calf serum in PBS, pH 7.2) and layered onto DM-L media followed by centrifugation at 380 g (1200 rpm) in a table-top centrifuge for 20 min with the break off.
3. After centrifugation, the buffy coat containing human CD4+ T cells was removed with a 10 mL pipette and the cells washed once with RT FACS buffer and once with RT complete RPMI media.
4. Cells were counted on a ViCell counter to determine cell number and viability and CD4+ T cells were suspended in complete RPMI media at a concentration of $1.0 \times 10^6$ per ml Primary activated human CD4+ T cells ($1.0 \times 10^6$ per mL in complete RPMI media) were cultured in a humidified tissue culture incubator at 37° C. and 5% $CO_2$ for 48 hours in the presence of 2 μg/mL PHA-L and 20 IU/mL rhIL-2 to activate T cells and up-regulate OX40 and subsequently used in OX40L IgG4P Fusion Protein ADCC assays. All donors in the tables and figures below represent separate individuals; that is, CD4+ T cells were not isolated from the same donor for repeat ADCC experiments.

After activation of the primary activated human CD4+ T cells, effector NK cells were isolated from sodium heparin anti-coagulated blood from the MedImmune Blood Donor Program using the same protocol as above for CD4+ T cells with the exception that 1 mL of RosetteSep NK cell isolation kit antibody mix was used in place of 1 mL of RosetteSep CD4+ T cell isolation kit antibody mix. Isolated primary activated human NK cells were washed two times with warm complete RPMI media (RPMI-1640 plus 10% FBS) and then suspended in complete RPMI at a concentration of $2.67 \times 10^6$ per ml. Likewise, activated primary activated human CD4+ T cells were also washed two times in warm complete RPMI and suspended at a concentration of $2.67 \times 10^5$ per ml Thereafter, 75 μL of primary activated human NK cells (200,000) and 75 μL of activated primary activated human CD4+ T cells (20,000) were added to wells of sterile non-TC treated round bottom 96-well plates for an effector-to-target ratio of 10:1. To the cells in the plate were added 50 μL of complete RPMI containing a dilution series of OX40L IgG4P Fusion Protein or OX40L fusion protein IgG1. 10 μg/mL of rituximab control antibody was used as a positive control in wells containing CD20-expressing Raji B cells in place of activated primary activated human $CD4^+$ T cells. Cells in the ADCC assay were gently pelleted by centrifugation (100 g for 2 min at RT) and subsequently cultured for 24 hours at 37° C. and 5% $CO_2$ in a humidified tissue culture incubator.

At the end of the incubation period, cells were pelleted by centrifugation at 380 g and then suspended in 100 μL FACS buffer containing 10 μg/mL propidium iodide for non-viable cell discrimination by flow cytometry analysis on a BD LSRII flow cytometer. For compensation, wells containing OX40-expressing cells bound to 10 μg/mL Ab (no PI), cells bound to secondary AlexaFluor® 647 labeled Ab reagent only or cells permeabilized with 0.1% saponin and treated with 10 μg/mL PI were prepared for single-stain compensation controls. For background subtraction, cells containing secondary antibody in the absence of primary activated antibody was also prepared as described above.

OX40L IgG4P Fusion Protein Binding to C1q

A ProteOn XPR36 instrument was used to determine the binding parameters of human complement protein C1q purified from a pool of human sera to OX40L IgG4P Fusion Protein. Standard amine coupling was used to immobilize OX40L IgG4P Fusion Protein to the surface of a GLC biosensor chip. Human C1q was suspended in PBS/0.005% Tween 20, pH 7.4 at five concentrations ranging from 26 nM to 1.6 nM. The samples were injected at 30 μL/min for 200 seconds, and the dissociation phase was followed for 600 seconds. Sensorgram data was processed using ProteOn Manager 2.1 software (Bio-Rad) using 1:1 fitting.

Materials used in this study are listed in Table 7-1.

TABLE 7-1

| Materials | |
| --- | --- |
| Item | Source |
| Bovine serum albumin (BSA) | Sigma, Saint Louis, MO |
| Complement protein C1q | Quidel, San Diego, CA |
| Complete RPMI media: RPMI-1640 + 10% FBS | Materials from Life Technologies, Carlsbad, CA |
| Deep well plates, polypropylene, 2 mL | VWR, Radnor, PA |
| DM-L media | Stem Cell Technologies, Vancouver, BC Canada |
| GLC biosensor chip | Bio-Rad, Hercules, CA |
| Heat inactivated newborn calf serum | Life Technologies, Carlsbad, CA |
| IL-2, recombinant human | Preprotech, Rocky Hill, NJ |
| LSR II flow cytometer | BD Biosciences, San Jose, CA |
| Newborn calf serum, heat inactivated (FBS) | Life Technologies, Carlsbad, CA |
| Non-TC treated round-bottom 96 well plates | VWR, Radnor, PA |
| PBS, phosphate buffered saline, pH 7.2 | Life Technologies, Carlsbad, CA |
| PHA-L | Roche Applied Science, Indianapolis, IN |
| Phosphate Buffer Saline (PBS) pH 7.2 without Calcium and Magnesium | Life Technologies, Carlsbad, CA |
| Phosphate Buffered Saline with Tween-20 | Bio-Rad, Hercules, CA, |
| Propidium iodide (1 mg/mL solution) | Sigma, Saint Louis, MO |
| ProteOn XPR36 instrument | Bio-Rad, Hercules, CA |
| RosetteSep CD4+ T cell enrichment kit | Stem Cell Technologies, Vancouver, BC Canada |
| RosetteSep Human NK cell enrichment | Stem Cell Technologies, Vancouver, BC Canada |
| RPMI-1640 | Life Technologies, Carlsbad, CA |
| ViCell counter | Beckman Coulter, Indianapolis, IN |
| Whole blood, sodium heparin anti-coagulated | MedImmune Blood Donor Program, MedImmune, Gaithersburg, MD |

Therapeutic antibodies can generally be classified into three categories (Jiang et al, 2011) based on their potential to elicit effector functions. Class I and Class II antibodies bind to cell-bound antigens, and Class III antibodies bind to and neutralize soluble antigens. Generally, the mechanism of action of Class I antibodies involves Fc effector functions, such as CDC and ADCC. In contrast, Fc effector functions are not expected to be part of the mechanism of action of Class II and Class III antibodies. OX40L IgG4P Fusion Protein is a human OX40 ligand IgG4P fusion protein that specifically binds to OX40, a cell surface-associated protein. IgG4P-containing molecules demonstrate relatively low affinity interactions with Fc gamma receptors and lack effector functions (Jiang et al, 2011). Thus, OX40L IgG4P Fusion Protein is classified as a Class II antibody, and is not expected to trigger measurable effector function. As part of this study, the lack of effector function of OX40L IgG4P Fusion Protein was confirmed in ADCC assays and a C1q binding assay.

The potential for OX40L IgG4P Fusion Protein-mediated ADCC was evaluated using enriched primary activated human NK cells as effector cells and activated human $CD4^+$ cells that express high levels of OX40 as target cells. The ADCC activity of OX40L IgG4P Fusion Protein and the OX40L fusion protein IgG1 was evaluated; anti-CD20 antibody (rituximab) was used as a positive control antibody. OX40L fusion protein IgG1 demonstrated concentration-dependent ADCC activity (FIGS. 14A and C; FIG. 15). In contrast, and as expected based on the IgG4P Fc domain, OX40L IgG4P Fusion Protein did not have any detectable ADCC (FIGS. 14A and C; FIG. 15). In addition, the F180A mutant versions of each OX40L fusion protein IgG1 and IgG4P did not have any detectable ADCC activity (FIGS. 14A and C; FIG. 15) confirming that ADCC activity was dependent on fusion protein engagement with OX40 on the target cells. A positive-control antibody against human CD20 also demonstrated ADCC (FIGS. 14B and D); this supports the validity of the assay. Collectively, the results of these experiments confirmed that OX40L IgG4P Fusion Protein does not trigger ADCC against target cells expressing high levels of OX40.

The potential for OX40L IgG4P Fusion Protein to bind to the human complement component C1q was assessed using a surface plasma resonance assay. In this assay, binding to C1q was used as a surrogate for complement dependent cytotoxicity assay (Dall'Acqua, W. F., K. E. Cook, M. M. Damschroder, R. M. Woods and H Wu. 2006. J. Immunol. 177:1129-1138.).

A human IgG1 antibody was used as a positive control antibody. The control human IgG1 demonstrated a concentration-dependent ability to bind to purified human C1q protein as expected (FIG. 16). OX40L IgG4P Fusion Protein did not have any detectable binding to C1q protein (FIG. 16).

Conclusions

OX40L IgG4P Fusion Protein does not bind to C1q or trigger ADCC against activated CD4$^+$ T cells that express high levels of OX40.

Example 8

Activity of OX40L IgG4P Fusion Protein in Mouse Models of Human Cancers

This example tests whether OX40L IgG4P Fusion Protein can be effective as a single-agent therapy for the treatment of cancers and if T cells contribute to the in vivo anticancer activity of OX40L IgG4P Fusion Protein. This study was conducted in xenograft models of human cancers in immunocompromised NOD/SCID (non-obese diabetic/severe combined immunodeficient, Table 8-1) mice.

Test Animals

TABLE 8-1

Test Animals

| | |
|---|---|
| Species | Mouse |
| Strain | NOD/SCID |
| Source | Harlan Laboratories, Inc., Indianapolis, IN |
| Total number (include number/sex if applicable) | 78/F |
| Age at start of study | 5 to 9 weeks |

Housing

The animals were humanely treated and housed according to Institutional Animal Care and Use Committee approved protocols in the Laboratory Animal Resources facility at MedImmune, an Association for Animal Accreditation of Laboratory Animal Care and United States Department of Agriculture-licensed facility. The animals were kept in sterile micro-isolator units, provided with sterile bedding and food, and acidified drinking water ad libitum. Environmental conditions were standardized (room temperature: 20° C.±1° C.; relative humidity: 50%±10%; 12-hour light-dark cycle). The animals were monitored daily for adverse clinical signs and weekly for body weight. Body weights were not collected weekly for the experiment testing the activity of OX40L IgG4P Fusion Protein with and without the presence of T cells. If hind limb paralysis, respiratory distress, 20% body weight loss, or tumor volume greater than 2000 mm$^3$ were noted, the animals were immediately sacrificed humanely by asphyxiation with CO$_2$.

Establishment of Xenografts

Human Cell Line Used in the Study

TABLE 8-2

Description of Cell Line: A375

| | |
|---|---|
| Cell line | A375 |
| Tissue origin | Human melanoma cell line |
| Source | ATCC, Manassas, VA |
| Growth media | DMEM, 10% FCS |
| Growth conditions | 37° C., 5% CO$_2$, humidified incubator |

DMEM = Dulbecco's modified Eagle medium;
FCS = fetal calf serum

Preparation of Cells for Implantation

Human cancerous A375 cells were harvested from cell cultures, washed once with and resuspended in phosphate buffered saline (PBS). A375 cells were subsequently mixed with CD4$^+$ and CD8$^+$ T cell lines alloreactive to A375 tumor cell lines before implanted into animals.

To generate CD4$^+$ and CD8$^+$ T cell lines, human peripheral blood mononuclear cells (PBMCs) from healthy donors were enriched for CD4$^+$ or CD8$^+$ T cells by the addition of 1 mL RosetteSep T cell enrichment product per 20 mL of whole blood. This was followed by a 20-minute incubation and subsequent isolation by density gradient centrifugation using RosetteSep DM-L density medium. After centrifugation, the cells were washed 3-times with PBS supplemented with 2% fetal bovine serum (FBS) and resuspended in RPMI1640 medium supplemented with 10% FBS. Enriched CD4$^+$ and CD8$^+$ T cells were cultured separately for 7 to 10 days in medium supplemented with recombinant human interleukin 2 (rhIL-2) and each combined with mitomyosin C-treated A375 cells. T cells were collected and separately cultured again for 7 to 10 days in medium supplemented with rhIL-2 and combined with mitomyosin C-treated A375 cells. CD4$^+$ and CD8$^+$ T cells were collected and combined at a 2:1 ratio.

A375 cells and PBMCs enriched for CD4$^+$ and CD8$^+$ T cells were mixed at a ratio of 6 A375 cells to 1 T cell immediately before implantation.

Implantation of Xenografts

Xenografts were established by subcutaneous (SC) injection of 3.5×10$^6$ cells (A375 cells mixed with human T cells at an effector-to-target [E:T] ratio of 1:6 and suspended in 200 μL of PBS) into the right flanks of the animals.

Randomization, Group Designation and Dose Levels

Six animals were randomly assigned to each experimental group prior to SC injection of cells. There were no animal substitutions. Group designations and dose levels for each experiment are listed in Table 8-3 and Table 8-4. Test and control articles were administered intraperitoneally (IP) in a total volume of 200 μL. The first dose of test and control articles was administered on Day 3 or 4 after implantation of cancerous/effector T cells. The animals received up to 3 additional doses of the test and control articles on days listed in the figure legends FIGS. 17 and 18. The formation of tumors was observed in each animal 1- or 2-times a week. The primary activated endpoint in this study was either a tumor volume of 2000 mm$^3$ or gross tumor necrosis.

Tumor Measurements

Tumors were measured by caliper and tumor volumes (V) were calculated using the following formula:

$$\text{tumor volume} = [\text{length (mm)} \times \text{width (mm)}^2]/2$$

For each group, the results are reported as the arithmetic mean.

Anticancer effects were expressed as percent tumor growth inhibition (% TGI), which was calculated as follows:

$$\% \text{ TGI} = (1 - [\text{mean tumor } V \text{ of treatment group}] \div [\text{mean tumor } V \text{ of control group}]) \times 100.$$

Statistical Methods

A comparison between OX40L IgG4P Fusion Protein-treated and isotype control-treated animals was made, and intergroup differences were analyzed for statistical significance by a Mann-Whitney rank sum test.

Significant p-values obtained from the Mann-Whitney rank sum test are presented in the summary tables and figures adjacent to the arithmetic mean and standard deviation of the mean.

Materials used in this study, and their source, are listed in Table 8-5.

TABLE 8-5

Materials

| Item | Source |
| --- | --- |
| DMEM medium | Invitrogen, Carlsbad, CA |
| FBS | Invitrogen, Carlsbad, CA |
| Lymphocyte separation medium | VWR, West Chester, PA |
| PBS | Invitrogen, Carlsbad, CA |
| RPMI 1640 | Invitrogen, Carlsbad, CA |
| RosetteSep CD4+ T cell enrichment kit | Stem Cell Technologies, Vancouver, BC, Canada |
| RosetteSep CD8+ T cell enrichment kit | Stem Cell Technologies, Vancouver, BC, Canada |
| RosetteSep DML media | Stem Cell Technologies, Vancouver, BC, Canada |
| Mitomycin C | Sigma-Aldrich, St. Louis, MO |

The activity of OX40L IgG4P Fusion Protein on growth of tumors in mouse models of human cancer was investigated in this study. Immunodeficient NOD/SCID female animals were implanted with human cancerous cell lines mixed with alloreactive human CD4+ and CD8+ T cell lines. CD4+ and CD8+ T cells were derived from PBMCs isolated from healthy human donors. Animals received the first dose of the test and control articles three or four days after implantation of xenografts, and were administered additional doses of the test and control articles as indicated.

OX40L IgG4P Fusion Protein significantly inhibited growth of A375 cells by up to 74% as compared to the isotype-control group (Table 8-3, Table 8-4, FIG. 17 and FIG. 18). Antitumor activity of OX40L IgG4P Fusion Protein was dependent on the addition of the alloreactive human T cells (Table 8-4 and FIG. 18). OX40L IgG4P Fusion Protein inhibited growth of A375 cells in the presence of human T cells, but not when T cells were absent.

TABLE 8-3

Treatment Groups and Percent TGI in A375 Xenograft Model on Day 28

| Group [a] | Test Article | Dose [b] (mg/kg) | % TGI [c] |
| --- | --- | --- | --- |
| 1 | None; no T cells | NA | NA |
| 2 | None | NA | NA |
| 3 | Isotype control | 3 | NA |
| 4 | OX40L IgG4P Fusion Protein | 3 | 74 |
| 5 | OX40L IgG4P Fusion Protein | 1 | 71 |
| 6 | OX40L IgG4P Fusion Protein | 0.3 | 61 |
| 7 | OX40L IgG4P Fusion Protein | 0.1 | 56 |

TGI = tumor growth inhibition;
NA = not applicable;
IP = intraperitoneal;
V = volume
[a] Number of animals per group: 6.
[b] All animals received 200 μL of test article IP on Days 4, 7, 9 and 12.
[c] % TGI = [1 − (mean tumor V of treatment group) ÷ (mean tumor V of control group)] × 100

TABLE 8-4

Treatment Groups and Percent TGI in A375 Xenograft Model on Day 30

| Group [a] | Test Article | Dose [b] (mg/kg) | % TGI [c] |
| --- | --- | --- | --- |
| 1 | None; no T cells | NA | NA |
| 2 | none | NA | NA |
| 3 | Isotype control; no T cells | 3 | NA |
| 4 | Isotype control | 3 | NA |
| 5 | OX40L IgG4P Fusion Protein; no T cells | 3 | <0 |
| 6 | OX40L IgG4P Fusion Protein | 3 | 61 |

TGI = tumor growth inhibition;
NA = not applicable;
IP = intraperitoneal;
V = volume
[a] Number of animals per group: 6.
[b] All animals received 200 μL of test article IP on Days 3, 6, 8 and 10.
[c] % TGI = [1 − (mean tumor V of treatment group) ÷ (mean tumor V of control group)] × 100

OX40L IgG4P Fusion Protein demonstrated potent anti-cancer activity in mouse models of human cancer. These results provide evidence that 1) OX40L IgG4P Fusion Protein can be effective as a single-agent therapy for the treatment of patients with cancer, 2) T cells thus contribute to the anticancer activity of OX40L IgG4P Fusion Protein in vivo.

Example 9

Murine OX40 Ligand Fusion Protein Inhibits the Growth of Mouse Cancer Cell Lines in Syngeneic Models OX40L IgG4P Fusion Protein does not cross-react to mouse (m)OX40 (See Example 2); therefore, it is impossible to test its activity in immunocompetent mouse models. To more fully study the effects of OX40 agonism, a mouse OX40 ligand mouse IgG1 fusion protein (mOX40L FP) that specifically binds to and triggers signaling by the mouse OX40 receptor was produced. The DNA and amino acid sequences are presented as SEQ ID NO: 9 and SEQ ID NO: 10, respectively.

mOX40L FP was selected as a surrogate mouse OX40L FP for OX40L IgG4P Fusion Protein. This non-GLP study was conducted to evaluate the single-agent activity of mOX40L FP in four mouse models of cancer.

```
SEQ ID NO: 9: DNA Sequence of mouse construct
mIgG1mTF2mOX40L (5' to 3' Open Reading Frame)
GTGCCTAGAGATTGCGGCTGCAAGCCCTGCATCTGCACCGTGCCCGAGGT

GTCCAGCGTGTTCATCTTCCCACCCAAGCCCAAGGACGTGCTGACCATCA

CCCTGACCCCCAAAGTGACCTGCGTGGTGGTGGACATCAGCAAGGACGAC

CCCGAGGTGCAGTTCAGTTGGTTCGTGGACGACGTGGAAGTGCACACCGC

CCAGACCCAGCCCAGAGAGGAACAGTTCAACAGCACCTTCAGAAGCGTGT

CCGAGCTGCCCATCATGCACCAGGACTGGCTGAACGGCAAAGAATTCAAG

TGCAGAGTGAACAGCGCCGCCTTCCCTGCCCCCATCGAGAAAACCATCAG

CAAGACCAAGGGCAGACCCAAGGCCCCCAGGTGTACACCATCCCCCCAC

CCAAAGAACAGATGGCCAAGGACAAGGTGTCCCTGACCTGCATGATCACC

GATTTCTTCCCAGAGGACATCACCGTGGAATGGCAGTGGAACGGCCAGCC

CGCCGAGAACTACAAGAACACCCAGCCCATCATGGACACCGACGGCAGCT

ACTTCGTGTACAGCAAGCTGAACGTGCAGAAGTCCAACTGGGAGGCCGGC
```

-continued

```
AACACCTTCACCTGTAGCGTGCTGCACGAGGGCCTGCACAACCACCACAC

CGAGAAGTCCCTGAGCCACAGCCCCGGCAAGCGGCTGGACCAGGACAAGA

TCGAGGCCCTGAGCAACAAGGTGCAGCAGCTGGAACGGTCTATCGGCCTG

AAGGACCTGGCTATGGCCGACCTGGAACAGAAAGTGTCTGAGCTGGAAGT

GTCCACCAGCAGCCCCGCCAAGGACCCTCCCATCCAGAGACTGAGAGGCG

CCGTGACCAGATGCGAGGACGGCCAGCTGTTCATCAGCAGCTACAAGAAC

GAGTACCAGACCATGGAAGTGCAGAACAACAGCGTGGTCATCAAGTGCGA

CGGCCTGTACATCATCTACCTCAAGGGCAGCTTCTTCCAGGAAGTGAAGA

TCGACCTGCACTTCAGAGAGGACCACAACCCCATCAGCATCCCCATGCTG

AACGACGGCAGACGGATCGTGTTCACCGTGGTGGCTAGCCTGGCCTTCAA

GGACAAAGTGTATCTGACCGTGAACGCCCCCGACACCCTGTGCGAGCATC

TGCAGATCAACGACGGCGAGCTGATCGTGGTGCAGCTGACCCCCGGCTAC

TGTGCCCCTGAGGGCAGCTACCACAGCACCGTGAACCAGGTGCCCCTG

SEQ ID NO: 10: Amino Acid Sequence of mouse
construct mIgG1FcmTF2mOX40L (N to C terminus)
VPRDCGKPCICTVPEVSSVFIFPPKPKDVLTITLTPKVTCVVVDISKDD

PEVQFSWFVDDVEVHTAQTQPREEQFNSTFRSVSELPIMHQDWLNGKEFK

CRVNSAAFPAPIEKTISKTKGRPKAPQVYTIPPPKEQMAKDKVSLTCMIT

DFFPEDITVEWQWNGQPAENYKNTQPIMDTDGSYFVYSKLNVQKSNWEAG

NTFTCSVLHEGLHNHHTEKSLSHSPGKRLDQDKIEALSNKVQQLERSIGL

KDLAMADLEQKVSELEVSTSSPAKDPPIQRLRGAVTRCEDGQLFISSYKN

EYQTMEVQNNSVVIKCDGLYIIYLKGSFFQEVKIDLHFREDHNPISIPML

NDGRRIVFTVVASLAFKDKVYLTVNAPDTLCEHLQINDGELIVVQLTPGY

CAPEGSYHSTVNQVPL
Mouse IgG 1Fc domain
mouse TRAF2 domain (bold)
mouse OX40L RBD domain
```

Test Animals are described in Tables 9-1 and 9-2.

TABLE 9-1

Test Animals: BALB/c Mice

| | |
|---|---|
| Species | *Mus musculus* |
| Strain | BALB/c |
| Source | Harlan Laboratories, Inc., Indianapolis, IN |
| Total number (include number/sex if applicable) | 150/Female |
| Age at receipt | 6-8 weeks |
| Age at start of study | 7-9 weeks |
| Body weight range | 15.4-23.4 grams |
| Identification | Microchip transponder |

TABLE 9-2

Test Animals: C57BL/6 Mice

| | |
|---|---|
| Species | *Mus musculus* |
| Strain | C57BL/6 |
| Source | Harlan Laboratories, Inc., Indianapolis, IN |
| Total number (include number/sex if applicable) | 70/Female |
| Age at receipt | 6-8 weeks |
| Age at start of study | 7-9 weeks |
| Body weight range | 17.3-23.5 grams |
| Identification | Microchip transponder |

Housing

The animals were humanely treated and housed according to Institutional Animal Care and Use Committee approved protocols in the Laboratory Animal Resources facility at MedImmune, an Association for Animal Accreditation of Laboratory Animal Care and United States Department of Agriculture-licensed facility. The animals were kept in sterile micro-isolator units, provided with sterile bedding and food, and acidified drinking water ad libitum. Environmental conditions were standardized (room temperature: 20° C.±1° C.; relative humidity: 50%±10%; 12-hour light-dark cycle). The animals were monitored daily for adverse clinical signs and weekly for body weight. If hind limb paralysis, respiratory distress, 20% body weight loss, or tumor volume greater than 2000 $mm^3$ were noted, the animals were immediately sacrificed humanely by asphyxiation with $CO_2$.

Establishment of Syngeneic Tumors

The cell lines used in the syngeneic tumor models are described in Tables 9-3 through 9-6.

TABLE 9-3

Description of Cell Line: Renca

| | |
|---|---|
| Cell line | Renca |
| Tissue origin | Kidney, mouse |
| Source | ATCC, Manassas, VA |
| Growth media | RPMI 1640 supplemented with 10% FBS |
| Growth conditions | 37° C., 5% $CO_2$ in humidified tissue culture chamber |

TABLE 9-4

Description of Cell Line: CT26

| | |
|---|---|
| Cell line | CT26 |
| Tissue origin | Colon, mouse |
| Source | ATCC, Manassas, VA |
| Growth media | RPMI 1640 supplemented with 10% FBS |
| Cell line | CT26 |
| Growth conditions | 37° C., 5% $CO_2$ in humidified tissue culture chamber |

TABLE 9-5

Description of Cell Line: 4T1

| | |
|---|---|
| Cell line | 4T1 |
| Tissue origin | Mammary gland, mouse |
| Source | ATCC, Manassas, VA |
| Growth media | RPMI 1640 supplemented with 10% FBS |
| Growth conditions | 37° C., 5% $CO_2$ in humidified tissue culture chamber |

TABLE 9-6

Description of Cell Line: MCA205

| | |
|---|---|
| Cell line | MCA205 |
| Tissue origin | Chemically induced soft tissue sarcoma, mouse |
| Source | Providence Cancer Center, Portland, OR |

TABLE 9-6-continued

Description of Cell Line: MCA205

| | |
|---|---|
| Growth media | RPMI 1640 supplemented with 10% FBS |
| Growth conditions | 37° C., 5% $CO_2$ in humidified tissue culture chamber |

RPMI 1640 = Roswell Park Memorial Institute 1640 medium;
FBS = fetal bovine serum Implantation of Syngeneic Tumors Allografts were established by subcutaneous (SC) injection of $5.0\times10^5$ Renca cells, $5.0\times10^5$ CT26 cells or $1.0\times10^5$ 4T1 cells suspended in 0.1 mL of PBS into the right flank of 7- to 9-week-old BALB/c mice that were randomly distributed into study groups, while $2.5\times10^6$ MCA205 cells suspended in 0.1 mL of PBS were injected into the right flank of 7- to 9-week-old C57BL/6 mice.

Randomization, Group Designation and Dose Levels

BALB/c (total of 150) and C57BL/6 (total of 70) female mice were used in this study. BALB/c mice were randomly assigned into treatment groups before injection of Renca and CT26 tumor cell lines. Balb/c mice implanted with 4T1 tumor cells were randomized by body weight 3 days post implantation. C57BL/6 mice were randomly assigned after tumors grew to a mean volume of 95 mm$^3$ per cohort, 11 days after implantation. Group designations, number of animals, dose levels and dose schedule are presented in Table 9-7, Table 9-8, Table 9-9 and Table 9-10.

All treatments were administered intraperitoneally (IP) on the appropriate study days as presented in Table 9-7, Table 9-8, Table 9-9 and Table 9-10. There were no animal substitutions.

Animals from each group were sacrificed when tumor volumes reached approximately 2000 mm$^3$.

TABLE 9-7

Group Designation and Dose Levels in Study OX40-013-029 (Renca cancer cell line)

| Group | Number of animals (M/F) | Treatment | Dose schedule (study day) | Dose level (mg/kg)$^a$ | ROA |
|---|---|---|---|---|---|
| 1 | 10 (F) | None | NA | NA | IP |
| 2 | 10 (F) | Isotype control (mouse IgG1 mAb) | 4, 7 | 7.5 | IP |
| 3 | 10 (F) | mOX40L FP | 4, 7 | 7.5 | IP |
| 4 | 10 (F) | mOX40L FP | 4, 7 | 2.5 | IP |
| 5 | 10 (F) | mOX40L FP | 4, 7 | 1.0 | IP |

F = female;
M = male;
NA = not applicable because the animals were not treated;
IP = intraperitoneal;
ROA = route of administration;
mOX40L FP = murine OX40 ligand murine IgG1 fusion protein
$^a$ Dose volume: 0.2 ml

TABLE 9-8

Group Designation and Dose Levels in Study OX40-013-039 (CT26 Cancer Cell Line)

| Group | Number of animals (M/F) | Treatment | Dose schedule (study day) | Dose level (mg/kg)$^a$ | ROA |
|---|---|---|---|---|---|
| 1 | 10 (F) | None | NA | NA | IP |
| 2 | 10 (F) | Isotype control (mOX40L FP Y182A) | 4, 6 | 7.5 | IP |
| 3 | 10 (F) | mOX40L FP | 4, 6 | 7.5 | IP |
| 4 | 10 (F) | mOX40L FP | 4, 6 | 2.5 | IP |

F = female;
M = male;
NA = not applicable because the animals were not treated;
IP = intraperitoneal;
ROA = route of administration;
mOX40L FP = murine OX40 ligand murine IgG1 fusion protein;
mOX40L FP (Y182A) = point mutation in the OX40L that renders the fusion protein incapable of binding to murine OX40
$^a$ Dose volume: 0.2 ml

TABLE 9-9

Group Designation and Dose Levels in Study IMT-14-003 (4T1 Cancer Cell Line)

| Group | Number of animals (M/F) | Treatment | Dose schedule (study day) | Dose level (mg/kg)$^a$ | ROA |
|---|---|---|---|---|---|
| 1 | 12 (F) | None | NA | NA | IP |
| 2 | 12 (F) | Isotype control (NIP228 mouse IgG1) | 4, 6 | 10 | IP |
| 3 | 12 (F) | mOX40L FP | 4, 6 | 12.5 | IP |
| 4 | 12 (F) | mOX40L FP | 4, 6 | 7.5 | IP |
| 5 | 12 (F) | mOX40L FP | 4, 6 | 2.5 | IP |

F = female;
M = male;
NA = not applicable because the animals were not treated;
IP = intraperitoneal;
ROA = route of administration;
mOX40L FP = murine OX40 ligand murine IgG1 fusion protein
$^a$ Dose volume: 0.2 ml

TABLE 9-10

Group Designation and Dose Levels in Study OX40-013-065 (MCA205 Cancer Cell Line)

| Group | Number of animals (M/F) | Treatment | Dose schedule (study day) | Dose level (mg/kg)$^a$ | ROA |
|---|---|---|---|---|---|
| 1 | 14 (F) | None | NA | NA | IP |
| 2 | 14 (F) | Isotype control (mOX40L FP Y182A) | 11, 14 | 12.5 | IP |
| 3 | 14 (F) | mOX40L FP | 11, 14 | 12.5 | IP |
| 4 | 14 (F) | mOX40L FP | 11, 14 | 7.5 | IP |
| 5 | 14 (F) | mOX40L FP | 11, 14 | 2.5 | IP |

F = female;
M = male;
IP = intraperitoneal;
ROA = route of administration;
mOX40L FP = murine OX40 ligand murine IgG1 fusion protein;
mOX40L FP (Y182A) = point mutation in the OX40L that renders the fusion protein incapable of binding to murine OX40
$^a$ Dose volume: 0.2 ml Tumor Measurements Tumors were measured by caliper and tumor volumes were calculated using the following formula:

$$\text{tumor volume} = [\text{length (mm)} \times \text{width (mm)}^2]/2$$

where length was defined as the larger side and width as the smaller side perpendicular to the length.

Antitumor effects of each group were expressed as tumor growth inhibition (TGI), which was calculated as follows:

percent TGI=$(1-T/C) \times 100$ where T=final tumor volumes from a treated group after the last dose and C=final tumor volumes from the control group after the last dose.

Tumor growth responses were categorized as a complete response (CR) if there was no measureable tumor.

Statistical Methods

One-way ANOVA was used to determine mean tumor volume differences. In the event of a significant F test a Dunnett's or Sidak's multiple comparison test was utilized (where appropriate). Where applicable, a log 10 transformation was applied to tumor volumes to account for heteroscedasticity. A p value <0.05 was considered significant.

Materials used in this study, and their source, are listed in Table 9-11.

TABLE 9-11

Materials

| Item | Source |
| --- | --- |
| Phosphate buffered saline, pH 7.2 | Life Technologies, Carlsbad, CA |
| Fetal bovine serum, heat inactivated | Life Technologies, Carlsbad, CA |
| Roswell Park Memorial Institute 1640 medium | Life Technologies, Carlsbad, CA |
| 0.25% Trypsin-EDTA (1X) | Life Technologies, Carlsbad, CA |

Treatment of mice with the murine OX40 ligand fusion protein IgG1 (mOX40L FP) results in significantly reduced growth of Renca, CT26, 4T1 and MCA205 tumor cells compared to isotype control (Table 9-7, Table 9-8, Table 9-9 and Table 9-10, FIG. 19, FIG. 20, FIG. 21 and FIG. 22).

Mixed response is often shown in syngeneic models. The response of the treatment with mOX40L FP is clearer from the individual animal tumor growth graphs (panel B in FIG. 19, FIG. 20, FIG. 12-3 and FIG. 21). Untreated and isotype control treated animals were euthanized by day 25 (FIG. 19, FIG. 21), day 42 (FIG. 22) or day 43 (FIG. 20) due to large tumor size. A dose-response was observed in mice treated with mOX40L FP based on tumor growth inhibition (Table 9-12, FIG. 19) or the number of animals with complete responses (Table 9-13, Table 9-14 and Table 9-15).

TABLE 9-12

Treatment Groups and Percent TGI on Day 26 and Number of Complete Responders in Renca Syngeneic Model

| Group [a] | Test/Control Article | Dose [b] (mg/kg) | % TGI [c] | Number of Complete Responders out of 10 mice [d] |
| --- | --- | --- | --- | --- |
| 1 | None | NA | NA | 0 |
| 2 | Isotype control | 7.5 mg/kg | NA | 0 |
| 3 | mOX40L FP | 7.5 mg/kg | 92 | 0 |
| 4 | mOX40L FP | 2.5 mg/kg | 73 | 0 |
| 5 | mOX40L FP | 1.0 mg/kg | 24 | 0 |

TGI = tumor growth inhibition;
NA = not applicable;
IP = intraperitoneal;
V = volume
[a] Number of animals per group: 10.
[b] All animals received 200 μL of test article IP on Days 4 and 7.
[c] % TGI = [1 − (mean tumor V of treatment group) ÷ (mean tumor V of control group)] × 100
[d] Number of animals in a group with a tumor volume measurement recorded as zero at the end of the study.

TABLE 9-13

Treatment Groups and Percent TGI on Day 22 and Number of Complete Responders in CT26 Syngeneic Model

| Group [a] | Test/Control Article | Dose [b] (mg/kg) | % TGI [c] | Number of Complete Responders out of 10 mice [d] |
| --- | --- | --- | --- | --- |
| 1 | None | NA | NA | 0 |
| 2 | Isotype control | 7.5 mg/kg | NA | 0 |
| 3 | mOX40L FP | 7.5 mg/kg | 88 | 8 |
| 4 | mOX40L FP | 2.5 mg/kg | 72 | 5 |

TGI = tumor growth inhibition;
NA = not applicable;
IP = intraperitoneal;
V = volume
[a] Number of animals per group: 10.
[b] All animals received 200 μL of test article IP on Days 4 and 7.
[c] % TGI = [1 − (mean tumor V of treatment group) ÷ (mean tumor V of control group)] × 100
[d] Number of animals in a group with a tumor volume measurement recorded as zero by the end of the study.

TABLE 9-14

Treatment Groups and Percent TGI on Day 25 and Number of Complete Responders in 4T1 Syngeneic Model

| Group [a] | Test/Control Article | Dose [b] (mg/kg) | % TGI [c] | Number of Complete Responders out of 12 mice [d] |
| --- | --- | --- | --- | --- |
| 1 | None | NA | NA | 0 |
| 2 | Isotype control | 10 mg/kg | NA | 0 |
| 3 | mOX40L FP | 12.5 mg/kg | 60 | 2 |
| 4 | mOX40L FP | 7.5 mg/kg | 62 | 1 |
| 5 | mOX40L FP | 2.5 mg/kg | 37 | 1 |

TGI = tumor growth inhibition;
NA = not applicable;
IP = intraperitoneal;
V = volume
[a] Number of animals per group: 12.
[b] All animals received 200 μL of test article IP on Days 4 and 7.
[c] % TGI = [1 − (mean tumor V of treatment group) ÷ (mean tumor V of control group)] × 100
[d] Number of animals in a group with a tumor volume measurement recorded as zero at the end of the study.

TABLE 9-15

Treatment Groups, Percent TGI and Number of Complete Responders in MCA205 Syngeneic Model on Day 22

| Group [a] | Test/Control Article | Dose [b] (mg/kg) | % TGI [c] | Number of Complete Responders out of 14 mice [d] |
| --- | --- | --- | --- | --- |
| 1 | None | NA | NA | 0 |
| 2 | Isotype control | 12.5 mg/kg | NA | 0 |
| 3 | mOX40L FP | 12.5 mg/kg | 62 | 6 |
| 4 | mOX40L FP | 7.5 mg/kg | 67 | 4 |
| 5 | mOX40L FP | 2.5 mg/kg | 54 | 1 |

TGI = tumor growth inhibition;
NA = not applicable;
IP = intraperitoneal;
V = volume
[a] Number of animals per group: 14.
[b] All animals received 200 μL of test article IP on Days 4 and 7.
[c] % TGI = [1 − (mean tumor V of treatment group) ÷ (mean tumor V of control group)] × 100
[d] Number of animals in a group with a tumor volume measurement recorded as zero at the end of the study.

Conclusions

Single-agent treatment of tumor-bearing mice with mOX40L FP resulted in a dose-dependent anti-tumor activity that significantly reduced growth of four different tumors as compared to untreated and isotype control treated groups.

Example 10

Response to OX40L IgG4P Fusion Protein in a Non-Human Primate Vaccination Model

In this example, the in vivo activity of OX40 agonists was evaluated in a non-human primate (NHP) vaccination model. The antigen used for this study was respiratory syncytial virus soluble F glycoprotein (RSV sF) antigen, which can induce both a T-cell response and an antibody response in cynomolgus macaques (data not shown).

An anti-human OX40 monoclonal antibody termed clone L106 has been shown to enhance both T and B cell responses in a nonhuman primate (NHP) model of simian immunodeficiency virus glycoprotein 130 (SIV gp1340) vaccination (Weinberg, A D et al, *J Immunother* 29:575-585 (2006)). In Phase 1 human clinical trials in patients with cancer, MEDI6469, a mouse anti-human OX40 monoclonal antibody also known as clone 9B 12, was shown to stimulate T-cell proliferative responses to co-administered antigen (both a recall response to tetanus toxoid and a de novo response to Keyhole limpet hemocyanin), with tumor regression occurring in some patients (Curti B D et al., *Cancer Res* 73:7189-98 (2013)).

Materials and Methods

Table 10-1 describes the group designations and dosing regimens. Two female and two male experimentally naïve Chinese cynomolgus monkeys were utilized in this study. Animals were randomized and assigned to groups. The animals were approximately 2.3 to 5.5 years of age at the time of dosing with body weights ranging from 2.5 to 3.5 kg. Animals were socialized during the study.

Isolation of Cynomolgus Monkey Peripheral Blood Mononuclear Cells from Whole Blood Peripheral blood mononuclear cells (PBMC) were isolated over a Percoll gradient. Briefly, whole blood (approximately 15 mL) was overlayed onto 30 mL of 60% Percoll working solution in a 50-mL conical tube and centrifuged at room temperature (RT) for 20 minutes at 1100×g. The PBMCs were harvested from the Percoll interface, transferred to a new conical tube and washed with 1× phosphate-buffered saline (PBS), pelleted and resuspended in 2 mL ammonium-chloride-potassium lysis buffer at RT to lyse the red blood cells. The PBMC were washed with 1×PBS then pelleted and resuspended in 25 mL of 1×PBS for counting on the Guava easyCyte-HT instrument (Millipore; Billerica, Mass.). The total viable PBMC count was attained using a 1:20 dilution into the ViaCount reagent. Before centrifuging, the PBMC sample from each animal was split into two tubes: one for the ELISpot assay and one for the Ki67 assays, because each assay type requires a different cell concentration. After centrifugation, the ELISpot PBMCs were resuspended at $2 \times 10^6$ PBMC/mL in CTL-test media (with L-glutamine) and the Ki67 PBMCs were resuspended at $5 \times 10^6$ PBMC/mL in media.

Intracellular Ki67 Staining Assay

Ki67 is an intracellular (nuclear) marker for proliferation that allows simultaneous evaluation of cell proliferation in multiple immune subsets in whole blood or purified PBMCs. Ki67 proliferation is an established pharmacodynamic marker for measuring in vivo activity of OX40 agonists in CD4+ and CD8+ memory T cells (Curti B D, et al. *Cancer Res.* 73:7189-98 (2013)).

All monkeys were evaluated for Ki67 levels in central memory (cM) CD4+T cells, effector memory (eM) CD8+T cells, NK cells, and B cells on Days −7, 42, and 56 using purified PBMCs and on Days 28, 35, and 38 using whole blood. An aliquot of 100 μL of whole blood or PBMCs ($10^6$ cells/well) was pipetted into multiple wells of a 96-well v-bottom plate, one well per immuno-phenotyping panel (i.e., one for memory T cells, one for NK cells, and one for

TABLE 10-1

Treatment Groups and Dosing Regimens

| Group No. | Group Name | Antigen Prime (Day 0) Dose/Route | Antigen Boost (Day 29) Dose/Route | OX40 Agonist Day 29/Route | OX40 Agonist/ Day 31/Route | OX40 Agonist/ Day 33/Route |
|---|---|---|---|---|---|---|
| 1 | RSV sF + mIgG1 Isotype | 100 μg RSV sF/IM | 100 μg RSV sF/IM | 5 mg/kg mIgG1 isotype control/IV | NA | NA |
| 2 | RSV sF + MEDI6469 | 100 μg RSV sF/IM | 100 μg RSV sF/IM | 5 mg/kg MEDI6469/ IV | NA | NA |
| 3 | PBS | PBS/IM | PBS/IM | PBS/IV | NA | NA |
| 4 | RSV sF + OX40L IgG4P fusion protein (3 doses) [a] | 100 μg RSV sF/IM | 100 μg RSV sF/IM | 5 mg/kg OX40L IgG4P fusion protein/IV | 5 mg/kg OX40L IgG4P fusion protein/IV | 5 mg/kg OX40L IgG4P fusion protein/IV |
| 5 | RSV sF + OX40L IgG4P fusion protein (1 dose) | 100 μg RSV sF/IM | 100 μg RSV sF/IM | 1 mg/kg OX40L IgG4P fusion protein /IV | NA | NA |

[a] Animals dosed on Days 29, 31, and 33.

B cells). The CD4+cM subset (CD95+, CCR5−) represents the majority of CD4+ memory T cells, while the CD8+eM (CD95+, CCR5+) subset represents the majority of CD8+ memory T cells. Focusing on these subsets increased the resolution of the assay.

Immuno-phenotyping antibody cocktails for NHP memory T cells and NK cells were prepared using antibodies listed in Table 10-2. Immuno-phenotyping antibody cocktails were incubated with 100 µL of whole blood or PBMCs at RT for 20 minutes. Wells were washed twice with fluorescence-activated cell sorting (FACS) staining buffer (FSB), followed by resuspension of the cell pellet with FACS™ Lyse at RT for 10 minutes. Cell pellets were then washed with FSB and permeabilized with FACS Perm for 10 minutes at RT (twice). Following another wash of the cell pellet with FSB, 10 µL of Ki67 fluorescein isothiocyanate antibody was added to each well for 45 minutes at RT in the dark. Cell pellets were washed twice with 200 µL FSB and resuspended in 200 µL FSB. One-hundred thousand events per sample were acquired on the flow cytometer and data were analyzed using FACS Diva and FlowJo 10.6 software (Tree Star; Ashland, Oreg.).

NHP IFN-Gamma ELISpot Assay

The IFNγ ELISpot is a 96-well assay used to detect frequency of antigen-specific T cells by capturing and quantitating individual membrane spots corresponding to individual cells secreting the IFNγ cytokine. This assay is the most sensitive assay in the field for detecting antigen-specific T cells.

Anti-monkey IFNγ kits including antibody-precoated plates and detection antibodies were purchased from Mabtech (Mariemont, Ohio) and used according to manufacturer's instructions. Plates were blocked with CTL-Test media. A sample of 200,000 PBMCs per well were stimulated in triplicate with mock (CTL-Test plus dimethyl sulfoxide) or RSV F peptide pools (2 µg/mL), while 20,000 PBMCs per well were stimulated in triplicate with staphylococcal enterotoxin B (1 µg/mL) as a positive control. Plates were incubated at 37° C. for 22±2 hours then washed 10 times with PBS. Detection of IFNγ spots was accomplished by incubation with detection antibody (7-B6-1-biotin, 1:1000) for 2 hours at RT, followed by another wash and incubation with secondary detection antibody (streptavidin-ALP, 1:1000) at RT for 1 hour. The spots were then visualized with the addition of BCIP/NBT-plus substrate for 4 minutes, with plates washed well with water to stop spot development and dried overnight at RT in the dark. The next day, the spots in each well were counted using the CTL Immunospot plate reader and Immunospot 5.1 software (CTL; Cleveland, Ohio). Results were graphed using GraphPad Prism 6 (GraphPad Software; La Jolla, Calif.) as F-specific spot forming counts (SFC)/$10^6$ PBMC after subtraction of dimethyl sulfoxide wells (background).

RSV-F-Specific Serum IgG Detection Assays

For RSV-F IgG enzyme-linked immunosorbent assay (ELISA), high-binding 96-well flat-bottom plates were coated at 4° C. overnight with 0.1 µg/mL RSV sF protein. Serum samples were manually diluted 1:100 in dilution buffer (PBS-Tween 20 [PBST] supplemented with 10% superblock), then 1:3 serially diluted 7 times in 96-well sample-dilution block (0.5 mL) using a Bravo liquid handler SRT. Each sample-dilution block also included both human serum as positive control and a negative control without antiserum for measuring the assay background. After the assay plates were washed 3 times with PBST and blocked for 1 hour at RT with superblock, serum dilutions in 96-well sample-dilution blocks were transferred to 96-well assay plates and further incubated for 1 hour at RT under constant shaking. At the end of incubation, the assay plates were washed 3 times with PBST, and incubated with horseradish peroxidase-conjugated anti-monkey IgG (1:80,000) for 1 hour at RT with constant shaking. The assay plates were washed 3 times with PBST then developed in 3,3',5,5'-tetramethylbenzidine (TMB) for 8-15 minutes. Color development was terminated with 1 N HCl and wells were read at optical density $(OD)_{450}$ on a plate reader. Serum titers were quantified as the reciprocal-fold serum dilution that gave $OD_{450}$ values 4-fold above that of the mean background of each assay plate. RSV-F antigen-specific IgG ELISA titers were $\log_2$ transformed and plotted. Limit of detection (LOD) for this assay was determined to be the reciprocal of the first serum dilution performed on the serum sample, i.e. 1:100 dilution means the LOD is 100 or $\log_2$ 6.6 and the imputed LOD value for samples that are <100 is one-half the LOD, which in this example case is 50 or $\log_2$ 5.6.

RSV A2 Microneutralization Assay

Serum RSV neutralization titers were determined by an RSV A2-green fluorescent protein (GFP) microneutralization assay. Control and test sample sera were heat-inactivated at 56° C. for an hour to inactivate complement. The heat-inactivated serum control and test samples were serially diluted 3-fold, for 8 dilutions, starting at 1:5 or 1:10, using the Bravo SRT liquid handler (Agilent; Santa Clara, Calif.). RSV A2 engineered to express GFP (RSV-GFP) was added to each serum dilution and virus-only control wells at a dilution to achieve approximately 500 fluorescent foci units per well. Meanwhile, Vero cells, plated in 96-well plates to achieve a 95%-100% confluent monolayer, were prepared. The serum-virus mixture was incubated at RT for 1 hour for neutralization and then added to duplicate, twice-washed Vero cell plates using the Bravo SRT liquid handler. The infected cell plates were incubated 22-24 hours in a 37° C., 5% $CO_2$ incubator. Fluorescent foci produced by non-neutralized RSV-GFP were enumerated after plate data were acquired by the ImageXpress Micro XL automated imaging platform (Molecular Devices; Sunnyvale, Calif.). Foci counts were logged into an automated data analysis worksheet to determine the $\log_2$ 50% inhibitory concentration titer using a 2-point interpolation from data normalized to the virus control on each plate. The 2-point interpolation was calculated from the linear regression of 2 points surrounding 50% neutralization of virus. For this assay, LOD was determined to be the reciprocal of the first dilution performed on the sample, i.e. 1:10 dilution means the LOD is 10 or $\log_2$ 3.3 and the imputed LOD value for samples that are <10 is one-half the LOD, which in this example case is 5 or $\log_2$ 2.3.

Statistical Methods

Significant p-values were obtained using the mixed-effects model (Brown H and Prescott R. Applied Mixed Models in Medicine, New York, N.Y.: John Wiley & Sons, 1999). Significance was set at p<0.05. Values that were near significance, p-values between 0.05 and 0.1, were also reported and identified for analysis and assessment purposes. Analysis of statistical significance was performed to compare across groups and across days using the calculated GeoMeans from the 4 individual animal assay values within a particular group at a particular time point.

Materials used in this study are listed in Table 10-2.

TABLE 10-2

Materials

| Reagent Name | Supplier | Location |
|---|---|---|
| Percoll | GE Life Sciences or MPBio | Piscataway, NJ |
| CryoABC | CTL | Shaker Heights, OH |
| BD FACS Lysing Solution | BD BioSciences, | San Jose, CA |
| BD FACS Staining Buffer (FSB) | BD BioSciences, | San Jose, CA |
| Anti-Ki-67 (clone B56)-fluorescein isothiocyanate Ab | BD BioSciences, | San Jose, CA |
| CD3 Alexa 700 | BD | San Jose, CA |
| CD4 PerCPCy5.5 | BD | San Jose, CA |
| CD8 BV605 | BioLegend | San Diego, CA |
| CD20 APC-H7 | BD | San Jose, CA |
| CD28 PE | BioLegend | San Diego, CA |
| CD95 PECy7 | BioLegend | San Diego, CA |
| CD195 APC | BD | San Jose, CA |
| CD197 BV785 | BioLegend | San Diego, CA |
| CD278/ICOS BV421 | BioLegend | San Diego, CA |
| CD11c APC | BioLegend | San Diego, CA |
| CD14 PECy7 | BioLegend | San Diego, CA |
| CD16 BV785 | BioLegend | San Diego, CA |
| CD20 PerCPCy5.5 | BioLegend | San Diego, CA |
| CD56 BV421 | BioLegend | San Diego, CA |
| HLA-DR BV605 | BioLegend | San Diego, CA |
| CD159a/NKG2a PE | Beckman | Brea, CA |
| CD25 APC | BD | San Jose, CA |
| Foxp3 PE | BioLegend | San Diego, CA |
| CD28 fluorescein isothiocyanate | BD | San Jose, CA |
| CD159a APC | Beckman | Brea, CA |
| OX40/CD134 PE | BD | San Jose, CA |
| ELISpot PLUS for NHP IFNγ | Mabtech | Cincinnati, OH |
| CTL Test Media (500 mL) | CTL | Shaker Heights, OH |
| CTL Wash Media (10×) | CTL | Shaker Heights, OH |
| Benzonase Nuclease | EMD | Billerica, MA |
| ViaCount Reagent | Millipore | Billerica, MA |
| Guava EasyCheck Beads | Millipore | Billerica, MA |
| RSV Fpp | JPT Peptides | Berlin, Germany |
| CEFpp | CTL | Shaker Heights, OH |
| Staphylococcal Enterotoxin B (SEB) | EMD | Billerica, MA |
| Goat-anti-monkey IgG-HRP | Thermo Scientific, | Rockford, IL |
| Superblock | Thermo Scientific, | Rockford, IL |
| TMB (3,3',5,5'-tetramethylbenzidene; SeeBlue Reserve) | KPL, | Gaithersburg, MD |
| Control human serum for RSV F ELISA | Innovative Research | Novi, MI |
| RSV sF protein | MedImmune | Gaithersburg, MD |
| Human Pooled Sera | Innovative Research | Novi, MI |
| RSV A2-GFP (Lot 87429-10) | MedImmune | Santa Clara, CA |

Results
Intracellular Ki67 Levels
Ki67 in CD4+cM T-Cells

Table 10-3 summarizes the CD4+cM T-cell proliferation results (percentage Ki67 induction). The optimal time point (based on peak Ki67 levels) for assessing CD4+cM T-cell proliferation is usually between Day 35 to 42.

Monkeys given 3 doses of OX40L IgG4P fusion protein on Days 29, 31, and 33 (Group 10) had the strongest enhancement in CD4+cM T-cell proliferation at Day 42, significantly greater than any other group. The increase in percentage Ki67 stimulation was highly significant compared with baseline at Day 28 (p=0.0003), and elicited CD4+cM T-cell proliferation of over 70% at Days 35 and 42. By Day 56, CD4+cM T-cell proliferation elicited by OX40L IgG4P fusion protein returned almost to baseline. Whereas animals in Group 4 were administered 3 doses of OX40L IgG4P fusion protein at 5 mg/kg, animals in Group 5 were administered OX40L IgG4P fusion protein in a single 1 mg/kg dose. The response elicited by one dose of OX40L IgG4P fusion protein was comparable to that elicited by the 3-dose OX40L IgG4P fusion protein regimen and was significantly stronger than those of the PBS or mIgG1 isotype control groups, indicating that OX40L IgG4P fusion protein can achieve significant OX40 agonism in the cynomolgus monkey following a single dose.

MEDI6469 showed no significant activity in the CD4+cM T-cell proliferation assay compared to PBS control group (see Table 10-3).

TABLE 10-3

Summary of CD4+ cM T-Cell Proliferation Results

| | | Mean % Ki67+ (n = 4/group) | | | |
|---|---|---|---|---|---|
| Group No. | Group Name | Day 28 (Baseline) | Day 35 | Day 42 | Day 56 |
| 1 | RSV sF + mIgG1 Isotype | 25.1 | 27.6 | 27.8 | 28.4 |
| 2 | RSV sF + MEDI6469 | 23.1 | 30.8 | 25.6 | 19.8 |
| 3 | PBS | 14.0 | 26.1 | 30.7 [a] | 32.0 |
| 4 | RSV sF + OX40L IgG4P fusion protein (3 doses) | 16.0 | 71.3 | 78.5 [a, b] | 30.1 |
| 5 | RSV sF + OX40L IgG4P fusion protein (1 dose) | 15.4 | 61.9 | 54.9 [a, b] | 22.8 |

Statistical significance for group changes from baseline and group-to-group comparisons was determined using the Day 42 time point.
[a] $p < 0.05$ vs. Day 28 (Baseline).
[b] $p < 0.05$ Test Group vs. Group 1.
Ki67 in CD8+ eM T Cells Table 10-4 summarizes the CD8+eM T-cell proliferation results (percentage Ki67 induction). CD8+eM T-cell proliferation was optimal at Day 42. OX40L IgG4P fusion protein showed the strongest CD8+eM T-cell proliferation response at Day 42 compared with baseline (p=0.0095). MEDI6469 also induced strong CD8+eM T-cell proliferation by Day 42 compared with baseline (p=0.007) and the isotype control, mIgG1 (p=0.015). The peak magnitude of CD8+eM T-cell proliferative response, observed for OX40L IgG4P fusion protein (3 doses), was over 50% (% Ki67+ cells among CD8+eM T cells). OX40L IgG4P fusion protein and MEDI6469 were the only OX40 agonists whose activity reached significance compared with the PBS and mIgG1 isotype control groups in CD8+eM T-cell proliferation.

TABLE 10-4

Summary of CD8+ eM T-cell Proliferation Results

| | | Mean % Ki67+ (n = 4) | | | |
|---|---|---|---|---|---|
| Group No. | Group Name | Day 28 (Baseline) | Day 35 | Day 42 | Day 56 |
| 1 | RSV sF + mIgG1 Isotype | 27.1 | 13.0 | 17.2 | 18.9 |
| 2 | RSV sF + MEDI6469 (CHO material/no delay) | 18.7 | 20.9 | 49.8 [a, b] | 11.8 |

TABLE 10-4-continued

Summary of CD8+ eM T-cell Proliferation Results

| Group No. | Group Name | Mean % Ki67+ (n = 4) | | | |
|---|---|---|---|---|---|
| | | Day 28 (Baseline) | Day 35 | Day 42 | Day 56 |
| 3 | PBS | 11.0 | 19.7 | 25.0 [c, d] | 24.7 |
| 4 | RSV sF + OX40L IgG4P fusion protein (3 doses) | 12.6 | 28.8 | 55.1 [a, b] | 19.0 |
| 5 | RSV sF + OX40L IgG4P fusion protein (1 dose) | 14.0 | 20.9 | 31.7 [a, d] | 16.4 |

Statistical significance for group changes from baseline and group-to-group comparisons was determined using the Day 42 time point.
[a] $p < 0.05$ vs. Day 28 (Baseline).
[b] $p < 0.05$ Test Group vs. Group 1.
[c] $p < 0.1$ vs. Day 28 (Baseline).
[d] $p < 0.1$ Test Group vs, Group 1.
Ki67 in NK Cells Table 10-5 summarizes the NK cell proliferation results (percentage of Ki67+NK cells). OX40 is reported to be expressed on NK cells at low levels (Croft M, et al. *Immunol Rev.* 229:173-91 (2009)), so NK cells can be direct targets of OX40 agonism or can be influenced by interactions with T cells. OX40L IgG4P fusion protein elicited the highest NK cell proliferation response at Day 42 of all the groups tested; the response was significant compared with PBS control ($p=0.020$) and mIgG1 isotype control ($p=0.032$), and was similar to MEDI6469 ($p=0.74$). The single 1 mg/kg dose of OX40L IgG4P fusion protein was similar to the 3-dose (5 mg/kg) regimen ($p=0.48$). MEDI6469 enhanced NK cell proliferation by Day 42, which was significantly higher than the PBS control ($p=0.0083$) and mIgG1 isotype control ($p=0.042$) groups.

TABLE 10-5

Summary of NK Cell Proliferation Results

| Group No. | Group Name | Mean % Ki67+ (n = 4) | | | |
|---|---|---|---|---|---|
| | | Day 28 (Baseline) | Day 35 | Day 42 | Day 56 |
| 1 | RSV sF + mIgG1 Isotype | 27.7 | 9.3 | 25.0 | 27.5 |
| 2 | RSV sF + MEDI6469 | 20.0 | 31.3 | 64.8 [a, b] | 11.8 |
| 3 | PBS | 15.4 | 21.9 | 26.8 [a] | 26.5 |
| 4 | RSV sF + OX40L IgG4P fusion protein (3 doses) | 15.6 | 33.8 | 63.3 [a, b] | 7.4 |
| 5 | RSV sF + OX40L IgG4P fusion protein (1 dose) | 10.8 | 26.0 | 49.5 [a, d] | 17.7 |

Statistical significance for group changes from baseline and group-to-group comparisons was determined using the Day 42 time point.
[a] $p < 0.05$ vs. Day 28 (Baseline).
[b] $p < 0.05$ Test Group vs. Group 1.
[c] $p < 0.1$ vs. Day 28 (Baseline).
[d] $p < 0.1$ Test Group vs. Group 1.
Ki67 in B Cells Table 10-6 summarizes the B-cell proliferation results (percentage Ki67+B cells). B cells are not known to express OX40, but they can be influenced by interactions with activated T cells. Significant B-cell proliferation was observed by Day 42 compared with baseline ($p<0.05$) with the 3-dose OX40L IgG4P fusion protein regimen and the 1-dose OX40L IgG4P fusion protein regimen. In the 3-dose OX40L IgG4P fusion protein regimen, a difference from baseline was observed, but possibly due to missing baseline values for 2 animals and a small sample size, the result was not statistically significant. The PBS control group also showed increases in B-cell proliferation that were significantly different from baseline ($p=0.0007$). Because of this, the only group with significantly higher B-cell proliferation than the PBS control group was the 1-dose OX40L IgG4P fusion protein group ($p=0.0316$). The only group showing significant B-cell proliferation increases over the mIgG1 isotype control group was the 1-dose OX40L IgG4P fusion protein regimen. The 1-dose OX40L IgG4P fusion protein regimen was similar to the 3-dose OX40L IgG4P fusion protein regimen.

TABLE 10-6

Summary of B-Cell Proliferation Results

| Group No. | Group Name | Mean % Ki67+ (n = 4/group) | | | |
|---|---|---|---|---|---|
| | | Day 28 (Baseline) | Day 35 | Day 42 | Day 56 |
| 1 | RSV sF + mIgG1 Isotype | 21.1 | 15.1 | 28.2 | 31.0 |
| 2 | RSV sF + MEDI6469 | 21.2 | 33.7 | 40.9 [a] | 17.2 |
| 3 | PBS | 12.7 | 21.2 | 34.1 [a] | 30.5 |
| 4 | RSV sF + OX40L IgG4P fusion protein (3 doses) | 15.8 | 30.6 | 53.1 [e] | 22.8 |
| 5 | RSV sF + OX40L IgG4P fusion protein (1 dose) | 10.7 | 24.8 | 55.5 [a, b] | 20.2 |

Statistical significance for group changes from baseline and group-to-group comparisons was determined using the Day 42 time point.
[a] $p < 0.05$ vs. Day 28 (Baseline).
[b] $p < 0.05$ Test Group vs. Group 1.
[c] $p < 0.1$ vs. Day 28 (Baseline).
[d] $p < 0.1$ Test Group vs. Group 1.

RSV-F IFN-Gamma ELISpot

Table 10-7 summarizes the RSV-F-specific IFNγ T-cell responses as measured by ELISpot. Optimal T-cell responses to an RSV sF prime-boost vaccination regimen can be observed 14-28 days after administration of booster antigen, which correspond to Days 42-56 in this study. An animal was considered a responder if it had a response level 4 times its baseline (pre-vaccination) level and ≥50 spots/million PBMCs.

The 3-dose OX40L IgG4P fusion protein regimen demonstrated the strongest induction of RSV-F-specific T-cell response, which was detected at Days 42 and 56, with 4/4 monkeys having a positive response at each time point. Responses were significant versus baseline at Day 42 ($p=0.012$) and Day 56 ($p=0.010$) and significantly different from PBS control ($p=0.0023$) and mIgG1 isotype control ($p=0.0024$) groups. The response in the animals given 1 dose of OX40L IgG4P fusion protein was similar to the response in the animals given 3 doses of OX40L IgG4P fusion protein at Day 42 ($p=0.47$) and Day 56 ($p=0.38$).

TABLE 10-7

Summary of RSV F-specific IFN-gamma T-Cell ELISpot Results

| Group No. | Group Name | Mean No. IFNγ Spots/1 million cells (n = 4/group) | | |
|---|---|---|---|---|
| | | Day 0 (Baseline) | Day 42 | Day 56 |
| 1 | RSV sF + mIgG1 Isotype | 40 | 2 | 4 |
| 2 | RSV sF + MEDI6469 | 6 | 34 [a] | 45 [b, c] |
| 3 | PBS | 0 | 1 | 2 |
| 4 | RSV sF + OX40L IgG4P fusion protein (3 doses) | 1 | 281 [d, b] | 359 [d, b] |
| 5 | RSV sF + OX40L IgG4P fusion protein (1 dose) | 2 | 394 [d, b] | 402 [d, b] |

Statistical significance for group changes from baseline and group-to-group comparisons was determined using the Day 42 time point.
[a] $p < 0.1$ Test Group vs. Group 1.
[b] $p < 0.05$ Test Group vs. Group 1.
[c] $p < 0.1$ Day 28 (Baseline).
[d] $p < 0.05$ vs. Day 28 (Baseline).

At Day 42, MEDI6469 elicited a 25% response rate, which was not significantly different from the PBS control (p=0.093) or mIgG1 isotope control (p=0.066) groups. By Day 56, MEDI6469 had a 50% response rate, significantly different from the mIgG1 isotype control group (p=0.039). This response was not significantly different from MEDI6469 given without delay after antigen boost.

Anti-RSV-F IgG Titers

Table 10-8 summarizes the anti-RSV-F IgG titers. B cells can be influenced by interactions with activated T cells to make more or higher-affinity antibodies to shared antigenic targets. As shown by the Ki67 data in Table 10-6, B cells were induced to proliferate by several OX40 agonist regimens. Antigen-specific antibody titers were assessed to determine whether this proliferation translated to a functional effect. RSV-F-specific IgG levels were below assay detection limits in most (or all) animals before the first immunization at Day 0. Low levels of anti-RSV-F IgG antibodies were detected at Day 14 in all the RSV sF-immunized groups but not in the PBS control group. The peak antibody responses were observed at Day 42, 14 days after OX40 agonist administration. The mIgG1 isotype control group demonstrated increases in RSV-F IgG titers (from baseline to approximately 1:256 titer or 8 $\log_2$) following priming (Days 14 and 28), which were further increased approximately 8-fold (approximately 1:2048 titer or 11 $\log_2$) by Days 42 and 56 following the RSV-F antigen-alone boost. OX40 agonism with MEDI6469 significantly enhanced anti-RSV-F IgG antibodies compared with the mIgG1 isotype control group (p=0.050) by Day 42 (approximately 1:16,400 titer or 14 $\log_2$) with a 300-fold increase from baseline. The 3-dose OX40L IgG4P fusion protein group showed strong induction of anti-RSV-F IgG antibodies by Day 42, which were similar to MEDI6469 (p=0.33 and p=0.44, respectively). Day 56 responses were equivalent to Day 42 responses in magnitude and significance for these 2 groups. Also, the 1-dose OX40L IgG4P fusion protein group was equivalent to the 3-dose OX40L IgG4P fusion protein group at eliciting anti-RSV-F IgG antibodies (p=0.23).

TABLE 10-8

Summary of RSV F-specific IgG Titers

| Group No. | Group Name | Mean ($\log_2$ transformed reciprocal serum dilution) (n = 4/group) | | | | |
|---|---|---|---|---|---|---|
| | | Day 0 | Day 14 | Day 28 (Baseline) | Day 42 | Day 56 |
| 1 | RSV sF + mIgG1 Isotype | 5.6 | 7.6 | 7.7 | 10.7 [a] | 10.1 |
| 2 | RSV sF + MEDI6469 | 5.6 | 8.3 | 8.6 | 13.9 [a, b] | 12.3 |
| 3 | PBS | 5.6 | 5.6 | 5.9 | 5.6 [b] | 5.6 |
| 4 | RSV sF + OX40L IgG4P fusion protein (3 doses) | 5.6 | 7.8 | 8.1 | 15.3 [a, b] | 14.3 |
| 5 | RSV sF + OX40L IgG4P fusion protein (1 dose) | 5.6 | 6.7 | 7.8 | 13.7 [a, b] | 13.2 |

Statistical significance for group changes from baseline and group-to-group comparisons was determined using the Day 42 time point.
[a] $p < 0.05$ vs. Day 28 (Baseline).
[b] $p < 0.05$ Test Group vs. Group 1.

RSV Neutralizing Antibody Titers

Table 10-9 summarizes the mean (per group) RSV neutralizing titer observed in the serum of the animals. This assay is less sensitive than the RSV-F IgG assay because it only assesses antibodies that can neutralize the RSV virus. A positive neutralizing response is defined as a 4-fold rise in neutralizing antibody titer over baseline. Maximum RSV neutralizing antibodies were observed at Days 42 and 56. Maximum responses in this assay were observed with the 3-dose OX40L IgG4P fusion protein group yielding a 100% response rate (4/4 animals). The 1-dose OX40L IgG4P fusion protein group reached a 75% response rate by Day 56 with magnitudes significantly higher than its baseline and similar to 3-dose OX40L IgG4P fusion protein at Day 42 (p=0.21) and Day 56 (p=0.45). The 1-dose and 3-dose OX40L IgG4P fusion protein groups were the only groups that showed statistical significance from the PBS control group at Day 56 (p=0.029 for both groups).

TABLE 10-9

Summary of RSV A2 Neutralizing Antibody Titers

| Group No. | Group Name | Mean RSV A2 Neutralizing Antibody Titers (n = 4/group) (log$_2$ transformed reciprocal dilution) | | | |
|---|---|---|---|---|---|
| | | Day 0 | Day 28 (Baseline) | Day 42 | Day 56 |
| 1 | RSV-F + mIgG1 Isotype | 2.32 | 2.32 | 2.76 | 2.71 |
| 2 | RSV-F + MEDI6469 | 2.32 | 2.32 | 4.23 | 3.31 |
| 3 | PBS | 2.32 | 2.32 | 2.32 | 2.32 |
| 4 | RSV-F + OX40L IgG4P fusion protein (3 doses) | 2.32 | 2.32 | 5.48 [a] | 5.32 |
| 5 | RSV-F + OX40L IgG4P fusion protein (1 dose) | 2.32 | 2.32 | 3.67 [a] | 4.52 |

Statistical significance for group changes from baseline and group-to-group comparisons was determined using the Day 42 time point.
[a] $p < 0.05$ vs. Day 28 (Baseline).

Conclusions

OX40L IgG4P fusion protein induced strong responses in terms of both Ki67 proliferation levels and in RSV-F antigen specific responses. MEDI6469 was active eliciting CD8+eM T cell proliferation similar to that of OX40L IgG4P fusion protein and eliciting RSV F specific T cell and B cell responses weaker than OX40L IgG4P fusion protein. Overall, one dose of OX40L IgG4P fusion protein (at 1 mg/kg) induced similar responses in most assays evaluated to three doses (at 5 mg/kg), although the 3 dose regimen was superior in Ki67 proliferation and in eliciting RSV neutralizing antibodies. OX40L IgG4P fusion protein administered with RSV sF resulted in significant F-specific IFNγ responses compared with baseline. The results of this NHP study provide evidence that administration of an OX40 agonist to NHP can drive defined antigen specific immune responses.

Example 11

Effect of Human OX40L IgG4P Fusion Protein on Treg-Mediated Suppression of Human CD4+Effector T Cells In this Example the effect of OX40L IgG4P fusion protein on the suppressive effect of human regulatory T cells was investigated.
Materials and Methods
Isolation of Effector and Regulatory T Cells Anonymized human leukocyte cones were supplied by the National Health Service Blood Transfusion Service (NHSBT) in the United Kingdom. Human peripheral blood mononuclear cells (PBMCs) were isolated from leukocyte cones by layering blood over Ficoll-Paque Plus and centrifuging as per manufacturer's instructions (GE Healthcare, Chalfont St Giles, UK). Human CD4+ effector and regulatory T cells were isolated from PBMCs using a human T-regulatory cell isolation kit as per manufacturer's instructions (Life Technologies, Paisley, UK). Briefly, this process involves negative selection of total CD4+ cells by antibody labelling of non-CD4+ cells and their removal through use of magnetic bead based depletion. Regulatory T cells are then separated from effector CD4+ cells by labelling with anti-CD25 followed by positive selection with magnetic beads, which are subsequently removed from the isolated cells.

Round bottom 96 well tissue culture plates were coated with anti-CD3 antibody and test articles in two sequential steps. In the first, 100 μL of 0.5 μg/mL anti-CD3 antibody was added to each well and plates were incubated overnight at 4° C. Plates were then washed with PBS, 100 μL of test or control articles were added to relevant wells at the appropriate concentration and plates were incubated overnight at 4° C. Following incubation the plates were washed again with PBS before use in subsequent suppression assays.

Effector CD4+T cells were labelled with carboxyfluorescein diacetate succinimidyl ester (CFSE) using the CellTrace™ CFSE cell proliferation kit according to manufacturer's instructions (Life Technologies, Paisley, UK).

Effector CD4+T cells and regulatory T cells were co-cultured at 1:1 or 1:2 ratios in the anti-CD3 coated plates. Culture media was RPMI-1640 Glutamax-I containing 1% v/v Penicillin and Streptomycin, 5% v/v Human AB serum and 1 μg/mL anti-CD28 antibody. Culture conditions were a temperature of 37° C. and an atmosphere of 5% $CO_2$.

After 4 days of culture cells were removed from the culture plates, washed twice in PBS and stained with Fixable Viability Dye eFluor® 780 according to the manufacturer's instructions (eBiosciences, Hatfield, UK). After staining cells were washed in FACS buffer (eBioscience) and fixed by resuspension in 100 μL of CellFix™ (Becton Dickinson, Oxford, UK) followed by incubation at room temperature for 15 minutes.

Fixed cells were suspended in FACS Buffer and analyzed using a Becton Dickinson FACSCanto II flow cytometer. The percentage of divided effector T cells (CFSE low) was assessed using FlowJo software (version vX.0.7) after fluorescence compensation. Non-viable (eFluor positive) cells and regulatory T cells (CFSE negative) were discriminated, and excluded from the analysis.

Graphical representation of the data, including determination of mean values and standard error of the mean, was generated using GraphPad Prism version 6.0 for Windows.

Materials used in this example are listed in Table 11-1.

TABLE 11-1

| Materials | |
|---|---|
| Item | Source |
| Leukocyte Cones | NHS Blood and Transplant Service, Watford, UK |
| Ficoll Paque Plus | GE Healthcare, Chalfont St Giles, UK |
| RPMI-1640 Glutamax-I | Life Technologies, Paisley, UK |
| Human AB serum | Life Technologies, Paisley, UK |
| Penicillin and Streptomycin | Life Technologies, Paisley, UK |
| 96-well U-bottomed culture plate | Corning B.V. Life Sciences, Amsterdam, Netherlands |
| Anti-human CD3 clone OKT3 | eBiosciences, Hatfield, UK |
| Anti-human CD28 clone CD28.2 | eBiosciences, Hatfield, UK |
| Human T-regulatory cell isolation kit | Life Technologies, Paisley, UK |
| CellTrace ® CFSE kit | Life Technologies, Paisley, UK |
| 96 well V-bottomed plate | Greiner Bio-One GmbH, Kremsmunster, Austria |
| FACS Buffer | eBiosciences, Hatfield, UK |
| CellFix ™ | Becton Dickinson, Oxford, UK |
| Fixable Viability Dye eFluor ® 780 | eBiosciences, Hatfield, UK |

Results
Human OX40L IgG4P Fusion Protein Overcomes Regulatory T-Cell Mediated Suppression of Human Effector CD4+ T-Cell Proliferation Human effector CD4+T cells did not divide in the absence of stimulation. The addition of anti-CD3 and anti-CD28 resulted in an increase in the percentage of divided cells to 33%. Addition of OX40L IgG1 fusion protein at a concentration of 40 nM or 10 nM significantly increased the percentage of divided cells to 41% and 61%, respectively (FIG. 23). Addition of a control construct (F180A OX40L FP IgG1; this phenylalanine (F) to Alanine (A) mutation ablates OX40 receptor binding activity of the OX40L protein, see Example 1) at a concentration of 40 nM or 01 nM did not significantly increase the % of divided cells relative to anti-CD3+anti-CD28 alone (FIG. 23 "isotype control" (F180A OX40L FP IgG1)).

The addition of regulatory T cells (Tregs) at a 1:1 effector to Treg ratio reduced the percentage of divided cells to 15%. The addition of regulatory T cells (Tregs) at a 1:2 effector to Treg ratio reduced the percentage of divided cells further to 12%. The addition of the control construct (F180A OX40L FP IgG1) at 40 nM or 10 nM did not significantly impact the suppression of effector T-cell division by Tregs when present at either a 1:1 or 1:2 effector to Treg ratio. In contrast the addition of OX40L IgG1 fusion protein at 40 nM or 10 nM significantly increased the percentage of divided effector CD4+T cells, to 52% and 67% respectively, when cultured in the presence of Tregs at an effector to Treg ratio of 1:1. The addition of OX40L IgG1 fusion protein at 40 nM and 10 nM significantly increased the percentage of divided effector CD4+T cells, to 53% and 66%, when cultured in the presence of Tregs at an effector to Treg ratio of 1:2 (FIG. 23). The Effects of OX40L IgG4P Fusion Protein on Regulatory T-Cell Mediated Suppression of Effector CD4+T-Cell Proliferation are Concentration Dependent In a subsequent assay, the concentration dependence of the OX40L IgG4P fusion protein mediated effects described above was assessed. In this assay the addition of anti-CD3 and anti-CD28 resulted in 3.4% divided CD4+ effector cells. This was increased by the addition of OX40L IgG4P fusion protein but these increases did not reach statistical significance except at 2.5 nM at which OX40L IgG4P fusion protein, increased the percentage of divided effector cells to 17% (FIG. 24).

The addition of Tregs at a 1:1 ratio reduced the percentage of divided effector T cells to 2.5%. The addition of OX40L fusion protein IgG4-FPat 40 nM and 2.5 nM, but not at 10 nM and 0.62 nM, significantly increased the percentage of dividing effector CD4+T cells to 6.7% and 24% respectively (FIG. 24).

Addition of control article (NIP228 IgG4P (see Table 1-1)) at a concentration of 40 nM did not significantly increase the % of divided CD4+ effector cells when cultured alone or in the presence of Tregs (FIG. 24).

Conclusions

OX40L fusion proteins can overcome the suppressive effects of Tregs cells on the proliferation of CD4+ effector T cells. The effects of OX40L fusion proteins on Treg cell mediated suppression are concentration dependent and require at least 2.5 nM of OX40L fusion protein.

Example 12

Pharmacodynamics of OX40 Agonists in Rhesus Monkeys

Pharmacodynamics of OX40 agonists were determined after intravenous administration to rhesus monkeys. Values were based on proliferation of peripheral blood T, B and NK cells (as changes in cell surface immunomodulatory proteins and intracellular Ki-67 on immune cells) following dosing with MEDI6469 (9B12 antibody) or OX40L fusion protein IgG4-FP. The expression Ki-67 as a marker of cell proliferation, as well as immunomodulatory proteins such as PD-1 and ICOS were examined on these cell populations. An additional group received saline as a control.

The study design was as follows (see also, FIG. 25):

TABLE 12-1

| Study Design and Groups | | | | | | |
|---|---|---|---|---|---|---|
| Study Groups | Dose (mg/kg) | Test Item | Route | No. of Doses | Dosing Days | No. of Animals |
| A | 0 | PBS | IV | 3 | 0, 2, 4 | 5 |
| B | 5 | 9B12 | IV | 1 | 0 | 5 |
| F | 1 | OX40L fusion protein IgG4-FP | IV | 3 | 0, 2, 4 | 5 |

Viable single cells were analyzed by flow cytometry to determine changes in pharmacodynamics markers. Total memory CD4 and CD8 T cells were defined as $CD3^+$ $CD4^+$ $CD95^+$ $CD20^-$ and $CD3^+$ $CD8^+$ $CD95^+$ $CD20^-$, respectively. Central memory CD4 and CD8 T cells were defined as $CD3^+$ $CD4^+$ $CD28^+$ $CD95^+CCR5^-CCR7^+$ CD20– and $CD3^+$ $CD8^+$ $CD28^+$ $CD95^+CCR5^-CCR7^+$ CD20–, respectively. Effector memory CD4 and CD8 T cells were defined as $CD3^+$ $CD4^+$ $CD28^-$ $CD95^+CCRTCD20-$ and $CD3^+$ $CD8^+$ $CD28^-$ $CD95^+CCRTCD20-$, respectively. B cells were defined as cells that were $CD3^-$ $CD20^+$ (see Table 12-2 below).

TABLE 12-2

| Immunotyping panels | | | | | | | | | | | |
|---|---|---|---|---|---|---|---|---|---|---|---|
| Tube No. | Tube Name | PacBlue | Am Cyan | FITC | PE | (ECD) TxR | TrR | PC7 | APC | A700 | AC7 |
| 1 | T cell | CCR7 | CD4 | ki-67 | CD95 | CD28 | CD8a | | CCR5 | CD3 | CD20 |
| 3 | T PD1 | CCR7 | CD4 | ki-67 | OX40 | CD28 | PD1 | CD8a | CD95 | CD3 | CD20 |

Results for MEDI6469 and OX40L fusion protein IgG4-FP were both quantitatively and qualitatively different at the peak biological effects compared to PBS control group. MEDI6469 showed a 3.5 fold mean increase in total memory CD4 T cell proliferation relative to the PBS treated group (30% compared to 7.6%). This was reflected in a 3.0 fold increase in central memory CD4 (23% compared to 7.7%) and a 3.2 fold increase (22% compared to 6.8%) in effector memory CD4 T cells. OX40L fusion protein IgG4-FP induced a 7-fold increase in proliferation of total memory CD4+T cells (52% compared to 7.6%). The peak increase in OX40L fusion protein IgG4-FP-induced effector memory CD4 T cell proliferation (day 14) was delayed relative to that observed for total and central memory CD4 T cell proliferation (day 10). The increase in proliferation of CD8+ total memory T cells in response OX40L fusion protein IgG4-FP (19% compared to 7.6%; 2.5 fold) were similar to that observed for MEDI6469 (17% compared to 9.2%, 1.8 fold). For OX40L fusion protein IgG4-FP, the increase in total memory CD8 T cells was reflected in a 3.3 fold change in central memory CD8 T cells (29% compared to 8.9%), and a 1.9 fold change in effector memory CD8 T cells (21% compared to 11%). Similar to that observed for CD4 T cells, the peak in effector memory CD8 T cell proliferation after OX40L fusion protein IgG4-FP treatment (day 14) was delayed relative to that for total and central memory CD8 T cell proliferation (day 10). No substantial changes in naïve CD4 or CD8 T cell proliferation were observed for OX40L fusion protein IgG4-FP nor MEDI6469 (FIG. 26).

An increase of ICOS+ cells in total memory CD4 T cells corresponded qualitatively with OX40-mediated proliferation of total memory CD4 T cells for OX40L fusion protein IgG4-FP, showing a 6.4 fold increase in mean % positive cells (15% vs 2.3% for PBS group), although representing lower overall gross percentage induction on cells. A 6.0 fold increase in ICOS+ memory CD8 T cells was also observed (3.8 vs 0.64%), higher than the relative increase in CD8 memory T cell proliferation (Ki67; 2.5 fold), but at low overall total % induction. In contrast to OX40L fusion protein IgG4-FP, MEDI6469 induced a lower 2.4 fold increase for ICOS induction, similar to the 3.5 fold induction of proliferation (Ki67) on total memory CD4 T cells. No ICOS induction was observed after MEDI6469 treatment on total memory CD8 T cells, which therefore differed from the results for OX40L fusion protein IgG4-FP. Changes in the expression of ICOS on naïve CD4 or CD8 T cells were not observed for OX40L fusion protein IgG4-FP or MEDI6469 (FIG. 27).

PD-1 expression on total memory CD4 T cells after OX40L fusion protein IgG4-FP administration increased by 3.1 fold (3.3% vs 1.1% PBS group), while for MEDI6469 administration that increase was approximately 5.1 fold (1.1 to 5.4%), although the induction on a gross percentage basis was low (2.0% and 4.0%, respectively). For total memory CD8 T cells, OX40L fusion protein IgG4-FP and MEDI6469 induced a 2.7 fold (2.5% compared to 0.92%) and a 5.0-fold (2.6% compared to 0.54%) peak increase in PD-1 expressing cells, respectively, although the increase on a gross percentage basis for each was quite low (1.6% and 2.1%, respectively). The greater induction of PD-1 by MEDI6469 on total memory CD4 and CD8 T cells differs qualitatively from that observed for ICOS, where OX40L fusion protein IgG4-FP-induced changes were greater. Changes in the expression of PD-1 on naïve CD4 or CD8 T cells were not observed for OX40L fusion protein IgG4-FP or MEDI6469 (FIG. 28).

OX40L fusion protein IgG4-FP and MEDI6469 induced the proliferation of CD20+B cells. At the peak, OX40L fusion protein IgG4-FP increased Ki67 expression in B cells by 2.8 fold (24% compared to 8.5%), and MEI6469 by 2.5 fold (17% compared to 6.7%) (FIG. 29).

Conclusions

OX40L fusion protein IgG4-FP induced the proliferation of total, central, and effector memory CD4 and CD8 T cells. The magnitude of effect was greater for CD4 than CD8 T cell populations. The induction of effector memory CD4 and CD8 T cell proliferation was delayed relative to that of total and central memory T cells, indicating either an indirect or delayed biological effect on the effector T cell populations. OX40L fusion protein IgG4-FP induced higher levels of proliferation of total memory CD4 T cells than MEDI6469, although the induction total memory CD8 T cell proliferation was similar at these doses and schedule of drug.

OX40L fusion protein IgG4-FP induced ICOS and PD-1 expression on total memory CD4 and CD8 T cells, with a higher gross percentage induction for each observed on total memory CD4 compared to total memory CD8 T cells. More ICOS induction on total memory CD4 and CD8 T cells was observed for OX40L fusion protein IgG4-FP than for MEDI6469. However, there was a greater induction of PD-1 by MEDI6469 than was observed for OX40L fusion protein IgG4-FP on total memory CD4 T cells, indicating a possible biological difference in the ability of the OX40L fusion protein OX40L fusion protein IgG4-FP to induce the PD-1 T cell inhibitory protein relative to the agonist mAb MEDI6469 on these cells.

The breadth and scope of the present disclosure should not be limited by any of the above-described exemplary embodiments, but should be defined only in accordance with the following claims and their equivalents.

What is claimed is:

1. A single-chain polypeptide subunit comprising: a human IgG4 Fc domain; a functional trimerization domain; and a receptor binding domain of OX40L, wherein the polypeptide subunit further comprises, from the amino terminus to the carboxy terminus, the human IgG4 Fc domain, followed by the trimerization domain, followed by the OX40L receptor binding domain, wherein the polypeptide subunit can self-assemble into a trimeric or hexameric protein, and wherein the polypeptide subunit comprises the amino acid sequence of SEQ ID NO: 4.

2. The polypeptide subunit of claim 1, wherein a hexameric protein assembled from six of the polypeptide subunits can specifically bind to human OX40.

3. The polypeptide subunit of claim 1, further comprising an associated heterologous agent.

4. The polypeptide subunit of claim 3, wherein the heterologous agent is a heterologous polypeptide and is fused to the polypeptide subunit via a peptide bond.

5. The polypeptide subunit of claim 4, wherein the heterologous polypeptide is fused to the N-terminus of the IgG4-Fc domain, is fused to the C-terminus of the receptor binding domain of OX40L, is fused to the C-terminus of the IgG4-Fc domain and to the N-terminus of the trimerization domain, or is fused to the C-terminus of the trimerization domain and to the N-terminus of the receptor binding domain of OX40L.

6. The polypeptide subunit of claim 3, wherein the heterologous agent is chemically conjugated to the polypeptide subunit.

7. The polypeptide subunit of claim 3, wherein the heterologous agent comprises a cytotoxic molecule, a stabilizing agent, an immune response modifier, or a detectable agent.

8. A trimeric protein comprising three polypeptide subunits of claim 1.

9. A hexameric protein comprising six polypeptide subunits of claim 1.

10. The hexameric protein of claim 9 comprising OX40L IgG4P Fusion Protein.

11. A composition comprising the hexameric protein of claim 9, and a carrier.

12. A polynucleotide comprising a nucleic acid that encodes the polypeptide subunit of claim 1, or the hexameric protein of claim 9.

13. The polynucleotide of claim 12, comprising SEQ ID NO: 3.

14. A vector comprising the polynucleotide of claim 12 or claim 13.

15. A host cell comprising the polynucleotide of claim 12 or claim 13 or the vector of claim 14.

16. A method of producing the polypeptide subunit of claim 1 or the hexameric protein of claim 9, comprising culturing the host cell of claim 15 under conditions in which the polypeptide subunit or hexameric protein encoded by the polynucleotide is expressed, and recovering the polypeptide subunit or hexameric protein.

17. A method to promote survival or proliferation of activated T cells, comprising contacting activated T cells with the hexameric protein of claim 9, wherein the hexameric protein can specifically bind to OX40 on the surface of the T cells.

18. A method to reduce regulatory T cell (Treg)-mediated suppression of activated T cell proliferation, comprising contacting a mixture of activated T cells and Treg cells with the hexameric protein of claim 9, wherein the hexameric protein can specifically bind to OX40 on the surface of the T cells.

19. A method of inducing cytokine release from activated T cells, wherein the cytokine is selected from the group consisting of IFNγ, TNFα, IL-10, IL-13 or any combination thereof, comprising contacting activated T cells with the hexameric protein of claim 9, wherein the hexameric protein can specifically bind to OX40 on the surface of the T cells.

20. The method of claim 19, wherein the cytokine is selected from the group consisting of IFNγ, TNFα, IL-10, IL-13 or any combination thereof.

21. The method of claim 17, wherein the activated T cells are activated CD4+ T cells, activated CD8+ T cells, or a combination thereof.

22. The method of any one of claim 21, wherein the activated CD4+ T cells are human CD4+ T cells, cynomolgus monkey CD4+ T cells, rhesus monkey CD4+ T cells, or a combination thereof.

23. A method of promoting T cell activation, comprising contacting T cells with the hexameric protein of claim 9, wherein the hexameric protein can specifically bind to OX40 on the surface of the T cells.

24. The method of claim 23, further comprising cross-linking of the hexameric protein through interaction of the IgG4-Fc domain with a cell expressing FcγR.

25. The method of claim 24, wherein the cell expressing FcγR is a B cell, a monocyte, a macrophage, a myeloid or plasmacytoid dendritic cell, a follicular dendritic cell, a Langerhans cell, an endothelial cell, an NK cell, an activated T cell, a neutrophil, a eosinophil, a platelet, a mast cell, a CD45+ cell from a primary human tumor or tumor-draining or non-draining lymph node, a CD45+ cell from other secondary or tertiary lymphoid structures, or a combination thereof.

26. The method of claim 23, wherein T cell activation can be measured through stimulation of the NFκB signal transduction pathway.

27. The method of claim 23, wherein the activated T cells are activated CD4+ T cells, activated CD8+ T cells, or a combination thereof.

28. The method of claim 27, wherein the activated CD4+ T cells are human CD4+ T cells, cynomolgus monkey CD4+ T cells, rhesus monkey CD4+ T cells, or a combination thereof.

29. The method of claim 17, wherein the contacting comprises administering an effective amount of the hexameric protein to a subject.

30. A method of treating cancer in a subject, wherein the cancer is selected from the group consisting of melanoma, renal cell carcinoma, colon carcinoma, mammary carcinoma, and sarcoma, comprising administering to a subject in need of treatment an effective amount of the hexameric protein of claim 9 or the composition of claim 11.

31. The method of claim 30, wherein administration of the hexameric protein or composition can inhibit tumor growth, can promote tumor reduction, or both.

32. The method of claim 30, wherein tumor growth inhibition is achieved in the presence of T-cells.

33. A method of enhancing an immune response in a subject comprising administering to a subject in need thereof a therapeutically effective amount of the hexameric protein of claim 9, or the composition of claim 11.

34. The method of claim 30, wherein the subject is a human subject.

35. A method of inducing expression of ICOS (inducible T-cell costimulator) on T cells, comprising contacting T cells with the hexameric protein of claim 9, wherein the hexameric protein can specifically bind to OX40 on the surface of the T cells.

36. A method of inducing expression of PD-1 on T cells, comprising contacting T cells with the hexameric protein of claim 9, wherein the hexameric protein can specifically bind to OX40 on the surface of the T cells.

* * * * *